United States Patent [19]

Lagu et al.

[11] Patent Number: 6,159,990
[45] Date of Patent: Dec. 12, 2000

[54] OXAZOLIDINONES AS $\alpha_{1A}$ RECEPTOR ANTAGONISTS

[75] Inventors: Bharat Lagu, Maywood, N.J.; T.G. Murali Dhar, Newark, Del.; Dhanapalan Nagarathnam, Ramsey, N.J.; Yoon T. Jeon; Mohammad R. Marzabadi, both of Ridgewood, N.J.; Wai C. Wong, Livingston, N.J.; Charles Gluchowski, Danville, Calif.

[73] Assignee: Synaptic Pharmaceutical Corporation, Paramus, N.J.

[21] Appl. No.: 09/099,225

[22] Filed: Jun. 17, 1998

Related U.S. Application Data

[60] Provisional application No. 60/050,096, Jun. 18, 1997.

[51] Int. Cl.$^7$ .................... A61K 31/445; C07D 413/12
[52] U.S. Cl. .................. 514/326; 546/208; 546/209; 546/210
[58] Field of Search .................. 546/208, 209, 546/210; 514/326

[56] References Cited

U.S. PATENT DOCUMENTS

| | | | |
|---|---|---|---|
| 3,193,559 | 7/1965 | Regnier et al. | 546/208 |
| 3,196,152 | 7/1965 | Wright et al. | 546/210 |
| 3,334,098 | 8/1967 | Wright | 546/210 |
| 3,576,808 | 4/1971 | Schut | 546/208 |
| 3,930,008 | 12/1975 | Manghisi et al. | 546/208 |
| 4,089,861 | 5/1978 | Kyburz | 544/369 |
| 4,145,347 | 3/1979 | L'Italien et al. | 546/208 |
| 4,377,578 | 3/1983 | Vandenberk et al. | 544/370 |
| 4,410,540 | 10/1983 | Schnettler et al. | 546/210 |
| 4,543,318 | 9/1985 | Maeda et al. | |
| 4,804,657 | 2/1989 | Kogure et al. | 514/218 |
| 4,882,431 | 11/1989 | Ishimitsu et al. | 540/603 |
| 5,202,345 | 4/1993 | Matsumura et al. | 514/423 |
| 5,436,264 | 7/1995 | Pfister et al. | 514/415 |
| 5,461,162 | 10/1995 | Ho et al. | 548/188 |
| 5,574,030 | 11/1996 | Masaki et al. | 514/212 |
| 5,637,729 | 6/1997 | Lacroix et al. | 548/316.7 |
| 5,698,573 | 12/1997 | Carling et al. | 514/326 |
| 5,726,188 | 3/1998 | Takano et al. | 514/326 |

FOREIGN PATENT DOCUMENTS

| | | |
|---|---|---|
| 0599749 | 6/1994 | European Pat. Off. |
| 0675114 | 4/1995 | European Pat. Off. |
| 0719773 | 7/1996 | European Pat. Off. |
| 871235 | 6/1961 | United Kingdom. |
| 9507904 | 3/1995 | WIPO. |
| 9507905 | 3/1995 | WIPO. |
| 9507906 | 3/1995 | WIPO. |
| 9510508 | 4/1995 | WIPO. |
| 95/33729 | 12/1995 | WIPO. |

OTHER PUBLICATIONS

Hasegawa et al. "2–oxazolidinone derivatives" CA 88:105311, 1977.

American Chemical Society Registry No 86217–68–7 (Exhibit 2).

Cascia, G., et al., "5–Peperazinylalkyl–2(3H)–Oxazolones With Neuroleptic Activity" *J. Med. Chem.* (1989) 32: 2241–2247.

Krieg, B. and Lautenschlager, H., "Uber die Umwandlung von 4–Oxazolin–2–onen in 1–(2–Oxoalkyl)–1,3,5–triazin–2,4,6 (1H,3H, 5H)–trione und umgekehrt" *Liebigs Ann. Chem.* (1976) 1465–1470.

Joshi, K. et al., Fluorine containing bioactive heterocycles. Part II. Synthesis of some new fluorine containing arylglyoxals, their hydrates and 1,5–disubstituted hydantoins. *J. Heterocyclic Chem.* (1981) 18: 1651–1653 (Exhibit K).

Sep. 3, 1998 International Search Report issued in connection with PCT International Application No. PCT/US98/12668 (Exhibit S).

Patent Family Information for EP 599749 from Dialog(R) (Exhibit T).

Hwang, K.J., et al., "Diastereoselcetive Synthesis Of Oxazolidinone Derivatives And Their Antifungal Activities" *Korean J. Of Med. Chem.* (1994) 4(1):52–56.

Krieg, B., and Lautenschlager, H., "Uber die saure Hydrolyse von N–tert–Butyl–2–oxo–4,5–dephenyl–4–oxazolin–3–carboxzmid" *Liebigs Ann. Chem.* (1976) 788–792.

Krieg, B. and Lautenschlager, H., "4–Imidazolin–2–one durch Umlagerung von 2–Oxo–4–oxaolin–3–caroxamiden" *Liebigs Ann. Chem* (1976) 208–221.

Pirkle, W.H. and Simmons, K.A., "Improved Chiral Derivatizing Agents For the Chromatographic Resolution Of Racemic Primary Amines" *J. Org. Chem.* (1983) 48: 2520–2527.

American Chemical Society Registry No. 52985–68–9; (1997).

American Chemical Society Registry No. 53291–72–8; (1997).

American Chemical Society Registry No. 59167–70–3; (1997).

American Chemical Society Registry No. 59167–71–4; (1997).

American Chemical Society Registry No. 59167–72–5; (1997).

American Chemical Society Registry No. 59167–85–0; (1997).

American Chemical Society Registry No. 86217–50–7; (1997).

(List continued on next page.)

*Primary Examiner*—Ceila Chang
*Attorney, Agent, or Firm*—John P. White; Cooper & Dunham LLP

[57] ABSTRACT

This invention is directed to oxazolidinone compounds which are selective antagonists for human $\alpha_{1A}$ receptors. This invention is also related to uses of these compounds for lowering intraocular pressure, inhibiting cholesterol synthesis, relaxing lower urinary tract tissue, the treatment of benign prostatic hyperplasia, impotency, cardiac arrhythmia and for the treatment of any disease where the antagonism of the $\alpha_{1A}$ receptor may be useful. The invention further provides a pharmaceutical composition comprising a therapeutically effective amount of the above-defined compounds and a pharmaceutically acceptable carrier.

38 Claims, 13 Drawing Sheets

OTHER PUBLICATIONS

American Chemical Society Registry No. 86217–51–8; (1997).
American Chemical Society Registry No. 86217–57–4; (1997).
American Chemical Society Registry No. 86217–58–5; (1997).
American Chemical Society REgistry No. 86217–60–9; (1997).
American Chemical Society Registry No. 86217–61–0; (1997).
American Chemical Society Registry No. 86217–62–1; (1997).
American Chemical Society Registry No. 86217–63–2; (1997).
American Chemical Society Registry No. 86217–65–4; (1997).
American Chemical Society Registry No. 86217–64–3; (1997).
American Chemical Society Registry No. 86217–66–5; (1997).
American Chemical Society Registry No. 86217–67–7; (1997).
American Chemical Society Registry No. 86217–69–8; (1997).
American Chemical Society Registry No. 86217–70–1; (1997).
American Chemical Society REgistry No. 86217–71–2; (1997).
American Chemical Society Registry No. 86217–72–3; (1997).
American Chemical Society Registry No. 86217–73–4; (1997).
American Chemical Society Registry No. 86217–74–5; (1997).
American Chemical Society Registry No. 86217–45–1; (1997).
American Chemical Society Registry No. 86238–45–1; (1997).
American Chemical Society Registry No. 120994–64–1; (1997).
American Chemical Society Registry No. 158323–69–4; (1997.
American Chemical Society Registry No. 158323–70–7; (1997).
American Chemical Society Registry No. 158323–71–8; (1997).
American Chemical Society Registry No. 158323–72–9; (1997).
American Chemical Society Registry No. 158323–41–0; (1997).
American Chemical Society Registry No. 158323–42–1; (1997).
American Chemical Society Registry No. 158323–43–2; (1997).
American Chemical Society Registry No. 167698–03–5; (1997).
American Chemical Society Registry No. 158267–05–1; (1997).
American Chemical Society Registry No. 158267–02–8; (1997).
American Chemical Society Registry No. 144253–21–4; (1997).
American Chemical Society Registry No. 144253–20–3; (1997).
American Chemical Society Registry No. 144253–19–0; (1997).
American Chemical Society Registry No. 144253–18–9; (1997).
American Chemical Society Registry No. 132659–25–7; (1997).
American Chemical Society Registry No. 132659–24–6; (1997).
American Chemical Society REgistry No. 132659–22–4; (1997).
American Chemical Society Registry No. 132659–21–3; (1997).
American Chemical Society Registry No. 132659–20–2; (1997).
American Chemical Society Registry No. 131478–61–0; (1997).
American Chemical Society Registry No. 131478–55–2; (1997).
American Chemical Society Registry No. 158731–63–8; (1997).

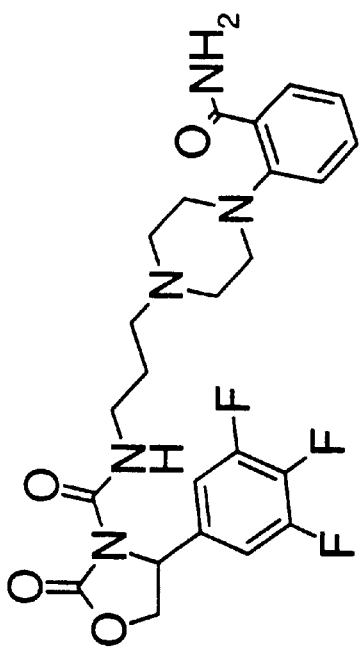
Compound 6
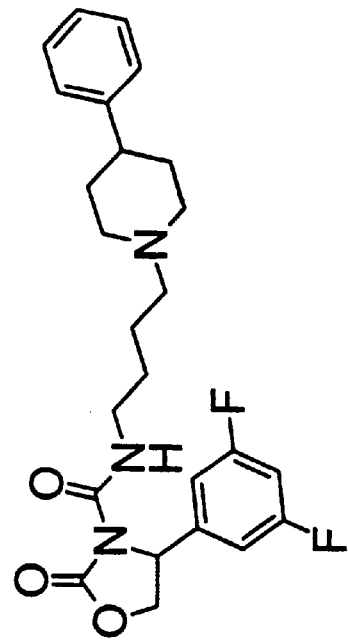
Compound 8
FIG. 1B
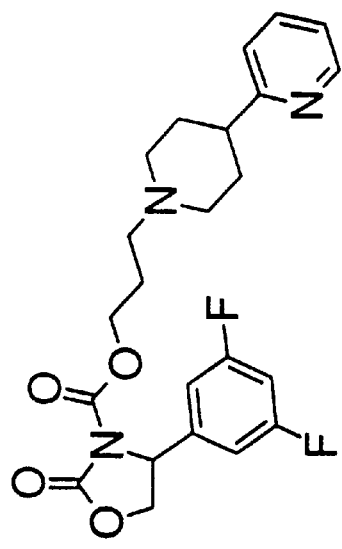
Compound 5
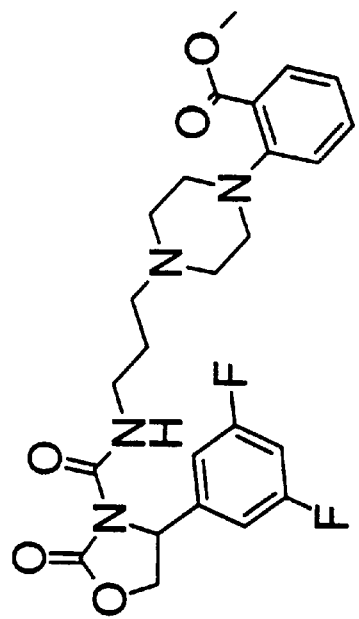
Compound 7

Compound 14

Compound 13

Compound 15

Compound 16

Compound 17

Compound 18

Compound 19

Compound 20

Compound 21

Compound 22

Compound 23

Compound 29

Compound 31

Compound 28

Compound 30

Compound 33

Compound 35

Compound 32

Compound 34

Compound 37

Compound 39

Compound 36

Compound 38

Compound 45

Compound 47

Compound 44

Compound 46

Compound 49

Compound 51

Compound 48

Compound 50

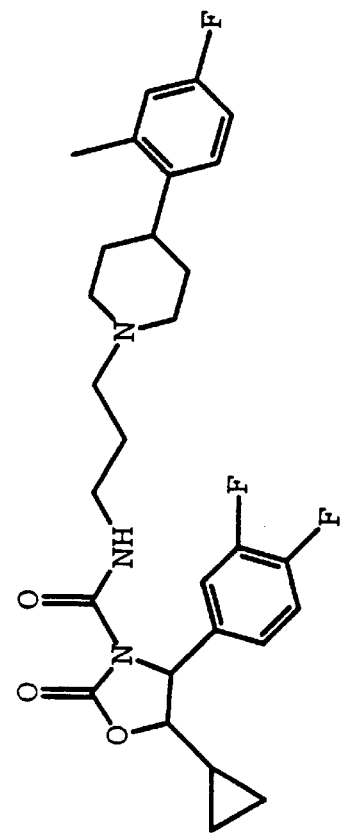
Compound 53
FIG. 1M
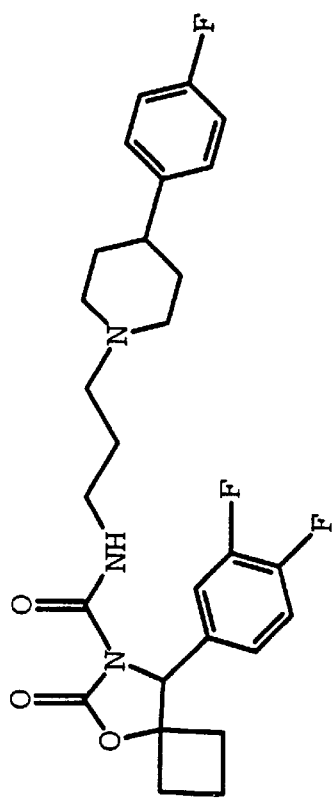
Compound 52

OXAZOLIDINONES AS $\alpha_{1A}$ RECEPTOR ANTAGONISTS

This application claims the benefit of U.S. Provisional application Ser. No. 60/050,096, filed Jun. 18, 1997, the contents of which are hereby incorporated in its entirety by reference into the present application.

Throughout this application, various references are referred to within parentheses. Disclosures of these publications in their entireties are hereby incorporated by reference into this application to more fully describe the state of the art to which this invention pertains.

BACKGROUND OF THE INVENTION

The designation "$\alpha_{1A}$" is the appellation recently approved by the IUPHAR Nomenclature Committee for the previously designated "$\alpha_{1C}$" cloned subtype as outlined in the 1995 Receptor and Ion Channel Nomenclature Supplement (Watson and Girdlestone, 1995). The designation $\alpha_{1A}$ is used throughout this application and the supporting tables and figures to refer to this receptor subtype. At the same time, the receptor formerly designated $\alpha_{1A}$ was renamed $\alpha_{1D}$. The new nomenclature is used throughout this application. Stable cell lines expressing these receptors are described herein; however, these cell lines were deposited with the American Type Culture Collection (ATCC) under the old nomenclature (infra).

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986).

Transurethral resection of the prostate (TURP) was used in approximately 180,000 men in the United States in 1996. This surgical procedure results in significant benefit. However, because of its potential adverse consequences, surgery is an unattractive alternative for many patients and is not recommended for elderly patients due to the potential for complications. Another surgical procedure, transurethral needle ablation (TUNA), was recently approved by the FDA and may have the advantage of possible use on an outpatient basis under local anesthesia. However, initial results of a recent study comparing TURP and TUNA show a lower level of efficacy in TUNA than in TURP with respect to increasing urinary flow.

A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

$\alpha$-Adrenergic receptors (McGrath, et. al. Med. Res. Rev., 9, 407–533, 1989) are specific neuroreceptor proteins located in the peripheral and central nervous systems on tissues and organs throughout the body. These receptors are important switches for controlling many physiological functions and, thus, represent important targets for drug development. In fact, many $\alpha$-adrenergic drugs have been developed over the past 40 years. Examples include clonidine, phenoxybenzamine and prazosin (treatment of hypertension), naphazoline (nasal decongestant), and apraclonidine (treating glaucoma). $\alpha$-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of $\alpha$-adrenergic receptors and their drugs has evolved through increased scientific scrutiny. Prior to 1977, only one $\alpha$-adrenergic receptor was known to exist. Between 1977 and 1988, it was accepted by the scientific community that at least two $\alpha$-adrenergic receptors—$\alpha_1$ and $\alpha_2$—existed in the central and peripheral nervous systems. Since 1988, new techniques in molecular biology have led to the identification of at least six $\alpha$-adrenergic receptors which exist throughout the central and peripheral nervous systems: $\alpha_{1A}$ (new nomenclature), $\alpha_{1B}$, $\alpha_{1D}$ (new nomenclature), $\alpha_{2A}$, $\alpha_{2B}$ and $\alpha_{2C}$ (Bylund, D. B., FASEB J., 6, 832 (1992)). In many cases, it is not known precisely which physiological responses in the body are controlled by each of these receptors. In addition, current $\alpha$-adrenergic drugs are not selective for any particular $\alpha$-adrenergic receptor. Many of these drugs produce untoward side effects which may be attributed to their poor $\alpha$-adrenergic receptor selectivity.

Since the mid 1970's, nonselective a-antagonists have been prescribed to treat BPH. In 1976, M. Caine, et al. (Brit. J. Urol., 48, 255 (1976)), reported that the nonselective $\alpha$-antagonist phenoxybenzamine was useful in relieving the symptoms of BPH. This drug may produce its effects by interacting with $\alpha$-receptors located on the prostate. However, this drug also produces significant side effects such as dizziness and asthenia which severely limit its use in treating patients on a chronic basis. More recently, the $\alpha$-adrenergic antagonists prazosin and terazosin have also been found to be useful for treating BPH. However, these drugs also produce untoward side effects. It has recently been discovered that the $\alpha_{1A}$ receptor is responsible for mediating the contraction of human prostate smooth muscle (Gluchowski, C. et. al., WO 94/10989, 1994; Forray, C. et. al., Mol. Pharmacol. 45, 703, 1994). This discovery indicates that the $\alpha_{1A}$ antagonists may be effective agents for the treatment of BPH with decreased side effects. Further studies have indicated that the $\alpha_{1A}$ receptor may also be present in other lower urinary tract tissues, such as urethral smooth muscle (Ford et al. Br. J. Pharmacol., 114, 24P, (1995)).

This invention is directed to oxazolidinone compounds which are selective antagonists for cloned human $\alpha_{1A}$ receptors. This invention is also related to uses of these compounds for lowering intraocular pressure (Zhan, et. al. Ophthalmol. Vis. Sci., 34 Abst. #1133, 928, 1993), inhibiting cholesterol synthesis (D'Eletto and Javitt, J. Cardiovascular Pharmacol., 13 (Suppl. 2) S1–S4, 1989), benign prostatic hyperplasia, impotency (Milne and Wyllie, EP 0 459 666 A2, 1991), sympathetically mediated pain (Campbell, WO 92/14453, 1992), cardiac arrhythmia (Spiers, et. al., J. Cardiovascular Pharmacol., 16, 824–830, 1990) and for the treatment of any disease where antagonism of the $\alpha_{1A}$ receptor may be useful.

SUMMARY OF THE INVENTION

This invention is directed to a compound having the structure:

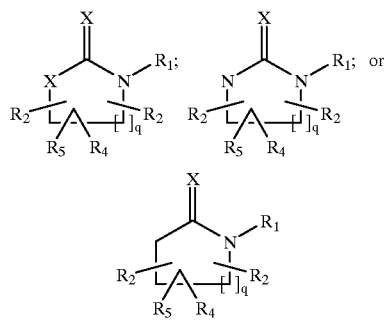

wherein each X is independently O or S;

wherein q is 1 or 2;

wherein each $R_2$ is independently H; —$(CH_2)_tXR_3$; —$(CH_2)_tC(X)NR_3$; —$(CH_2)_tCO_2R_3$; —$CO_2R_3$; straight chained or branched $C_1$–$C_7$ alkyl, aminoalkyl, carboxamidoalkyl; straight chained or branched $C_2$–$C_7$ alkenyl, or alkynyl; or $C_3$–$C_7$ cycloalkyl or $C_5$–$C_7$ cycloalkenyl;

wherein each t is an integer from 1 to 4 inclusive;

wherein each $R_3$ is independently H; straight chained or branched $C_1$–$C_7$ alkyl, straight chained or branched $C_2$–$C_7$ alkenyl, or alkynyl; or $C_3$–$C_7$ cycloalkyl or $C_5$–$C_7$ cycloalkenyl;

wherein $R_4$ is aryl, heteroaryl, $C_1$–$C_7$ alkyl substituted with one or two aryl, or $C_1$–$C_7$ alkyl substituted with one or two heteroaryl; wherein the aryl or heteroaryl may be substituted with one or more of F, Cl, Br, I, —CN, —$NO_2$, —$N(R_3)_2$, —$COR_3$, —$(CH_2)_tXR_3$, —$(CH_2)_nC(X)NR_3$, —$(CH_2)_nCO_2R_3$, straight chained or branched $C_1$–$C_7$ alkyl, monofluoroalkyl, polyfluoroalkyl or carboxamidoalkyl, or straight chained or branched $C_2$–$C_7$ aminoalkyl, alkenyl or alkynyl, or $C_3$–$C_7$ cycloalkyl or $C_5$–$C_7$ cycloalkenyl;

wherein each n independently is an integer from 0 to 7 inclusive;

wherein $R_5$ is H; aryl, $C_1$–$C_7$ alkyl substituted with aryl, heteroaryl, or $C_1$–$C_7$ alkyl substituted with heteroaryl; wherein the aryl or heteroaryl may be substituted with one or more of F, Cl, Br, I, —CN, —$NO_2$, —$N(R_3)_2$, —$COR_3$, —$(CH_2)_tXR_3$, —$(CH_2)_nC(X)NR_3$, —$(CH_2)_nCO_2R_3$, straight chained or branched $C_1$–$C_7$ alkyl, monofluoroalkyl, polyfluoroalkyl or carboxamidoalkyl, or straight chained or branched $C_2$–$C_7$ aminoalkyl, alkenyl or alkynyl, or $C_3$–$C_7$ cycloalkyl or $C_5$–$C_7$ cycloalkenyl;

where $R_5$ and one $R_2$ on adjacent carbon atoms together may form aryl, heteroaryl, indane or tetrahydronaphthyl, $C_3$–$C_7$ cycloalkyl, or heterocycloalkyl wherein one or two heteroatoms may be O, N or S;

wherein $R_1$ is

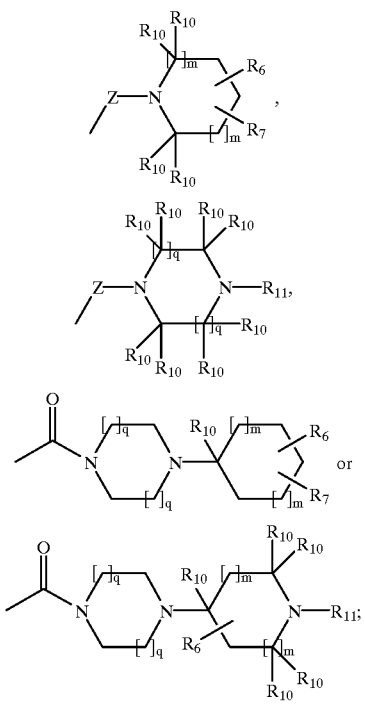

where each $R_6$ is independently H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;

where each $R_7$ is independently H; F; Cl; Br; I; —$COR_3$; —$CO_2R_3$; —$(CH_2)_nXR_3$; —$COR_3$; —$(CH_2)_nC(X)N(R_3)_2$; —$(CH_2)_nCO_2R_3$; —CN; —$NO_2$; —$N(R_3)_2$; straight chained or branched $C_1$–$C_7$ alkyl, hydroxyalkyl, aminoalkyl, carboxamidoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or $C_5$–$C_7$ cycloalkenyl, wherein the alkyl, aminoalkyl, carboxamidoalkyl, alkenyl, alkynyl, cycloalkyl or cycloalkenyl may be substituted with one or more aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, straight chained or branched $C_1$–$C_7$ monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;

wherein each $R_{10}$ is independently H; $(CH_2)_t XR_3$; $(CH_2)_t C(X)NR_3$; $(CH_2)_t CO_2 R_3$; straight chained or branched $C_1$–$C_7$ alkyl or carboxamidoalkyl; straight chained or branched $C_2$–$C_7$ aminoalkyl, alkenyl, or alkynyl; or $C_3$–$C_7$ cycloalkyl or $C_5$–$C_7$ cycloalkenyl;

wherein $R_{11}$ is aryl, heteroaryl, $C_1$–$C_7$ alkyl substituted with one or two aryl, or $C_1$–$C_7$ alkyl substituted with one or two heteroaryl; wherein any aryl or heteroaryl independently may be substituted with one or more of F, Cl, Br, I, —CN, —$NO_2$, —$N(R_3)_2$, —$COR_3$, —$(CH_2)_n XR_3$, —$(CH_2)_n C(X)NR_3$, —$(CH_2)_n CO_2 R_3$, straight chained or branched $C_1$–$C_7$ alkyl, monofluoroalkyl, polyfluoroalkyl, or carboxamidoalkyl, straight chained or branched $C_2$–$C_7$ aminoalkyl, alkenyl, or alkynyl, or $C_3$–$C_7$ cycloalkyl or $C_5$–$C_7$ cycloalkenyl;

wherein each m independently is an integer from 0 to 3 inclusive;

wherein Z is

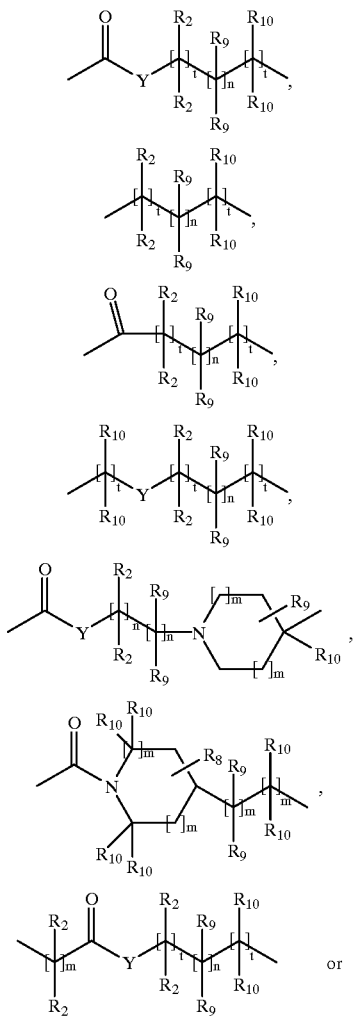

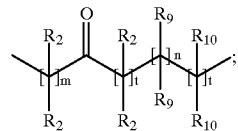

or $C_2$–$C_7$ alkenyl, wherein the $C_2$–$C_7$ alkenyl may be unsubstituted or substituted with one or more $R_9$ groups;

where $R_8$ is H; $(CH_2)_t XR_3$; $(CH_2)_t C(X)NR_3$; $(CH_2)_t CO_2 R_3$; straight chained or branched $C_1$–$C_7$ alkyl, carboxamidoalkyl; straight chained or branched $C_2$–$C_7$ aminoalkyl, alkenyl, or alkynyl; or $C_3$–$C_7$ cycloalkyl or $C_5$–$C_7$ cycloalkenyl;

where each $R_9$ is independently H; F; Cl; Br; I; $(CH_2)_m XR_3$; $(CH_2)_m C(X)NR_3$; $(CH_2)_m CO_2 R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, or alkynyl; or $C_3$–$C_7$ cycloalkyl or $C_5$–$C_7$ cycloalkenyl;

wherein Y is S, O, or $NR_8$;

or a pharmaceutically acceptable salt thereof.

The present invention is additionally directed to a compound having the structure:

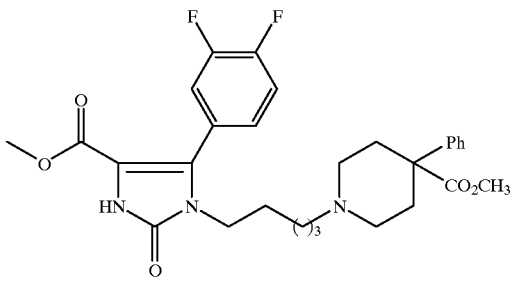

This invention is additionally directed to a compound having the structure:

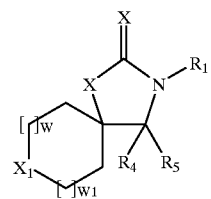

wherein each W is an integer from 0 to 3 inclusive;
wherein each W1 is an integer from 0 to 3 inclusive;
wherein each X is independently O or S;
wherein X1 is O, S, $NR_3$;
wherein each $R_2$ is independently H; —$(CH_2)_t XR_3$; —$(CH_2)_t C(X)NR_3$; —$(CH_2)_t CO_2 R_3$; —$CO_2 R_3$; straight chained or branched $C_1$–$C_7$ alkyl, aminoalkyl, carboxamidoalkyl; straight chained or branched $C_2$–$C_7$ alkenyl, or alkynyl; or $C_3$–$C_7$ cycloalkyl or $C_5$–$C_7$ cycloalkenyl;

wherein each t is an integer from 1 to 4 inclusive;

wherein each $R_3$ is independently H; straight chained or branched $C_1$–$C_7$ alkyl, straight chained or branched $C_2$–$C_7$ alkenyl, or alkynyl; or $C_3$–$C_7$ cycloalkyl or $C_5$–$C_7$ cycloalkenyl;

wherein $R_4$ is aryl, heteroaryl, $C_1$–$C_7$ alkyl substituted with one or two aryl, or $C_1$–$C_7$ alkyl substituted with one or two heteroaryl; wherein the aryl or heteroaryl may be substituted with one or more of F, Cl, Br, I, —CN, —NO$_2$, —N(R$_3$)$_2$, —COR$_3$, —(CH$_2$)$_t$XR$_3$, —(CH$_2$)$_n$C(X)NR$_3$, —(CH$_2$)$_n$CO$_2$R$_3$, straight chained or branched C$_1$–C$_7$ alkyl, monofluoroalkyl, polyfluoroalkyl or carboxamidoalkyl, or straight chained or branched C$_2$–C$_7$ aminoalkyl, alkenyl or alkynyl, or C$_3$–C$_7$ cycloalkyl or C$_5$–C$_7$ cycloalkenyl;

wherein each n independently is an integer from 0 to 7 inclusive;

wherein R$_5$ is H; aryl, C$_1$–C$_7$ alkyl substituted with aryl, heteroaryl, or C$_1$–C$_7$ alkyl substituted with heteroaryl; wherein the aryl or heteroaryl may be substituted with one or more of F, Cl, Br, I, —CN, —NO$_2$, —N(R$_3$)$_2$, —COR$_3$, —(CH$_2$)$_t$XR$_3$, —(CH$_2$)$_n$C(X)NR$_3$, —(CH$_2$)$_n$CO$_2$R$_3$, straight chained or branched C$_1$–C$_7$ alkyl, monofluoroalkyl, polyfluoroalkyl or carboxamidoalkyl, or straight chained or branched C$_2$–C$_7$ aminoalkyl, alkenyl or alkynyl, or C$_3$–C$_7$ cycloalkyl or C$_5$–C$_7$ cycloalkenyl;

wherein R$_1$ is

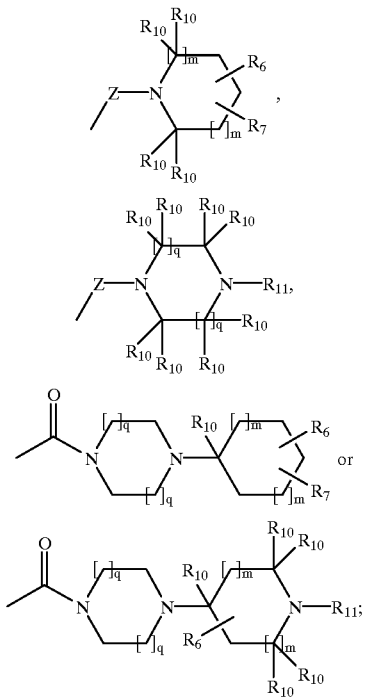

where each R$_6$ is independently H; straight chained or branched C$_1$–C$_7$ alkyl, hydroxyalkyl, aminoalkyl, alkoxyalkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or C$_5$–C$_7$ cycloalkenyl; aryl or heteroaryl, wherein the aryl or heteroaryl may be substituted with one or more of F, Cl, Br, I, —(CH$_2$)$_n$XR$_3$, —COR$_3$, —(CH$_2$)$_n$C(X)N(R$_3$)$_2$, —(CH$_2$)$_n$CO$_2$R$_3$, —CN, —NO$_2$, —N(R$_3$)$_2$, —SO$_2$R$_3$, straight chained or branched C$_1$–C$_7$ alkyl, monofluoroalkyl or polyfluoroalkyl, straight chained or branched C$_2$–C$_7$ alkenyl or alkynyl, or C$_3$–C$_7$ cycloalkyl, monofluorocycloalkyl, polyfluorocycloalkyl or C$_5$–C$_7$ cycloalkenyl;

where each R$_7$ is independently H; F; Cl; Br; I; —COR$_3$; —CO$_2$R$_3$; —(CH$_2$)$_n$XR$_3$; (CH$_2$)$_n$C(X)N(R$_3$)$_2$; —(CH$_2$)$_n$CO$_2$R$_3$; —CN; —NO$_2$; —N(R$_3$)$_2$; straight chained or branched C$_1$–C$_7$ alkyl, hydroxyalkyl, aminoalkyl, carboxamidoalkyl, alkoxyalkyl, monofluoroalkyl or polyfluoroalkyl; straight chained or branched C$_2$–C$_7$ alkenyl or alkynyl; C$_3$–C$_7$ cycloalkyl, monofluorocycloalkyl, polyfluorocycloalkyl or C$_5$–C$_7$ cycloalkenyl, wherein the alkyl, aminoalkyl, carboxamidoalkyl, alkenyl, alkynyl, cycloalkyl or cycloalkenyl may be substituted with one or more aryl or heteroaryl, wherein the aryl or heteroaryl may be substituted with one or more of F, Cl, Br, I, —(CH$_2$)$_n$XR$_3$, —COR$_3$, —(CH$_2$)$_n$C(X)N(R$_3$)$_2$, —(CH$_2$)$_n$CO$_2$R$_3$, —CN, —NO$_2$, —N(R$_3$)$_2$, —SO$_2$R$_3$, straight chained or branched C$_1$–C$_7$ alkyl, monofluoroalkyl or polyfluoroalkyl, straight chained or branched C$_2$–C$_7$ alkenyl or alkynyl, or C$_3$–C$_7$ cycloalkyl, monofluorocycloalkyl, polyfluorocycloalkyl or C$_5$–C$_7$ cycloalkenyl; aryl or heteroaryl, wherein the aryl or heteroaryl may be substituted with one or more of F, Cl, Br, I, —(CH$_2$)$_n$XR$_3$, —COR$_3$, —(CH$_2$)$_n$C(X)N(R$_3$)$_2$, —(CH$_2$)$_n$CO$_2$R$_3$, —CN, —NO$_2$, —N(R$_3$)$_2$, —SO$_2$R$_3$, straight chained or branched C$_1$–C$_7$ alkyl, straight chained or branched C$_1$–C$_7$ monofluoroalkyl or polyfluoroalkyl, straight chained or branched C$_2$–C$_7$ alkenyl or alkynyl, or C$_3$–C$_7$ cycloalkyl, monofluorocycloalkyl, polyfluorocycloalkyl or C$_3$–C$_7$ cycloalkenyl;

wherein each R$_{10}$ is independently H; (CH$_2$)$_t$XR$_3$; (CH$_2$)$_t$C(X)NR$_3$; (CH$_2$)$_t$CO$_2$R$_3$; straight chained or branched C$_1$–C$_7$ alkyl or carboxamidoalkyl; straight chained or branched C$_2$–C$_7$ aminoalkyl, alkenyl, or alkynyl; or C$_3$–C$_7$ cycloalkyl or C$_5$–C$_7$ cycloalkenyl;

wherein R$_{11}$ is aryl, heteroaryl, C$_1$–C$_7$ alkyl substituted with one or two aryl, or C$_1$–C$_7$ alkyl substituted with one or two heteroaryl; wherein any aryl or heteroaryl independently may be substituted with one or more of F, Cl, Br, I, —CN, —NO$_2$, —N(R$_3$)$_2$, —COR$_3$, —(CH$_2$)$_n$XR$_3$, —(CH$_2$)$_n$C(X)NR$_3$, —(CH$_2$)$_n$CO$_2$R$_3$, straight chained or branched C$_1$–C$_7$ alkyl, monofluoroalkyl, polyfluoroalkyl, or carboxamidoalkyl, straight chained or branched C$_2$–C$_7$ aminoalkyl, alkenyl, or alkynyl, or C$_3$–C$_7$ cycloalkyl or C$_5$–C$_7$ cycloalkenyl;

wherein each m independently is an integer from 0 to 3 inclusive;

wherein Z is

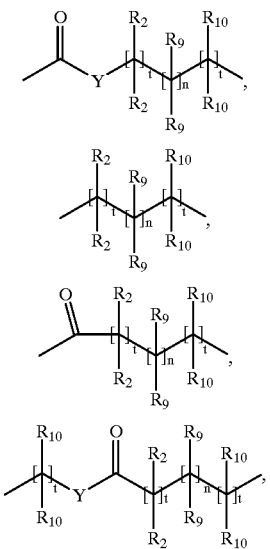

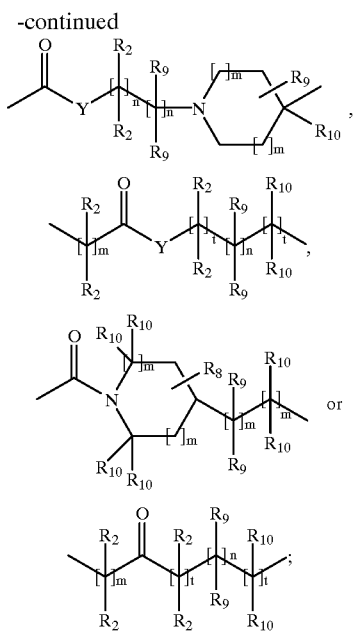

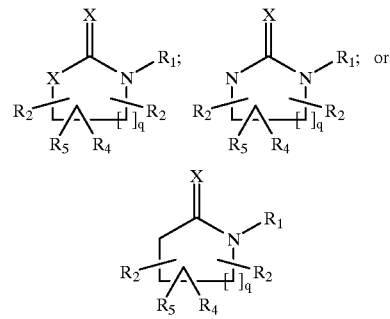

or C$_2$–C$_7$ alkenyl, wherein the C$_2$–C$_7$ alkenyl may be unsubstituted or substituted with one or more R$_9$ groups;

where R$_8$ is H; (CH$_2$)$_t$XR$_3$; (CH$_2$)$_t$C(X)NR$_3$; (CH$_2$)$_t$CO$_2$R$_3$; straight chained or branched C$_1$–C$_7$ alkyl, carboxamidoalkyl; straight chained or branched C$_2$–C$_7$ aminoalkyl, alkenyl, or alkynyl; or C$_3$–C$_7$ cycloalkyl or C$_5$–C$_7$ cycloalkenyl;

where each R$_9$ is independently H; F; Cl; Br; I; (CH$_2$)$_m$XR$_3$; (CH$_2$)$_m$C(X)NR$_3$; (CH$_2$)$_m$CO$_2$R$_3$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl, or alkynyl; or C$_3$–C$_7$ cycloalkyl or C$_5$–C$_7$ cycloalkenyl;

wherein Y is S, O, or NR$_8$;

or a pharmaceutically acceptable salt thereof.

This invention is also related to uses of these compounds for lowering intraocular pressure, inhibiting cholesterol synthesis, relaxing lower urinary tract tissue, the treatment of benign prostatic hyperplasia, impotency, cardiac arrhythmia and for the treatment of any disease where antagonism of the α$_{1A}$ receptor may be useful. The invention further provides pharmaceutical compositions comprising a therapeutically effective amount of the above-defined compounds and a pharmaceutically acceptable carrier.

BRIEF DESCRIPTION OF THE FIGURES

FIG. 1 FIGS. 1A–1M show the structures of the compounds described hereinbelow in the Examples.

DETAILED DESCRIPTION OF THE INVENTION

Figure 1A:
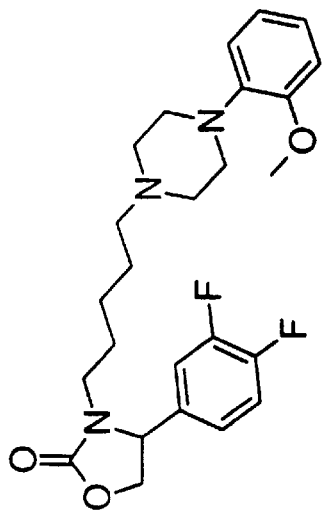
Figure 1A:
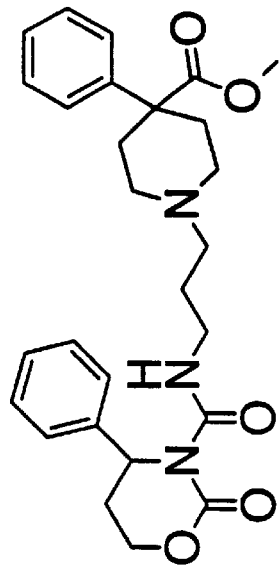
Figure 1A:
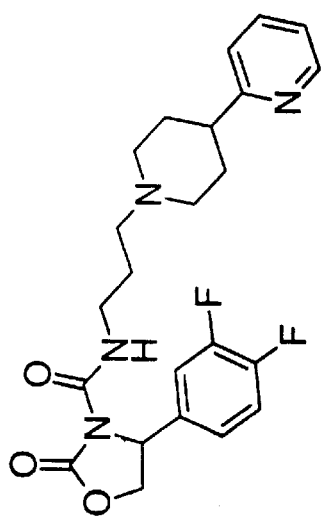
Figure 1A:
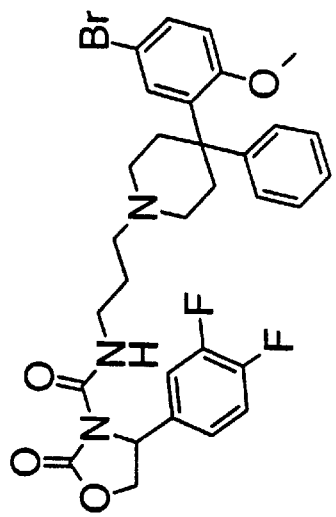
Figure 1C:
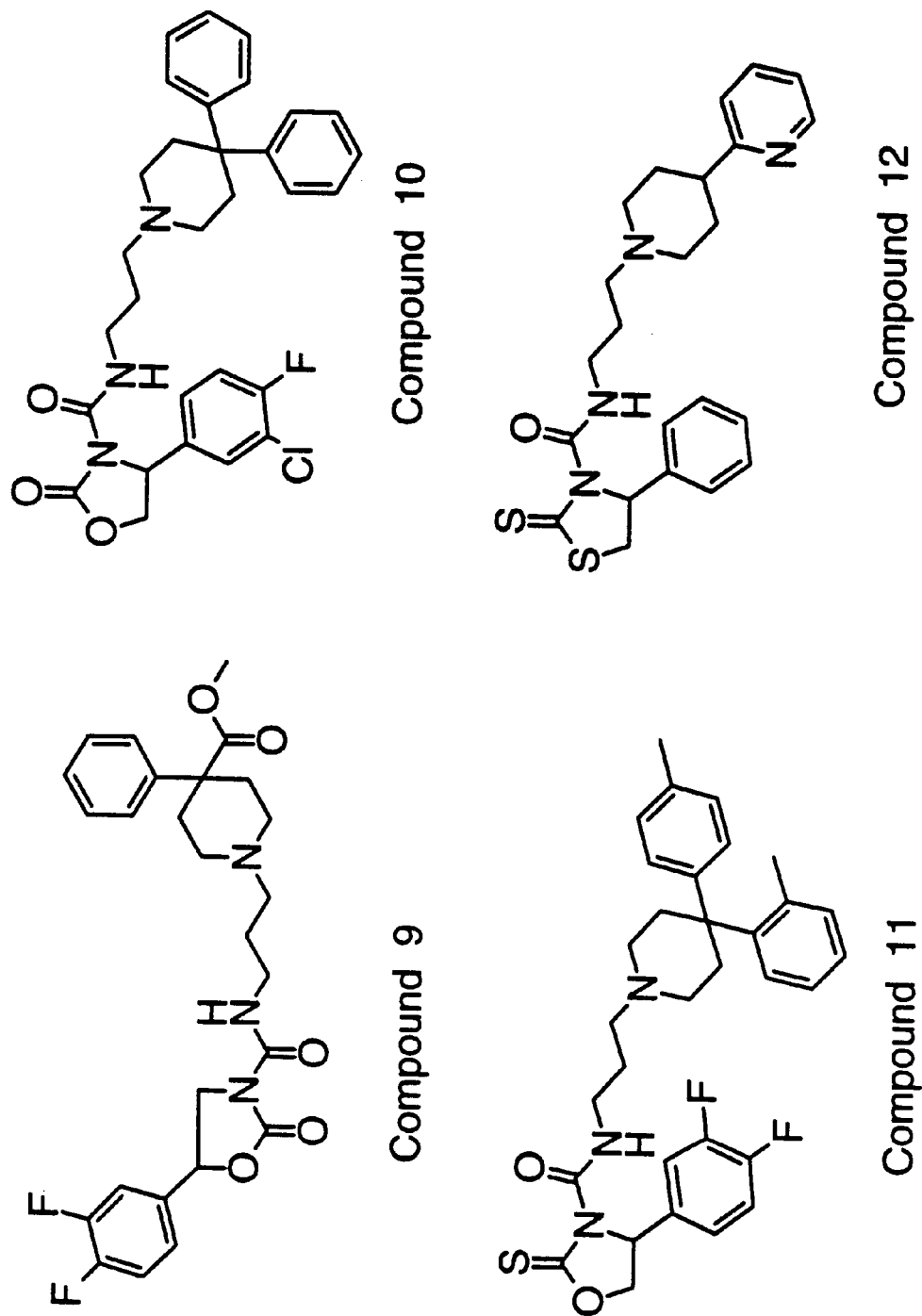
Figure 1D:
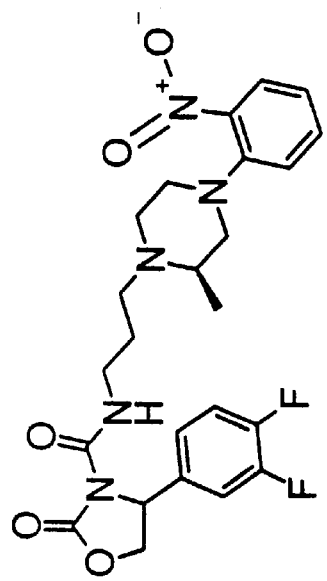
Figure 1D:
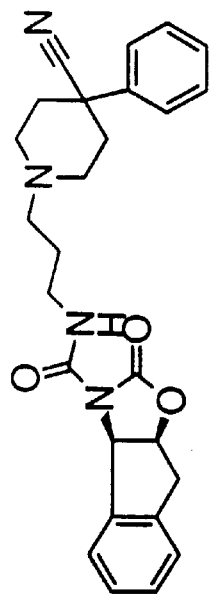
Figure 1D:
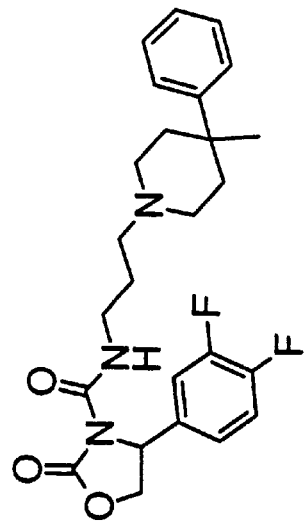
Figure 1E:
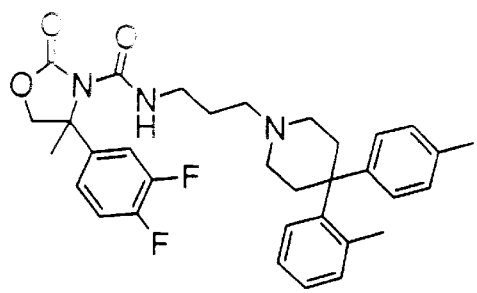
Figure 1E:
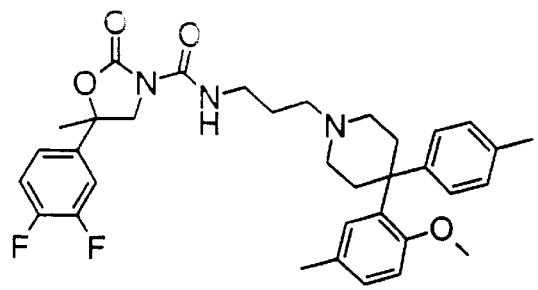
Figure 1E:
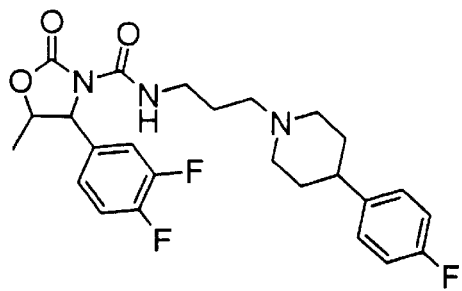
Figure 1E:
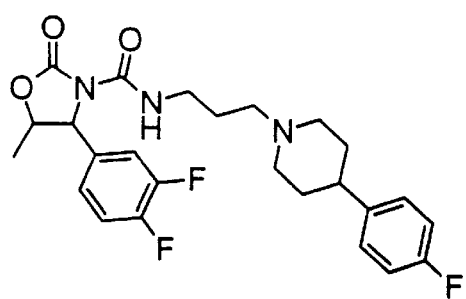
Figure 1E:
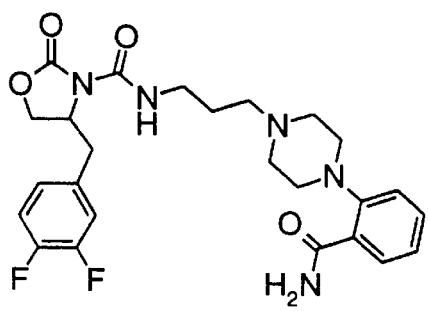
Figure 1E:
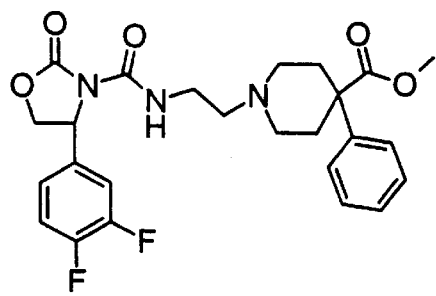
Figure 1E:
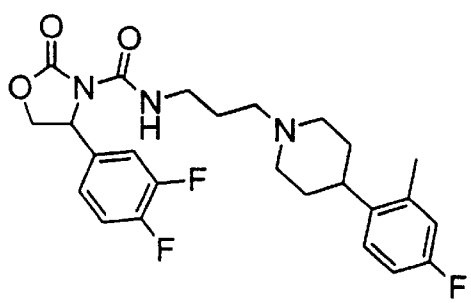
Figure 1E:
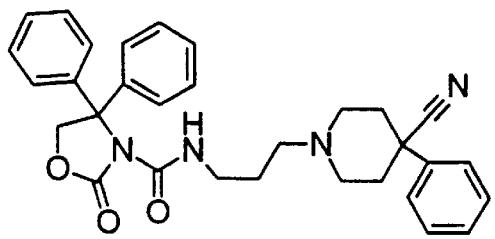
Figure 1F:
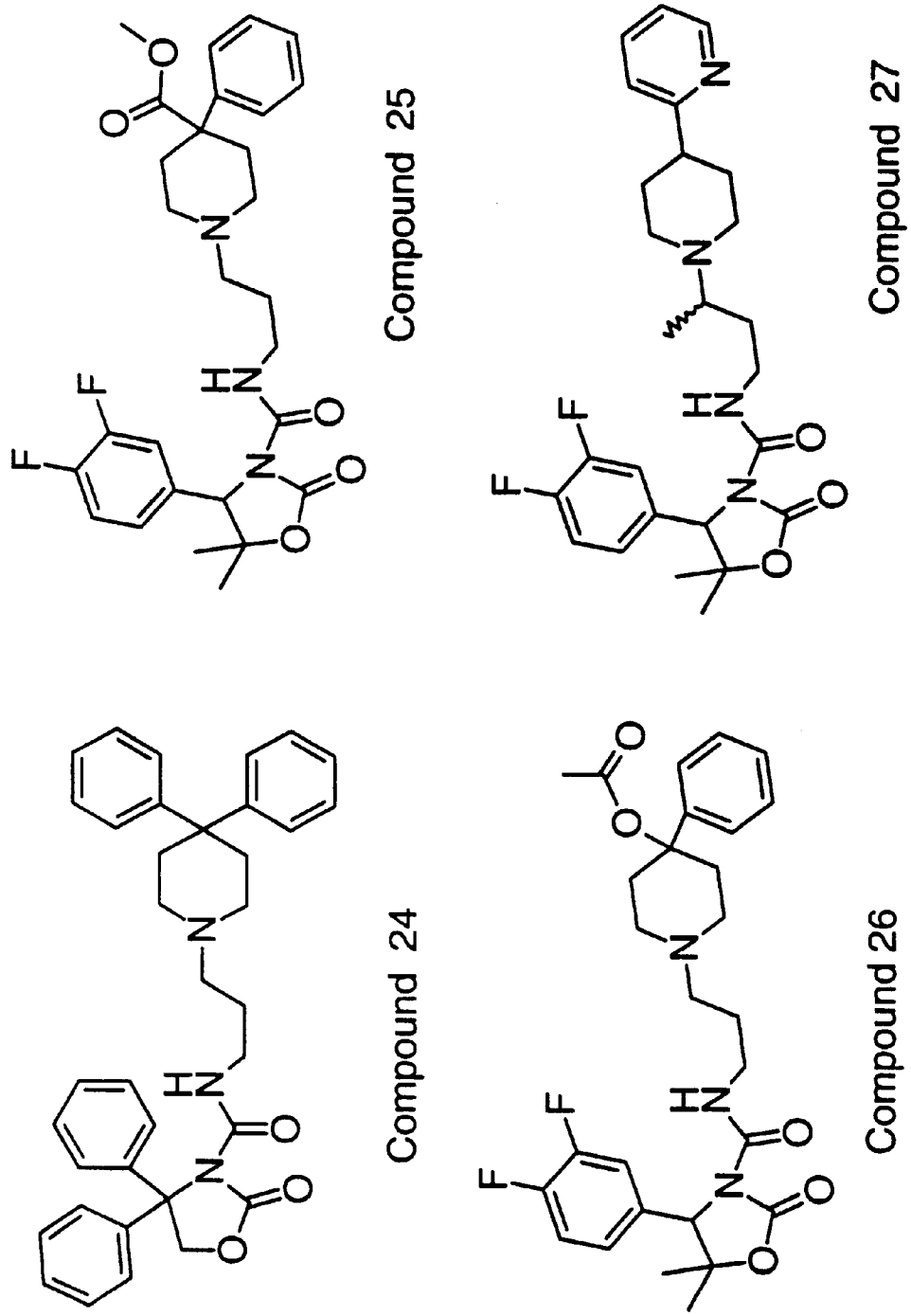
Figure 1G:
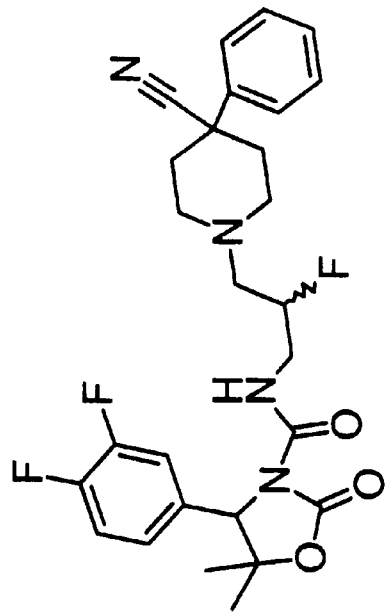
Figure 1G:
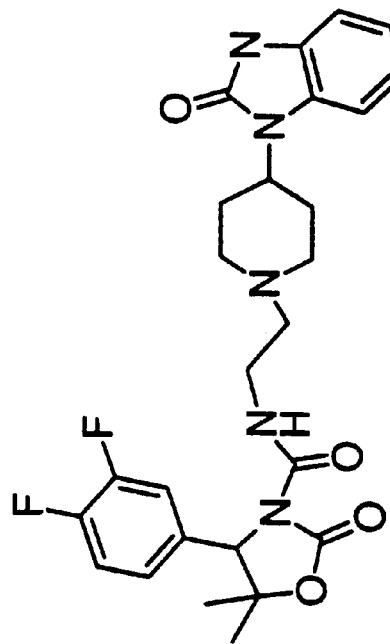
Figure 1G:
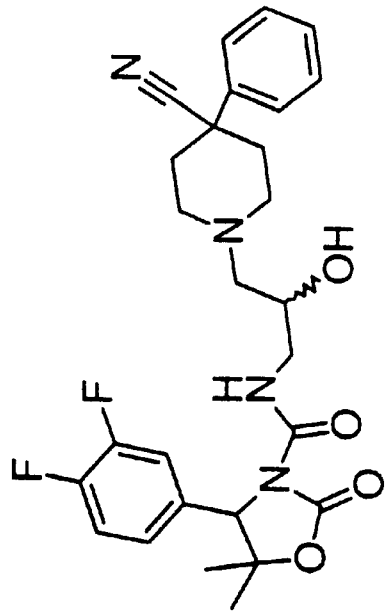
Figure 1G:
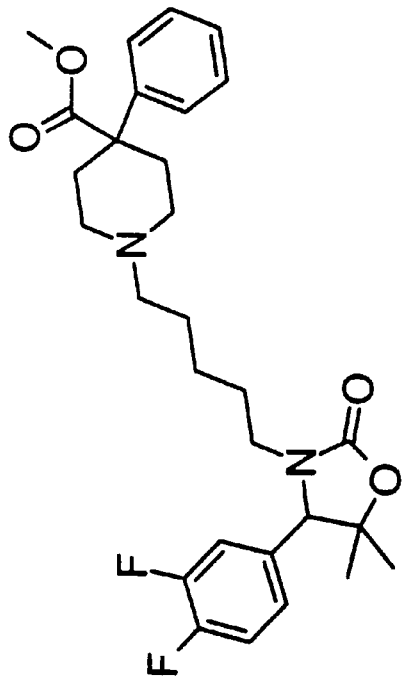
Figure 1H:
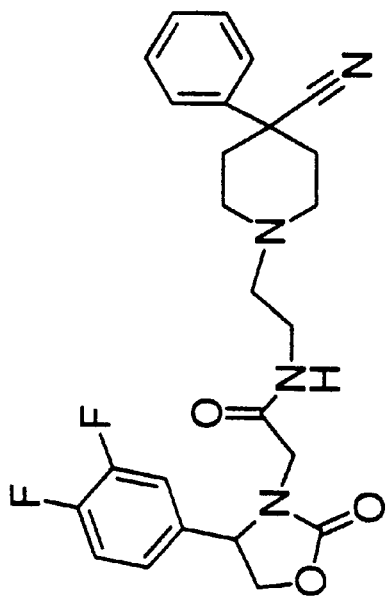
Figure 1H:
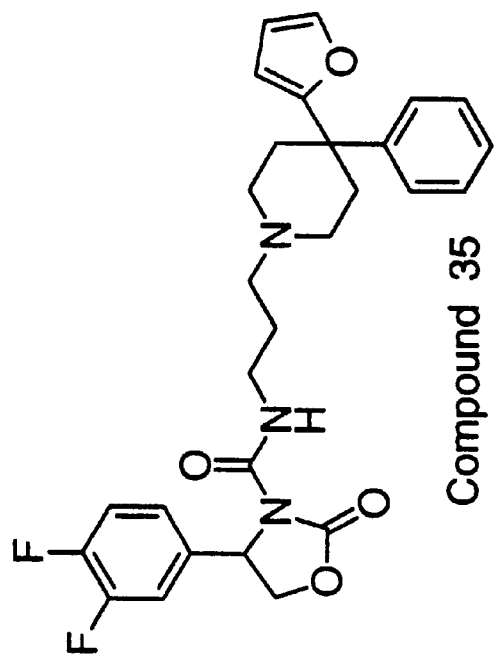
Figure 1H:
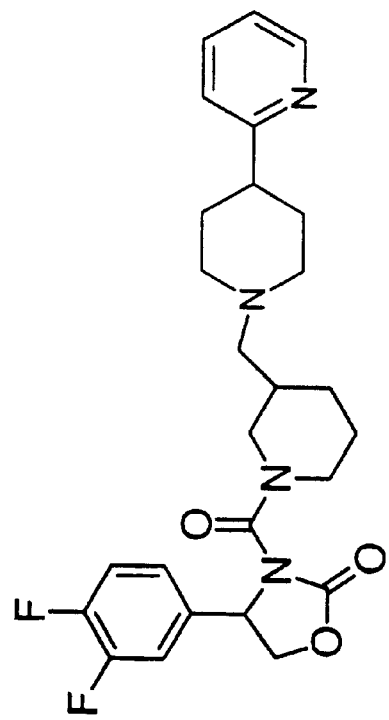
Figure 1H:
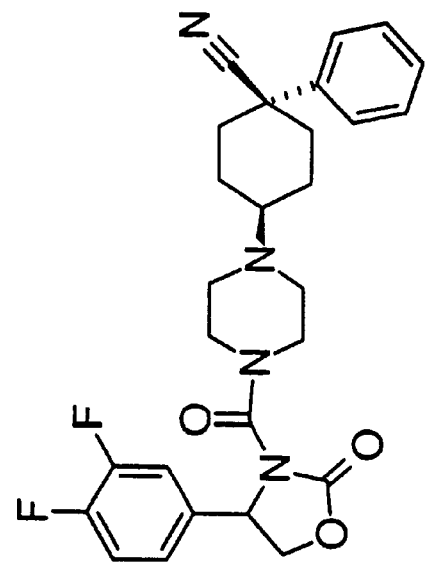
Figure 1I:
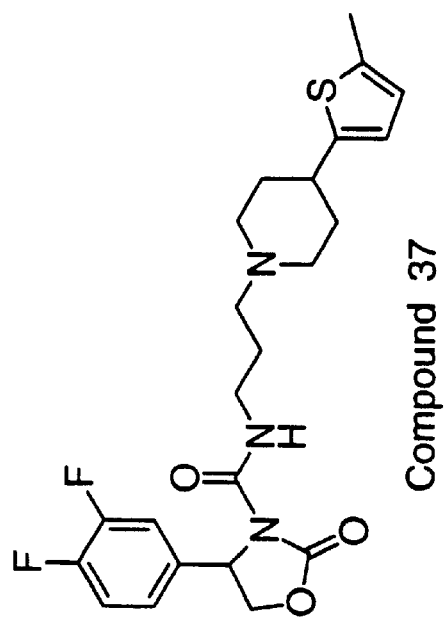
Figure 1I:
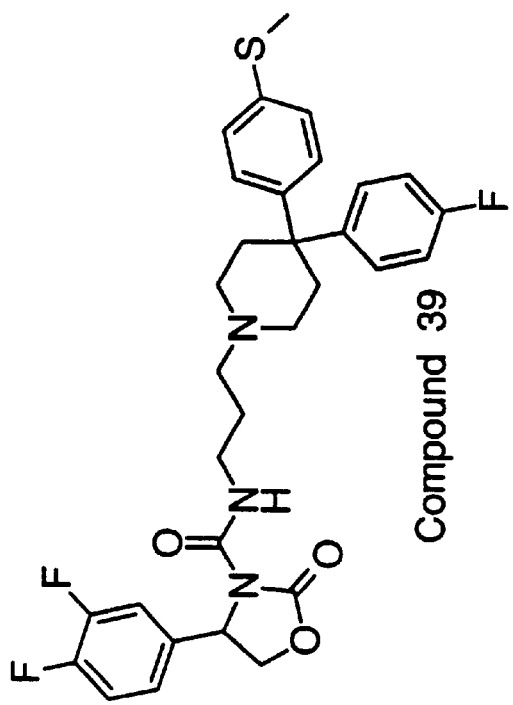
Figure 1I:
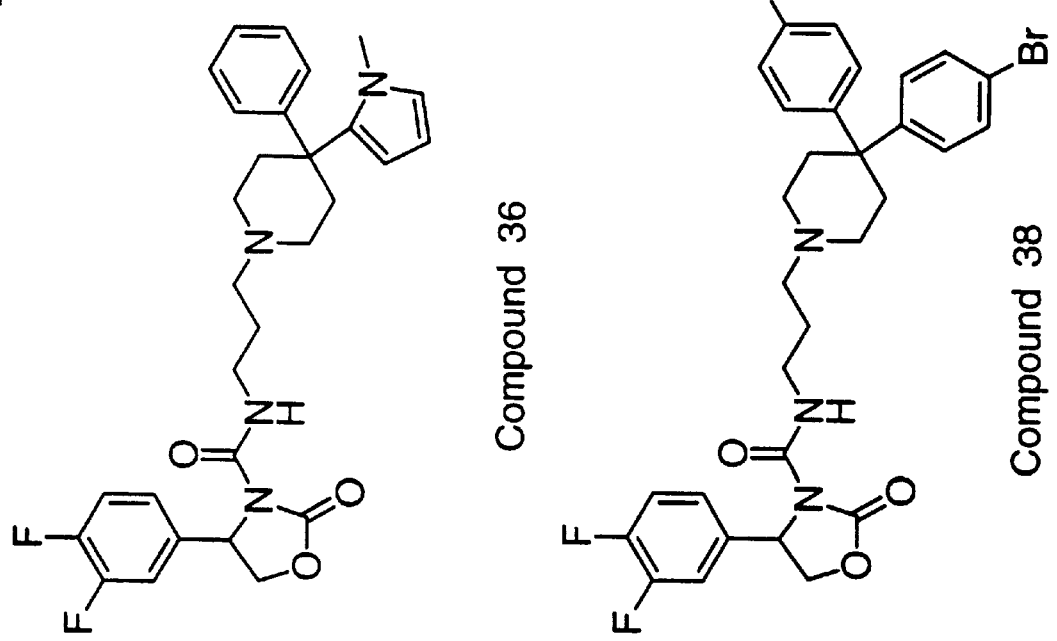
Figure 1J:
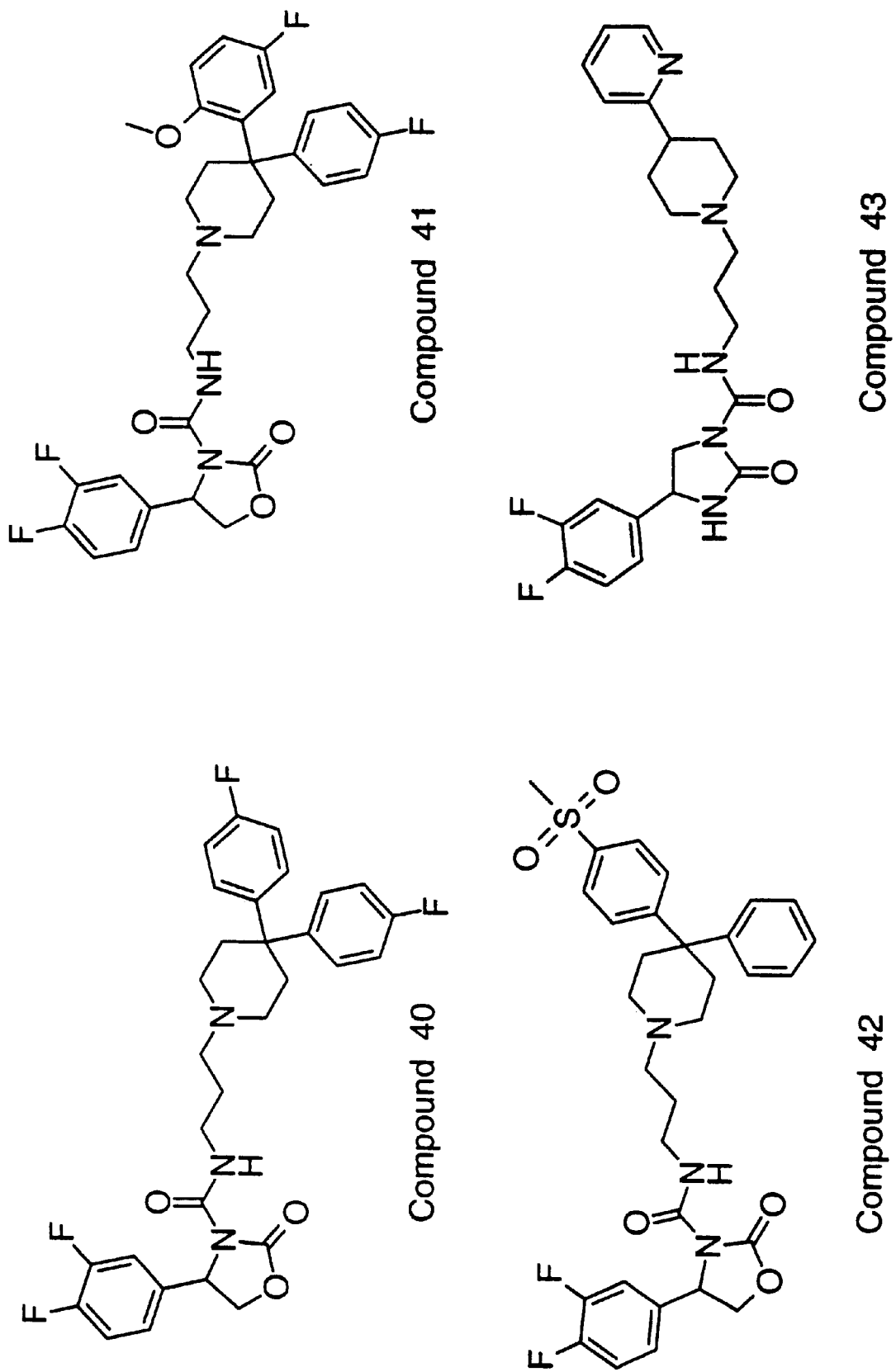
Figure 1K:
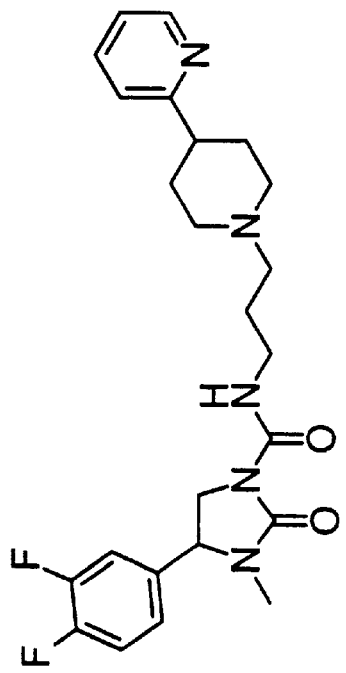
Figure 1K:
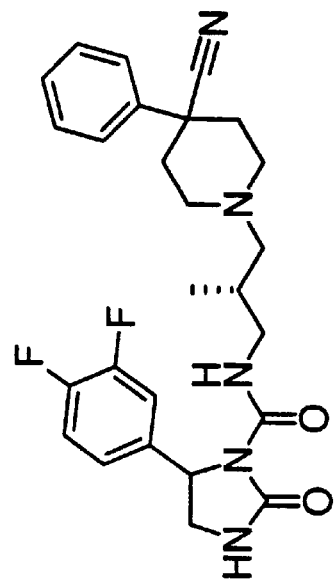
Figure 1K:
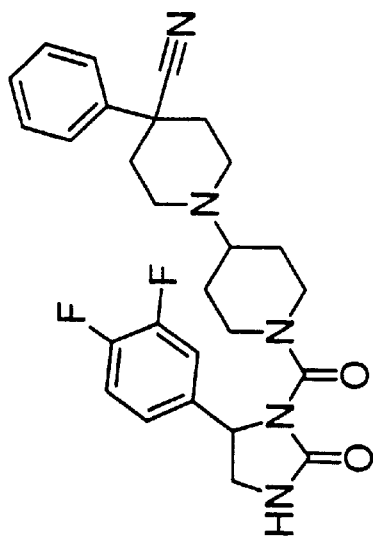
Figure 1K:
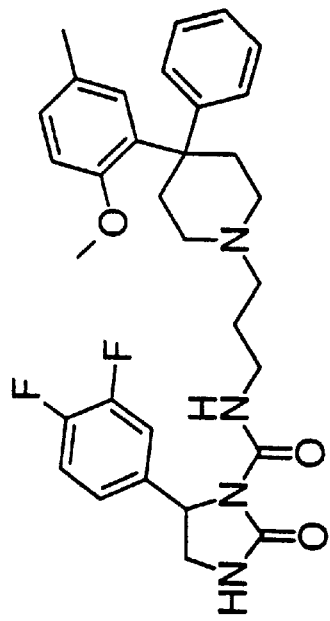
Figure 1L:
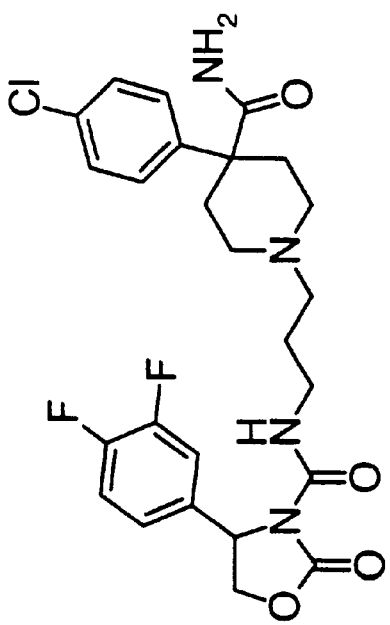
Figure 1L:
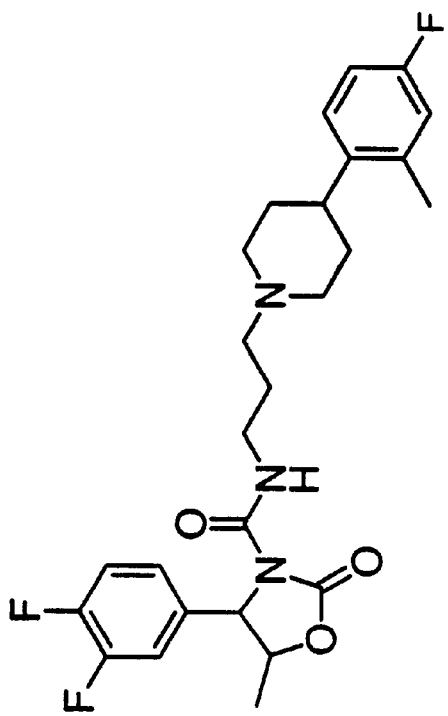
Figure 1L:
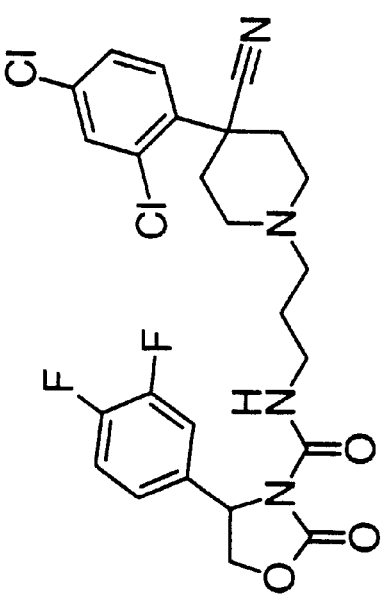
Figure 1L:
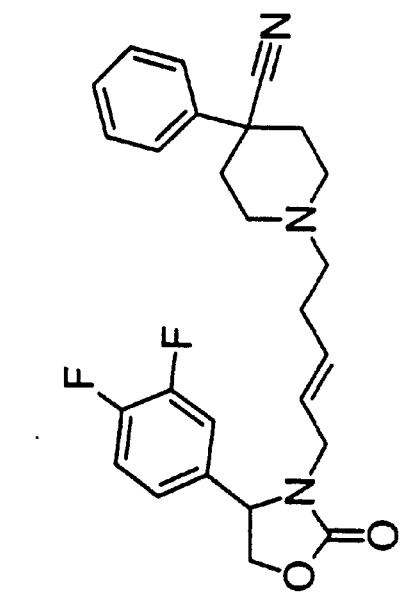

The present invention is directed to compounds having the structure:

wherein each X is independently O or S;

wherein q is 1 or 2;

wherein each R$_2$ is independently H; —(CH$_2$)$_t$XR$_3$; —(CH$_2$)$_t$C(X)NR$_3$; —(CH$_2$)$_t$CO$_2$R$_3$; —CO$_2$R$_3$; straight chained or branched C$_1$–C$_7$ alkyl, aminoalkyl, carboxamidoalkyl; straight chained or branched C$_2$–C$_7$ alkenyl, or alkynyl; or C$_3$–C$_7$ cycloalkyl or C$_2$–C$_7$ cycloalkenyl;

wherein each t is an integer from 1 to 4 inclusive;

wherein each R$_3$ is independently H; straight chained or branched C$_1$–C$_7$ alkyl, straight chained or branched C$_2$–C$_7$ alkenyl, or alkynyl; or C$_3$–C$_7$ cycloalkyl or C$_5$–C$_7$ cycloalkenyl;

wherein R$_4$ is aryl, heteroaryl, C$_1$–C$_7$ alkyl substituted with one or two aryl, or C$_1$–C$_7$ alkyl substituted with one or two heteroaryl; wherein the aryl or heteroaryl may be substituted with one or more of F, Cl, Br, I, —CN, —NO$_2$, —N(R$_3$)$_2$, —COR$_3$, —(CH$_2$)$_t$XR$_3$, —(CH$_2$)$_n$C(X)NR$_3$, —(CH$_2$)$_n$O$_2$R$_3$, straight chained or branched C$_1$–C$_7$ alkyl, monofluoroalkyl, polyfluoroalkyl or carboxamidoalkyl, or straight chained or branched C$_2$–C$_7$ aminoalkyl, alkenyl or alkynyl, or C$_3$–C$_7$ cycloalkyl or C$_5$–C$_7$ cycloalkenyl;

wherein each n independently is an integer from 0 to 7 inclusive;

wherein R$_5$ is H; aryl, C$_1$–C$_7$ alkyl substituted with aryl, heteroaryl, or C$_1$–C$_7$ alkyl substituted with heteroaryl; wherein the aryl or heteroaryl may be substituted with one or more of F, Cl, Br, I, —CN, —NO$_2$, —N(R$_3$)$_2$, —COR$_3$, —(CH$_2$)$_t$XR$_3$, —(CH$_2$)$_n$C(X)NR$_3$, —(CH$_2$)$_n$CO$_2$R$_3$, straight chained or branched C$_1$–C$_7$ alkyl, monofluoroalkyl, polyfluoroalkyl or carboxamidoalkyl, or straight chained or branched C$_2$–C$_7$ aminoalkyl, alkenyl or alkynyl, or C$_3$–C$_7$ cycloalkyl or C$_5$–C$_7$ cycloalkenyl;

where R$_5$ and one R$_2$ on adjacent carbon atoms together may form aryl, heteroaryl, indane or tetrahydronaphthyl, C$_3$–C$_7$ cycloalkyl, or heterocycloalkyl wherein one or two heteroatoms may be O, N or S;

wherein R$_1$ is

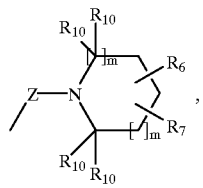

-continued

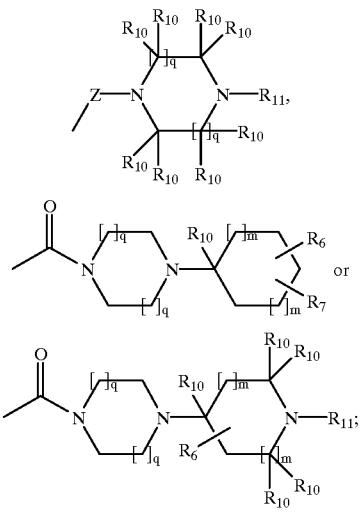

where each $R_6$ is independently H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;

where each $R_7$ is independently H; F; Cl; Br; I; —$COR_3$; —$CO_2R_3$; —$(CH_2)_nXR_3$; —$COR_3$; —$(CH_2)_nC(X)N(R_3)_2$; —$(CH_2)_nCO_2R_3$; —CN; —$NO_2$; —$N(R_3)_2$; straight chained or branched $C_1$–$C_7$ alkyl, hydroxyalkyl, aminoalkyl, carboxamidoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or $C_5$–$C_7$ cycloalkenyl, wherein the alkyl, aminoalkyl, carboxamidoalkyl, alkenyl, alkynyl, cycloalkyl or cycloalkenyl may be substituted with one or more aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, straight chained or branched $C_1$–$C_7$ monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;

wherein each $R_{10}$ is independently H; $(CH_2)_tXR_3$; $(CH_2)_tC(X)NR_3$; $(CH_2)_tCO_2R_3$; straight chained or branched $C_1$–$C_7$ alkyl or carboxamidoalkyl; straight chained or branched $C_2$–$C_7$ aminoalkyl, alkenyl, or alkynyl; or $C_3$–$C_7$ cycloalkyl or $C_5$–$C_7$ cycloalkenyl;

wherein $R_{11}$ is aryl, heteroaryl, $C_1$–$C_7$ alkyl substituted with one or two aryl, or $C_1$–$C_7$ alkyl substituted with one or two heteroaryl; wherein any aryl or heteroaryl independently may be substituted with one or more of F, Cl, Br, I, —CN, —$NO_2$, —$N(R_3)_2$, —$COR_3$, —$(CH_2)_nXR_3$, —$(CH_2)_nC(X)NR_3$, —$(CH_2)_nCO_2R_3$, straight chained or branched $C_1$–$C_7$ alkyl, monofluoroalkyl, polyfluoroalkyl, or carboxamidoalkyl, straight chained or branched $C_2$–$C_7$ aminoalkyl, alkenyl, or alkynyl, or $C_3$–$C_7$ cycloalkyl or $C_5$–$C_7$ cycloalkenyl;

wherein each m independently is an integer from 0 to 3 inclusive;

wherein Z is

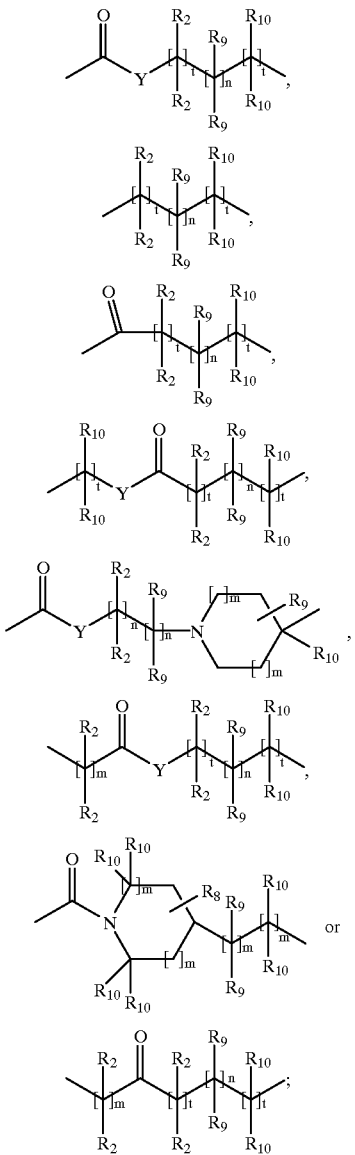

or $C_2$–$C_7$ alkenyl, wherein the $C_2$–$C_7$ alkenyl may be unsubstituted or substituted with one or more $R_9$ groups;

where $R_8$ is H; $(CH_2)_tXR_3$; $(CH_2)_tC(X)NR_3$; $(CH_2)_tCO_2R_3$ straight chained or branched $C_1$–$C_7$ alkyl, carboxamidoalkyl; straight chained or branched $C_2$–$C_7$ aminoalkyl, alkenyl, or alkynyl; or $C_3$–$C_7$ cycloalkyl or $C_5$–$C_7$ cycloalkenyl;

where each $R_9$ is independently H; F; Cl; Br; I; $(CH_2)_mXR_3$; $(CH_2)_mC(X)NR_3$; $(CH_2)_mCO_2R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, or alkynyl; or $C_3$–$C_7$ cycloalkyl or $C_5$–$C_7$ cycloalkenyl;

wherein Y is S, O, or $NR_8$;

or a pharmaceutically acceptable salt thereof.

The invention further provides for the (+) enantiomer of any of the compounds described herein which may be a cis isomer or a trans isomer. The invention also provides for the (−) enantiomer of any of the compounds described herein which may be a cis or a trans isomer.

The compounds of the present invention are preferably at least 80% pure, more preferably at least 90% pure, and most preferably at least 95% pure.

In the present invention the term "aryl" is used to include phenyl, benzyl, benzoyl or naphthyl and the term "heteroaryl" is used to include pyrazinyl, pyrryl, furanyl, thiophenyl, pyridyl, imidazolyl, indolyl, aminophenyl, benzamidyl, benzimidazolyl, benzfurazanyl, benzfuranyl, 2-keto-1-benzimidazolinyl or quinolyl.

The compounds of this invention exhibit at least ten-fold greater affinity for the human $\alpha_{1A}$ receptor than for the human $\alpha_{1B}$ or human $\alpha_{1D}$ receptor.

In one embodiment of the present invention $R_1$ is

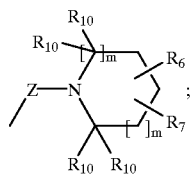

$R_4$ is aryl or heteroaryl, where the aryl may be substituted with one or more of F, Cl, —$(CH_2)_tOR_3$, —$(CH_2)_nCONR_3$, —$(CH_2)_nCO_2R_3$, straight chained or branched $C_1$–$C_7$ alkyl or monofluoroalkyl; and Z is

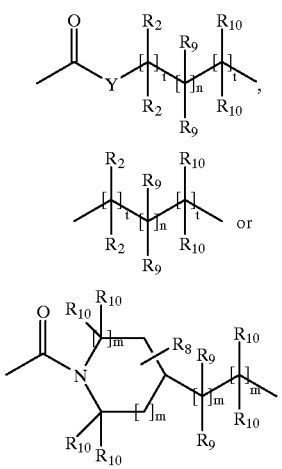

In another embodiment of the present invention $R_4$ is pyridyl or phenyl, where the phenyl may be substituted with one or more of F, Cl, —$(CH_2)_tOR_3$, —$(CH_2)_nC(O)NR_3$, —$(CH_2)_nCO_2R_3$, straight chained or branched $C_1$–$C_7$ alkyl or monofluoroalkyl.

In yet another embodiment of the present invention each $R_6$ is independently aryl or heteroaryl, where the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl.

In a further embodiment of the present invention $R_7$ is H; —CN; —$CO_2R_3$; —$C(O)NR_3$; —$(CH_2)_mXR_3$; unsubstituted or substituted aryl; $C_1$–$C_3$ alkyl; or —$OCOR_3$.

In another embodiment of the present invention $R_4$ is phenyl which may be substituted with at least one of F or Cl.

In yet another embodiment of the present invention the compound has the structure:

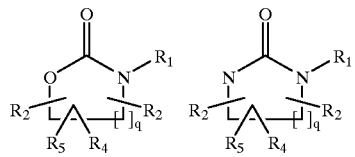

In another embodiment of the present invention Z is:

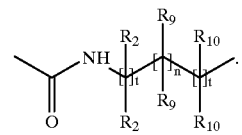

In a further embodiment of the present invention q is 1 and $R_1$ is

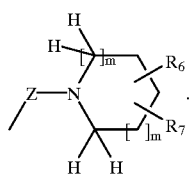

In a further embodiment of the present invention at least one $R_2$ is $C_1$–$C_3$ alkyl.

In another embodiment of the present invention $R_4$ is phenyl substituted with at least one of F or Cl.

In a further embodiment of the present invention $R_4$ is phenyl substituted with at least two F.

In an embodiment of the present invention $R_4$ is 3,4-difluorophenyl.

In an additional embodiment of the present invention $R_6$ is pyridyl, phenyl, or phenyl substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl.

In a further embodiment of the present invention $R_7$ is H; —CN; or —$CO_2R_3$.

In another embodiment of the present invention $R_9$ is F; —OH; $C_1$–$C_3$ alkyl; or —$(CH_2)_mXR_3$.

In an embodiment, when $R_9$ is —OH or F, the other $R_9$ on the same carbon atom is not —OH. In yet another embodiment, when $R_9$ is F, the other $R_9$ on the same carbon atom is $C_1$–$C_3$ alkyl, F, Cl, Br, or I.

In yet another embodiment of the present invention $R_6$ is 4-fluorophenyl.

In a presently preferred embodiment of the invention, the compound is a trans (+) isomer having the structure:

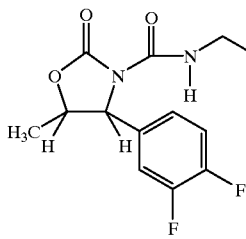

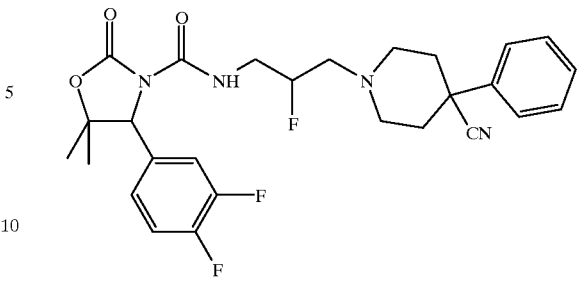

This invention is additionally directed to a compound having the structure:

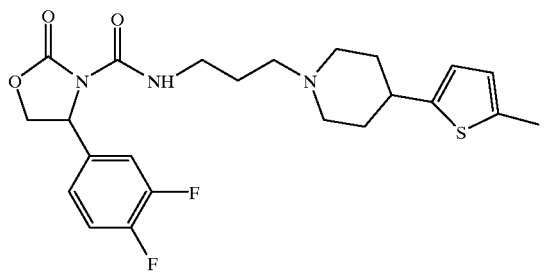

This invention is additionally directed to a compound having the structure:

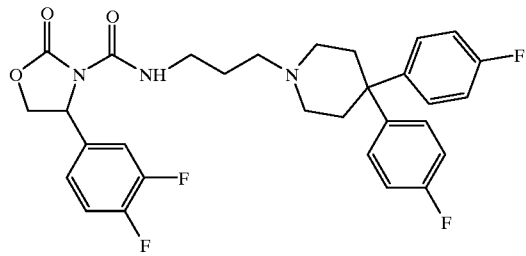

This invention is additionally directed to a compound having the structure:

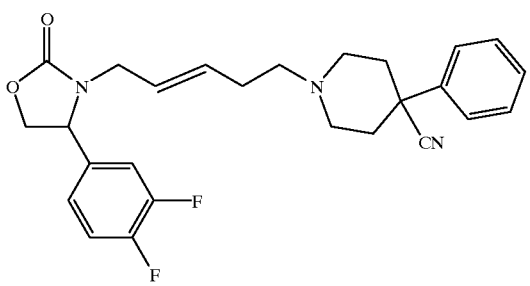

This invention is additionally directed to a compound having the structure:

This invention includes a compound having the structure:

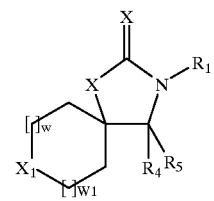

wherein each W is an integer from 0 to 3 inclusive;

wherein each W1 is an integer from 0 to 3 inclusive;

wherein each X is independently O or S;

wherein each X1 is O, S, $NR_3$;

wherein each $R_2$ is independently H; —$(CH_2)_tXR_3$; —$(CH_2)_tC(X)NR_3$; —$(CH_2)_tCO_2R_3$; —$CO_2R_3$; straight chained or branched $C_1$–$C_7$ alkyl, aminoalkyl, carboxamidoalkyl; straight chained or branched $C_2$–$C_7$ alkenyl, or alkynyl; or $C_3$–$C_7$ cycloalkyl or $C_5$–$C_7$ cycloalkenyl;

wherein each t is an integer from 1 to 4 inclusive;

wherein each $R_3$ is independently H; straight chained or branched $C_1$–$C_7$ alkyl, straight chained or branched $C_2$–$C_7$ alkenyl, or alkynyl; or $C_3$–$C_7$ cycloalkyl or $C_5$–$C_7$ cycloalkenyl;

wherein $R_4$ is aryl, heteroaryl, $C_1$–$C_7$ alkyl substituted with one or two aryl, or $C_1$–$C_7$ alkyl substituted with one or two heteroaryl; wherein the aryl or heteroaryl may be substituted with one or more of F, Cl, Br, I, —CN, —$NO_2$, —N $(R_3)_2$, —$COR_3$, —$(CH_2)_tXR_3$, —$(CH_2)_nC(X)NR_3$, —$(CH_2)_nCO_2R_3$, straight chained or branched $C_1$–$C_7$ alkyl, monofluoroalkyl, polyfluoroalkyl or carboxamidoalkyl, or straight chained or branched $C_2$–$C_7$ aminoalkyl, alkenyl or alkynyl, or $C_3$–$C_7$ cycloalkyl or $C_5$–$C_7$ cycloalkenyl;

wherein each n independently is an integer from 0 to 7 inclusive;

wherein $R_5$ is H; aryl, $C_1$–$C_7$ alkyl substituted with aryl, heteroaryl, or $C_1$–$C_7$ alkyl substituted with heteroaryl; wherein the aryl or heteroaryl may be substituted with one or more of F, Cl, Br, I, —CN, —$NO_2$, —$N(R_3)_2$, —$COR_3$, —$(CH_2)_tXR_3$, —$(CH_2)_nC(X)NR_3$, —$(CH_2)_nCO_2R_3$, straight chained or branched $C_1$–$C_7$ alkyl, monofluoroalkyl, polyfluoroalkyl or carboxamidoalkyl, or straight chained or branched $C_2$—$C_7$ aminoalkyl, alkenyl or alkynyl, or $C_3$–$C_7$ cycloalkyl or $C_5$–$C_7$ cycloalkenyl;

wherein $R_1$ is

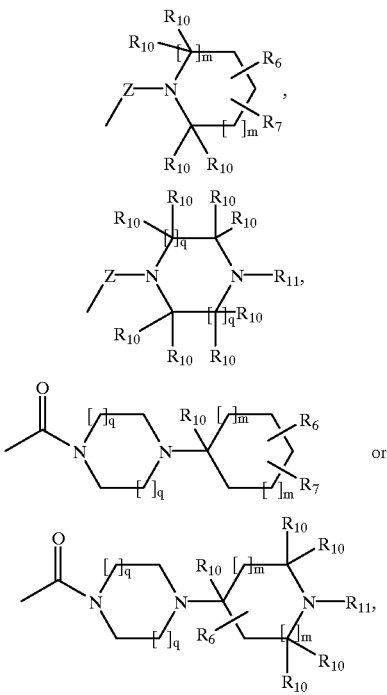

wherein each $R_6$ is independently H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or $C_5$–$C_7$ cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;

wherein each $R_7$ is independently H; F; Cl; Br; I; —$COR_3$; —$CO_2R_3$; —$(CH_2)_nXR_3$; $(CH_2)_nC(X)N(R_3)_2$; —$(CH_2)_nCO_2R_3$; CN; —$NO_2$; —$N(R_3)_2$; straight chained or branched $C_1$–$C_7$ alkyl, hydroxyalkyl, aminoalkyl, carboxamidoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or $C_5$–$C_7$ cycloalkenyl, wherein the alkyl, aminoalkyl, carboxamidoalkyl, alkenyl, alkynyl, cycloalkyl or cycloalkenyl may be substituted with one or more aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, straight chained or branched $C_1$–$C_7$ monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;

wherein each $R_{10}$ is independently H; $(CH_2)_tXR_3$; $(CH_2)_tC(X)NR_3$; $(CH_2)_tCO_2R_3$; straight chained or branched $C_1$–$C_7$ alkyl or carboxamidoalkyl; straight chained or branched $C_2$–$C_7$ aminoalkyl, alkenyl, or alkynyl; or $C_3$–$C_7$ cycloalkyl or $C_5$–$C_7$ cycloalkenyl;

wherein $R_{11}$ is aryl, heteroaryl, $C_1$–$C_7$ alkyl substituted with one or two aryl, or $C_1$–$C_7$ alkyl substituted with one or two heteroaryl; wherein any aryl or heteroaryl independently may be substituted with one or more of F, Cl, Br, I, —CN, —$NO_2$, —$N(R_3)_2$, —$COR_3$, —$(CH_2)_nXR_3$, —$(CH_2)_nC(X)NR_3$, —$(CH_2)_nCO_2R_3$, straight chained or branched $C_1$–$C_7$ alkyl, monofluoroalkyl, polyfluoroalkyl, or carboxamidoalkyl, straight chained or branched $C_2$–$C_7$ aminoalkyl, alkenyl, or alkynyl, or $C_3$–$C_7$ cycloalkyl or $C_5$–$C_7$ cycloalkenyl;

wherein each m independently is an integer from 0 to 3 inclusive;

wherein Z is

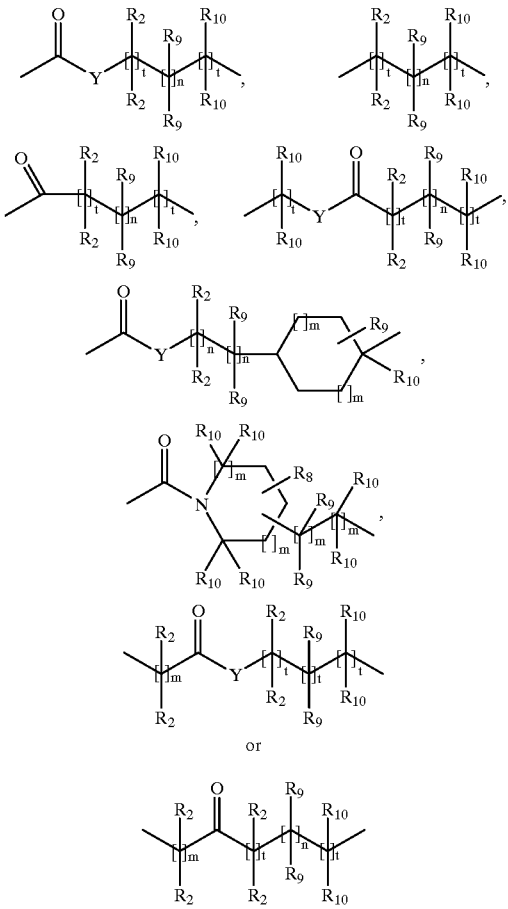

or $C_2$–$C_7$ alkenyl, wherein the $C_2$–$C_7$ alkenyl may be unsubstituted or substituted with one or more $R_9$ groups;

where $R_8$ is H; $(CH_2)_tXR_3$; $(CH_2)_tC(X)NR_3$; $(CH_2)_tCO_2R_3$; straight chained or branched $C_1$–$C_7$ alkyl, carboxamidoalkyl; straight chained or branched $C_2$–$C_7$ aminoalkyl, alkenyl, or alkynyl; or $C_3$–$C_7$ cycloalkyl or $C_5$–$C_7$ cycloalkenyl;

where each $R_9$ is independently H; F; Cl; Br; I; $(CH_2)_m XR_3$; $(CH_2)_m C(X)NR_3$; $(CH_2)_m CO_2R_3$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl, or alkynyl; or $C_3$–$C_7$ cycloalkyl or $C_5$–$C_7$ cycloalkenyl;

wherein Y is S, O, or $NR_8$;

or a pharmaceutically acceptable salt thereof.

The present invention is additionally directed to a compound having the structure:

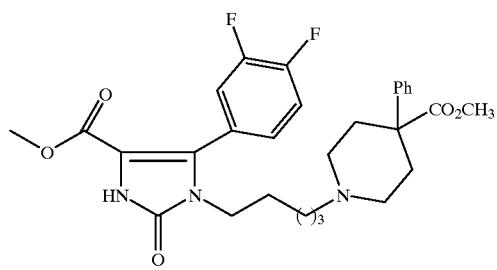

The invention also encompasses the (−) and (+) enantiomers of all compounds described herein. The invention further includes cis and trans isomers of all of the compounds described herein, the terms "cis" and "trans" corresponding to relative stereochemistry, as determined, for example, by NOE (Nuclear Overhauser Effect) experiments. In one embodiment, cis and trans designate the relative positions of aryl and alkyl on adjacent carbons in the oxazolidinone ring (see Examples 18 and 19).

Included in this invention are pharmaceutically acceptable salts and complexes of all of the compounds described herein. The salts include but are not limited to the following acids and bases: inorganic acids such as hydrochloric acid, hydrofluoric acid, hydrobromic acid, hydroiodic acid, sulfuric acid and boric acid; organic acids such as acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid and mandelic acid; inorganic bases such as ammonia and hydrazine; and organic bases such as methylamine, ethylamine, hydroxyethylamine, propylamine, dimethylamine, diethylamine, trimethylamine, triethylamine, ethylenediamine, hydroxyethylamine, morpholine, piperazine and guanidine. This invention further encompasses hydrates and polymorphs of all of the compounds described herein.

The invention further provides pharmaceutical compositions comprising a therapeutically effective amount of any of the compounds described above and a pharmaceutically acceptable carrier. In the subject invention a "therapeutically effective amount" is any amount of a compound which, when administered to a subject suffering from a disease against which the compounds are effective, causes reduction, remission, or regression of the disease. In one embodiment, the therapeutically effective amount is an amount from about 0.01 mg to about 800 mg. In another embodiment, the therapeutically effective amount is an amount from about 0.01 mg to about 500 mg. In another embodiment, the therapeutically effective amount from about 0.01 mg to about 250 mg. In another embodiment, the therapeutically effective amount is an amount from about 0.1 mg to about 60 mg. In another embodiment, the therapeutically effective amount is an amount from about 1 mg to about 20 mg. In one embodiment the therapeutically effective amount is an amount from about 0.01 mg per subject per day to about 500 mg per subject per day, preferably from about 0.1 mg per subject per day to about 100 mg per subject per day, e.g., from about 1 mg per subject per day to about 50 mg per subject per day. In the practice of this invention the "pharmaceutically acceptable carrier" is any physiological carrier known to those of ordinary skill in the art as being useful in formulating pharmaceutical compositions.

In one embodiment the pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The invention also provides a method of treating a subject suffering from benign prostatic hyperplasia which comprises administering to the subject any one of the compounds described herein in an amount effective to treat benign prostatic hyperplasia. In a preferred embodiment the compound of the pharmaceutical composition additionally does not cause a fall in blood pressure at dosages effective to alleviate benign prostatic hyperplasia. In one preferred embodiment the compound effects treatment of benign prostatic hyperplasia by relaxing lower urinary tract tissue and in particular where lower urinary tract tissue is prostatic smooth muscle.

The invention further provides a method of treating a subject suffering from elevated intraocular pressure which comprises administering to the subject one of the compounds described herein effective to lower intraocular pressure.

The invention further provides a method of treating a subject suffering from a disorder associated with elevated blood cholesterol which comprises administering to the subject one of the compounds described herein effective to inhibit cholesterol synthesis.

The invention also provides a method of treating a disease which is susceptible to treatment by antagonism of the $\alpha_{1A}$ receptor which comprises administering to the subject one of the compounds described herein effective to treat the disease.

The invention further provides a method of treating a subject suffering from impotency which comprises administering to the subject one of the compounds described herein effective to treat impotency.

The invention further provides a method of treating a subject suffering from sympathetically mediated pain which comprises administering to the subject one of the compounds described herein effective to treat sympathetically mediated pain.

The invention provides a method of treating a subject suffering from cardiac arrhythmia which comprises administering to the subject one of the compounds described herein effective to treat cardiac arrhythmia.

The invention provides a method of treating a subject suffering from benign prostatic hyperplasia which comprises administering to the subject one of the compounds described herein in combination with a 5 alpha-reductase inhibitor effective to treat benign prostatic hyperplasia. In one preferred embodiment the 5-alpha reductase inhibitor is finasteride. The dosage administered to the subject is about 0.01 mg per subject per day to 50 mg per subject per day of finasteride in combination with an $\alpha_{1A}$ antagonist. A more preferred dosage administered to the subject is about 1 mg per subject per day to 7 mg per subject per day of finasteride in combination with an $\alpha_{1A}$ antagonist. The most preferred dosage administered to the subject is about 5 mg per subject per day of finasteride in combination with an $\alpha_{1A}$ antagonist.

The invention also provides a pharmaceutical composition comprising a therapeutically effective amount of a combination of any of the compounds described herein in combination with finasteride and a pharmaceutically acceptable carrier. In one embodiment the pharmaceutical composition is a therapeutically effective amount of a combination comprising an amount from about 0.01 mg per subject per day to about 500 mg per subject per day of any one of the compounds described herein and an amount of finasteride of about 5 mg per subject per day. A more preferred embodiment of the pharmaceutical composition is a therapeutically effective amount of a combination comprising an amount from about 0.1 mg per subject per day to about 60 mg per subject per day of any one of the compounds described herein and an amount of the finasteride of about 5 mg per subject per day. The most preferred embodiment of the pharmaceutical composition is a therapeutically effective amount of a combination comprising from about 1 mg per subject per day to about 20 mg per subject per day of any one of the compounds described herein and an amount of finasteride of about 5 mg per subject per day.

The invention further provides a method of relaxing lower urinary tract tissue which comprises contacting the lower urinary tract tissue with an amount of one of the compounds described herein effective to relax lower urinary tract tissue. In one embodiment the lower urinary tract tissue is prostatic smooth muscle. In one preferred embodiment the compound additionally does not cause a fall in blood pressure when it is effective to relax lower urinary tract tissue.

The invention provides a method of relaxing lower urinary tract tissue in a subject which comprises administering to the subject an amount of one of the compounds described herein effective to relax lower urinary tract tissue. In one preferred embodiment the compound does not cause a fall in blood pressure and the lower urinary tract tissue is prostatic smooth muscle.

The invention further provides for a method of inhibiting contraction of prostatic tissue, which comprises administering to the subject an amount of any of the compounds described herein effective to inhibit contraction of prostatic tissue. In one preferred embodiment the prostatic tissue is prostatic smooth muscle and the compound additionally does not cause a fall in blood pressure.

The invention provides for the use of the compounds described herein for the preparation of a pharmaceutical composition for lowering intraocular pressure, inhibiting cholesterol synthesis, and the treatment of: benign prostatic hyperplasia, impotency, cardiac arrhythmia and any disease where antagonism of the $\alpha_{1A}$ receptor may be useful. The invention provides for the use of the compounds described herein for the preparation of a pharmaceutical composition for relaxing lower urinary tract tissue and in particular prostatic smooth muscle. The invention further provides for the use of any of compounds described herein for the preparation of a pharmaceutical composition, where the compound additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1A}$ receptor may be useful.

The invention provides for the use of the compounds described herein in the preparation of a medicament for lowering intraocular pressure, inhibiting cholesterol synthesis, and for the treatment of: benign prostatic hyperplasia, impotency, cardiac arrhythmia and any disease where antagonism of the $\alpha_{1A}$ receptor may be useful. The invention provides for the use of the compounds described herein in the preparation of a medicament for relaxing lower urinary tract tissue and in particular prostatic smooth muscle. The invention further provides for the use of any of compounds described herein in the preparation of a medicament, where the compound additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1A}$ receptor may be useful.

The invention provides a drug which is useful for lowering intraocular pressure, inhibiting cholesterol synthesis, and the treatment of: benign prostatic hyperplasia, impotency, cardiac arrhythmia and any disease where antagonism of the $\alpha_{1A}$ receptor may be useful, the effective ingredient of the said drug being any of the compounds described herein. The invention further provides the drug described herein additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1A}$ receptor may be useful.

The invention provides a drug which is useful for relaxing lower urinary tract tissue and in particular prostatic smooth muscle, the effective ingredient of the drug being any of the compounds described herein. The invention further provides a drug which is useful for relaxing lower urinary tract tissue additionally does not cause a fall in blood pressure at dosages effective to relax lower urinary tract tissue.

In the preceding methods the compound may be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound may also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

In the practice of this invention, the term "lower urinary tract tissue" is used to include prostatic capsule, prostate urethra, and bladder neck.

One skilled in the art will readily appreciate that appropriate biological assays will be used to determine the therapeutic potential of the claimed compounds for the treating the above noted disorders.

This invention will be better understood from the Experimental Details which follow. However, one skilled in the art will readily appreciate that the specific methods and results discussed are merely illustrative of the invention as described more fully in the claims which follow thereafter.
Experimental Details

EXAMPLE 1
4-(3,4-Difluoro-phenyl)-2-oxo-oxazolidine-3-carboxylic acid [3-(3-(3',4',5',6'-tetrahydro-2'H-[2,4']bipyridinyl-1'-yl)-propyl]-amide (Schemes 5 and 6)

It is a typical procedure for the synthesis of oxazolidinone compounds which are described below.
METHOD A
a. Amino-(3,4-difluorophenyl)-acetonitrile Through a solution of 3,4-difluorobenzaldehyde (25.0 g, 0.18 mol) in MeOH (500 mL)in a round bottom flask, was bubbled ammonia gas for two hours at room temperature. The flask was then cooled to 0° C. and trimethylsilyl cyanide (1.3 eq., 0.23 mmol) was then added slowly. The reaction mixture was stirred for 2 h when TLC analysis indicated that the reaction was complete ($R_f$=0.35, 3:2 hexane/EtOAc). Solvent was removed in vacuo and the residue was subjected to flash column chromatography on silica gel to obtain 25.0 g (81%) of amino-(3,4-difluorophenyl)-acetonitrile as a yellow syrup.

b. Amino-(3,4-difluorophenyl)-acetic acid methyl ester

To a well stirred solution of amino-(3,4-difluorophenyl)-acetonitrile (22.0 g, 0.130 mol), a solution of HCl in MeOH(200 mL) was added at room temperature. The resulting yellow solution was stirred at room temperature for 10 h and then heated to reflux for 1.5 h. After cooling, the solvent was removed in vacuo and the resulting yellow solid was dissolved in water (200 mL). The aqueous solution was then carefully basified with 20% NaOH solution to pH 9. The aqueous layer was extracted with $CH_2Cl_2$ (3×100 mL). The organic layer was separated and dried over $Na_2SO_4$, filtered and the solvent was removed in vacuo to obtain 22.2 g (84%)of amino-(3,4-difluorophenyl)-acetic acid methyl ester as a brownish yellow liquid. It was used in the next step without purification.

c. 2-Amino-2-(3,4-difluorophenyl)-ethanol

To a well stirred suspension of $LiAlH_4$ (4.7 g, 0.125 mol) in THF (120 mL) in a 3-necked round bottom flask fitted with a condenser and a dropping funnel, was added a solution of amino-(3,4-difluorophenyl)-acetic acid methyl ester (10.0 g, 0.05 mol) in THF (100 mL) dropwise at 0° C. The resulting greenish brown suspension was then heated to reflux for 2 h. The reaction mixture was cooled to 0° C. and then carefully quenched sequentially with 5 mL of water, 5 mL of 3N NaOH followed by 15 mL of water. The resulting suspension was filtered through a fritted glass funnel. To the residue was added 100 mL $Et_2O$ and the suspension was heated to reflux for 20 min. The suspension was filtered and was combined with the previous filtrate, dried over $MgSO_4$, filtered and the solvent was removed in vacuo. 2-amino-2-(3,4-difluorophenyl)-ethanol was obtained as a yellow glassy syrup (8.6 g, 99%) which was used in the next step without further purification.

METHOD B: Synthesis of 2-amino-2-(3,4-difluorophenyl)-ethanol by different route. (Scheme 6)
a. 1-Hydroxy-(3,4-difluorophenyl)-acetophenone To a solution of KOH (56 g, 1.0 mol) in MeOH (500 mL) was added 3,4-difluoroacetophenone (15.6 g, 0.1 mol) dropwise over 15 min at 0° C. Phenyliodosodiacetate (64.4 g, 0.2 mol) was added in small portions over 20 min period and the resulting yello-orange solution was stirred overnight at room temperature. The solvent was removed in vacuo to obtain yellow-orange gum. The residue was dissolved in 100 mL of water and 100 mL of brine and was thoroughly extracted with ethyl acetate (3×150 mL). The organic layer was dried over $Na_2SO_4$ and was decanted. The solvent was removed in vacuo to obtain 31.0 g of the acetal as thick yellow oil. It was dissolved in 200 mL of acetone and about 10 drops of conc. sulfuric acid. The reaction mixture was stirred at room temperature for 2 h till tlc analysis showed complete consumption of the starting material. The solvent was removed in vacuo and the solid that was obtained was basified by adding sat. $NaHCO_3$ solution and then it was extracted with ethyl acetate (300 mL). The organic layer was separated and washed with brine. The organic layer was dried over $MgSO_4$, filtered and the solvent was removed in vacuo to obtain yellow solid. The yellow solid was washed with cold hexane (to remove iodobenzene impurities) and dried to obtain 11.4 g (66% yield) of 1-hydroxy-(3,4-difluorophenyl)-acetophenone as pale yellow solid. The product was shown to be >90% pure by NMR and was used in the next step without further purification.

b. 1-Hydroxy-(3,4-difluorophenyl)-acetophenone oxime

To a solution of 1-hydroxy-(3,4-difluorophenyl)-acetophenone (6.0 g, 34.9 mmol) in 150 mL of MeOH was added hydroxylamine hydrochloride (3.16 g, 45.6 mmol) and sodium acetate (9.6 g, 69.6 mmol) at room temperature and the resulting solution was stirred overnight. The solvent was removed and the residue was dissolved in methylene chloride (150 mL) and was washed with 100 mL of sat. $NaHCO_3$ solution followed by brine. The organic layer was separated and dried over $MgSO_4$, filtered and the solvent was removed in vacuo to obtain 1-hydroxy-(3,4-difluorophenyl)-acetophenone-oxime as a yellow solid (5.6 g, 86%). It was used in the next step without any purification.

c. 2-Amino-2-(3,4-difluorophenyl)-ethanol

To a well stirred suspension of $LiAlH_4$ (3.4 g, 89.5 mmol) in THF (120 mL) in a 3-necked round bottom flask fitted with a condenser and a dropping funnel, was added a solution of 1-hydroxy-(3,4-difluorophenyl)-acetophenone-oxime (4.6 g, 24.6 mmol) in THF (50 mL) dropwise at 0° C. The resulting greyish yellow suspension was then heated to reflux for 2 h. The reaction mixture was cooled to 0° C. and then carefully quenched sequentially with 3.4 mL of water, 3.4 mL of 3N NaOH followed by 10 mL of water. The resulting suspension was filtered thro' a fritted glass funnel. To the residue was added 100 mL $Et_2O$ and the suspension was heated to reflux for 20 min. The suspension was filtered and was combined with the previous filtrate, dried over $MgSO_4$, filtered and the solvent was removed in vacuo. 2-Amino-2-(3,4-difluorophenyl)-ethanol was obtained as a yellow glassy syrup (4.1 g, 96%) which was used in the next step without further purification.

d. [1-(3,4-Difluorophenyl)-2-hydroxy-ethyl]-carbamic acid-tert-butyl ester

To a solution of 2-amino-2-(3,4-difluorophenyl)-ethanol (8.6 g, 49.7 mmol) in $CHCl_3$ (150 mL) at 0° C. was added a solution of di-tert-butyl dicarbonate (11.4 g, 52.0 mmol) in $CHCl_3$ (50 mL) in one portion and the resulting solution was stirred overnight at room temperature. The solvent was removed in vacuo and the residue was subjected to column chromatography on silica gel (2:1 hexane-EtOAc followed by EtOAc) to obtain [1-(3,4-difluorophenyl)-2-hydroxy-ethyl]-carbamic acid-tert-butyl ester as white solid (10.0 g,74%).

e. (+)-4-(3,4-Difluorophenyl)-oxazolidin-2-one

To a well stirred suspension of NaH (1.1 g, 45.8 mmol) in THF (40 mL) at room temperature was added a solution of [1-(3,4-difluorophenyl)-2-hydroxy-ethyl]-carbamic acid-tert-butyl ester (5.0 g, 18.3 mmol) in THF 20 mL via a dropping funnel at room temperature. The resulting suspension was stirred for 3 h and then quenched carefully with 10 mL of water. The biphasic mixture was extracted with 100 mL of $Et_2O$, washed with brine, filtered and the solvent was removed in vacuo. The gummy residue thus obtained was purified by column chromatography over silica gel ($R_f$=0.15, 3:2 hexane-EtOAc) to obtain (+)-4-(3,4-difluorophenyl)-oxazolidin-2-one as a white flaky solid (2.8 g, 77%). The enantiomers were separated by using Chiralcel OD (4.6×250 mm) using 80% hexane/20% isopropyl alcohol/0.1% Diethylamine as the eluting system under isothermal conditions (U.V. 254 nM). The retention times for the two isomers were 16.19 min and 20.08 min respectively. First isomer:$[\alpha]_D$=+62.9 (c=0.67, acetone); Anal. Calcd. for $C_9H_7NO_2F_2$: C, 54.28; H, 3.54; N, 7.03. Found: C, 54.16; H, 3.44; N, 6.96. Second isomer:$[\alpha]_D$=−56.9 (c=0.75, acetone); Anal. Calcd. for $C_9H_7NO_2F_2$: C, 54.28; H, 3.54; N, 7.03. Found: C, 54.31; H, 3.46; N, 6.98. The first isomer was used in the next step.

f. 4-(3,4-Difluorophenyl)-2-oxo-oxazolidine-3-carboxylic acid-4-nitro-phenyl ester To a suspension of NaH (0.14 g, 5.30 mmol) in 20 mL of anhydrous THF under argon, a solution of (+)-4-(3,4-difluorophenyl)-oxazolidin-2-one (0.88 g, 4.42 mmol) in THF was added dropwise via an dropping funnel. The resulting suspension was stirred at room temperature for 30 min. This suspension was then added dropwise via cannula into another round bottom flask containing a solution of 4-nitrophenylchloroformate (1.11 g, 5.30 mmol) in 25 mL of THF and cooled at −78° C. over a period of 15 min. The stirring was continued for 2 h after which the solvent was removed and the residue was purified by column chromatography on silica gel with 1:1 hexane/$CH_2Cl_2$ followed by $CH_2Cl_2$ ($R_f$=0.4, $CH_2Cl_2$) to obtain 4-(3,4-difluorophenyl)-2-oxo-oxazolidine-3-carboxylic acid-4-nitro-phenyl ester as a white solid (1.55 g, 86%).

g. 3-Amino-propyl-4-pyridyl-piperidine 1-(3-Aminopropyl)-4-[pyrid-2-yl]pyridinium bromide hydrobromide Method A: A solution of 2,4'-dipyridyl (5.0 g, 32.0 mmol) and 3-bromopropylamine hydrobromide (7.0 g, 32.0 mmol) in DMF (50.0 mL) and acetonitrile (50.0 mL) was heated at 90–95° C. for 1 h. After cooling, the white solid that came out was filtered, washed with $Et_2O$ and dried. The mother liquor was concentrated to remove $Et_2O$ and then heated to 90–95° C. for 4 h. The solvent was evaporated and the white residue was triturated with $Et_2O$ (100.0 mL) and filtered. The combined weight of the salt was 11.6 g (97%).

Method B: A well-stirred solution of 2,4'-dipyridyl (12.8 g, 0.08 mol) and N-tert-butoxycarbonyl-3-bromo-propylamine (21.3 g, 0.09 mol) in acetonitrile (40.0 mL) was heated to reflux for 6 h. The reaction mixture was cooled to room temperature and filtered. The white solid thus obtained was washed with acetone (2×20.0 mL) and chloroform (2×20.0 mL) to yield 10.9 g as the first crop. Anal. Calcd. for $C_{13}H_{16}N_3Br.HBr.0.5\ H_2O$: C, 40.65; H, 4.72; N, 10.94. Found: C, 40.83; H, 4.37; N, 11.05.

3-(3',6'-Dihydro-2'-H-[2,4']bipyridinyl-1'-yl)-propylamine

To a solution of 1-(3-aminopropyl)-4-[pyrid-2-yl] pyridinium bromide hydrobromide (0.66 g, 1.75 mmol) in 20.0 mL MeOH was added $NaBH_4$ (0.101 g, 2.62 mmol) in small portions. The reaction mixture was stirred for 30 min and then quenched with 6M HCl solution. The solution was concentrated to 20.0 mL and basified with 50% NaOH solution to pH 12. Extracted with $CHCl_3$ (5×30.0 mL), dried over $MgSO_4$ and the solvent was removed to give 3-(3',6'-Dihydro-2'-H-[2,4']bipyridinyl-1'-yl)-propylamine as an oil (0.37 g, 96% yield). It is used in the next step immediately without purification.

3-(3',4',5',6'-Tetrahydro-2'-H-[2,4']bipyridinyl-1'-yl)-propylamine

To a solution of 3-(3',6'-Dihydro-2'-H-[2,4']bipyridinyl-1'-yl)-propylamine (3.48 g crude, 15.9 mmol) in MeOH (40 mL), was added 1.0 g of Pearlman's catalyst. The suspension was hydrogenated under 120 psi for 10 h after which the reaction mixture was filtered thro' a pad of celite and the solvent was removed. The residue was purified by column chromatography over silica gel using $CH_2Cl_2$/methanol/2M $NH_3$ in MeOH (90:8:4 to 90:40:40) as the eluting system. The product was obtained as a pale yellow oil (3.21 g, 91%).

3-(3',4',5',6'-Tetrahydro-2'-H-[2,4']bipyridinyl-1'-yl)-propylamine

To a solution of 1-(3-aminopropyl)-4-[pyrid-2-yl] pyridinium bromide hydrobromide (0.53 g) 10.0 mL of 2M NH$_3$ in MeOH was added PtO$_2$ (0.1 g) and the reaction mixture was hydrogenated at 110 psi for 6 h and then at 130 psi for 12 h. The catalyst was removed via filtration thro' a pad of celite, washed with MeOH and the solvent was removed. The NMR showed it to be the required product although the accurate weight of the product was not determined due to the presence of ammonium bromide generated during the course of the reaction.

h. (+)-4-(3,4-Difluoro-phenyl)-2-oxo-oxazolidine-3-carboxylic acid [3-(3',4',5',6'-tetrahydro-2'H-[2,4'] bipyridinyl-1'-yl)-propyl]-amide To a solution of 3-amino-propyl-4-pyridyl piperidine (1.1 g, 5.1 mmol) in 100 mL of THF 4-(3,4-difluorophenyl)-2-oxo-oxazolidine-3-carboxylic acid-4-nitro-phenyl ester (1.55 g, 4.24 mmol) was added and the resulting yellow solution was stirred under argon atmosphere for 10 h at room temperature. The solvent was removed in vacuo and the residue was purified by column chromatography over silica gel with EtOAC followed by 15% MeOH in EtOAC as the eluting systems (R$_f$=0.4, 1:1 MeOH/EtOAC) to obtain a pale yellow glassy oil. It was dissolved in EtOAc (150 mL) and washed throughly with 5% KOH solution (4×25 mL) in order to remove traces of 4-nitrophenol in the product. The organic layer was separated, washed with brine (25 mL) and then dried over Na$_2$SO$_4$. The solvent was removed and 4-(3,4-Difluoro-phenyl)-2-oxo-oxazolidine-3-carboxylic acid [3-(3',4',5',6'-tetrahydro-2'H-[2,4']bipyridinyl-1'-yl)-propyl]-amide was obtained as a colorless glassy oil(1.55 g, 82%) which develops some brownish color after 2 h.

To a solution of 4-(3,4-Difluoro-phenyl)-2-oxo-oxazolidine-3-carboxylic acid [3-(3',4',5',6'-tetrahydro-2'H-[2,4']bipyridinyl-1'-yl)-propyl]-amide (1.53 g, 3.45 mmol) in 10.0 mL of anhydrous EtOH was added a warm solution of 95% fumaric acid (0.48 g, 4.06 mmol) in 8.0 mL EtOH and the resulting solution was kept under a gentle stream of argon for 30 min. Hexane (5×1.0 mL) was added over 2 h and the solution was kept under argon atmosphere overnight. Pale yellowish-white small crystals thus obtained were filtered, washed successively with EtOH (10.0 mL) and hexane (10.0 mL). The crystals were pulverized and dried under vacuum at 40° C. The white non-hygroscopic powder (1.6 g, 84%) was found out to be the monofumarate salt after NMR and elemental analysis as shown below. M.P. 142–144° C.; [α]$_D$=+47.4 (c=0.52, MeOH); Anal. Calcd. for C$_{27}$H$_{30}$N$_4$O$_7$F$_2$.H$_2$O: C, 56.05; H, 5.57; N, 9.68. Found: C, 56.18; H, 5.51; N, 9.54.

EXAMPLE 2

4-(3,4-Difluorophenyl)-3-{5-[4-(2-methoxy-phenyl)-piperazin-1-yl]-pentyl}-oxazolidin-2-one a. 4-(3,4-Difluorophenyl)-1-(5-bromopentyl) oxazolidinone To a stirred suspension of sodium hydride (203 mg, 8.04 mmol) in THF(5 mL) at 0° C. under argon, was added a solution of 4-(3,4-difluorophenyl)oxazolidinone (800 mg, 4.02 mmol) in the mixed solvent of THF(4 ml) and HMPA (0.7 ml, 4.02 mmol) and stirred for 30 min. To this 1,5-dibromopentane (2.17 ml, 16 mmol) was added and the mixture was heated to reflux for 70 min, after which the reaction mixture was cooled to room temperature and the solvent was removed in vacuo. The residue was purified by column chromatography over silica gel with CH$_2$Cl$_2$ followed by 5% EtOAc in CH$_2$Cl$_2$ as the eluting system (R$_f$=0.72, CH$_2$Cl$_2$:EtOAc=3:1) to obtain 4-(3,4-difluorophenyl)-1-(5-bromopentyl) oxazolidinone as a brown liquid (0.70 g, 50%).

b. 4-(3,4-Difluorophenyl)-3-{5-[4-(2-methoxy-phenyl)-piperazin-1-yl]-pentyl}-oxazolidin-2-one To a solution of 4-(3,4-difluorophenyl)-1-(5-bromopentyl) oxazolidinone (60 mg, 0.17 mmol) in 1,6-dioxane (20 ml) at room temperature, were added 1-(2-methoxyphenyl)-piperazine (33.8 mg, 0.17 mmol) and K$_2$CO$_3$ (23.8 mg, 0.52 mmol). The resulting mixture was heated to reflux for 12 h after which the reaction mixture was cooled to room temperature and the solvent was removed in vacuo. The residue was dissolved in water and extracted with CH$_2$Cl$_2$ (2×30 ml), dried over Na$_2$SO$_4$. The solvent was then removed in vacuo and the residue was purified by column chromatography over silica gel with EtOAc followed by 5% MeOH in EtOAc as the eluting system (R$_f$=0.24, MeOH:EtOAc=1:8) to obtain 4-(3,4-difluorophenyl)-3-{5-[4-(2-methoxy-phenyl)-piperazin-1-yl]-pentyl}-oxazolidin-2-one as a brown oil (69 mg, 88%). The compound was dissolved in CH$_2$Cl$_2$ (3 mL) and was treated with 1N HCl in ether (1 mL). The solvent was removed in vacuo to give the corresponding hydrochloride salt as a yellow solid. M.P. 174–178° C.; Anal. Calcd. For C$_{25}$H$_{33}$N$_3$O$_3$F$_2$Cl$_2$.0.65 CH$_2$Cl$_2$: C, 52.43; H, 5.88; N, 7.15. Found: C, 52.12; H, 6.36; N, 6.84.

EXAMPLE 3

4-(3,4-Difluoro-phenyl)-2-oxo-oxazolidine-3-carboxylic acid {3-[4-(5-bromo-2-methoxy-phenyl)-4-phenyl-piperidin-1-yl]-propyl}-amide a. 4-(5-bromo-2-methoxy)-phenyl-4-phenyl-piperidine hydrochloride To a 100 mL round bottom flask equipped with a rubber septum and a stirring bar was added 4-hydroxy-4-phenyl-piperidine (5 g, 30.0 mmol) followed by 30 mL of 4-bromoanisole. The resulting solution was stirred at room temperature under argon atmosphere and then AlCl$_3$ (8.0 g, 60.0 mmol) was added in one portion. An exotherm was observed. The reaction mixture was stirred for 8 h (brownish green color), then poured carefully over 600 ml of ice-water and stirred for 10 h. The white suspension was diluted with 100 mL of diethyl ether. The white solid that precipitated out was filtered and washed thoroughly with water (600 mL) followed by diethyl ether (500 mL) to obtain 4-(5-bromo-2-methoxy)-phenyl-4-phenyl-piperidine hydrochloride as a greyish white solid (6.0 g, 52%).

b. 3-[4-(5-bromo-2-methoxy)phenyl-4-phenyl-piperidin-1-yl]propylamine

To a solution of 4-(5-bromo-2-methoxy)-phenyl-4-phenyl-piperidine hydrochloride (2.5 g, 6.3 mmol) in 100 mL dioxane was added 3-bromo-N-tert-butoxycarbonyl-propylamine (2.25 g, 9.4 mmol) and K$_2$CO$_3$ (3.48 g, 25.2 mmol) and the resulting suspension was heated to reflux for 10 h. The suspension was allowed to cool, filtered and the solvent was evaporated to obtain yellow residue which was purified by column chromatography (Rf=0.4, 3:1 EtOAc/MeOH) to obtain 3-[4-(5-bromo-2-methoxy)phenyl-4-phenyl-piperidin-1-yl]-N-tert-butoxycarbonyl-propylamine as a yellow oil (3.15 g). It was dissolved in 35 mL of CH$_2$Cl$_2$ and 6.0 mL of trifluoroacetic acid was added with stirring at room temperature under argon atmosphere. After 1 h the solvent was evaporated in vacuo and the residue was basified to pH 10 by adding minimum amount of 1 N KOH solution. The product was extracted with CH$_2$Cl$_2$ (3×35 mL), dried over MgSO4, filtered and the solvent was removed in vacuo to obtain 3-[4-(5-bromo-2-methoxy) phenyl-4-phenyl-piperidin-1-yl]propylamine as a viscous yellow oil (2.26 g, 89% for two steps). It was used in the next step without further purification. The above mentioned steps a and b are representative examples of synthesis of all the 4,4-diaryl piperidine containing side chains described in this document.

c. 4-(3,4-Difluoro-phenyl)-2-oxo-oxazolidine-3-carboxylic acid {3-[4-(5-bromo-2-methoxy-phenyl)-4-phenyl-piperidin-1-yl]-propyl}-amide To a solution of 3-amino-propyl-4-(5-bromo-2-methoxy) phenyl-4-phenyl piperidine (2.0 g, 4.96 mmol) in 100 mL of THF was added 4-(3,4-difluorophenyl)-2-oxo-oxazolidine-3-carboxylic acid-4-nitro-phenyl ester (1.81 g, 4.96 mmol) and the resulting yellow solution was stirred under argon atmosphere for 3 h at room temperature. The solvent was removed in vacuo and the residue was purified by column chromatography over silica gel with 50% hexane/EtOAC followed by 5% MeOH in EtOAC as the eluting systems ($R_f$=0.4, 1:3 MeOH/EtOAC) to obtain the product as white foam (wt=2.2 g). It was dissolved in EtOAc (150 mL) and washed throughly with 5% NaOH solution (4×25 mL) in order to remove traces of 4-nitrophenol from the product. The organic layer was separated, washed with brine (25 mL) and then dried over $Na_2SO_4$. The solvent was removed after filtration and (+)-1-{3-{3,4-difluorophenyl)-2-oxo-oxazolidine-3-carbonyl)-amino-propyl}(5-bromo-2-methoxy)phenyl-4-phenyl-piperidine was obtained as a colorless glassy oil(1.84 g, 60%). $[\alpha]_D$=+34.3 (c=0.3, MeOH); The compound was dissolved in $CHCl_3$ (10 mL) and was treated with 1N HCl in ether (5 mL). The solvent was removed in vacuo to give the corresponding hydrochloride salt as a white solid (2.0 g). M.P. 142–144° C.; Anal. Calcd. for $C_{31}H_{33}N_4O_4BrClF_2$.0.3 $CHCl_3$: C, 53.65; H, 4.79; N, 6.00. Found: C, 53.89; H, 4.73; N, 5.74.

EXAMPLE 4

1-{3-[(2-Oxo-4-phenyl-[1,3]oxazinane-3-carbonyl)-amino-propyl}-4-phenyl-piperidine-4-carboxylic acid methyl ester (Scheme 7)

a. 3-Amino-3-phenyl-propan-1-ol

To a well stirred suspension of $LiAlH_4$ (1.3 g, 35.0 mmol) in THF (75 mL) in a round bottom flask fitted with a condenser was added 3-amino-3-phenyl-propionic acid (2.5 g, 15.0 mmol) in small portions at 0° C. The resulting grey suspension was then heated to reflux for 2 h. The reaction mixture was cooled to 0° C. and then carefully quenched sequentially with 1.3 mL of water, 1.3 mL of 3N NaOH followed by 4.0 mL of water. The resulting suspension was filtered thro' a fritted glass funnel. To the residue was added 100 mL $Et_2O$ and the suspension was heated to reflux for 20 min. The suspension was filtered and was combined with the previous filtrate, dried over $MgSO_4$, filtered and the solvent was removed in vacuo. 3-amino-3-phenyl-propan-1-ol was obtained as a white solid (2.30 g, 100%) which was used in the next step without further purification.

b. (3-Hydroxy-1-phenyl-propyl)-carbamic acid-tert-butyl ester

To a solution of 3-amino-3-phenyl-propan-1-ol (2.30 g, 15.0 mmol) in $CHCl_3$ (50 mL) at 0° C. was added a solution of di-tert-butyl dicarbonate (3.75 g, 17.1 mmol) in $CHCl_3$ (25 mL) in one portion and the resulting solution was stirred overnight at room temperature. The solvent was removed in vacuo and the residue was subjected to column chromatography on silica gel (2:1 hexane-EtOAc followed by EtOAc) to obtain (3-hydroxy-1-phenyl-propyl)-carbamic acid-tert-butyl ester as white solid (4.0 g, 100%).

c. 4-Phenyl-oxazinan-2-one

To a well stirred suspension of 95% NaH (0.24 g, 10.0 mmol) in THF (20 mL) at r.t. was added a solution of (3-hydroxy-1-phenyl-propyl)-carbamic acid-tert-butyl ester (1.0 g, 4.0 mmol) in 10 mL THF via a dropping funnel at room temperature. The resulting suspension was stirred for 3 h and then quenched carefully with 10 mL of water. The biphasic mixture was extracted with 100 mL of $Et_2O$, washed with brine, filtered and the solvent was removed in vacuo. The gummy residue thus obtained was purified by column chromatography over silica gel ($R_f$=0.2, 3:2 hexane-EtOAc) to obtain 4-phenyl-oxazinan-2-one as a white flaky solid (0.44 g, 62%).

d. 2-Oxo-4-phenyl-[1,3]-oxazinane-3-carboxylic acid-4-nitro-phenyl ester

To a suspension of NaH (0.07 g, 2.78 mmol) in 10 mL of anhydrous THF under argon, a solution of 4-phenyl-oxazinan-2-one (0.41 g, 2.31 mmol) in THF was added dropwise via an dropping funnel. The resulting suspension was stirred at room temperature for 30 min. This suspension was then added dropwise via cannula into another round bottom flask containing a solution of 4-nitrophenylchloroformate (0.60 g, 3.0 mmol) in 20 mL of THF and cooled at −78° C. over a period of 15 min. The stirring was continued for 2 h after which the solvent was removed and the residue was purified by column chromatography on silica gel with 1:1 hexane/$CH_2Cl_2$ followed by $CH_2Cl_2$ ($R_f$=0.4, $CH_2Cl_2$) to obtain 2-oxo-4-phenyl-[1,3]-oxazinane-3-carboxylic acid-4-nitro-phenyl ester as a white solid (0.65 g, 82%).

e. 1-{3-[(2-Oxo-4-phenyl-[1,3]oxazinane-3-carbonyl)-amino-propyl}-4-phenyl-piperidine-4-carboxylic acid methyl ester To a solution of 3-amino-propyl-(4-carbomethoxy-4-phenyl) piperidine (55 mg, 0.20 mmol) in 5 mL of THF, 2-oxo-4-phenyl-[1,3]-oxazinane-3-carboxylic acid-4-nitro-phenyl ester(51 mg, 0.15 mmol) was added and the resulting yellow solution was stirred under argon atmosphere for 10 h at room temperature. The solvent was removed in vacuo and the residue was purified by column chromatography over silica gel with EtOAC followed by 15% MeOH in EtOAC as the eluting systems ($R_f$=0.4, 1:1 MeOH/EtOAC) to obtain 2-oxo-4-phenyl-[1,3]-oxazinane-3-carboxylic acid-3-(4-carbomethoxy-4-phenyl)-piperidin-1-yl]-propyl amide as a pale yellow glassy oil (35 mg, 49% yield). It was converted into hydrochloride salt for characterization. Hygroscopic yellow solid. Anal. Calcd. for $C_{27}H_{34}N_3O_5Cl$.2.5 $H_2O$: C, 57.80; H, 7.01; N, 7.49. Found: C, 57.98; H, 6.68; N, 6.86.

EXAMPLE 5

4-(3,5-Difluoro-phenyl)-2-oxo-oxazolidine-3-carboxylic acid [3-(3',4',5',6'-tetrahydro-2'H-[2,4']bipyridinyl-1'-yl)-propyl]-ester a. 1-(3-hydroxypropyl)-4-[pyrid-2-yl]pyridinium bromide A solution of 2,4'-dipyridyl (3.0 g, 18.6 mmol) and 3-bromo-1-propanol (2.02 ml, 22.4 mmol) in acetonitrile (100 mL) was heated to reflux for 2 days. After cooling, the solvent was removed in vacuo and the yellow-brown liquid (8.0 g) was directly used for next step without further purification.

b. 3-(3',6'-Dihydro-2'-H-[2,4']bipyridinyl-1'-yl)-propanol

To a solution of 1-(3-hydroxypropyl)-4-[pyrid-2-yl] pyridinium bromide (8 g) in 100 mL EtOH was added $NaBH_4$ (1.41 g, 37.2 mmol) in small portions. The reaction mixture was stirred at room temperature for 12 h and then quenched with drops of water. The solvent was removed in vacuo and the residue was purified by column chromatography over silica gel with 1:4 MeOH/EtOAc followed by 1:4 (2M $NH_3$ in MeOH)/EtOAc as the eluting system ($R_f$=0.6, (2M $NH_3$ in MeOH)/EtOAc=1:4) to obtain 3-(3',6'-dihydro-2'-H-(2,4']bipyridinyl-1'-yl)-propanol as an oil (1.58 g, 39% over two steps).

c. 3-hydroxy-propyl-4-pyridyl-piperidine

To a solution of 3-(3',6'-dihydro-2'-H-[2,4']bipyridinyl-1'-yl)-propanol (1.30 g, 5.93 mmol) in mixed solvent (40 mL)

of MeOH and 2N Hcl (1:1), was added 0.5 g of Pearlman's catalyst. The suspension was hydrogenated under 80 psi at 50° C. for 10 h after which the reaction mixture was filtered through a pad of celite and the solvent was removed. The residue was basified by 20% NaOH and extracted by $CHCl_3$ (7×40 ml), dried over $Na_2SO_4$. The solvent was removed in vacuo to obtain a brown oil (785 mg, 60%).

d. 4-(3,5-Difluoro-phenyl)-2-oxo-oxazolidine-3-carboxylic acid [3-(3',4',5',6'-tetrahydro-2'H-[2,4'] bipyridinyl-1'-yl)-propyl]-ester To a solution of 4-(3,5-difluorobenzyl)-2-oxo-oxazolidine-3-carboxylic acid-4-nitro-phenyl ester (50 mg, 0.137 mmol) in 1,6-dioxane (20 ml) at room temperature, were added 3-hydroxy-propyl-4-pyridyl-piperidine (30 mg, 0.136 mmol) and $K_2CO_3$ (23.8 mg, 0.52 mmol). The resulting mixture was heated to reflux for 12 h after which the reaction mixture was cooled to room temperature and the solvent was removed in vacuo. The residue was purified by column chromatography over silica gel with EtOAc followed by 15% MeOH in EtOAc as the eluting system ($R_f$=0.30, MeOH:EtOAc=1:1) to obtain 4-(3,5-difluoro-phenyl)-2-oxo-oxazolidine-3-carboxylic acid [3-(3',4',5',6'-tetrahydro-2'H-[2,4']bipyridinyl-1'-yl)-propyl]-ester (20 mg, 33%). The compound was dissolved in anhydrous EtOH (1 mL) and was treated with a warm solution of 95% fumaric acid (5.3 mg, 0.045 mmol) in EtOH (3 ml). The resulting solution was kept under gentle stream of argon for 30 min after which hexane (2 ml) was added over 1 h and the solution was kept under argon overnight. Grey small crystals thus obtained were filtered, washed with EtOH (1 ml) and hexane (1 ml) and dried under vacuum. M.P. 171–173° C.; Anal. Calcd. For $C_{27}H_{29}N_3O_8F_2$.0.27$CHCl_3$: C, 55.16; H, 4.97; N, 7.08. Found: C, 55.17; H, 4.98; N, 6.53.

EXAMPLE 6

2-Oxo-4-(3,4,5-trifluoro-phenyl)-oxazolidine-3-carboxylic acid{3-[4-(2-carbamoyl-phenyl)-piperazin-1-yl]-propyl}-amide a. 2-[4-(3-amino-propyl)-piperazin-1-yl]-benzamide Concentrated sulfuric acid (15 mL) was added to 1-(2-cyanophenyl)piperazine (1.5 g, 8.0 mmol) placed in a round bottom flask and the resulting slurry was stirred at room temperature for 48 h. The reaction mixture was poured on crushed ice very slowly and then basified (pH 9) with 50% solution of NaOH. The aqueous layer was extracted several times with EtOAc, dried over $K_2CO_3$, filtered and the solvent was evaporated. 1-(2-carboxamidophenyl) piperazine was obtained as an off-white solid (1.2 g, 73%). It was used in the next step without further purification.

b. 2-Oxo-4-(3,4,5-trifluoro-phenyl)-oxazolidine-3-carboxylic acid{3-[4-(2-carbamoyl-phenyl)-piperazin-1-yl]-propyl}-amide To a solution of 1-(3-amino-propyl)-4-(2-carboxamido)-phenyl-piperazine (100 mg, 0.38 mmol) in 10 mL of THF, 4-(3,4,5-trifluorophenyl)-2-oxo-oxazolidine-3-carboxylic acid-4-nitro-phenyl ester(130 mg, 0.34 mmol) was added and the resulting yellow solution was stirred under argon atmosphere for 2 h at room temperature. The solvent was removed in vacuo and the residue was purified by column chromatography over silica gel with 1:1 hexane/EtOAc followed by 1:9 MeOH/EtOAc ($R_f$=0.64, MeOH/EtOAc= 1:3) to obtain (+)-1-{3-{3,4,5-trifluorophenyl)-2-oxo-oxazolidine-3-carboxylic acid{3-[4-(2-carbomoyl-phenyl)-piperazin-1-yl]-propyl}-amide (135 mg, 79%). The compound was dissolved in $CH_2Cl_2$ (3 mL) and was treated with 1N HCl in ether (1 mL). The solvent was removed in vacuo to give the corresponding hydrochloride salt as a yellow solid. M. P. 164–168° C.; $[\alpha]_D$=+50.5, (c=0.28, MeOH); Anal. Calcd. For $C_{24}H_{28}N_5O_4F_3Cl_2$.0.25 $CHCl_3$: C, 47.89; H, 4.68; N, 11.51. Found: C, 48.18; H, 5.03; N, 11.14.

EXAMPLE 7

2-[4-(3-{[4-(3,5-Difluoro-phenyl)-2-oxo-oxazolidine-3-carbonyl]-amino}-propyl)-piperazin-1-yl]-benzoic acid methyl ester (Schemes 1 and 5)

a. 1-(2-Carbomethoxyphenyl)-piperazine

To a solution of methyl 2-bromobenzoate (1.63 g, 17.8 mmol) in 1,4-dioxane (100 ml) at room temperature, were added piperazine (15.3 g, 178 mmol) and $K_2CO_3$ (4.92 g, 35 mmol). The resulting mixture was heated to reflux for 7 days after which the reaction mixture was cooled to room temperature and the solvent and the excess piperazine were removed in vacuo and heating with a hot water bath. The residue was dissolved in 1N NaOH solution and extracted with $CH_2Cl_2$ (6×30 ml), dried over $Na_2SO_4$. The solvent was removed in vacuo to obtain 1-(2-carbomethoxyphenyl)-piperazine as a yellow oil (1.0 g, 26%).

b. 2-[4-(3-{[4-(3,5-Difluoro-phenyl)-2-oxo-oxazolidine-3-carbonyl]-amino}-propyl)-piperazin-1-yl]-benzoic acid methyl ester To a solution of 1-(3-amino-propyl)-4-(2-carbomethoxyphenyl)-piperazine (25 mg, 0.090 mmol) in 10 mL of THF, 4-(3,5-difluorophenyl)-2-oxo-oxazolidine-3-carboxylic acid-4-nitro-phenyl ester(30 mg, 0.082 mmol) was added and the resulting yellow solution was stirred under argon atmosphere for 2 h at room temperature. The solvent was removed in vacuo and the residue was purified by column chromatography over silica gel with 1:1 hexane/EtOAc followed by 1:9 MeOH/EtOAc ($R_f$=0.75, MeOH/EtOAc=1:3) to obtain 2-[4-(3-{[4-(3,5-difluoro-phenyl)-2-oxo-oxazolidine-3-carbonyl]-amino}-propyl)-piperazin-1-yl]-benzoic acid methyl ester (31 mg, 69%). The compound was dissolved in $CH_2Cl_2$ (3 mL) and was treated with 1N HCl in ether (1 mL). The solvent was removed in vacuo to give the corresponding hydrochloride salt as a yellow solid. M. P. 93–96° C.; $[\alpha]_D$=+45.3, (c=0.29, MeOH); Anal. Calcd. For $C_{25}H_{30}N_4O_5F_2Cl_2$.0.58 $CH_2Cl_2$: C, 50.48; H, 5.16; N, 9.20. Found: C, 50.46; H, 5.56; N,8.91.

EXAMPLE 8

4-(3,4-Difluoro-phenyl)-2-oxo-oxazolidine-3-carboxylic acid [4-(4-phenyl-piperidin-1-yl)-butyl]-amide To a solution of 1-(4-amino-butyl)-4-phenyl-piperidine (35 mg, 0.151 mmol) in 10 mL of THF, 4-(3,5-difluorophenyl)-2-oxo-oxazolidine-3-carboxylic acid-4-nitro-phenyl ester(40 mg, 0.110 mmol) was added and the resulting yellow solution was stirred under argon atmosphere for 2 h at room temperature. The solvent was removed in vacuo and the residue was purified by column chromatography over silica gel with 1:1 hexane/EtOAc followed by 1:19 MeOH/EtOAc ($R_f$=0.33, MeOH/EtOAc= 1:3) to obtain 4-(3,4-difluoro-phenyl)-2-oxo-oxazolidine-3-carboxylic acid [4-(4-phenyl-piperidin-1-yl)-butyl]-amide (42 mg, 83%). The compound was dissolved in $CH_2Cl_2$ (3 mL) and was treated with 1N HCl in ether (1 mL). The solvent was removed in vacuo to give the corresponding hydrochloride salt as a yellow solid. M.P. 80–84° C.; Anal. Calcd. For $C_{25}H_3O_3N_{30}N_3F_2Cl$.0.5 $CH_2Cl_2$: C, 57.09; H, 5.82; N, 7.83. Found: C, 57.08; H, 6.21; N, 7.36.

EXAMPLE 9
1-(3-{[5-{3-(3,4-Difluorophenyl)-2-oxo-oxazolidine-3-carbonyl]-amino}-propyl)-4-phenyl-piperidine-4-carboxylic acid methyl ester (Scheme 8)

a. Hydroxy-(3,4-difluorophenyl)-acetonitrile

To a solution of 3,4-difluorobenzaldehyde (2.86 g, 20.0 mmol) in MeOH (20 mL)in a round bottom flask was added trimethylsilyl cyanide (4.0 mL., 30.0 mmol) at 0° C. The reaction mixture was stirred at room temperature for 10 h when TLC analysis indicated that the reaction was complete ($R_f$=0.4, 3:2 hexane/EtOAc). Solvent was removed in vacuo and hydroxy-(3,4-difluorophenyl)-acetonitrile was obtained as a colorless liquid (crude wt.=3.4 g). It was used in the next step without purification.

b. 2-Amino-1-(3,4-difluorophenyl)-ethanol

To a well stirred solution of hydroxy-(3,4-difluorophenyl)-acetonitrile (3.34 g, 20 mmol), was added a 1.0 M solution of $LiAlH_4$ in ether (40 mL, 40 mmol) dropwise at 0° C. The resulting yellow solution was then stirred at room temperature for 2 h. The reaction mixture was cooled to 0° C. and then carefully quenched sequentially with 1.5 mL of water, 1.5 mL of 3N NaOH followed by 4.5 mL of water. The resulting suspension was filtered thro' a fritted glass funnel. To the residue was added 100 mL $Et_2O$ and the suspension was heated to reflux for 20 min. The suspension was filtered and was combined with the previous filtrate, dried over $MgSO_4$, filtered and the solvent was removed in vacuo. 2-amino-1-(3,4-difluorophenyl)-ethanol was obtained as a yellow glassy syrup (3.3 g, 99%) which was used in the next step without further purification.

c. [1-(3,4-Difluorophenyl)-2-hydroxy-ethyl]-carbamic acid-tert-butyl ester

To a solution of 2-amino-1-(3,4-difluorophenyl)-ethanol (3.2 g, 19.8 mmol) in $CHCl_3$ (15 mL) at 0° C. was added a solution of di-tert-butyl dicarbonate (4.36 g, 20.0 mmol) in $CHCl_3$ (10 mL) in one portion and the resulting solution was stirred overnight at room temperature. The solvent was removed in vacuo and the residue was subjected to column chromatography on silica gel (2:1 hexane-EtOAc followed by EtOAc) to obtain [2-(3,4-difluorophenyl)-2-hydroxy-ethyl]-carbamic acid-tert-butyl ester as white solid (3.2 g, 59.4%).

d. 5-(3,4-Difluorophenyl)-oxazolidin-2-one

To a well stirred suspension of 95% NaH (0.55 g, 11.8 mmol) in THF (20 mL) at room temperature was added a solution of [2-(3,4-difluorophenyl)-2-hydroxy-ethyl]-carbamic acid-tert-butyl ester (3.2 g, 23.0 mmol) in THF via a dropping funnel at room temperature. The resulting suspension was stirred for 3 h and then quenched carefully with 10 mL of water. The biphasic mixture was extracted with 100 mL of $Et_2O$, washed with brine, filtered and the solvent was removed in vacuo.

The gummy residue thus obtained was purified by column chromatography over silica gel ($R_f$=0.15, 3:2 hexane-EtOAc) to obtain 5-(3,4-difluoro-phenyl)-oxazolidin-2-one as a white solid (1.1 g, 47%).

e. 5-(3,4-Difluorophenyl)-2-oxo-oxazolidine-3-carboxylic acid-4-nitro-phenyl ester To a suspension of 95% NaH (0.08 g, 3.0 mmol) in 5.0 mL of anhydrous THF under argon, a solution of 5-(3,4-difluorophenyl)-oxazolidin-2-one (0.5 g, 2.51 mmol) in 5.0 mL THF was added dropwise via an dropping funnel. The resulting suspension was stirred at room temperature for 30 min. This suspension was then added dropwise via cannula into another round bottom flask containing a solution of 4-nitrophenylchloroformate (0.07 g, 3.26 mmol) in 20 mL of THF, cooled at −78° C., over a period of 15 min. The stirring was continued for 2 h after which the solvent was removed and the residue was purified by column chromatography on silica gel with 1:1 hexane/$CH_2Cl_2$ followed by $CH_2Cl_2$ ($R_f$=0.4, $CH_2Cl_2$) to obtain 5-(3,4-difluorophenyl)-2-oxo-oxazolidine-3-carboxylic acid-4-nitro-phenyl ester as a white solid (0.7 g, 76%).

f. 1-(3-{[5-{3-(3,4-Difluorophenyl)-2-oxo-oxazolidine-3-carbonyl]-amino}-propyl)-4-phenyl-piperidine-4-carboxylic acid methyl ester To a solution of 3-amino-propyl-4-carbomethoxy-4-phenyl piperidine (0.04 g, 0.13 mmol) in 10 mL of THF 5-(3,4-difluorophenyl)-2-oxo-oxazolidine-3-carboxylic acid-4-nitro-phenyl ester (0.04 g, 0.10 mmol) was added and the resulting yellow solution was stirred under argon atmosphere for 10 h at room temperature. The solvent was removed in vacuo and the residue was purified by column chromatography over silica gel with EtOAC followed by 15% MeOH in EtOAC as the eluting systems ($R_f$=0.4, 1:1 MeOH/EtOAC) to obtain 1-(3-{[5-{3-(3,4 -difluorophenyl)-2-oxo-oxazolidine-3-carbonyl]-amino}-propyl)-4-phenyl-piperidine-4-carboxylic acid methyl ester as a pale yellow glassy oil(0.03 g, 60%). It was converted into its hydrochloride salt. M.P.=121–125° C.; Anal. Calcd. for $C_{26}H_{80}N_3O_4F_2Cl_2.0.2\ H_2O$: C, 57.66; H, 5.66; N, 7.76. Found: C, 57.80; H, 6.15; N, 7.95.

EXAMPLE 10
4-(3-Chloro-4-fluoro-phenyl)-2-oxo-oxazolidine-3-carboxylic acid [3-(4,4-diphenyl-piperidin-1-yl)-propyl]-amide (Schemes 2 and 5)

To a solution of 3-amino-propyl-4,4-diphenyl piperidine (0.04 g, 0.1 mmol) in 5 mL of THF was added 4-(3-chloro-4-fluorophenyl)-2-oxo-oxazolidine-3-carboxylic acid-4-nitro-phenyl ester (0.04 g, 0.12 mmol) and the resulting yellow solution was stirred under argon atmosphere for 3 h at room temperature. The solvent was removed in vacuo and the residue was purified by column chromatography over silica gel with 50% hexane/EtOAC followed by 5% MeOH in EtOAC as the eluting systems ($R_f$=0.45, 1:3 MeOH/EtOAC) to obtain 4-(3-Chloro-4-fluoro-phenyl)-2-oxo-oxazolidine-3-carboxylic acid [3-(4,4-diphenyl-piperidin-1-yl)-propyl]-amide as white foam (wt=0.03 g). It was converted into its hydrochloride salt. M.P. 112–115° C.; Anal. Calcd. for $C_{30}H_{32}N_3O_3Cl_2F.0.5\ CHCl_3$: C, 57.95; H, 5.18; N, 6.65. Found: C, 58.06; H, 5.74; N, 6.30.

EXAMPLE 11
4-(3,4-Difluoro-phenyl)-2-thioxo-oxazolidine-3-carboxylic acid [3-(4-o-toluyl-4-p-toluyl-piperidin-1-yl)-propyl]-amide (Scheme 9)

a. 4-(3,4-Difluorophenyl)-oxazolidine-2-thione

To a solution of 2-amino-2-(3,4-difluorophenyl)-ethanol (600 mg, 3.46 mmol) in $CH_2Cl_2$ (20 ml) at room temperature, was added 1,1'-thiocarbonyldiimadazole (755 mg, 3.81 mmol). The resulting solution was heated by a pre-heated oil-bath (110° C.) to reflux for 10 h after which the reaction mixture was cooled to room temperature and the solvent was removed in vacuo. The residue was purified by column chromatography over silica gel with $CH_2Cl_2$ as the eluting system ($R_f$=0.68, $CH_2Cl_2$:EtOAc=3:1) to obtain 4-(3,4-difluorophenyl)-oxazolidine-2-thione a brown oil (290 mg, 39%).

b. 4-(3,4-Difluorophenyl)-2-thione-oxazolidine-3-carboxylic acid-4-nitro-phenyl ester To a suspension of NaH (41 mg, 1.62 mmol) in 20 mL of anhydrous THF under argon, a solution of 4-(3,4-difluorophenyl)-oxazolidine-2-thione (290 mg, 1.35 mmol) in THF was added dropwise via an dropping funnel. The resulting suspension was stirred at room temperature for 30 min. This suspension was then added dropwise via cannula into another round bottom flask containing a solution of 4-nitrophenylchloroformate (336 mg, 1.62 mmol) in 20 mL of THF and cooled at −78° C. over a period of 15 min. The stirring was continued for 2 h after which the solvent was removed and the residue was purified by column chromatography on silica gel with 1:1 hexane/$CH_2Cl_2$, then 3:7 hexane/$CH_2Cl_2$ followed by $CH_2Cl_2$ ($R_f$=0.50) to obtain 4-(3,4-difluorophenyl)-2-thione-oxazolidine-3-carboxylic acid-4-nitro-phenyl ester as a yellow solid (130 mg, 25%).

c. 4-(3,4-Difluoro-phenyl)-2-thioxo-oxazolidine-3-carboxylic acid [3-(4-o-toluyl-4-p-toluyl-piperidin-1-yl)-propyl]-amide To a solution of 1-(3-amino-propyl)-4-(4-methyl)-phenyl-4-(2-methyl)-phenyl-piperidine (60 mg, 0.186 mmol) in 10 mL of THF,4-(3,4-Difluorophenyl)-2-thione-oxazolidine-3-carboxylic acid-4-nitro-phenyl ester(30 mg, 0.079 mmol) was added and the resulting yellow solution was stirred under argon atmosphere for 2 h at room temperature. The solvent was removed in vacuo and the residue was purified by column chromatography over silica gel with 1:1 hexane/EtOAc followed by 1:19 MeOH/EtOAc ($R_f$=0.66, MeOH/EtOAc=1:3) to obtain 4-(3,4-Difluoro-phenyl)-2-thioxo-oxazolidine-3-carboxylic acid [3-(4-o-toluyl-4-p-toluyl-piperidin-1-yl)-propyl]-amide (16 mg, 36%). The compound was dissolved in $CH_2Cl_2$ (3 mL) and was treated with 1N HCl in ether (1 mL). The solvent was removed in vacuo to give the corresponding hydrochloride salt as a yellow solid. M.P.=132–136° C.; Anal. Calcd. for $C_{32}H_{36}N_3O_2SCl.0.60$ $CH_2Cl_2$: C, 60.14; H, 5.76; N, 6.45. Found: C, 59.97; H, 6.14; N, 6.12.

EXAMPLE 12

4-phenyl-2-thioxo-thiazolidine-3-carboxylic acid [3-(3',4',5',6'-tetrahydro-2'H-[2,4']bipyridinyl-1'-yl)-propyl]-amide (Scheme 9)

a. 4-(S)-Phenyl-thiazolidine-2-thione

To a solution of (S)-(+)-2-Phenylglycinol(1.40 g, 10 mmol) in 1N $KOH/H_2O$ (10 ml) at room temperature, was added carbon disulfide (3 ml, 50 mmol). The resulting solution was heated by a pre-heated oil-bath (110° C.) to reflux for 20 h after which the reaction mixture was cooled to room temperature and extracted with $CH_2Cl_2$ (3×30 ml), dried over $Na_2SO_4$. The solvent was removed in vacuo and the residue was purified by column chromatography over silica gel with 1:1 hexane/$CH_2Cl_2$ followed by $CH_2Cl_2$ as the eluting system ($R_f$=0.09, $CH_2Cl_2$:hexane=7:3) to obtain 4(S)-phenyl-thiazolidine-2-thione (170 mg, 9%).

b. 4-(S)-Phenyl-2-thione-thiazolidine-3-carboxylic acid-4-nitro-phenyl ester

To a suspension of NaH (26 mg, 1.04 mmol) in 10 mL of anhydrous THF under argon, a solution of 4(S)-Phenyl-thiazolidine- 2-thione (170 mg, 0.87 mmol) in THF was added dropwise via an dropping funnel. The resulting suspension was stirred at room temperature for 30 min. This suspension was then added dropwise via cannula into another round bottom flask containing a solution of 4-nitrophenylchloroformate (217 mg, 1.04 mmol) in 20 mL of THF and cooled at −78° C. over a period of 15 min. The stirring was continued for 2 h after which the solvent was removed and the residue was purified by column chromatography on silica gel with 1:1 hexane/$CH_2Cl_2$ then 3:7 hexane/$CH_2Cl_2$ followed by $CH_2Cl_2$ ($R_f$=0.50) to obtain (+)-4(S)-phenyl-2-thione-thiazolidine-3-carboxylic acid-4-nitro-phenyl ester as a pale yellow solid (200 mg, 64%).

c. 4-phenyl-2-thioxo-thiazolidine-3-carboxylic acid [3-(3',4',5',6'-tetrahydro-2'H-[2,4']biphenyl-1'-yl)-propyl]-amide To a solution of 3-amino-propyl-4-pyridyl-piperidine (35 mg, 0.159 mmol) in 10 mL of THF,(+)-4(S)-Phenyl-2-thione-thiazolidine-3-carboxylic acid-4-nitro-phenyl ester (50 mg, 0.139 mmol) was added and the resulting yellow solution was stirred under argon atmosphere for 2 h at room temperature. The solvent was removed in vacuo and the residue was purified by column chromatography over silica gel with 1:1 hexane/EtOAc followed by 1:9 MeOH/EtOAc ($R_f$=0.21, MeOH/EtOAc=1:3) to obtain 4-(3,4-Difluoro-phenyl)-2-thioxo-thiazolidine-3-carboxylic acid [3-(3',4',5',6'-tetrahydro-2'H-[2,4']bipyridinyl-1'-yl)-propyl]-amide (10 mg, 14%). The compound was dissolved in $CH_2Cl_2$ (3 mL) and was treated with 1N HCl in ether (1 mL). The solvent was removed in vacuo to give the corresponding hydrochloride salt as a yellow solid. M.P.=67–70° C.; Anal. Calcd. for $C_{23}H_{31}N_4OS_2Cl_2.0.67$ $CHCl_3$: C, 47.82; H, 5.37; N, 9.42. Found: C, 47.85; H, 6.12; N, 6.52.

EXAMPLE 13

(−)-2-Oxo-8,8a-dihydro-3aH-1-(S)-oxa-3-(R)-aza-cyclopent[1]indene-3-carboxylic acid-[3-(1-4-cyano-4-phenyl-piperidin-1-yl)-propyl-amide (Scheme 10)

a. Synthesis of (+)-3,3a,8,8a-tetrahydro-1(S)-oxa-3(R)-aza-cyclopenta[a]inden-2-one To a solution of (1R,2S)-(+)-cis-1-amino-2-indanol (1.0 g, 6.7 mmol) in 30 ml methylene chloride in 100-ml round bottom flask equipped with a stirring bar, was added 1,1'-carbonyldimidazole (1.20 g, 7.4 mmol) at room temperature. The resulting solution was heated by a pre-heated oil-bath (110° C.) to reflux for 10 h after which the reaction mixture was cooled to room temperature and the formation of white crystal was observed. The white crystal was filtered off, washed with minimum $CH_2Cl_2$ (2 mL) and then dried in vacuo. (+)-3,3a,8,8a-Tetrahydro-1(S)-oxa-3(R)-aza-cyclopenta[a]inden-2-one was obtained as a white crystal (500 mg, 43%). $[\alpha]_D$=−71.1 (c=0.28, acetone). M.P. 203–204° C. Anal. Calcd. for $C_{10}H_9NO_2$: C, 68.56; H, 5.18; N, 8.00. Found: C, 68.44; H, 5.12; N, 7.98.

b. 2-Oxo-1,3a,8,8a-tetrahydro-2H-3-aza-cyclopenta[a]indene-3-carboxylic acid 4-nitro-phenyl ester To a suspension of NaH (73 mg, 2.88 mmol) in 20 mL of anhydrous THF under argon, a solution of 3,3a,8,8a-tetrahydro-1(R)-oxa-3(S)-aza-cyclopenta[a]inden-2-one (420 mg, 2.40 mmol) in THF was added dropwise via an dropping funnel. The resulting suspension was stirred at room temperature for 30 min. This suspension was then added dropwise via cannula into another round bottom flask containing a solution of 4-nitrophenylchloroformate (598 mg, 2.88 mmol) in 25 mL of THF and cooled at −78° C. over a period of 15 min. The stirring was continued for 2 h after which the solvent was removed and the residue was purified by column chromatography on silica gel with 4:1 hexane/EtOAc followed by 3:2 hexane/EtOAc ($R_f$=0.51, hexane/EtOAc=1:1) to obtain a white solid (680 mg, 83%).

c. (−)-2-Oxo-8,8a-dihydro-3aH-1-(S)-oxa-3-(R)-aza-cyclopent[1]indene-3-carboxylic acid-[3-(1-4-cyano-4-phenyl-piperidin-1-yl)-propyl-amide To a solution of 1-(3-amino-propyl)-4-cyano-4-phenyl-piperidine (25 mg, 0.103 mmol) in 10 mL of THF, 2-Oxo-1,3a,8,8a-tetrahydro-2H-3-aza-cyclopenta[a]indene-3-carboxylic acid 4-nitro-phenyl ester (40 mg, 0.118 mmol) was added and the resulting yellow solution was stirred under argon atmosphere for 2 h at room temperature. The solvent was removed in vacuo and the residue was purified by column chromatography over silica gel with 1:1 hexane/EtOAc followed by EtOAc ($R_f$=0.35) to obtain (−)-2-Oxo-8,8a-dihydro-3aH-1-(S)-oxa-3-(R)-aza-cyclopent[1]indene-3-carboxylic acid-[3-(1-4-cyano-4-phenyl-piperidin-1-yl)- propyl-amide (19 mg, 35%). The compound was dissolved in $CH_2Cl_2$ (3 mL) and was treated with 1N HCl in ether (1 mL). The solvent was removed in vacuo to give the corresponding hydrochloride salt as a white solid. M. P. 98–102° C.; $[\alpha]_D$=−96.5, (c=0.21, MeOH); Anal. Calcd. For $C_{26}H_{29}N_4O_3Cl.0.48$ $CH_2Cl_2$: C, 60.96; H, 5.79; N, 10.74. Found: C, 60.94; H, 6.69; N, 8.02.

EXAMPLE 14

4-(3,4-Difluoro-phenyl)-2-oxo-oxazolidine-3-carboxylic acid {3-[2-methyl-4-(2-nitro-phenyl)-piperazin-1-yl)-propyl}-amide a. (S)-(+)-3-methyl-1-(2-nitrophenyl)-piperazine To a solution of 2-bromo-nitrobenzene (0.6 g, 3.0 mmol) in 1,4-dioxane (15 mL) was added (S)-(+)-2-methylpiperazine (0.5 g, 0.5 mmol) and powdered $K_2CO_3$ (15.0 mmol, 1.5 g) and the resulting suspension was heated at reflux for 10 h. After the suspension was cooled, it was filtered through a sintered glass funnel and the solvent was evaporated in vacuo. The resulting residue was purified by column chromatography on silica gel (1:1 hexane/EtOAc followed by 4:1 EtOAc/MeOH) to yield (S)-(+)-3-methyl-1-(2-nitrophenyl)-piperazine as an orange oil (0.53 g, 80%). It was converted into (S)-(+)-3-methyl-1-(2-nitrophenyl)-4-(3-aminopropyl)-piperazine by the usual procedure.

b. 4-(3,4-Difluoro-phenyl)-2-oxo-oxazolidine-3-carboxylic acid {3-[2-methyl-4-(2-nitro-phenyl)-piperazin-1-yl)-propyl}-amide To a solution of (S)-(+)-3-methyl-1-(2-nitrophenyl)-4-(3-aminopropyl)-piperazine (35 mg, 0.126 mmol) in 10 mL of THF, 4-(3,4-difluorophenyl)-2-oxo-oxazolidine-3-carboxylic acid-4-nitro-phenyl ester (50 mg, 0.137 mmol) was added and the resulting yellow solution was stirred under argon atmosphere for 2 h at room temperature. The solvent was removed in vacuo and the residue was purified by column chromatography over silica gel with 1:1 hexane/EtOAc followed by MeOH:EtOAc=1:9 ($R_f$=0.58, MeOH:EtOAc=1:3) to obtain 4-(3,4-Difluoro-phenyl)-2-oxo-oxazolidine-3-carboxylic acid {3-[2-methyl-4-(2-nitro-phenyl)-piperazin-1-yl)-propyl}-amide (55 mg, 87%) The compound was dissolved in $CH_2Cl_2$ (3 mL) and was treated with 1N HCl in ether (1 mL). The solvent was removed in vacuo to give the corresponding hydrochloride salt as a pale yellow solid. M. P. 115–119° C.; $[\alpha]_D$=+38.3, (c=0.22, $CH_2Cl_2$); Anal. Calcd. For $C_{24}H_{28}N_5O_5F_2Cl.0.72$ $C_6H_{12}$: C, 56.50; H, 6.38; N, 11.63. Found: C, 56.63; H, 6.35; N, 10.08.

EXAMPLE 15

4-(3,4-Difluoro-phenyl)-2-oxo-oxazolidine-3-carboxylic acid {3-[4-methyl-4-phenyl-piperidin-1-yl)-propyl}-amide a. 1-Benzyl-4-methyl-4-piperidinol To a solution of 1-benzyl-4-piperidone (5.6 mL, 30.0 mmol) in 50 mL THF was added a solution of methyllithium in THF (24.0 mL, 36 mmol) dropwise at 0° C. over 15 min. The reaction mixture was allowed to warm to room temperature over 3 h and then quenched with 30 mL of sat. $NH_4Cl$ solution. The organic layer was extracted with diethyl ether (2×100 mL) and the combined organic layer was washed with brine (100 mL). The organic layer was separated, dried over $Na_2SO_4$, filtered and the solvent was removed in vacuo to obtain yellow gum. It was purified by column chromatography over silica gel with 9:1 EtOAc-MeOH as the eluting system to obtain 1-benzyl-4-methyl-4-piperidinol as a yellow thick oil (3.6 g, 59% yield).

b. 1-Benzyl-4-methyl-4-phenyl piperidine

To a solution of 1-benzyl-4-methyl-4-piperidinol (3.6 g, 17.5 mmol) in 75 mL of benzene was added $AlCl_3$ (11.7 g, 87.7 mmol) in one portion at room temperature. After stirring at room temperature for 30 min, the reaction mixture was heated to reflux for 8 h. The red colored solution was allowed to cool and then poured over 100 g of ice-water. It was extracted with EtOAc (2×100 mL) and the organic layer was washed with solution of Rochelle's salt. The organic layer was separated, dried over $Na_2SO_4$, filtered and the solvent was removed in vacuo to obtain 1-benzyl-4-methyl-4-phenyl piperidine as a red oil (4.5 g, 97% yield). It was used in the next step without further purification.

c. 4-Methyl-4-phenyl piperidine

To a cooled suspension of 10% Pd-C (0.5 g) in 10 mL methanol was added a solution of 1-benzyl-4-methyl-4-phenyl piperidine (4.5 g, 17.0 mmol) in 40 mL of methanol and the resulting suspension was hydrogenated in a Parr bomb under 250 psi of hydrogen for two days. The suspension was filtered through a pad of celite and the solvent was removed from the filtrate to obtain 4-methyl-4-phenyl piperidine as a yellow solid (3.3 g, 99% yield).

d. 4-(3,4-Difluoro-phenyl)-2-oxo-oxazolidine-3-carboxylic acid {3-[4-methyl-4-phenyl-piperidin-1-yl)-propyl}-amide To a solution of 1-(3-amino-propyl)-4-methyl-4-phenyl-piperidine (60 mg, 0.258 mmol) in 10 mL of THF, 4-(3,4-difluorophenyl)-2-oxo-oxazolidine-3-carboxylic acid-4-nitro-phenyl ester (60 mg, 0.165 mmol) was added and the resulting yellow solution was stirred under argon atmosphere for 2 h at room temperature. The solvent was removed in vacuo and the residue was purified by column chromatography over silica gel with 1:1 hexane/EtOAc followed by MeOH:EtOAc=1:19 ($R_f$=0.45, MeOH:EtOAc=1:3) to obtain 4-(3,4-difluoro-phenyl)-2-oxo-oxazolidine-3-carboxylic acid {3-[4-methyl-4-phenyl-piperidin-1-yl)-propyl}-amide (56 mg, 74%). The compound was dissolved in $CH_2Cl_2$ (3 mL) and was treated with 1N HCl in ether (1 mL). The solvent was removed in vacuo to give the corresponding hydrochloride salt as a pale yellow solid. M. P. 176–178° C.; $[\alpha]_D$=+76.9, (c=0.23, MeOH); Anal. Calcd. For $C_{25}H_{30}N_3O_3F_2Cl.0.60$ $CH_2Cl_2$: C, 56.32; H, 5.94; N, 7.70. Found: C, 56.30; H, 5.80; N, 7.35.

EXAMPLE 16

4-(3,4-Difluorophenyl)-4-methyl-2-oxo-oxazolidine-3-carboxylic acid {3-[4-(2-methylphenyl)-4-(4-methylphenyl)-piperidin-1-yl]-propyl}amide (Scheme 11)

a. 2-(3,4-Difluorophenyl)propan-2-ol

To a solution of ethylmagnesium bromide in ether (38.0 mL, 38.0 mmol) at 0° C., was added a solution of 3',4'-difluoroacetophenone (5.0 g, 32.0 mmol) in diethyl ether (35 mL). The reaction mixture was stirred at 0° C. for 1 h when TLC analysis indicated that the reaction was complete ($R_f$=0.3, 3:1 hexane/EtOAc). The reaction was quenched carefully by adding 38 mL of water. It was extracted with diethyl ether (2×30 mL), washed with Rochelle's salt followed by brine and the organic layer was dried over $Na_2SO_4$. The solvent was removed in vacuo after filtration and 2-(3,4-difluorophenyl)propan-2-ol was obtained as a colorless oil (crude wt.=5.4 g, 97%) which looked >90% pure by NMR. It was used in the next step without purification.

b. 1,2-Difluoro-4-isopropenyl-benzene

To a solution of 2-(3,4-difluorophenyl)propan-2-ol (1.0 g, 5.8 mmol) in 40 mL benzene was added 0.1 g of p-toluenesulfonic acid and the solution was heated to 60° C. TLC analysis showed disappearance of the starting material. After cooling, the solution was extracted with EtOAc, washed with saturated $NaHCO_3$, dried over $Na_2SO_4$, filtered and the solvent was removed in vacuo. 1,2-difluoro-4-isopropenyl-benzene was obtained as a yellow oil (0.82 g, 92% yield).

c. 2-(3,4-Difluorophenyl)-2-methyl-oxirane

To a biphasic solution of 1,2-difluoro-4-isopropenyl-benzene (0.81 g, 5.1 mmol) in $CH_2Cl_2$ (50 mL) and 50 mL of phosphate buffer (made by dissolving 0.3 g of $NaHPO_4$ and 0.35 g of $NaH_2PO_4$ in 50 mL water, pH=8) at 0° C., was added a solution of 3-chloroperoxybenzoic acid (approx. 75% solid, 3.32 g, 10.2 mmol) via a dropping funnel fitted with a cotton plug dropwise in two batches. The solution was stirred at room temperature overnight. It was extracted with $CH_2Cl_2$, washed with sat. $Na_2S_2O_4$ solution followed by water. The organic layer was finally washed with sat. $NaHCO_3$, separated, dried over $Na_2SO_4$, filtered and solvent was removed in vacuo. 2-(3,4-Difluorophenyl)-2-methyl-oxirane was obtained as a pale yellow oil (0.65 g, 74% yield). It was used in the next step without purification.

d. 1-Amino-2-(3,4-difluorophenyl)-propan-2-ol and 2-Amino-2-(3,4-difluorophenyl)-propan-1-ol To a solution of 2-(3,4-difluorophenyl)-2-methyl-oxirane (1.2 g, 7.06 mmol) in 10 mL of acetonitrile was added sodium azide (0.69 g, 10.6 mmol) followed by lithium perchlorate (1.13 g, 10.6 mmol) and the suspension was heated to reflux overnight. After cooling, it was extraced with EtOAc, washed with saturated $NaHCO_3$, dried over $Na_2SO_4$, filtered and the solvent was removed in vacuo. The light bron oil that was obtained was a 10:1 mixture of 1-azido-2-(3,4-difluorophenyl)-propan-2-ol and 2-azido-2-(3,4-difluorophenyl)-propan-1-ol (crude wt 2.0 g). It was dissolved in 40 mL of diethyl ether, cooled to 0° C. and then treated with a solution of lithium aluminum hydride (20.0 mL, 20 mmol). The resulting yellow suspension was then stirred at room temperature for 2 h. The reaction mixture was cooled to 0° C. and then carefully quenched sequentially with 0.8 mL of water, 0.8 mL of 3N NaOH followed by 2.5 mL of water. The resulting suspension was filtered thro' a fritted glass funnel. To the residue was added 100 mL $Et_2O$ and the suspension was heated to reflux for 20 min. The suspension was filtered and was combined with the previous filtrate, dried over $MgSO_4$, filtered and the solvent was removed in vacuo. 1-Amino-2-(3,4-difluorophenyl)-propan-2-ol and 2-amino-2-(3,4-difluorophenyl)-propan-1-ol was obtained as a yellow glassy syrup (1.16 g, 87%) which was used in the next step immediately without further purification.

e. [2-(3,4-Difluorophenyl)-2-hydroxy-propyl]-carbamic acid-tert-butyl ester and [1-(3,4-Difluorophenyl)-2-hydroxy-propyl]-carbamic acid-tert-butyl ester To a solution of 1-amino-2-(3,4-difluorophenyl)-propan-2-ol and 2-amino-2-(3,4-difluorophenyl)-propan-1-ol (1.2 g, 6.4 mmol) in $CHCl_3$ (50 mL) at 0° C. was added a solution of di-tert-butyl dicarbonate (1.74 g, 7.9 mmol) in $CHCl_3$ (10 mL) in one portion and the resulting solution was stirred overnight at room temperature. The solvent was removed in vacuo and the residue was subjected to column chromatography on silica gel (2:1 hexane-EtOAc followed by EtOAc) to obtain [2-(3,4-difluorophenyl)-2-hydroxy-propyl]-carbamic acid-tert-butyl ester and [1-(3,4-Difluorophenyl)-2-hydroxy-propyl]-carbamic acid-tert-butyl ester as a white solid (1.1 g, 60.1%).

f. 5-(3,4-Difluorophenyl)-5-methyl-oxazolidin-2-one and 4-(3,4-Difluorophenyl)-4-methyl-oxazolidin-2-one To a well stirred solution of [2-(3,4-difluorophenyl)-2-hydroxy-propyl]-carbamic acid-tert-butyl ester and [1-(3,4-Difluorophenyl)-2-hydroxy-propyl]-carbamic acid-tert-butyl ester (1.1 g, 3.8 mmol) THF (50 mL) was added 95% NaH (0.23 g, 9.6 mmol) at room temperature. The resulting suspension was heated to reflux for 1 h and then stirred at room temperature overnight. It was quenched carefully with ice. The biphasic mixture was extracted with 100 mL of EtOAc, washed with brine, dried over $Na_2SO_4$, filtered and the solvent was removed in vacuo. The two diastereomers were separated by column chromatography over silica gel. The first diastereomer that came out was 4-(3,4-difluorophenyl)-4-methyl-oxazolidin-2-one (0.05 g, $R_f$=0.3, 3:2 hexane-EtOAc) and the second isomer was 5-(3,4-difluorophenyl)-5 -methyl-oxazolidin-2-one (0.61 g, $R_f$=0.2, 3:2 hexane-EtOAc).

g. 4-(3,4-Difluorophenyl)-4-methyl-2-oxo-oxazolidine-3-carboxylic acid-4-nitro-phenyl ester To a a solution of 4-(3,4-Difluorophenyl)-4-methyl-oxazolidin-2-one(0.05 g, 0.23 mmol) in 5.0 mL THF was added 95% NaH (0.01 g, 0.28 mmol) in one portion. The resulting suspension was stirred at room temperature for 20 min. This suspension was then added dropwise via a syringe into another round bottom flask containing a solution of 4-nitrophenylchloroformate (0.06 g, 0.28 mmol) in 5 mL of THF, cooled at −78° C., over a period of 15 min. The stirring was continued for 1 h after which the solvent was removed and the residue was purified by column chromatography on silica gel with 3:2 hexane/EtOAc ($R_f$=0.5) to obtain 4-(3,4-difluorophenyl)-4-methyl-2-oxo-oxazolidine-3-carboxylic acid-4-nitro-phenyl ester as a white solid (0.06 g, 69%).

h. 5-(3,4-Difluorophenyl)-5-methyl-2-oxo-oxazolidine-3-carboxylic acid-4-nitro-phenyl ester To a a solution of 4-(3,4-Difluorophenyl)-4-methyl-oxazolidin-2-one (0.61 g, 2.86 mmol) in 20 mL THF was added 95% NaH (0.07 g, 3.0 mmol) in one portion. The resulting suspension was stirred at room temperature for 20 min. This suspension was then added dropwise via a cannula into another round bottom flask containing a solution of 4-nitrophenylchloroformate (0.62 g, 3.1 mmol) in 20 mL of THF, cooled at −78° C., over a period of 15 min. The stirring was continued for 1 h after which the solvent was removed and the residue was purified by column chromatography on silica gel with 3:2 hexane/EtOAc ($R_f$=0.6) to obtain 4-(3,4-difluorophenyl)-4-methyl-2-oxo-oxazolidine-3-carboxylic acid-4-nitro-phenyl ester as a white solid (0.7 g, 67%).

i. 4-(3,4-Difluorophenyl)-4-methyl-2-oxo-oxazolidine-3-carboxylic acid (3-[4-(2-methylphenyl)-4-(4-methylphenyl)-piperidin-1-yl]-propyl)amide To a solution of 3-amino-propyl-4-(2-methyl)phenyl-4-(4-methyl)phenyl-piperidine (0.09 g, 0.27 mmol) in 10 mL of THF, 4-(3,4-Difluorophenyl)-4-methyl-2-oxo-oxazolidine-3-carboxylic acid-4-nitro-phenyl ester (0.06 g, 0.15 mmol) was added and the resulting yellow solution was stirred under argon atmosphere for 10 h at room temperature. The solvent was removed in vacuo and the residue was purified by column chromatography over silica gel with EtOAC followed by 15% MeOH in EtOAC as the eluting systems ($R_f$=0.3, 1:3 MeOH/EtOAC) to obtain 4-(3,4-difluorophenyl)-4-methyl-2-oxo-oxazolidine-3-carbonyl)-amino-propyl}-4-(2-methyl)phenyl-4-(4-methyl)phenyl-piperidine as a pale yellow glassy oil (0.06 g, 73%) as a viscous oil. It was converted into its hydrochloride salt. M.P.=98–101° C.; Anal. Calcd. for $C_{33}H_{38}N_3O_3F_2Cl.1.0$ $CH_2Cl_2$: C, 59.79; H, 5.90; N, 6.15. Found: C, 59.40; H, 5.99; N, 5.92.

EXAMPLE 17

5-(3,4-Difluorophenyl)-5-methyl-2-oxo-oxazolidine-3-carboxylic acid {3-[4-(2-methoxy-5-methyl)phenyl-4-(4-methylphenyl)-piperidin-1-yl]propyl}amide (Scheme 11)

To a solution of 3-amino-propyl-4-(2-methoxy-5-methyl)phenyl-4-(4-methyl)phenyl-piperidine (0.09 g, 0.27 mmol) in 10 mL of THF, 5-(3,4-Difluorophenyl)-5-methyl-2-oxo-oxazolidine-3-carboxylic acid-4-nitro-phenyl ester (0.04 g, 0.11 mmol) was added and the resulting yellow solution was stirred under argon atmosphere for 10 h at room temperature. The solvent was removed in vacuo and the residue was purified by column chromatography over silica gel with EtOAC followed by 15% MeOH in EtOAC as the eluting systems ($R_f$ =0.3, 1:3 MeOH/EtOAC) to obtain 4-(3,4-difluorophenyl)-4-methyl-2-oxo-oxazolidine-3-carboxylic acid {3-[4-(2-methoxy-5-methyl)phenyl-4-(4-methylphenyl)-piperidin-1-yl]propylyl}amide as a pale yellow glassy oil (0.06 g, 85%) as a viscous oil. It was converted into its hydrochloride salt. M.P.=82–85° C.; Anal. Calcd. for $C_{34}H_{40}N_3O_4F_2Cl.0.7\ CH_2Cl_2$: C, 60.61; H, 6.07; N, 6.11. Found: C, 60.73; H, 6.46; N, 6.12.

EXAMPLE 18 cis (+)-4-(3,4-Difluorophenyl)-5-methyl-2-oxo-oxazolidine-3-carboxylic acid{3-[4-(4-fluorophenyl)-piperidin-1-yl]propyl}amide (Scheme 12)

a. 1-(3,4-Difluorophenyl)propan-1-ol

To a solution of 3,4-difluorobenzaldehyde (5.0 g, 35.2 mmol) in diethyl ether (35 mL)in a round bottom flask was added a solution of ethylmagnesium bromide in THF (38.0 mL, 38.0 mmol) at 0° C. The reaction mixture was stirred at 0° C. for 1 h when TLC analysis indicated that the reaction was complete ($R_f$=0.5, 8:1 hexane/EtOAc). The reaction was quenched carefully by adding 38 mL of water. It was extracted with diethyl ether (2×30 mL), washed with brine and the organic layer was dried over $Na_2SO_4$. The solvent was removed in vacuo after filtration and 1-(3,4-difluorophenyl)propan-1-ol was obtained as a yellow oil (crude wt.=6.0 g) which looked >90% pure by NMR. It was used in the next step without purification.

b. 1-(3,4-Difluorophenyl)propan-1-one

In a round bottom flask containing pyridinium chlorochromate (12.5 g, 58.1 mmol) was added celite 545 (25 g) and with the help of a magnetic stirrer the solids were mixed together. 200 mL of $CH_2Cl_2$ was added followed by a solution of 1-(3,4-difluoro-phenyl)propan-1-ol (5.0 g, 29.1 mmol) in 10 mL of $CH_2Cl_2$ and the resulting brown suspension was stirred overnight at room temperature. The suspension was filtered through a sintered glass funnel and the solvent was removed in vacuo from the pale green colored filtrate. The green oil was then diluted with diethyl ether (200 mL) and it was filtered through a pad of celite to remove the metal impurities. The solvent was removed in vacuo to obtain 1-(3,4-difluorophenyl)propan-1-one as a pale yellow oil (3.4 g, 69% yield). It was used in the next step without purification.

c. 1-(3,4-Difluorophenyl)-2-hydroxy-propan-1-one

In a round bottom flask containing 200 mL of MeOH was added pellets of potassium hydroxide (23.0 g, 410.0 mmol). The solution was cooled to 0° C. and 1-(3,4-difluorophenyl)-2-hydroxy-propan-1-one (7.0 g, 41.2 mmol) in 10 mL MeOH was added dropwise. The solution was stirred for 10 min and then iodobenzene diacetate (22.5 g, 70 mmol) was added in two portions. The solution first became orange and then turned yellow. It was stirred overnight at room temperature and then solvent was removed in vacuo. The residue was dissolved in water and was extracted with ethyl acetate (3×100 mL). The combined organic extracts were washed with brine and then dried over $Na_2SO_4$. After filteration, the solvent was removed in vacuo to get 1-(3,4-difluorophenyl)-2-hydroxy-propan-1-one dimethyl acetal as a yellow viscous oil (crude wt.=9.2 g). It was dissoled in 150 mL of acetone and 10 drops of concentrated sulfuric acid were added. After stirring for 3 h, TLC analysis indicated that the reaction was complete. Acetone was removed in vacuo and after basification with saturated $NaHCO_3$, the residue was extracted in EtOAc and was washed with brine. The organic layer was separated, dried over $Na_2SO_4$ and then filtered. The solvent was removed in vacuo and the residue was purified by silica gel chromatography (Rf=0.4, 3:2 hexane/EtOAc) to obtain 1-(3,4-difluorophenyl)-2-hydroxy-propan-1-one as a pale yellow oil (3.3 g, 51% yield over two steps).

d. 1-(3,4-Difluorophenyl)-2-hydroxy-propan-1-one-oxime

To a well stirred solution of 1-(3,4-difluorophenyl)-2-hydroxy-propan-1-one (5.5 g, 29.6 mmol) in MeOH (200 mL) was added hydroxylamine hydrochloride (2.6 g, 38.4 mmol) and sodium acetate (8.1 g, 59.2 mmol) and the the turbid solution was stirred overnight at room temperature. The solvent was evaporated and the residue was extracted with $CH_2Cl_2$. The organic layer was washed with sat. $NaHCO_3$, separated, dried over $Na_2SO_4$ and then filtered. The solvent was removed in vacuo to obtain 1-(3,4-difluorophenyl)-2-hydroxy-propan-1-one-oxime as an orangish yellow oil (5.8 g, 97%). It was used in the next step without purification.

e. 1-Amino-1-(3,4-difluorophenyl)-propan-2-ol

To a well stirred solution of 1-(3,4-difluorophenyl)-2-hydroxy-propan-1-one-oxime (5.8 g, 28.4 mmol), was added a 1.0 M solution of $LiAlH_4$ in ether (90 mL, 90 mmol) dropwise at 0° C. The resulting yellow solution was then stirred at room temperature for 2 h. The reaction mixture was cooled to 0° C. and then carefully quenched sequentially with 3.5 mL of water, 3.5 mL of 3N NaOH followed by 10.5 mL of water. The resulting suspension was filtered thro' a fritted glass funnel. To the residue was added 100 mL $Et_2O$ and the suspension was heated to reflux for 20 min. The suspension was filtered and was combined with the previous filtrate, dried over $MgSO_4$, filtered and the solvent was removed in vacuo. 1-amino-1-(3,4-difluorophenyl)-propan-2-ol was obtained as a yellow glassy syrup (3.6 g, 66%) which was used in the next step without further purification.

f. [1-(3,4-Difluorophenyl)-2-hydroxy-propyl]-carbamic acid-tert-butyl ester

To a solution of 1-amino-1-(3,4-difluorophenyl)-propan-2-ol (3.5 g, 19.1 mmol) in $CHCl_3$ (15 mL) at 0° C. was added a solution of di-tert-butyl dicarbonate (5.1 g, 23.6 mmol) in $CHCl_3$ (10 ML) in one portion and the resulting solution was stirred overnight at room temperature. The solvent was removed in vacuo and the residue was subjected to column chromatography on silica gel (2:1 hexane-EtOAc followed by EtOAc) to obtain [1-(3,4-difluorophenyl)-2-hydroxy-propyl]-carbamic acid-tert-butyl ester as a viscous oil (3.3 g, 60.2%).

g. 4-(3,4-Difluorophenyl)-5-methyl-oxazolidin-2-one

To a well stirred solution of [1-(3,4-difluorophenyl)-2-hydroxy-propyl]-carbamic acid-tert-butyl ester (0.43 g, 1.5 mmol) THF (20 mL) was added 95% NaH (0.09 g, 3.8 mmol) at room temperature. The resulting suspension was stirred for 3 h at about 35° C. (warm water bath) and then quenched carefully with ice. The biphasic mixture was extracted with 100 mL of EtOAc, washed with brine, dried over $Na_2SO_4$, filtered and the solvent was removed in vacuo. The two diastereomers were separated by column chromatography over silica gel (First isomer: 0.11 g, $R_f$=0.6, 3:1 hexane-EtOAc; second isomer: 0.23 g, $R_f$=0.5, 3:1 hexane-EtOAc). NOE experiment suggested that the first diastereomer had the methyl and the aryl group in trans configuration while the second diastereomer had cis relationship between the two groups.

Enantiomers of each of these diastereoisomers were separated by HPLC by using Chiralcel OD (4.6×250 mm) using 80% hexane/20% isopropyl alcohol/0.1% diethylamine as the eluting system (12 mL/min) under isothermal conditions (U.V. 254 nM). The retention times for the two isomers of the trans-oxazolidinone were 12.1 min $\{[\alpha]_D=+36.4$ (c=o.25, acetone)$\}$ and 15.6 min $\{[\alpha]_D=-30.8$ (c=o.20, acetone)$\}$, respectively. The retention times for the two isomers of the cis-oxazolidinone were 13.7 min $\{[\alpha]_D=+65.8$ (c=o.92, acetone)$\}$ and 19.9 min $\{[\alpha]_D=-65.8$ (c=o.74, acetone)$\}$ respectively. The next steps may be performed on each of the four enantiomers individually in the following manner, which describes the synthesis of the cis (+) enantiomer.

h. 4-(3,4-Difluorophenyl)-5-methyl-2-oxo-oxazolidine-3-carboxylic acid-4-nitro-phenyl ester To a suspension of 95% NaH (0.01 g, 0.38 mmol) in 5.0 mL of anhydrous THF under argon, a solution of 4-(3,4-difluorophenyl)-5-methyl-oxazolidin-2-one (0.07 g, 0.33 mmol) in 5.0 mL THF was added dropwise via a syringe. The resulting suspension was stirred at room temperature for 20 min. This suspension was then added dropwise via a syringe into another round bottom flask containing a solution of 4-nitrophenylchloroformate (0.08 g, 0.4 mmol) in 10 mL of THF, cooled at −78° C., over a period of 15 min. The stirring was continued for 1 h after which the solvent was removed and the residue was purified by column chromatography on silica gel with 1:1 hexane/$CH_2Cl_2$ followed by $CH_2Cl_2$ ($R_f$=0.4, $CH_2Cl_2$) to obtain 4-(3,4-difluorophenyl)-5-methyl-2-oxo-oxazolidine-3-carboxylic acid-4-nitro-phenyl ester as a white solid (0.07 g, 56%).

i. 3-[4-(4-Fluoro-phenyl)-piperidin-1-yl]-propylamine

To a solution of 4-fluorophenylmagnesium bromide (110.0 mmol, 55.0 mL of 2.0 M solution) in 150.0 mL THF at 0° C. was added 1-benzyl-4-piperidone (55.0 mmol, 10.2 mL) dropwise. The resulting solution was stirred under argon atmosphere for 1.5 h and then quenched with 100.0 mL of saturated $NH_4Cl$ solution. The organic layer was separated and the aqueous layer was extracted with 100.0 mL of $Et_2O$. The combined organic extracts were washed with brine, separated and dried over $Na_2SO_4$. The solution was filtered and the solvent was removed in vacuo to obtain a yellow oil which was purified by passing through a silica gel column with 4:1 hexane/EtOAc followed by 1:1 hexane/EtOAc as the eluting system. 1-Benzyl-4-(4-fluoro-phenyl)-piperidin-4-ol was obtained as a pale yellow oil in 89% yield (13.9 g). It was dissolved in 150.0 mL of toluene and p-toluenesulfonic acid monohydrate (50.0 mmol, 9.5 g) was added. The resulting suspension was heated to reflux for 8 h. After the suspension was cooled, it was basified with 3 N NaOH solution and was extracted with $Et_2O$ (2×50 mL). The organic extracts were combined, washed with brine and the oraganic layer was dried over $Na_2SO_4$. The solvent was removed in vacuo to obtain 1-benzyl-4-(4-fluoro-phenyl)-1,2,3,6-tetrahydro-pyridine as a yellow viscous oil (12.0 g, 92% yield) which was used in the next step without further purification.

To a solution of 1-benzyl-4-(4-fluoro-phenyl)-1,2,3,6-tetrahydro-pyridine (45.0 mmol, 12.0 g) in 100 mL MeOH was added 1.0 g of Pd(OH)2 and the resulting suspension was hydrogenated under 200 psi of $H_2$ in a stainless steel bomb for two days. The suspension was passed through a pad of celite and the filterate was concentrated in vacuo to obtain 4-(4-fluoro)-phenyl-piperidine (7.5 g, 94%) as a viscous oil. It was converted into 3-[4-(4-fluoro-phenyl)-piperidin-1-yl]-propylamine by the route described previously in Example 1.

j. cis (+)-(4-(3,4-Difluorophenyl)-5-methyl-2-oxo-oxazolidine-3-carboxylic acid$\{$3-[4-(4-fluorophenyl)-piperidin-1-yl]propyl$\}$amide To a solution of 3-amino-propyl-4-(4-fluoro)phenyl-piperidine (0.04 g, 0.12 mmol) in 10 mL of THF (+)-4-(3,4-Difluorophenyl)-5-methyl-2-oxo-oxazolidine-3-carboxylic acid-4-nitro-phenyl ester (0.03 g, 0.08 mmol) (made from the (+)-enantiomer from HPLC of the cis diastereomer separated by column chromatography) was added and the resulting yellow solution was stirred under argon atmosphere for 10 h at room temperature. The solvent was removed in vacuo and the residue was purified by column chromatography over silica gel with EtOAC followed by 15% MeOH in EtOAC as the eluting systems ($R_f$=0.4, 1:3 MeOH/EtOAC) to obtain (+)-(4-(3,4-Difluorophenyl)-5-methyl-2-oxo-oxazolidine-3-carboxylic acid$\{$3-[4-(4-fluorophenyl)-piperidin-1-yl]propyl$\}$amide as a pale yellow glassy oil(0.03 g, 66%). It was converted into its hydrochloride salt. M. P. 108–112° C.; $[\alpha]_D$=+56.7, (c=0.20, MeOH); Anal. Calcd. For $C_{25}H_{29}N_3O_3F_3Cl.0.36$ $CH_2Cl_2$: C, 56.14; H, 5.52; N, 7.75. Found: C, 56.17; H, 5.90; N, 7.20.

EXAMPLE 19 trans (+)-4-(3,4-Difluorophenyl)-5-methyl-2-oxo-oxazolidine-3-carboxylic acid$\{$3-[4-(4-fluorophenyl)-piperidin-1-yl]propyl$\}$amide (Scheme 12)

In an analogous manner as described above for Example 18, Steps h–j, the trans (+)-4-(3,4-difluorophenyl)-5-methyl-2-oxo-oxazolidine-3-carboxylic acid-4-nitro-phenyl ester (0.03 g, 0.08 mmol) (made from the (+)-enantiomer from HPLC of the trans diastereomer separated by column chromatography) was converted into trans (+)-4-(3,4-difluorophenyl)-5-methyl-2-oxo-oxazolidine-3-carboxylic acid$\{$3-[4-(4-fluorophenyl)-piperidin-1-yl]propyl$\}$amide in 70% yield. It was converted into hydrochloride salt.

M.P.=80–83° C. (shrinks around 58° C.); $[\alpha]_D$=+27.4 (c=0.49, MeOH); Anal. Calcd. for $C_{25}H_{29}N_3O_3F_3Cl.1.0$ $H_2O$: C, 56.55; H 6.07; N 7.91 Found: C, 56.49; H, 5.88; N 7.80.

EXAMPLE 20

4-(3,4-Difluoro-benzyl)-2-oxo-oxazolidine-3-carboxylic acid $\{$3-[4-(2-carbamoylphenyl)-piperazin-1-yl]-propyl$\}$amide a. 2-Amino-3-(3,4-difluoro)-phenyl-propan-1-ol To a well stirred suspension of $LiAlH_4$ (0.48 g, 12.5 mmol) in THF (30 mL) in a round bottom flask fitted with a condenser was added 3,4-difluorophenyl alanine (1.0 g, 5.0 mmol) in small portions at 0° C. The resulting grey suspension was then heated to reflux for 2 h. The reaction mixture was cooled to 0° C. and then carefully quenched sequentially with 0.5 mL of water, 0.5 mL of 3N NaOH followed by 1.5 mL of water. The resulting suspension was filtered through a fritted glass funnel. To the residue was added 50 mL $Et_2O$ and the suspension was heated to reflux for 20 min. The suspension was filtered and was combined with the previous filtrate, dried over $MgSO_4$, filtered and the solvent was removed in vacuo. 2-Amino-3-(3.4-difluoro)-phenyl-propan-1-ol was obtained as a white solid (0.5 g, 100%) which was used in the next step without further purification.

b. (+)-[1-(3,4-Difluorobenzyl)-2-hydroxy-ethyl]-carbamic acid-tert-butyl ester

To a solution of 2-amino-3-(3.4-difluoro)-phenyl-propan-1-ol (0.5 g, 2.62 mmol) in $CHCl_3$ (20 mL) at 0° C. was added a solution of di-tert-butyl dicarbonate (0.64 g, 2.90 mmol) in $CHCl_3$ (10 mL) in one portion and the resulting solution was stirred overnight at room temperature. The solvent was removed in vacuo and the residue was subjected to column chromatography on silica gel (2:1 hexane-EtOAc followed by EtOAc) to obtain (+)-[1-(3,4-difluorobenzyl)-2-hydroxy-ethyl]-carbamic acid-tert-butyl ester as white solid (0.64 g, 99%).

c. (+)-4-(3,4-Difluoro-benzyl)-oxazolidin-2-one

To a well stirred suspension of 95% NaH (0.12 g, 5.0 mmol) in THF (20 mL) at r.t. was added a solution of (+)-[1-(3,4-difluorobenzyl)-2-hydroxy-ethyl]-carbamic acid-tert-butyl ester (1.0 g; 4.0 mmol) in 10 mL THF via a dropping funnel at room temperature. The resulting suspension was stirred for 3 h and then quenched carefully with 10 mL of water. The biphasic mixture was extracted with 50 mL of Et$_2$O, washed with brine, filtered and the solvent was removed in vacuo. The gummy residue thus obtained was purified by column chromatography over silica gel ($R_f$=0.25, 3:2 hexane-EtOAc) to obtain (+)-4-(3,4-difluoro-benzyl)-oxazolidin-2-one as a white solid (0.32 g, 76%).

d. (+)-4-(3,4-Difluoro-benzyl)-oxazolidin-2-one-3-carboxylic acid-4-nitro-phenyl ester To a suspension of NaH (0.03 g, 1.30 mmol) in 10 mL of anhydrous THF under argon, a solution of (+)-4-(3,4-difluoro-benzyl)-oxazolidin-2-one (0.21 g, 1.0 mmol) in 10 mL THF was added dropwise via an dropping funnel. The resulting suspension was stirred at room temperature for 30 min. This suspension was then added dropwise via cannula into another round bottom flask containing a solution of 4-nitrophenylchloroformate (0.30 g, 1.5 mmol) in 20 mL of THF and cooled at −78° C. over a period of 15 min. The stirring was continued for 2 h after which the solvent was removed and the residue was purified by column chromatography on silica gel with 1:1 hexane/CH$_2$Cl$_2$ followed by CH$_2$Cl$_2$ ($R_f$=0.4, CH$_2$Cl$_2$) to obtain (+)-4-(3,4-difluoro-benzyl)-oxazolidin-2-one-3-carboxylic acid-4-nitro-phenyl ester as a yellow solid (0.35 g, 82%).

e. 4-(3,4-Difluoro-benzyl)-2-oxo-oxazolidine-3-carboxylic acid {3-[4-(2-carbamoylphenyl)-piperazin-1-yl]-propyl}amide To a solution of 1-(3-amino-propyl)-4-(2-carboxamido)-phenyl-piperazine (30 mg, 0.114 mmol) in 10 mL of THF, 4-(3,4-difluorobenzyl)-2-oxo-oxazolidine-3-carboxylic acid-4-nitro-phenyl ester (30 mg, 0.079 mmol) was added and the resulting yellow solution was stirred under argon atmosphere for 2 h at room temperature. The solvent was removed in vacuo and the residue was purified by column chromatography over silica gel with 1:1 hexane/EtOAc followed by 1:19 MeOH/EtOAc ($R_f$=0.70, MeOH/EtOAc=1:3) to obtain 4-(3,4-Difluoro-benzyl)-2-oxo-oxazolidine-3-carboxylic acid {3-[4-(2-carbamoylphenyl)-piperazin-1-yl]-propyl}amide (20 mg, 44%). The compound was dissolved in CH$_2$Cl$_2$ (3 mL) and was treated with 1N HCl in ether (1 mL). The solvent was removed in vacuo to give the corresponding hydrochloride salt as a yellow solid. M. P. 82–85° C.; [α]$_D$=+34.3, (c=0.49, MeOH); Anal. Calcd. For C$_{25}$H$_{31}$N$_5$O$_4$F$_2$Cl$_2$.3.5 H$_2$O: C, 47.10; H, 6.01; N, 10.99. Found: C, 47.12; H, 5.94; N,10.94.

EXAMPLE 21

4-(3,4-difluorophenyl)-2-oxo-oxazolidine-3-carboxylic acid{2-[4-phenylpiperidine-4-(carboxylic acid methyl ester)]ethyl}amide (Scheme 5)

To a solution of 2-amino-ethyl-4-carbomethoxy-4-phenyl piperidine (0.03 g, 0.12 mmol) in 5 mL of THF was added 4-(3,4-difluorophenyl)-2-oxo-oxazolidine-3-carboxylic acid-4-nitro-phenyl ester (0.04 g, 0.10 mmol) and the resulting yellow solution was stirred under argon atmosphere for 3 h at room temperature. The solvent was removed in vacuo and the residue was purified by column chromatography over silica gel with 50% hexane/EtOAC followed by 5% MeOH in EtOAC as the eluting systems ($R_f$=0.5, 1:3 MeOH/EtOAC) to obtain the product as colorless oil (wt=0.02 g). The compound was converted into its hydrochloride salt. M.P. 80–85° C.; [α]$_D$=+51.6, (c=0.11, MeOH); Anal. Calcd. for C$_{25}$H$_{28}$N$_3$O$_5$ClF$_2$.0.5 CHCl$_3$: C, 52.48; H, 4.92; N, 7.20. Found: C, 52.54; H, 5.13; N, 7.27.

EXAMPLE 22

4-(3,4-Difluoro-phenyl)-2-oxo-oxazolidine-3-carboxylic acid{3-[4-(4-fluoro-2-methyl-phenyl)-piperidin-1-yl3-propyl} amide a. 1-Benzyl-4-(5-fluoro-2-methyl)-phenyl-4-piperidinol To a cooled solution of n-BuLi (6.0 mL, 15.0 mmol) in 20 mL THF was added 2-Bromo-5-fluoro toluene (1.9 mL, 15.0 mmol) dropwise at −78° C. over 15 min. The reaction mixture was allowed to warm to 0° C. over 1 h and then cooled to −78° C. 1-Benzyl-4-piperidone (1.48 mL, 8.0 mmol) was added the white slurry and the reaction mixture was warmed to 0° C. over 2 h. The reaction was then quenched with 10 mL of sat. NH$_4$Cl solution. The oragnic layer was extracted with diehtyl ether (2×50 mL) and the combined organic layer was washed with brine (100 mL). The organic layer was separated, dried over Na$_2$SO$_4$, filtered and the solvent was removed in vacuo to obtain yellow oil. It was purified by column chromatography over silica gel with 3:2 hexane-EtOAc as the eluting system to obtain 1-benzyl-4-(5-fluoro-2-methyl)-phenyl-4-piperidinol as a yellow thick oil (1.1 g, 46% yield).

b. 1-Benzyl-4-(4-Fluoro-2-methyl)-phenyl-1,2,3,6-tetrahydropyridine

To a solution of 1-benzyl-4-(5-fluoro-2-methyl)-phenyl-4-piperidinol (1.1 g, 3.68 mmol) in 100 mL toluene was added p-toluenesulfonic acid monohydrate (1.39 g, 7.35 mmol) and the resulting solution was heated to reflux for 8 h. The suspension was cooled and the basified with 10% KOH solution and extracted with EtOAc (2×50 mL). The organic layer was washed with brine (30 mL). The organic layer was separated, dried over Na$_2$SO$_4$, filtered and the solvent was removed in vacuo to obtain 1-benzyl-4-(4-Fluoro-2-methyl)-phenyl-1,2,3,6-tetrahydropyridine as a pale yellow oil (0.9 g, 87% yield). It was used in the next step without further purification.

c. 3-amino-propyl-4-(4-fluoro-2-methyl)phenyl-piperidine

To a cooled suspension of 10% Pd-C (0.1 g) in 10 mL methanol was added a solution of 1-benzyl-4-(4-Fluoro-2-methyl)-phenyl-1,2,3,6-tetrahydropyridine (0.9 g, 3.2 mmol) in 20 mL of methanol and the resulting suspension was hydrogenated at room temperature under 1 atm of hydrogen for 10 h. The suspension was filtered through a pad of celite and the solvent was removed from the filtrate to obtain 4-(4-fluoro-2-methyl)-phenyl-piperidine which was converted into its hydrochloride salt (0.62 g, 99% yield). It was used in the next step without further purification. It was converted into 3-amino-propyl-4-(4-fluoro-2-methyl) phenyl-piperidine by the usual procedure.

d. 4-(3,4-Difluoro-phenyl)-2-oxo-oxazolidine-3-carboxylic acid{3-[4-(4-fluoro-2-methyl-phenyl)-piperidin-1-yl]-propyl}amide To a solution of 3-amino-propyl-4-(4-fluoro-2-methyl) phenyl-piperidine (0.03 g, 0.11 mmol) in 5 mL of THF was added 4-(3,4-difluorophenyl)-2-oxo-oxazolidine-3-carboxylic acid-4-nitro-phenyl ester (0.04 g, 0.10 mmol) and the resulting yellow solution was stirred under argon atmosphere for 8 h at room temperature. The solvent was removed in vacuo and the residue was purified by column chromatography over silica gel with 50% hexane/EtOAC followed by 5% MeOH in EtOAC as the eluting systems ($R_f$=0.4, 1:3 MeOH/EtOAC) to obtain the product as colorless oil (wt=0.02 g). The compound was converted into its hydrochloride salt. Off-white solid. M.P.=60–64° C.; [α]$_D$=+36.6 (c=0.15, MeOH); Anal. Calcd. for $C_{25}H_{29}N_3O_3F_3Cl.0.25$ $CHCl_3$: C, 55.97; H, 5.44; N, 7.76. Found: C, 55.91; H, 5.66; N, 7.87.

Preparation of Side Chains 1. 3-(4,4-Diphenylpiperidin-i-yl)propylamine a. 4,4-Diphenylpiperidine hydrochloride A mixture of 4-piperidone monohydrate hydrochloride (15.0 g, 0.0976 mol) and $AlCl_3$ (130 g, 0.976 mol, 10.0 eq) in anhydrous benzene (600 mL) were stirred at reflux for 4 hours. The mixture was cooled to room temperature, poured into ice (300 g) and water (50 mL), and filtered. The solid was washed with toluene and dried to afford 19.2 g (72%) of an off-white solid, which was characterized spectroscopically.

b. 3-(4,4-Diphenylpiperidin-1-yl)propionitrile

To a suspension of 4,4-diphenylpiperidine hydrochloride (0.195 g, 0.712 mmol) in EtOH (1.5 mL) was added $Et_3N$ (0.25 mL, 1.8 mmol, 2.6 eq) followed by acrylonitrile (0.13 mL, 2.01 mmol, 2.8 eq). The resulting solution was stirred at room temperature under argon for 15 min and then concentrated. Water was added, and the mixture was extracted with EtOAc (3×10 mL). The combined organic extracts were dried ($MgSO_4$) and concentrated to give 170 mg (87%) of a tan solid, which was characterized spectroscopically and used in the next reaction without purification.

c. 3-(4,4-Diphenylpiperidin-1-yl)propylamine

To a stirred solution of 3-(4,4-diphenylpiperidin-1-yl) propionitrile (2.00 g, 6.89 mmol) in anhydrous THF (20 mL) under argon was added a solution of $BH_3$ in THF (1.0 M, 24.1 mL, 24 mmol, 3.5 eq) at room temperature. The mixture was refluxed for 4.5 hours and then cooled to room temperature. Aqueous HCl (6 N, 50 mL) was added and stirring was continued for 1 hour. The mixture was basified to pH 9 by addition of 6 N aq. NaOH, extracted with $CH_2CL_2$ (3×10 mL), dried ($MgSO_4$) and concentrated. The residue was purified by flash chromatography ($SiO_2$, EtOAc-MeOH-isopropylamine 9:1:0 to 4:1:0.2) to give 1.35 g (66%) of tan solid, which was characterized spectroscopically.

2. 3-(4-Cyano-4-phenylpiperidin-1-yl)propylamine a. 3-(4-Cyano-4-phenylpiperidin-1-yl)propylphthalimide A mixture of 4-cyano-4-phenylpiperidine hydrochloride (111 g, 0.5 mol), 3-bromopropylphthalimide (135.39 g, 0.505 mol), potassium carbonate (276.42 g, 2 mol), and potassium iodide (5.4 g) in DMF (1 L) was stirred and heated at 100–110° C. for 8 h. About 80% of the solvent was evaporated at reduced pressure, the residue was diluted with dichloromethane (1 L) and washed with brine (3×300 mL) and dried ($Na_2SO_4$). Solvent was evaporated from the dichloromethane solution and the residue was treated with isopropanol (400 mL) and cooled. The pale yellow crystalline product formed was filtered, washed with ice-cold isopropanol and dried (168.6 g, 90%); M.p. 96–98° C.

b. 3-(4-Cyano-4-phenylpiperidin-1-yl)propylamine

To a solution of 3-(4-cyano-4-phenylpiperidin-1-yl) propylphthalimide (112 g, 0.3 mol) in methanol (1. 5 L), hydrazine (30 mL) was added and the mixture was stirred and refluxed for 20 h. It was cooled, the white solid formed was filtered and washed with more methanol (200 mL). Solvent was evaporated from the filtrate and residue was dried under vacuum for 4 h. Chloroform (500 mL) was added to this, stirred for 1 h and filtered. The white solid was washed with more chloroform (200 mL), the solvent was evaporated from the combined filtrates to leave the product as an oil (70 g, 96%).

3. 3-(4-Methoxycarbonyl-4-phenylpiperidin-1-yl) propylamine a. 4-Methoxycarbonyl-4-phenylpiperidine To a stirred solution of $H_2SO_4$ (16 mL) in MeOH (400 mL), 4-phenyl-4-piperidinecarboxylic acid 4-methylbenzenesulfonate (37.7 g, 0.1 mole) was added and the mixture was stirred and refluxed for 8 hours. Excess methanol was evaporated at reduced pressure and the residue was poured into a mixture of ice and 6 N NaOH. The pH was adjusted to 10–11 by adding more 6 N NaOH and extracted with $CH_2Cl_2$ (3×150 mL). The combined $CH_2Cl_2$ extracts were dried ($MgSO_4$) and the solvent evaporated to leave the desired product as a viscous oil. The product (20.2 g, 92%) was used without further purification.

b. 3-(4-Methoxycarbonyl-4-phenylpiperidin-1-yl) propylamine

A mixture of 4-methoxycarbonyl-4-phenylpiperidine (8.5 g, 0.039 mol), 3-bromopropylamine hydrobromide (12.7 g, 0.058 mol), potassium carbonate (13.475 g, 0.0957 mole), and KI (3.24 g, 0.0195 mol) in 1,4-dioxane (200 mL) was stirred and refluxed for 24 hours. Dioxane was evaporated at reduced pressure, the residue was treated with ice-cold 6 N NaOH (400 mL) and extracted with $CH_2Cl_2$ (4×120 mL). Solvent was evaporated from the combined dried ($K_2CO_3$) extracts and the residue was purified by column chromatography on silica gel using $CHCl_3$/MeOH/2 M $NH_3$ in MeOH (20:2:1) as the eluent to afford the product as a viscous oil (7.8 g, 72%).

4. 3-Aminopropyl-4-pyridyl-piperidine a. 1-(3-Aminopropyl)-4-[pyrid-2-yl]pyridinium bromide hydrobromide A solution of 2,4'-dipyridyl (5.0 g, 32.0 mmol) and 3-bromopropylamine hydrobromide (7.0 g, 32.0 mmol) in DMF (50.0 mL) and acetonitrile (50.0 mL) was heated at 90–95° C. for 1 h. After cooling, the white solid that came out was filtered, washed with $Et_2O$ and dried. The mother liquor was concentrated to remove $Et_2O$ and then heated at 90–95° C. for 4 h. The solvent was evaporated and the white residue was triturated with $Et_2O$ (100.0 mL) and filtered. The combined weight of the salt was 11.6 g (97%).

b. 3-(3',6'-Dihydro-2'-H-[2,4']bipyridinyl-1'-yl)-propylamine

To a solution of 1-(3-aminopropyl)-4-[pyrid-2-yl] pyridinium bromide hydrobromide (0.66 g, 1.75 mmol) in 20.0 mL MeOH was added $NaBH_4$ (0.101 g, 2.62 mmol) in small portions. The reaction mixture was stirred for 30 min and then quenched with 6M HCl solution. The solution was concentrated to 20.0 mL and basified with 50% NaOH solution to pH 12. Extracted with $CHCl_3$ (5×30.0 mL), dried over $MgSO_4$ and the solvent was removed to give 3-(3',6'-dihydro-2'-H-[2,4']bipyridinyl-1'-yl)-propylamine as an oil (0.37 g, 96% yield). It is used in the next step immediately without purification.

c. 3-Aminopropyl-4-(2-pyridyl)piperidine

To a solution of 3-(3',6'-dihydro-2'-H-[2,4']bipyridinyl-1'-yl)-propylamine (3.48 g crude, 15.9 mmol) in MeOH (40 mL), was added 1.0 g of Pearlman's catalyst. The suspension was hydrogenated under 120 psi for 10 h after which the reaction mixture was filtered through a pad of celite and the solvent was removed. The residue was purified by column chromatography over silica gel using $CH_2Cl_2$/methanol/2M $NH_3$ in MeOH (90:8:4 to 90:40:40) as the eluting system. The product was obtained as a pale yellow oil (3.21 g, 91%).

5. 3-(4-Acetoxy-4-phenylpiperidin-1-yl)propylamine a. N-Benzyloxycarbonyl-3-(4-hydroxy-4-phenylpiperidin-1-yl)propylamine A mixture of 4-hydroxy-4-phenylpiperidine (5 g, 0.0282 mol), N-benzyloxycarbonyl-3-bromopropylamine (8.445 g, 0.031 mol), and potassium carbonate (7.795 g, 0.0564 mole) in acetone (200 mL) was stirred and refluxed for 12 hours. Acetone was evaporated at reduced pressure, the residue was treated with ice-cold water (400 mL) and extracted with CH$_2$Cl$_2$ (4×120 mL). Solvent was evaporated from the combined dried (sodium sulfate) extracts and the residue was found to be almost pure desired product (9.5 g, 91%) by tlc and $^1$H-NMR and was used as such without any further purification.

b. N-Benzyloxycarbonyl-3-(4-acetoxy-4-phenylpiperidin-1-yl)propylamine

To a solution of N-benzyloxycarbonyl-3-(4-hydroxy-4-phenylpiperidin-1-yl)propylamine (0.5 g, 1.36 mmol) in THF (20 mL) at 0° C., sodium hydride (60% suspension in paraffin, 65 mg, 1.63 mmol, 1.2 eq.) was added and the mixture was stirred for 1.5 h. To this acetyl bromide (0.12 mL, 1.63 mmol) was injected and the mixture was stirred at 0° C. for 30 minutes and at room temperature for 3 h. Solvent was evaporated, the residue was mixed with dichloromethane (100 mL), and washed with water (2×20 mL). Solvent was evaporated from the dried dichloromethane solution gave the product as a viscous oil (0.485 g, 87%). The $^1$H-NMR showed this product to be pure and was used in the next step without any further purification.

c. 3-(4-Acetoxy-4-phenylpiperidin-1-yl)propylamine

A mixture of N-benzyloxycarbonyl-3-(4-acetoxy-4-phenylpiperidin-1-yl)propylamine (3.0 g, 7.3 mmol) and 10% Pd-C (0.3 g) in 1M ammonia in methanol(50 mL) was hydrogenated at 70 psi at room temperature for 4 h. The catalyst was removed by filtration and the solvent was evaporated to leave the product as a viscous oil (2.01 g, 99%), the $^1$H-NMR showed it to be very pure and was used in the next step without any purification.

6. 3-(4-Cyano-4-phenylpiperidin-1-yl)-2-hydroxypropylamine a. 3-(4-Cyano-4-phenylpiperidin-1-yl)(2-hydroxypropyl)phthalimide A mixture of 4-cyano-4-phenylpiperidine (10.0 g, 45 mmol) and 2,3-epoxypropylphthalimide (10.94 g, 54 mmol) in DMF (100 mL) was stirred and heated at 70° C. for 72 h. The solvent was evaporated under reduced pressure and the residue was purified by column chromatography on silica gel using chloroform-methanol-2M ammonia in methanol (1000/28/14) as the eluent, to obtain the desired product as a viscous oil (16.45 g, 86%).

b. 3-(4-Cyano-4-phenylpiperidin-1-yl)-2-hydroxypropylamine

A mixture of 3-(4-cyano-4-phenylpiperidin-1-yl)-(2-hydroxypropyl)phthalimide (10 g, 23.48 mmol) and hydrazine (6.01 g, 188 mmol, 8 eq.) in methanol (100 mL) was stirred and refluxed for 4.5 h. It was cooled, filtered, and the solid was washed with methanol (30 mL). Evaporation of solvent from the filtrate gave the product as a viscous oil (5.53 g, 94%).

7. 3-(4-Cyano-4-phenylpiperidin-1-yl)-2-fluoropropylamine a. 3-(4–Cyano-4-phenylpiperidin-1-yl)(2-fluoropropyl)phthalimide A mixture of 3-(4-cyano-4-phenylpiperidin-1-yl)-(2-hydroxypropyl)phthalimide (2.60 g, 6.1 mmol) and diethylaminosulfur trifluoride (DAST, 1.96 g, 12.2 mmol) in benzene (100 mL) was stirred and heated at 70° C. under argon atmosphere for 24 h. The solvent was evaporated under reduced pressure and the residue was purified by column chromatography on silica gel using chloroform-methanol-2M ammonia in methanol (1000/28/14) as the eluent, to obtain the desired product as a viscous oil (1.30 g, 50%).

b. 3-(4-Cyano-4-phenylpiperidin-1-yl)-2-fluoropropylamine.

A mixture of 3-(4-cyano-4-phenylpiperidin-1-yl)-(2-fluoropropyl)phthalimide (3.80 g, 8.88 mmol) and hydrazine (2.27 g, 71.04 mmol, 8 eq.) in methanol (100 mL) was stirred and refluxed for 4.5 h. It was cooled, filtered, and the solid was washed with methanol (30 mL). Evaporation of solvent from the filtrate gave the product as a viscous oil (1.9 g, 85%).

8. 3-[4-(2-Pyridyl)-piperidin-1-yl)-3-methylpropylamine.

a. 3-[4-(2-Pyridyl)-piperidin-1-yl)-2-methylpropionitrile. A mixture of 4-(2-pyridyl)-piperidine (1.56 g, 10 mmol) and crotononitrile (1.34 g, 20 mmol, 2 eq) in ethanol (100 mL) was strirred and refluxed for 16 h and the solvent and excess crotononitrile were evaporated under vacuum. The residue was purified by column chromatography on silica gel using dichloromethane-methanol-2M ammonia in methanol (45/4/2) as the eluent to give the desired product as a viscous oil (2.09 g, 94%), which got solidified on standing.

b. 3-[4-(2-Pyridyl)-piperidin-1-yl)-3-methylpropylamine.

To a stirred solution of 3-[4-(2-pyridyl)-piperidin-1-yl)-3-methylpropionitrile (0.446 g, 2 mmol) in anhydrous THF (10 mL) under argon was added a solution of BH$_3$ in THF (1.0M, 10 mL, 10 mmol, 5 eq) at room temperature. The mixture was refluxed for 4.5 hours and then cooled to room temperature. Aqueous HCl (6N, 50 mL) was added and stirring was continued for 1 hour. The mixture was basified to pH 9 by addition of 6N aq. NaOH, extracted with CH$_2$Cl$_2$ (3×10 mL), dried (potassium carbonate) and the solvent evaporated to leave the product as a viscous oil (0.42 g, 93%) the $^1$H-NMR of it showed it to be pure enough to use it in the next step.

9. 3-[4-(2-Pyridyl)-piperidin-1-yl)-2-methylpropylamine.

a. 3-[4-(2-Pyridyl)-piperidin-1-yl)-2-methylpropionitrile. A mixture of 4-(2-pyridyl)-piperidine (3.12 g, 20 mmol) and 1-methylacrylononitrile (5 mL) in methanol (100 mL) was strirred and refluxed for 48 h and the solvent and excess 1-methylacrylonitrile were evaporated under vacuum. The residue was purified by column chromatography on silica gel using dichloromethane-methanol-2M ammonia in methanol (45/4/2) as the eluent to give the desired product as a viscous oil (3.30 g, 74%), which got solidified on standing.

b. 3-[4-(2-Pyridyl)-piperidin-1-yl)-2-methylpropylamine.

To a stirred solution of 3-[4-(2-pyridyl)-piperidin-1-yl)-2-methylpropionitrile (0.446 g, 2 mmol) in anhydrous THF (10 mL) under argon was added a solution of BH$_3$ in THF (1.0M, 10 mL, 10 mmol, 5 eq) at room temperature. The mixture was refluxed for 4.5 hours and then cooled to room temperature. Aqueous HCl (6N, 50 mL) was added and stirring was continued for 1 hour. The mixture was basified to pH 9 by addition of 6N aq. NaOH, extracted with CH$_2$Cl$_2$ (3×10 mL), dried (potassium carbonate) and the solvent evaporated to leave the product as a viscous oil (0.436 g, 96%) the $^1$H-NMR of it showed it to be pure enough to use it in the next step.

EXAMPLES 23 and 24

N3-[3-(4-Cyano-4-phenylpiperidino)propyl]-2-oxo-4,4-diphenyl-oxazolidine-3-carboxamide hydrochloride and N3-[3-(4,4-Diphenylpiperidino)propyl]-2-oxo-4,4-diphenyl-oxazolidine-3-carboxamide hydrochloride a) 1,1-Diphenyl-2-hydroxyethylamine.

To stirred a solution of 2,2-diphenylglycine (5.0 g, 22 mmol) in THF (100 mL) at 0° C. under argon atmosphere, a solution of LAH in THF (1M, 50 mL, 50 mmol) was added over a period of 15 minutes and the mixture was allowed to warm to room temperature. After 12 h, it was poured onto a mixture of ice (300 g) and 6N HCl (20 mL) and stirred for 1 h. The mixture was basified to pH 10–11 by the addition of 6N NaOH and extracted with dichloromethane (4×100 mL). The combined extracts were dried (sodium sulfate) and the solvent evaporated to leave the product as a pale yellow viscous oil, which on trituration with hexane became white powder (4.7 g, ~100%). The $^1$H-NMR showed this product to be pure and was used as is in the next step.

b) 4,4-Diphenyl-2-oxo-oxazolidine.

A mixture of 1,1-diphenyl-2-hydroxyethylamine (4.26 g, 20 mmol), CDI (3.24 g, 20 mmol) in dichloromethane (200 mL) was refluxed for 20 h and the solvent evaporated. The residue was purified by column chromatography on silica gel using dichloromethane/ethyl acetate (9:1) to give the product as a viscous oil which solidified on standing (4.25 g, 89%).

c) 4,4-Diphenyl-1-(4-nitrophenyloxycarbonyl)-2-oxo-oxazolidine.

To a stirred suspension of sodium hydride (60% suspension in paraffin, 0.6 g, 15 mmol, 1.5 eq.) in THF (20 mL) at 0° C., a solution of 4,4-diphenyl-2-oxo-oxazolidine (2.39 g, 10 mmol) in THF (5 mL) was added and stirred for 30 minutes. This suspension was added to a solution of 4-nitrophenyl chloroformate (2.41 g, 12 mmol) in THF (20 mL) at −78° C. under argon and the stirring was continued for 2 h. It was slowly warmed to room temperature and after 4 h the solvent was evaporated. The residue was mixed with dichloromethane (150 mL), washed with 0.05N sodium hydroxide (3×10 mL), and dried (sodium sulfate). Solvent was evaporated and the residue was purified by column chromatography on silica gel using chloroform/ethyl acetate (9:1) as the eluent to give the product as a white powder (3.72 g, 92%).

d) General procedure: Examples 23 and 24.

A mixture of 4,4-diphenyl-3-(4-nitrophenyloxycarbonyl)-2-oxo-oxazolidine (40 mg, 0.1 mmol) and an appropriate amine (0.15 mmol, 1.5 eq.) in THF (5 mL) was stirred at room temperature and the product formed was purified by preparative TLC on silica gel using ethyl acetate as the eluent. The HCl salt was made by treatment with 1N HCl in ether.

N3-[3-(4-Cyano-4-phenylpiperidino)propyl]-2-oxo-4,4-diphenyl-oxazolidine-3-carboxamide hydrochloride Yield 93%; m.p.139°–141° C.; Anal. Calcd. For: $C_{31}H_{32}N_4O_3$.HCl .0.8$CH_2Cl_2$: C, 60.77; H, 5.92; N, 9.51. Found: C, 60.90; H, 5.80; N, 9.66.

N3-[3-(4,4-Diphenylpiperidino)propyl]-2-oxo-4,4-diphenyl-oxazolidine-3-carboxamide hydrochloride Yield 92%; m.p.145°148° C.; Anal. Calcd. For: $C_{34}H_{37}N_3O_3$.HCl .1.3$CH_2Cl_2$: C, 62.12; H, 6.00; N, 6.16. Found: C, 62.19; H, 5.64; N, 6.14.

EXAMPLES 25, 26, 27, 28 and 29 a. 1-(3,4-Difluorophenyl)-2-methyl-2-hydroxypropylamine.

To a well-stirred solution of methyl 2-amino-2-(3,4-difluorophenyl)acetate (10.5 g, 52.19 mmol) in anhydrous ether (200 mL) at 0° C. a solution of methylmagnesium bromide (3M, 87 mL, 261 mmol) in ether was added in 10 minutes. The mixture was stirred at 0° C. for 2.5 h and allowed to warm to room temperature. After 12 h, the mixture was carefully poured onto a mixture of ice (300 g) and saturated ammonium chloride (50 g). The ether layer was separated and the aqueous layer was extracted with more ether (4×200 mL). The combined extracts were dried with magnesium sulfate and the solvent evaporated. The crude product was purified by column chromatography on silica gel using chloroform/methanol/2M ammonia in methanol (1000:20:10 mL, 1000:40:20 mL, 1000:80:40 mL) as eluents to give the product as an oil (6.5 g, 62%). The $^1$H-NMR and MS confirmed this to be the desired product.

b. 4-(3,4-Difluorophenyl)-5,5-dimethyl-2-oxo-oxazolidine.

A mixture of 1-(3,4-difluorophenyl)-2-methyl-2-hydroxypropylamine (3.00 g, 14.9 mmol), CDI (2.418 g, 14.9 mmol) in dichloromethane (150 mL) was refluxed for 36 h and the solvent evaporated. The residue was purified by column chromatography on silica gel using chloroform/ethyl acetate (9:1) to give the product as a viscous oil which solidified on standing (1.80 g, 50%).

c. 4-(3,4-Difluorophenyl)-5,5-dimethyl-2-oxo-3-(4-nitrophenyloxycarbonyl)oxazolidine.

To a stirred suspension of sodium hydride (60% suspension in paraffin 203 mg, 1.4 eq.) in THF (20 mL) at 0° C., a solution of 4-(3,4-difluorophenyl)-5,5-dimethyl-2-oxo-oxazolidine (870 mg, 3.622 mmol) in THF (5 mL) was added and stirred for 30 minutes. This suspension was added to a solution of 4-nitrophenyl chloroformate (950 mg, 4.71 mmol) in THF (20 mL) at −78° C. under argon and the stirring was continued for 2 h. It was slowly warmed to room temperature and after 4 h the solvent was evaporated. The residue was mixed with dichloromethane (150 mL), washed with 0.05N sodium hydroxide (3×10 mL), and dried (sodium sulfate). Solvent was evaporated and the residue was purified by column chromatography on silica gel using chloroform/ethyl acetate (9:1) as the eluent to give the product as a white powder (860 mg, 59%).

d. General procedure:

A mixture of 4-(3,4-difluorophenyl)-5,5-dimethyl-3-(4-nitrophenyloxycarbonyl)-2-oxo-oxazolidine (50 mg, 0.123 mmol) and an appropriate amine (0.16 mmol, 1.3 eq.) in dichloromethane (6 mL) was stirred at room temperature and the product formed was purified by preparative TLC on silica gel using two elutions, first with chloroform/ethyl acetate (9:1) and then with chloroform/methanol (9:1) as eluents. The HCl salt was made by treatment with 1N HCl in ether.

EXAMPLE 25

Methyl 1-[3-([4-(3,4-difluorophenyl)-5,5-dimethyl-2-oxo-oxazolidine-3-yl]carbonylamino)propyl]-4-phenyl-4-piperidinecarboxylate hydrochloride Yield 56%; m.p. 208°–210° C.; Anal. Calcd. For: $C_{28}H_{33}F_2N_3O_5$.HCl: C, 59.41; H, 6.05; N, 7.42. Found: C, 59.06; H, 5.83; N, 7.27.

EXAMPLE 26

1-[3-([4-(3,4-Difluorophenyl)-5,5-dimethyl-2-oxo-oxazolidine-3-yl]carbonylamino)propyl]-4-phenyl-4-piperidyl acetate hydrochloride Yield 29%; m.p. 116°–118° C.; Anal. Calcd. For: $C_{28}H_{33}F_2N_3O_5$.HCl .0.3$CH_2Cl_2$: C, 57.46; H, 5.90; N, 7.50. Found: C, 57.38; H, 6.18; N, 7.67.

EXAMPLE 27

N3-[4-(2-Pyridyl)piperidino]-3-methylpropyl-4-(3,4-difluorophenyl)-5,5-dimethyl-2-oxo-oxazolidine-3-carboxamide dihydrochloride Yield 64%; m.p. 87°–90° C.; Anal. Calcd. For: $C_{26}H_{32}F_2N_4O_3$.2HCl .1.1$CHCl_3$.1.1$H_2O$: C, 45.81; H, 5.29; N, 7.88. Found: C, 45.73; H. 5.50; N, 8.07.

EXAMPLE 28

N3-[3-(4-Cyano-4-phenylpiperidino)-2-hydroxypropyl]-4-(3,4-difluorophenyl)-5,5-dimethyl-2-oxo-oxazolidine-3-carboxamide hydrochloride Yield 63%; m.p. 135°–137° C.; Anal. Calcd. For: $C_{27}H_{30}F_2N_4O_4$.HCl .1.2$H_2O$: C, 56.83; H, 5.90; N, 9.82. Found: C, 56.88; H, 5.98; N, 9.58.

EXAMPLE 29

N3-[3-(4-Cyano-4-phenylpiperidino)-2-fluoropropyl]-4-(3,4-difluorophenyl)-5,5-dimethyl-2-oxo-oxazolidine-3-carboxamide hydrochloride Yield 39%; m.p. 120°–122° C.; Anal. Calcd. For: $C_{27}H_{29}F_3N_4O_3 \cdot HCl \cdot 0.8CH_2Cl_2$: C, 53.95; H, 5.15; N, 9.05. Found: C, 53.89; H, 5.33; N, 8.95.

EXAMPLE 30

Methyl 1-5-[4-(3,4-difluorophenyl)-5,5-dimethyl-2-oxo-oxazolidin-3-yl]pentyl-4-phenyl-4-piperidinecarboxylate hydrochloride a. 4-(3,4-Difluorophenyl)-5,5-dimethyl-1-(5-bromopentyl)-2-oxo-oxazolidine.

To a stirred suspension of sodium hydride (60% suspension in paraffin 205 mg, 1.4 eq) in THF (20 mL) at 0° C., a solution of 4-(3,4-difluorophenyl)-5,5-dimethyl-2-oxo-oxazolidine (880 mg, 3.622 mmol) in THF (5 mL) was added and stirred for 30 minutes. To this 1,5-dibromopentane (3.37 g, 14.64 mmol, 4 eq.) and HMPA (179 mg, 3.66 mmol) were added and the mixture was warmed to room temperature. It was heated at 55°–60° C. for 12 h and the solvent evaporated. The residue was purified by column chromatography on silica gel using chloroform/ethyl acetate (9:1) as the eluent to give the product as a viscous oil (1.1 g).

b. Methyl 1-5-[4-(3,4-difluorophenyl)-5,5-dimethyl-2-oxo-oxazolidin-3-yl]pentyl-4-phenyl-4-piperidinecarboxylate hydrochloride A mixture of 4-(3,4-difluorophenyl)-5,5-dimethyl-1-(5-bromopentyl)oxazolidinone (50 mg, 0.123 mmol), 4-phenyl-4-methoxycarbonylpiperidine (0.16 mmol, 1.3 eq.), potassium iodide (11.6 mg), and potassium carbonate (58 mg, 0.42 mmol, 3 eq.) in acetone (6 mL) was stirred and refluxed for 12 h and the product formed was purified by preparative TLC on silica gel using ethyl acetate as the eluent. The HCl salts were made by treatment with 1N HCl in ether. Yield 50%; m.p. 58–60° C.; Anal. Calcd. For: $C_{29}H_{36}F_2N_2O_4 \cdot HCl \cdot 0.8CH_2Cl_2$: C, 57.82; H, 6.28; N, 4.53. Found: C, 58.01; H, 6.53; N, 4.45.

EXAMPLE 31

N3-2-[4-(2-Oxo-2,3-dihydro-1H-benzo[d]imidazol-1-yl)piperidino]ethyl-4-(3,4-difluorophenyl)-5,5-dimethyl-2-oxo-oxazolidine-3-carboxamide hydrochloride a. N-(2-[(4-(2-Keto-1-benzimidazolinyl)piperidin-1-yl]-ethyl)phthalimide.

To a solution of 4-(2-keto-1-benzimidazolinyl)piperidine (5 g, 23 mmol) and N-(2-bromoethyl)phthalimide (5.85 g, 23 mmol) in DMF (100 mL) was added potassium carbonate (10 g) and potassium iodide (250 mg) and the mixture was stirred and heated at 65°–70° C. for 2 h. It was poured into ice-water (500 mL), extracted with ether (4×75 mL) and dried (sodium sulfate). Solvent was evaporated and the product was crystallized from methanol (8 g, 89%).

b. N-(2-[(4-(2-Keto-1-benzimidazolinyl)piperidin-1-yl]-ethyl)amine

A mixture of N-(2-[(4-(2-keto-1-benzimidazolinyl)piperidin-1-yl]-ethyl)phthalimide (3.9 g, 10 mmol) and hydrazine (2 mL) in methanol was refluxed for 10 h and the solvent was evaporated. The residue was suspended in chloroform (50 mL) and filtered. The residue was washed with more chloroform (50 mL). Solvent was evaporated from the combined filtrate and the residue was dried under vacuum to leave is the desired product, which was used in the next step without further characterization.

c. N3-2-[4-(2-Oxo-2,3-dihydro-1H-benzo[d]imidazol-1-yl)piperidinolethyl-4-(3,4-difluorophenyl)-5,5-dimethyl-2-oxo-oxazolidine-3-carboxazaide hydrochloride Prepared from 4-(3,4-difluorophenyl)-5,5-dimethyl-3-(4-nitrophenyloxycarbonyl)-2-oxo-oxazolidine (20 mg) and N-(2-[(4-keto-1-benzimidazolinyl)piperidin-1-yl]-ethyl) amine (20 mg) as described earlier. Yield 25 mg; $[\alpha]_D$=+58.8 (c=0.40 g, methanol); m.p. 227°–230° C.; Anal. Calcd. For: $C_{26}H_{29}F_2N_2O_3 \cdot HCl \cdot 0.4\ CH_2Cl_2$: C, 54.30; H, 5.32; N, 11.99. Found: C, 54.52; H, 5.40; N, 11.82.

EXAMPLE 32

4-(3,4-Difluorophenyl)-3-[(3-[4-(2-pyridyl)piperidino]methylpiperidino)carbonyl]-oxazolidine-2-one dihydrochloride.

a. 1-Benzyl-4-[pyrid-2-yl]pyridinium bromide.

A solution of 2,4'-dipyridyl (15.62 g, 0.1 mol) and benzyl bromide (17.104 g, 0.1 mol) in anhydrous EtOAc (600 mL) for 24 h. The pale yellow crystalline product formed was filtered and dried (32.7 g, 100%).

b. 1-Benzyl-4-(2-pyridyl)-1,2,3,6-tetrahydropyridine.

To a stirred solution of 1-benzyl-4-[pyrid-2-yl]pyridinium bromide (50 g, 0.152 mol) in ethanol (500 mL) at 0°–5° C., was added $NaBH_4$ (23 g) in small portions over a period of 4 h. The mixture was allowed to warm to room temperature and the stirring continued for overnight. Solvent was evaporated the residue was mixed with ether (500 mL), washed with 6N sodium hydroxide solution (200 mL), brine (500 mL), and dried (potassium carbonate). Solvent was evaporated and the oily residue was used in the next step immediately without purification (33.4 g, 88%).

c. 4-(2-Pyridyl)piperidine.

To a solution of 1-benzyl-4-(2-pyridyl)-1,2,3,6-tetrahydropyridine (25 g, 0.1 mol) in MeOH (400 mL) and 2M ammonia in methanol (100 mL), was added Pearlman's catalyst (6 g). The suspension was hydrogenated under 200 psi for 24 h after which the reaction mixture was filtered through a pad of celite and the solvent was removed. The residue was purified by column chromatography over silica gel using $CH_2Cl_2$/methanol/2M $NH_3$ in MeOH (45:4:2 to 9:4:4) as the eluting system. The product was obtained as a pale yellow oil (12.4 g, 79%).

d. N-(t-Butyl-carbonate)-nipecotic acid. To a solution of nipecotic acid (3.865 g, 29.9 mmol)in dioxane (20 mL) at 0° C. was added $(Boc)_2O$ (6.53 g, 29.9 mmol) and a solution of NaOH (2.63 g, 6.60 mmol)in water (10 mL). The resulting mixture was stirred overnight while warmed up to room temperature. The mixture was concentrated and the residue was acidified to pH=3 with 1N HCl and then extracted with EtOAc (3×50 mL), dried ($MgSO_4$) to afford crude product which was used in the next step without further purification.

e. 4-(2-Pyridyl)piperidine-N-(t-butyl-carbonate)-nipecotamide. To a solution of N-(t-butyl-carbonate)-nipecotic acid (6.85 g, 29.8 mmol) in $CH_2Cl_2$ (40 mL) was added 1-(3-dimethylaminopropyl)-3-ethylcarbodiimide hydrochloride (DMAPECD) (11.426 g, 59.6 mmol)and DMAP (9.102 g, 74.5 mmol), then 4-(2-pyridyl)piperidine (4.834 g, 29.8 mmol) was added. The resulting mixture was stirred for 24 hours and quenched with water (40 mL). The mixture was extracted with $CH_2Cl_2$ (3×40 mL) and the combined extracts was dried ($K_2CO_3$) and concentrated. The residue was purified by flash chromatography on silica gel($CHCl_3$-MeOH-$NH_3$ 100:4:1) to afford the product as an oil (5.469 g, 49%).

f. 4-(2-Pyridyl)-N-(2-piperidinyl)methyl-piperidine. A solution of 4-(2-pyridyl)piperidine-N-(t-butyl-carbonate)-nipecotamide (1.904 g, 5.084 mmol) in TFA (5.0 mL) was stirred at 0° C. overnight. The mixture was concentrated and the residue was dissolved in THF (30 mL). The mixture was cooled to 0° C. and lithium aluminium hydride (LAH) (193 mg, 5.084 mmol) was added slowly. The reaction mixture was stirred for 12 hours while warmed to r.t. before quenched with water (1.0 mL) and 1N NaOH (0.5 mL). The mixture was basified to pH=10 with 1N NaOH and extracted with $CH_2Cl_2$ (5×20 mL), dried ($K_2CO_3$) and concentrated. The residue was purified by flash chromatography ($CHCl_3$-$MeOH$-$NH_3$ 100:10:2 to 100:20:5) to afford the product as an oil (0.804 g, 61%).

g. 4-(3,4-Difluorophenyl)-3-[(3-[4-(2-pyridyl)piperidino]methylpiperidino)carbonyl]-oxazolidine-2-one dihydrochloride.

Prepared from 4-(3,4-difluorophenyl)-3-(4-nitrophenyloxycarbonyl)-2-oxo-oxazolidine and 4-(2-pyridyl)-N-(2-piperidinyl)methyl-piperidine following the procedure described earlier.

Yield 90%; m.p.=176°–178° C.; Anal. Calcd. For $C_{26}H_{31}N_4O_3F_2$·2HCl·1.2$H_2O$·0.1.2$CH_2Cl_2$: C,47.90; H, 5.59, N,8.21. Found: C, 47.27; H, 5.41; N, 8.21.

EXAMPLE 33

N1-[2-(4-Cyano-4-phenylpiperidino)ethyl]-2-[4-(3,4-difluorophenyl)-2-oxo-oxazolidin-3-yl]acetamide hydrochloride a. (+)-(2-[(4-(3,4-Difluorophenyl)-2-oxo-oxazolidine-1-acetic acid benzyl ester. To a stirred a solution of 4-(3,4-difluorophenyl)-2-oxo-oxazolidinone (398 mg, 2 mmol) in THF (20 mL) at 0° C. under argon atmosphere, LiHMDS (1M solution in THF, 2.2 mL, 2.2 mmol) was added and the mixture was warmed to room temperature. After 30 minutes it was cooled to 0° C. and to this benzyl bromoacetate (0.504 g, 2.2 mmol, 1.1 eq.) was added and the mixture was warmed to room temperature. After 12 h, solvent was evaporated and the residue was purified by column chromatography on silica gel using chloroform/ethyl acetate (9:1) as the eluent to give the product as a viscous oil (0.695 g, 88%).

b. (+)-(2-[(4-(3,4-Difluorophenyl)-2-oxo-oxazolidine-1-acetic acid

The product obtained from the above reaction (0.592 g, 1.5 mmol) was dissolved in methanol/water (25/5 mL), mixed with Pearlman's catalyst (120 mg) and hydrogenated at 100 psi for 3 h. The catalyst was removed by filtration and washed with methanol (20 mL). Solvent was evaporated from the combined filtrate to obtain the product as a white powder (0.375 g, 97%).

c. N1-[2-(4-Cyano-4-phenylpiperidino)ethyl]-2-[4-(3,4-difluorophenyl)-2-oxo-oxazolidin-3-yl]acetamide hydrochloride A mixture of (+)-(2-[(4-(3,4-difluorophenyl)-2-oxo-oxazolidine-1-acetic acid (51.4 mg, 0.2 mmol), 1-(3-dimethylaminopropyl)-3-ethylcarbodiimide hydrochloride (100 mg), and 4-(N,N-dimethylamino)pyridine (100 mg), 2-[(4-cyano-4-phenyl)piperidin-1-yl]propylamine (55 mg) in anhydrous dichloromethane (15 mL) was stirred at room temperature for 12 h. The mixture was diluted with 10 mL of dichloromethane and washed with saturated aqueous ammonium chloride solution (6×10 mL). Solvent was evaporated from the dried (sodium sulfate) dichloromethane solution and the residue was purified by column chromatography on silica gel using chloroform-methanol-2M ammonia in methanol (100/2/1) as the eluent, to obtain the desired product as a white powder (82 mg); $[\alpha]_D$=+168.40 (c=0.42 g, methanol). The HCl salt was prepared by treatment of a solution of the free base in ether with 1N HCl in ether. M.p. 136°–139° C.; Anal. Calcd. for $C_{25}H_{27}N_4O_3F_2Cl$·0.4$CH_2Cl_2$: C, 56.38; H, 5.20; N, 10.40. Found: C, 56.38; H; 5.30; N, 10.52.

EXAMPLE 34

4-{4-[4-(3,4-Difluoro-phenyl)-2-oxo-oxazolidine-3-carbonyl]-piperazin-1-yl}-1-phenyl-cyclohexanecarbonitrile a. 1-Phenyl-4-piperazin-1-yl-cyclohexanecarbonitrile A mixture of 4-cyano-4-phenyl-cyclohexanone (0.23 g, 1.2 mmol) and piperazine (0.30 g, 3.5 mmol) in 20 ml of toluene was stirred at reflux for 2 h in presence of catalytic amount of p-toluenesulfonic acid. The reaction mixture was concentrated in vacuo to provide a white solid, which was redissolved in 20 ml of EtOH and stirred with $NaBH_4$ (0.30 g, 80 mmol) for 12 h at 25° C. Reaction mixture was diluted with 100 ml of EtOAc and washed with brine several times. Organic layer was dried over $MgSO_4$ and concentrated in vacuo, to provide oily residue, which was subjected to column chromatography (10% MeOH/EtOAc) to yield 0.13 g (40%) of the desired product as an oil.

b. 4-{4-[4-(3,4-Difluoro-phenyl)-2-oxo-oxazolidine-3-carbonyl]-piperazin-1-yl}-1-phenyl-cyclohexanecarbonitrile To a solution of 4-(3,4-difluoro-phenyl)-2-oxo-oxazolidine-3-carboxylic acid 4-nitrophenyl ester (80 mg, 0.21 mmol) in 5 ml of THF was added 1-phenyl-4-piperazin-1-yl-cyclohexanecarbonitrile (80 mg, 0.29 mmol) in a portion and the resulting solution was stirred for 12 h at 25° C. Reaction mixture was concentrated in vacuo yielding a yellow oil, which was subjected to column chromatography (50% Hexane/EtOAc) to provide 53 mg (51%) of the desired product as a colorless oil. The product obtained was converted to the HCl salt and recrystallized from EtOAc-$Et_2O$ to afford 43 mg of the product as white solid: mp 148°151° C.; Anal. Calc. For $C_{27}H_{28}F_2N_4O_3$·1.0HCl requires C, 61.07; H, 5.50; N, 10.55. Found: C, 59.48; H, 5.41; N, 10.34.

EXAMPLE 35

(+)-4-(3,4-Difluoro-phenyl)-2-oxo-oxazolidine-3-carboxylic acid [3-(4-furan-2-yl-4-phenyl-piperidin-1-yl)-propyl]-amide a. 4-Phenyl-4-furan-2-yl-piperidine To a solution of 4-hydroxy-4-phenyl-piperidine(0.50 g, 2.8 mmol) in 10 ml of $CH_2Cl_2$ at 25° C. was added furan (0.40 ml, 5.6 mmol) and aluminum chloride (0.75 g, 5.6 mmol) in a portion and the resulting heterogeneous solution was stirred for 3 h. Reaction mixture was poured into cold aqueous $NaHCO_3$ and extracted with EtOAc. Organic layer was dried over $Na_2SO_4$ and concentrated in vacuo to provide oily residue, which was purified by column chromatography (30% $NH_3$ sat'd MeOH/EtOAc) to yield 0.48 g (76%) of the desired product as an oil.

b. 3-[4-(4-furan-2-yl-4-Phenyl-phenyl)-piperidin-1-yl)]-propyl-1-amine

A solution of the amine (0.15 g, 0.66 mmol), (3-bromopropyl)-carbamic acid tert-butyl ester (0.30 g, 1.3 mmol) and $K_2CO_3$ (1.0 g, 7.4 mmol) in 10 ml of dioxane was stirred at reflux for 12 h. Reaction mixture was diluted with EtOAc and washed with brine several times. Organic layer was dried over $Na_2SO_4$ and concentrated in vacuo to provide oily residue, which was purified by column chromatography (EtOAc, neat) to yield 120 mg of the desired product as tert-butyl carbamic ester. The ester was diluted in 5 ml of $CH_2Cl_2$ and 1 ml of trifluoroacetic acid, and stirred for 2 h at 25° C. Reaction mixture was concentrated in vacuo, yielding an oil, which was diluted with EtOAc and washed with aqueous $NaHCO_3$. Organic layer was dried over $Na_2SO_4$ and concentrated in vacuo to provide 86 mg (33%) of the desired product as a colorless oil.

c. (+)-4-(3,4-Difluoro-phenyl)-2-oxo-oxazolidine-3-carboxylic acid [3-(4-furan-2-yl-4-phenyl-piperidin-1-yl)-propyl]amide To a solution of (+)-4-(3,4-difluoro-phenyl)-2-oxo-oxazolidine-3-carboxylic acid 4-nitrophenyl ester (19 mg, 0.05 mmol) in 5 ml of $CH_2Cl_2$ was added 3-[4-(4-Phenyl-4-furan-2-yl-phenyl)-piperidin-1-yl)]-propyl-1-amine (12 mg, 0.04 mmol) in a portion and the resulting solution was stirred for 4 h at 25° C. Reaction mixture was concentrated in vacuo yielding a yellow oil, which was subjected to column chromatography (5% $MeOH/CHCl_3$) to provide 18 mg (88%) of the desired product as a colorless oil. The product obtained was converted to the HCl salt and recrystallized from $EtOAc-Et_2O$ to afford 19 mg of the product as white solid: mp 149°151° C.; $[\alpha]_D$=+49.4 (c=0.11, MeOH); Anal. Calc. For $C_{28}H_{29}F_2N_3O_4 \cdot 1.0HCl$ requires C, 62.42; H, 5.42; N, 7.53. Found: C, 60.79; H, 5.49; N, 7.43.

EXAMPLE 36

(+)-4-(3,4-Difluoro-phenyl)-2-oxo-oxazolidine-3-carboxylic acid (3-[4-(1-methyl-1H-pyrrol-2-yl)-4-phenyl-piperidin-1-yl]-propyl)-amide a. 4-Phenyl-4-(1-methyl-pyrrol)-2-yl-piperidine To a solution of 4-hydroxy-4-phenyl-piperidine(0.50 g, 2.8 mmol) in 10 ml of $CH_2Cl_2$ was added 1-methyl-pyrrole (0.51 ml, 5.6 mmol) and aluminum chloride (0.75 g, 5.6 mmol) in a portion and the resulting heterogeneous solution was stirred for 4 h at −78° C. Reaction mixture was poured into cold aqueous $NaHCO_3$ and extracted with EtOAc. Organic layer was dried over $Na_2SO_4$ and concentrated in vacuo to provide oily residue (0.81 g), which was identified as the desired product by NMR analysis and subjected to the following reaction without any further purification.

b. 3-[4-(1-methyl-1H-pyrrol-2-yl)-4-phenyl-piperidin-1-yl]-propyl-1-amine

A solution of the amine (0.81 g, 2.8 mmol), (3-bromo-propyl)-carbamic acid tert-butyl ester (1.0 g, 4.2 mmol), $K_2CO_3$ (1.0 g, 7.4 mmol) and NaI (0.05 g) in 10 ml of dioxane was stirred at reflux for 12 h. Reaction mixture was diluted with EtOAc and washed with brine several times. Organic layer was dried over $Na_2SO_4$ and concentrated in vacuo to provide oily residue, which was purified by column chromatography (2% $MeOH/CHCl_3$) to yield 0.87 g (78%) of the desired product as tert-butyl carbamic ester. The ester was diluted in 10 ml of $CH_2Cl_2$ and 1 ml of trifluoro-acetic acid, and stirred for 2 h at 25° C. Reaction mixture was concentrated in vacuo, yielding an oil, which was diluted with EtOAc and washed with aqueous $NaHCO_3$. Organic layer was dried over $Na_2SO_4$ and concentrated in vacuo to provide 0.63 g (75% for two steps) of the desired product as a colorless oil.

c. (+)-4-(3,4-Difluorophenyl)-2-oxo-oxazolidine-3-carboxylic acid {3-[4-(1-methyl-1H-pyrrol-2-yl)-4-phenyl-piperdin-1-yl]-propyl}-amide To a solution of (+)-4-(3,4-difluoro-phenyl)-2-oxo-oxazolidine-3-carboxylic acid 4-nitrophenyl ester (30 mg, 0.08 mmol) in 5 ml of $CH_2Cl_2$ was added 3-{[4-phenyl-4-(1-methyl-pyrrol)-2-yl-phenyl]-piperidin-1-yl}-propyl-1-amine (24 mg, 0.08 mmol) in a portion and the resulting solution was stirred for 4 h at 25° C. Reaction mixture was concentrated in vacuo yielding a yellow oil, which was subjected to column chromatography (5% $MeOH/CHCl_3$) to provide 14.4 mg (34%) of the desired product as a colorless oil. The product obtained was converted to the HCl salt and recrystallized from $EtOAc-Et_2O$ to afford 13.0 mg of the product as white solid: mp 135°–138° C.; $[\alpha]_D$=+34.1 (c=0.11, MeOH); Anal. Calc. For $C_{28}H_{29}F_2N_3O_4 \cdot 1.0HCl$ requires C, 62.42; H, 5.42; N, 7.53. Found: C, 60.79; H, 5.49; N, 7.43.

EXAMPLE 37

(+)-4-(3,4-Difluoro-phenyl)-2-oxo-oxazolidine-3-carboxylic acid {3-[4-(5-methyl-thiophen-2-yl)-piperidin-1-yl]-propyl}-amide a. 4-[4-Hydroxy-4-(5-methyl-thiophen-2-yl)]-piperidine To a solution of 2-methyl-thiophene (1.0 ml, 10 mmol) in 40 ml of dry THF was added tert-butyl lithium (1.7M solution in ether, 6.5 ml, 11 mmol) dropwise and the resulting solution was stirred for 1 h at −40° C. To the solution was added N-tert-butoxycarbonyl-4-piperidinone (1.0 g, 5.0 mmol) in a portion and the resulting solution was stirred for 2 h. Reaction was quenched by adding a few drops of water. Reaction mixture was diluted with EtOAc and washed with brine several times. Organic layer was dried over $Na_2SO_4$ and concentrated in vacuo to provide an oil, which was identified as the desired product by NMR analysis and subjected to the following reaction without any further purification.

b. 4-(5-Methyl-thiophen-2-yl)-piperidine

A solution of the carbamic ester (1.3 g, 4.4 mmol) and triisopropylsilane (1.0 ml, 8.2 mmol) in 10 ml of $CH_2Cl_2$ was added 10 ml of trifluoroacetic acid and the resulting solution was stirred for 2 h at 0° C. Reaction mixture was concentrated in vacuo, yielding a dark oil, which was redissolved in EtOAc and washed with aqueous $NaHCO_3$. Organic layer was dried over Na2SO4 and concentrated in vacuo to provide oily residue, which was purified by column chromatography (5% MeOH/CHCl3) to yield 0.73 g (87%) of the desired product as an oil.

c. 3-[4-(5-methyl-thiophene-2-yl)-piperidin-1-yl]-propyl-1-amine

A solution of the amine (0.73 g, 4.0 mmol), (3-bromo-propyl)-carbamic acid tert-butyl ester (1.8 g, 7.5 mmol), $K_2CO_3$ (1.0 g, 7.4 mmol) and NaI (0.05 g) in 25 ml of acetone was stirred at reflux for 12 h. Reaction mixture was diluted with EtOAc and washed with brine several times. Organic layer was dried over $Na_2SO_4$ and concentrated in vacuo to provide oily residue, which was purified by column chromatography (5% $MeOH/CHCl_3$) to yield 0.60 g (44%) of the desired product as tert-butyl carbamic ester. The ester was diluted in 10 ml of $CH_2Cl_2$ and 1 ml of trifluoroacetic acid, and stirred for 2 h at 25° C. Reaction mixture was concentrated in vacuo, yielding an oil, which was diluted with EtOAc and washed with aqueous $NaHCO_3$. Organic layer was dried over $Na_2SO_4$ and concentrated in vacuo to provide 0.40 g of the desired product as a colorless oil.

d. (+)-4-(3,4-Difluoro-phenyl)-2-oxo-oxazolidine-3-carboxylic acid {3-[4-(5-methyl-thiophen-2-yl)-piperidin-1-yl-propyl}-amide To a solution of (+)-4-(3,4-difluoro-phenyl)-2-oxo-oxazolidine-3-carboxylic acid 4-nitrophenyl ester (46 mg, 0.12 mmol) in 5 ml of $CH_2Cl_2$ was added 3-[4-(5-methyl-thiophen-2-yl)-piperidin-1-yl]-propyl-1-amine (30 mg, 0.13 mmol) in a portion and the resulting solution was stirred for 12 h at 25° C. Reaction mixture was concentrated in vacuo yielding a yellow oil, which was subjected to column chromatography (5% $MeOH/CH_2Cl_2$) to provide 41 mg (74%) of the desired product as a colorless oil. The product obtained was converted to the HCl salt and recrystallized from $EtOAc-Et_2O$ to afford 43 mg of the product as white solid: mp 143°–146° C.; $[\alpha]_D$=+41.0 (c=0.11, MeOH); Anal. Calc. For $C_{23}H_{27}F_2N_3O_4 \cdot 1.0$ HCl requires C, 55.25; H, 5.64; N, 8.40. Found: C, 57.01; H, 5.54; N, 8.29.

General Procedure for the Preparation of the 4,4-Diaryl Piperidines: A mixture of 0.5 g of 4-aryl-4-hydroxy piperidine, 3 mL of the aromatic substrate, and 1 g of aluminum chloride were stirred at room temperature for 3 days. The reaction mixture was poured over 10 mL of ice, diluted with t-butyl-methyl ether, the resulting hydrochloride salt was filtered, washed with water and ether, dried, and used in the next step after spectral characterization.

4-Phenyl-4-(4-thiomethoxy-phenyl)-piperidine, Hydrochloride: From 4-phenyl-4-hydroxy-piperidine and thioanisole (82%), Anal. Calc. for $C_{18}H_{21}N_1S_1$+HCl+0.2$H_2O$: C, 66.83; H, 6.98; N, 4.33. Found: C, 66.71; H, 6.81; N, 4.24.

4-(4-Fluoro-phenyl-4-(4-thiomethoxy-phenyl)-piperidine, Hydrochloride: From 4-(4-fluoro-phenyl-4-hydroxy-piperidine and thioanisole (59%), Anal. Calc. for $C_{18}H_{20}F_1N_1S_1$+HCl+0.35$CH_2Cl_2$: C, 60.14; H, 5.56; N, 3.90. Found: C, 59.96; H, 5.95; N, 3.81.

4-(4-Fluoro-phenyl-4-(2-methoxy-5-fluoro-phenyl)-piperidine, Hydrochloride: From 4-(4-fluoro-phenyl)-4-hydroxy-piperidine and 4-fluoroanisole (78%), Anal. Calc. for $C_{18}H_{19}N_1F_2O_1$+HCl+0.2$H_2O$: C, 62.96; H, 5.99; N, 4.08. Found: C, 62.72; H, 6.06; N, 4.06.

Bis-(4-fluoro-phenyl)piperidine, Hydrochloride: From 4-(4-fluoro-phenyl)-4-hydroxy-piperidine and 3 mL of fluorobenzene (69%).

4-(4-Bromo-phenyl-4-(4-methoxy-phenyl)-piperidine, Hydrochloride: From 4-(4-bromo-phenyl-4-hydroxy-piperidine and thioanisole (66%), Anal. Calc. for $C_{18}H_{20}Br_1N_1S_1$+HCl: C, 54.21; H, 5.30; N, 3.51. Found: C, 54.43; H, 5.22; N, 3.41.

General Procedure for the Preparation of the 4,4-Diaryl-1-(3-amino-propyl)Piperidines: A solution of 1.00 mmol of diarylpiperidine, 1.30 mmol of N-BOC-3-bromopropylamine, 1.00 mL of diisopropylethylamine and 2 mL of dioxane were heated at reflux temperature for 36 hours, cooled, applied to prep-tlc plates and eluted with the appropriate solvent. The product was used in the next step after spectral characterization. A solution of the N-BOC protected amine in 1:1 TFA-water was stirred at room temperature for 2 hours (monitored by tlc), solvent removed in vacuo, the product was dissolved in dichloromethane, washed with saturated $Na_2CO_3$ solution, dried ($Na_2SO_4$), solvent removed in vacuo, and the product was used after spectral characterization.

[4-(4-methanesulfonyl-phenyl)-4-phenyl]-3-aminopropyl-piperidine: A mixture of 644 mg of [4-(4-thiomethyl-phenyl)-4-phenyl]-3-aminopropyl-piperidine (TFA salt, 1.13 mmol), 853 mg of 50–60% 3-chlorophenylperbenzoic acid (2.72 mmol, assuming 55% purity), 2 mL of trifluoroacetic acid and 10 mL of chloroform were stirred at room temperature for 36 hours, solvent removed in vacuo, and the product was chromatographed (X2) ($NH_3$-MeOH-$CHCl_3$) to give 270 mg of the desired product.

General procedure for the synthesis of Examples 38, 39, 40, 41 and 42.

A solution of (+)-4-(3,4-difluoro-phenyl)-2-oxo-oxazolidine-3-carboxylic acid 4-nitro-phenyl ester (25 mg, 0.069 mmol), the 4,4-diaryl-1-(3-amino-propyl) piperidine (1.2 eqiv.) in 5 ml of methylene chloride were stirred at room temperature for 12 hours. The reaction mixture was washed with 3N KOH solution. The organic phase was chromatographed on preparative TLC ($CH_2Cl_2$/methanol/ 2N $NH_3$ in methanol=40 /2/1) to obtain the title compound. The hydrochloride salt of the free base was prepared by addition of 1N HCl in ether to a solution of the free base in ethyl acetate until no more precipitate was observed.

EXAMPLE 38
4-(3,4-Difluoro-phenyl)-2-oxo-oxazolidine-3-carboxylic acid {3-[4-(4-bromo-phenyl)-4-(4-methoxy-phenyl)-piperidin-1-yl]-propyl}-amide 33 mg of the free base was obtained (55% yield). Anal. Calc. For $C_{31}H_{32}BrF_2N_3O_4$+1.5 HCl: C, 54.50%; H. 4.94%; N, 6.15%. Found: C, 54.62%; H, 4.88%; N, 5.88%. M.p. of the salt: 123°~126° C. $[\alpha]_D^{22}$=+53.93.

EXAMPLE 39
4-(3,4-difluoro-phenyl) -2-oxo-oxazolidine-3-carboxylic acid {3-[4-(4-fluoro-phenyl)-4-(4-methylsulfanyl-phenyl)-piperidin-1-yl]-propyl}-amide 20 mg of the free base was obtained (55% yield). Anal. Calc. For $C_{31}H_{32}F_3N_3O_3S$+1.75 HCl+0.75 EtOAc: C, 57.23%; H, 5.61%; N, 5.89%. Found: C, 57.28%; H, 5.73%; N, 5.83%. M.p. of the salt: 121°~124° C. $[\alpha]_D^{22}$=+33.33.

EXAMPLE 40
4-(3,4-difluoro-phenyl)-2-oxo-oxazolidine-3-carboxylic acid {3-[4,4-bis-(4-fluoro-phenyl)-piperidin-1-yl]-propyl}-amide. 24 mg of the free base was obtained (63% yield). Anal. Calc. For $C_{30}H_{21}IF_4N_3O_3$+2.0 HCl+0.125 $CHCl_3$: C, 56.24%; H, 4.88%; N, 6.52%. Found: C, 56.39%; H, 4.88%; N, 6.10%. M.p. of the salt: 124°~126° C. $[\alpha]_D^{22}$=+47.33.

EXAMPLE 41
4-(3,4-difluoro-phenyl)-2-oxo-oxazolidine-3-carboxylic acid {3-[4-(4-fluoro-phenyl)-4-(2-methoxy-5-fluoro-phenyl)-piperidin-1-yl]-propyl}-amide 24 mg of the free base of the tittle product was obtained (59% yield). Anal. Calc. For $C_{31}H_{31}F_4N_3O_4$+2.0 HCl+0.5 EtOAc: C, 56.42%; H, 5.31%; N, 5.98%. Found: C, 56.61%; H, 5.18%; N, 5.77%. M.p. of the salt: 130°~133° C. $[\alpha]_D^{22}$=+38.86.

EXAMPLE 42
(+)-4-(3,4-Difluoro-phenyl)-2-oxo-oxazolidine-3-carboxylic acid
{3-[4-(4-methanesulfonyl-phenyl)-4-phenyl-piperidin-1-yl]-propyl}-amide, hydrochloride 18 mg of the free base was obtained: Anal. Calc. For $C_{31}H_{31}F_4N_3O_4$+2.0 HCl+EtOAc: C, 55.41%; H, 5.71%; N, 5.54%. Found: C, 55.82%; H, 5.19%; N, 5.49%.

EXAMPLE 43
4-(3,4-Difluorophenyl)-1-(3-(4-(2-pyridyl)piperidin-1-yl)-propyl)aminocarbonyl-2-imidazolidone.

a. 2-Amino-2-(3,4-difluorophenyl)-acetonitrile:

To a mixture of 3,4-difluorobenzaldehyde (2.0 g, 14.07 mmol) and trimethylsilylcyanide (2.34 ml, 17.59 mmol), catalytic amount of Zinc Iodide was added at 0° C. After stirring for 15 minutes at room temperature a saturated solution of methanolic ammonia (15 ml) was added in one lot at 0° C. The reaction mixture was then stirred for 4 hours at 40° C. After evaporation of the solvent the residue was purified by column chromatography (hexanes:ethyl acetate;3:2) to yield 1.98 g of the product as a brown syrup.

b. 1-(3,4-Difluorophenyl)ethane-1,2-diamine:

To Lithium aluminium hydride in ether (50.7 ml, 50.76 mmol), at 0° C., cyano amine in ether (80 ml) slowly over a period of 10 minutes. The solution was then allowed to stir at room temperature for 1 hour. The reaction mixture was cooled to 0° C. and quenched with water (2 ml), 15% NaOH (2 ml) and water (10 ml). The mixture was then filtered, the residue was repeatedly washed with ethylacetate. The solution was then concentrated to yied 2.71 g (93%) of the crude product as an oil which was then used for the subsequent step.

c. 4-(3,4-Difluorophenyl)-2-imidazolidone:

To the diammine (1.667 g, 9.68 mmol) in dichloromethane (20 ml), triethylamine (1.34 ml, 9.68 mmol) was added slowly and the reaction was cooled to −78° C. Then triphosgene (3.01 g, 10.16 mmol) was added to the solution over a period of 30 minutes. The reaction mixture was then stirred at −78° C. for 5 minutes. The reaction mixture was quenched with water and partitioned between dichloromethane (20 ml) and water, washed with 10 ml 10% KOH solution, dried over sodium sulfate, filtered and concentrated. The product was then purified by column purified (hexanes:ethyl acetate 2:3) to yield 0.995 g (52%) of a yellow solid.

d. 4-(3,4-Difluorophenyl)-2-imidazolidone-1-carboxylic acid 4-nitrophenyl ester:

To sodium hydride (0.069 g, 2.74 mmol) in THF (10 ml), 4-(3,4-difluorophenyl)-2-imidazolidone (0.5 g, 2.49 mmol) was added at 0° C. The solution was then stirred at room temperature for 15 minutes. It was then added to a solution of 4-nitrophenyl chloroformate (0.552 g, 2.74 mmol) at −78° C. via a cannula. The reaction mixture was then allowed to stir at room temperature for 8 hours. It was then concentrated and partitioned between ethyl acetate (20 ml) and water (5 ml), washed with 10% KOH (10 ml), dried over sodium sulfate, filtered and concentrated. Purification by column chromatography (hexanes:ethylacetate 2:3) yielded 0.04 g (4.4%) of the product as a light brown syrup.

e. 4-(3,4-Difluorophenyl)-1-(3-(4-(2-pyridyl)piperidin-1-yl)-propyl)aminocarbonyl-2-imidazolidone:

To 4-(3,4-difluorophenyl)-1-(4-nitrophenoxy)carbonyl-2-imidazolidone (0.05 g, 0.137 mmol) in THF (10 mL) was added 1-(3-aminopropyl)-4-(2-pyridyl)piperidine (0.036 g, 0.165 mmol) and the solution was stirred at room temperature for 16 hours. The solution was then concentrated and the residue flash chromatographed (ethyl acetate:methanol 4:1) to yield 0.038 g (59%) of the product as a brown syrup. It was dissolved in dichloromethane (2 mL) and treated with 1N HCl in ether (0.5 mL). The solution was concentrated under reduced pressure. Recrystallization of the residue from ether gave 0.029 g (60%) of the hydrochloride salt as a brown solid: mp 148°–150° C. Anal. Calcd. for $C_{23}H_{29}F_2N_4O_3Cl_2.0.5\ CCl_4$: C, 51.90; H, 4.90; N, 11.0. Found: C, 54.23; H 5.17; N, 10.84.

EXAMPLE 44

3-(4-(4-Cyano-4-phenylpiperidin-1-yl)piperidin-1-yl) carbonyl-4-(3,4-difluorophenyl)-2-imidazolidone.

a. 4-(3,4-Difluorophenyl)-2-imidazolidone-3-carboxylic acid 4-nitrophenyl ester:

To sodium hydride (0.069 g, 2.74 mmol) in THF (10 ml), 4-(3,4-difluorophenyl)-imidazolidin-2-one (0.5 g, 2.49 mmol) was added at 0° C. The solution was then stirred at room temperature for 15 minutes. It was then added to a solution of 4-nitrophenylchloroformate (0.552 g, 2.74 mmol) at −78° C. via a cannula. The reaction mixture was then allowed to stir at room temperature for 8 hours. It was then concentrated and partitioned between ethyl acetate (20 ml) and water (5 ml), washed with 10 % KOH (10 ml), dried over sodium sulfate, filtered and concentrated. Purification by column chromatography (hexanes:ethylacetate; 2:3) to yield 0.04 g (4.4%) of the product as a light brown syrup.

b. 3-(4-(4-Cyano-4-phenylpiperidin-1-yl)piperidin-1-yl) carbonyl-4-(3,4-difluorophenyl)-2-imidazolidone.

To 4-(3,4-difluorophenyl)-3-(4-nitrophenoxy)carbonyl-2-imidazolidone (0.04 g, 0.110 mmol) in THF (10 mL) was added 4-(4-cyano-4-phenylpiperidin-1-yl)piperidine (0.0355 g, 0.132 mmol) and the solution was stirred at room temperature for 16 hours. The solution was then concentrated and the residue flash chromatographed (ethyl acetate-:methanol 4:1) to yield 0.024 g (44%) of the product as a brown syrup. It was dissolved in dichloromethane (2 mL) and treated with 1N HCl in ether (0.5 mL). The solution was concentrated under reduced pressure. Recrystallization of the residue from ether gave 0.029 g (96%) of the hydrochloride salt as a white solid: mp 243°–245° C. Anal. Calcd. for $C_{27}H_{30}ClF_2N_5O_2.0.4\ CHCl_3$: C, 56.96; H, 5.30; N, 12.12. Found: C, 57.08; H 5.20; N, 11.90.

EXAMPLE 45

4- (3,4-Difluorophenyl)-3-methyl-1-(3-(4-(2-pyridyl) piperidin-1-yl)propyl)aminocarbonyl-2-imidaxolidons.

a. 2-(3,4-Difluorophenyl)-2-methylamino-acetonitrile:

To a mixture of 3,4-difluorobenzaldehyde (4.0 g, 28.0 mmol) and trimethylsilylcyanide (4.69 mL, 35.1 mmol), catalytic amount of Zinc Iodide was added at 0° C. After stirring for 15 minutes at room temperature a saturated solution of methylammonia (15 mL) was added in one lot at 0° C. The reaction mixture was then stirred for 4 hours at 40° C. After evaporation of the solvent the residue was purified by column chromatography (hexanes:ethylacetate 3:2) to yield 4.719 g (92%) of the product as a brown syrup.

b. 2-(3,4-Difluorophenyl)-2-methylamino-ethylamine:

To Lithium aluminum hydride in ether (49.41 mL, 49.4 mmol), at 0° C., 2-(3,4-difluorophenyl)-2-methylamino-acetonitrile (3.0 g, 16.47 mmol) in ether (80 mL) slowly over a period of 10 minutes. The solution was then allowed to stir at room temperature for 1 hour. The reaction mixture was cooled to 0° C. and quenched with water (2 mL), 15% NaOH (2 mL) and water (10 mL). The mixture was then filtered, the residue was repeatedly washed with ethylacetate. The solution was then concentrated to yield 2.71 g (93%) of the crude product as an oil.

c. 4-(3,4-Difluorophenyl)-3-methyl-2-imidazolidone:

To 2-(3,4-difluorophenyl)-2-methylamino-ethylamine (1.048 g, 5.68 mmol) in dichloromethane (20 mL), 1,1-carbonyldiimidazole (1.09 g, 6.75 mmol) was added slowly and the reaction was stirred at room temperature for 24 hours. It was then concentrated and purified by column chromatography (hexanes:ethylacetate; 1:4) to yield 0.876 g (73%) of a yellow solid.

d. 4-(3,4-Difluorophenyl)-3-methyl-1-(3-(4-(2-pyridyl) piperidin-1-yl)propyl)aminocarbonyl-2-imidazolidone.

To a solution of 4-(3,4-difluorophenyl)-3-methyl-2-imidazolidone (0.15 g, 0.706 mmol) in THF (10 mL) cooled at 0° C., lithium bis(trimethylsilyl)amide in THF (0.848 mL, 0.848 mmol) was added slowly and the solution was stirred at room temperature for 15 minutes. After cooling to −78° C., phosgene (0.729 g, 7.06 mmol) was added and the solution was stirred at −78° C. for 1 hour. It was then concentrated to give an intermediate (0.194 g, 0.703 mmol) which was immediately dissolved in THF (10 mL) at −78° C. and treated with 1-(3-aminopropyl)-4-(2-pyridyl) piperidine (0.231 g, 1.05 mmol) and triethylamine (0.106 g, 1.055 mmol), and the solution was stirred at room temperature for 24 hours. It was then concentrated, and the residue partitioned between dichloromethane (25 mL) and water (5 mL). The organic layer was washed with 10% KOH solution (5 mL), dried over sodium sulfate, filtered and concentrated. Purification of the residue by flash chromatography (ethyl acetate: methanol 24:1) yielded 0.030 g (9%) of the product as a syrup. It was dissolved in dichloromethane (2 mL) and treated with 1N HCl in ether (0.5 mL). The solution was concentrated under reduced pressure. Recrystallization of the residue from ether gave 0.030 g (88%) of the dihydrochloride salt as a pale yellow solid: mp 120°–122° C. Anal. Calcd. for $C_{24}H_{31}ClF_2NSO_2.0.95\ CHCl_3$: C, 46.54; H, 5.00; N, 10.88. Found: C, 46.30; H 5.35; N, 11.20.

EXAMPLE 46

4-(3,4-Difluorophenyl)-3-(3-(4-(2-methoxyl-5-methyl) phenyl-4-phenylpiperidin-1-yl)propyl)aminocarbonyl-2-imidazolidone.

a. 1-(3,4-Difluorophenyl)-2-tritylazino-ethylamine:

To a solution of 1-(3,4-difluorophenyl)-ethane-1,2-diamine (6 g, 35.6 mmol) in dichloromethane (100 ml), diazabicycloundecane (DBU)(5.87 mL, 39.2 mmol) was added and the solution cooled to 0° C. Trityl chloride (10.94 g, 39.2 mmol) in dichloromethane (100 ml) was added slowly to the cooled solution. After addition the solution was stirred at room temperature for 24 hours. The soution was then concentrated, partitioned between chloroform (100 ml) and water (25 ml), washed with 1N KOH (10 mL), filtered, and concentrated. Purification by column chromatography (hexanes:ethyl acetate 3:2) yielded 6.75 g (46%) of the product as a brown syrup.

b. 4-(3,4-Difluorophenyl)-1-trityl-2-imidazolidone:

To a solution of 1-(3,4-difluorophenyl)-2-tritylamino-ethylamine (6.75 g, 16.44 mmol) in THF (200 mL), 1,1-carbonyldiimidazole (3.2 g, 19.7 mmol) was added and the solution was stirred at room temperature for 12 hours. The solution was concentrated and purified by column chromatography (hexanes:ethylacetate 3:2) to yield 5.55 g (77%) of the product as a white solid.

c. 4-(3,4-Difluorophenyl)-1-trityl-2-imidazolidone-3-carboxylic acid 4-nitrophenyl ester:

To sodium hydride (95%)(0.189 g, 7.49 mmol) in THF (150 ml), 4-(3,4-Difluorophenyl)-1-trityl-2-imidazolidone (3.0 g, 6.81 mmol) was added at 0° C. The solution was then stirred at room temperature for 15 minutes. It was then added to a solution of 4-nitrophenylchloroformate (1.647 g, 8.17 mmol) at −78° C. via a cannula. The reaction mixture was then allowed to stir at room temperature for 12 hours. It was then concentrated and partitioned between ethyl acetate (30 ml) and water (5 ml), washed with 10% KOH (10 ml), dried over sodium sulfate, filtered and concentrated. Purification by column chromatography (hexanes:ethylacetate; 2:3) to yield 2.1 g (51%) of the product as a light brown syrup.

d. 4-(3,4-Difluorophenyl)-3-(3-(4-(2-methoxy-5-methyl)phenyl-4-phenylpiperidin-1-yl)propyl)aminocarbonyl-1-trityl-2-imidazolidone:

To 4-(3,4-difluorophenyl)-3-(4-nitrophenoxy)carbonyl-1-trityl-2-imidazolidone (0.089, 0.147 mmol) in THF (5 mL) was added 3-(4-(2-methoxy-5-methyl)phenyl-4-phenylpiperidin-1-yl)propylamine (0.055 g, 0.162 mmol) and the solution was stirred at room temperature for 16 hours. The solution was then concentrated and the residue flash chromatographed (hexanes:ethyl acetate 1:4) to yield 0.08 g (68%) of the product as a syrup.

e. 4-(3,4-Difluorophenyl)-3-(3-(4-(2-methoxyl-5-methyl)phenyl-4-phenylpiperidin-1-yl)propyl)aminocarbonyl-2-imidazolidone:

To 4-(3,4-Difluorophenyl)-3-(3-(4-(2-methoxyl-5-methyl)phenyl-4-phenylpiperidin-1-yl)propyl)aminocarbonyl-1-trityl-2-imidazolidone (0.100 g, 0.124 mmol) in dichloromethane (2 mL) at 0° C., trifluoroacetic acid (4 mL) in dichloromethane (2 mL) was slowly added and the solution was stirred at room temperature for 20 minutes. The solution was then concentrated, neutralized with 10% KOH and extracted into dichloromethane (20 mL). The organic layer was dried over sodium sulfate, filtered and concentrated. Purification of the residue by flash chromatography (ethyl acetate) yielded 0.06 g (87%) of a white foam. To it in dichloromethane (2 mL), 1N HCl in ether (0.5 mL) was added, and the solution concentrated under reduced pressure. Recrystallization of the residue from ether gave 0.061 g (96%) of a hydrochloride salt as a white solid: mp 173°–175° C. Anal. Calcd. for $C_{32}H_{36}ClF_2N_4O_3 \cdot 1.20$ $CHCl_3$: C, 53.72; H, 5.19; N, 7.55. Found: C, 53.76; H 5.01; N, 7.36.

EXAMPLE 47

(−)-3-(3-(4-Cyano-4-phenylpiperidin-1-yl)-2(S)-methylpropyl)-aminocarbonyl-4-(3,4-difluorophenyl)-2-imidazolidone.

a. 4-Cyano-1-(3-hydroxy-2(S)-methylpropyl)-4-phenylpiperidine:

A mixture of 4-cyano-4-phenylpiperidine hydrochloride (1.89 g, 8.49 mmol) and (S)-3-bromo-2-methyl-1-propanol (1.0 g, 6.53 mmol), potassium carbonate (2.709 g, 19.6 mmol) and sodium iodide (1.17 g, 7.84 mmol) in acetone (20 mL) was refluxed for 12 hours. The solution was cooled to room temperature and concentrated. The residue was partitioned between ethyl acetate (25 mL) and water (10 mL). The organic layer was dried over sodium sulfate, filtered and concentrated. Purification of the residue by flash chromatography (hexanes:ethyl acetate 2:3) yielded 1.45 g (86%) of the product as a syrup.

b. 1-(3-Azido-2(S)-methylpropyl)-4-cyano-4-phenylpiperidine:

To a solution of 4-cyano-1-(3-hydroxy-2(S)-methylpropyl)-4-phenylpiperidine (1.0 g, 3.87 mmol), triphenyl phospine (1.01 g, 3.87 mmol) and diethyl azodicarboxylate (0.609 g, 3.87 mmol) in THF (20 mL) was slowly added diphenylphosporylazide (0.83 mL, 3.87 mmol) and the solution was stirred at room temperature for 24 hours. The solution was then concentrated and flash chromatographed (hexanes:ethyl acetate 3:2) to yield 0.963 g (88%) of the product as a light brown syrup.

c. 1-(3-Amino-2(S)-methylpropyl)-4-cyano-4-phenylpiperidine:

To a solution of 1-(3-azido-2(S)-methylpropyl)-4-cyano-4-phenylpiperidine (0.96 g, 3.39 mmol) in ethyl acetate (10 mL) was added trimethylphosphine (8.4 mL, 8.49 mmol) and water (0.30 mL, 16.9 mmol) and the solution was stirred at room temperature for 24 hours. The solution was then concentrated and flash chromatographed (ethyl acetate-:methanol:methanolic ammonia 3:1:1) to yield 0.60 g (69%) of the crude product as a syrup.

d. (−)-3-(3-(4-Cyano-4-phenylpiperidine-1-yl)-2(S)-methylpropyl)-aminocarbonyl-4-(3,4-difluoro)phenyl-1-trityl-2-imidazolidone:

To 4-(3,4-difluoro)phenyl-3-(4-nitrophenoxy)carbonyl-1-trityl-2-imidazolidone (0.49 g, 0.809 mmol) in THF (10 mL) was added 1-(3-amino-2(S)-methyl)propyl-4-cyano-4-phenylpiperidine (0.250 g, 0.92 mmol) and the solution was stirred at room temperature for 16 hours. The solution was then concentrated and flash chromatographed (ethyl acetate-:methanol 4:1) to yield 0.441 g (73%) of the product as a syrup.

e. (−)-3-(3-(4-Cyano-4-phenylpiperidin-1-yl)-2(S)-methyl)propyl-aminocarbonyl-4-(3,4-difluorophenyl)-2-imidazolidone:

To (−)-3-(3-(4-Cyano-4-phenylpiperidine-1-yl)-2(S)-methylpropyl)-aminocarbonyl-4-(3,4-difluoro)phenyl-1-trityl-2-imidazolidone (0.441 g, 0.607 mmol) in dichloromethane (2 mL) at 0° C. was added trifluoroacetic acid (4 mL) in dichloromethane (2 mL) and the solution was stirred at room temperature for 20 minutes. The solution was then concentrated, neutralized with 10% KOH and extracted into dichloromethane (20 mL). The organic layer was dried over sodium sulfate, filtered and concentrated. Purification of the residue by column chromatography (ethyl acetate) yielded 0.293 g (100%) of the product as a syrup. The two diastereomers were seperated by using Chiralcel OD (20×250 mm) column with hexanes/2-propanol/diethylamine (60:40:0.1)as the eluent.

To the desired diastereomer (0.016 g, 0.0332 mmol) in dichloromethane (2 mL) was added 1N HCl in ether (0.5 mL) and the solution concentrated under reduced pressure. Recrystallization of the residue from ether gave 0.016 g (94%) of the hydrochloride salt as a white solid: $[\alpha]_D$=−5.32 (8.0 mg/mL MeOH); mp 265°–267° C. Anal.Calcd. for $C_{26}H_{30}ClF_2N_5O_2.0.15\ CHCl_3$: C, 58.61; H, 5.67; N, 12.07. Found: C, 58.50; H 5.90; N, 12.10.

EXAMPLE 48

(+)-3-(3-(4-cyano-4-(2,4-dichloro)phenylpiperidin-1-yl)propyl)aminocarbonyl-4-(3,4-difluorophenyl)-2-oxazolidinone.

a. 4-Cyano-4-(2,4-dichlorophenyl)-piperidine-1-carboxylic acid tert-butyl ester:

To bis(2-chloroethyl)-carbamic acid tert-butyl ester (1.0 g, 3.8 mmol) and (2,4-dichloro)phenyl acetonitrile (0.708 g, 3.8 mmol) in DMF (35 mL) was added NaH (95%)(0.258 g, 9.68 mmol) in one lot at 0° C. The solution was stirred for 10 minutes at room temperature. When the foaming subsided, the solution was heated at 60° C. for 24 hours. It was then quenched with water at 0° C. and concentrated. The residue was extracted with ethyl acetate (25 mL) and washed with water (3×15 mL). The organic layer was dried over sodium sulfate, filtered and concentrated. Purification of the residue by column chromatography (hexane:ethyl acetate 4:1) yielded 0.620 g (45%) of the product as a syrup.

b. {3-[4-Cyano-4(2,4-dichlorophenyl)-piperidin-1-yl}-propyl)-carbamic acid tert-butyl ester:

To 4-cyano-4-(2,4-dichlorophenyl)-piperidine-1-carboxylic acid tert-butyl ester (0.620 g, 1.74 mmol) in dichloromethane (5 mL), trifluoroacetic acid (2 mL) was added and the solution stirred at room temperature for 1 hour. The solution was concentrated, neutralized with 10% KOH solution and extracted into 25 ml of dichloromethane. The organic layer was dried over sodium sulfate, filtered and concentrated to give 0.442 g (99%) of 4-(2,4-dichlorophenyl)-piperidine-4-carbonitrile which was used as such for the subsequent step.

To a stirred solution of the 4-(2,4-dichlorophenyl)piperidine-4-carbonitrile (0.736 g, 2.88 mmol) in acetone (20 mL) was added N-(tert-butoxycarbonyl)-3-bromopropylamine (0.754 g, 3.17 mmol, potassium carbonate (1.594 g, 11.53 mmol) and sodium iodide (0.865 g, 5.7 mmol) and the solution refluxed for 24 hours. The reaction mixture was cooled to room temperature, concentrated and partitioned between chloroform (30 mL) and water (5 mL). The organic layer was dried over sodium sulfate, filtered and concentrated. The crude product was purified by column chromatography (ethyl acetate) to yield 0.925 g (78%) of the required product as a colorless oil.

c. (+)-3-(3-(4-cyano-4-(2,4-dichloro)phenylpiperidin-1-yl)propyl)aminocarbonyl-4-(3,4-difluorophenyl)-2-oxazolidinone:

To 3-[4-cyano-4-(2,4-dichlorophenyl)-piperidin-1-yl]-propyl-carbamic acid tert-butyl ester (0.589, 1.42 mmol) in dichloromethane (5 mL), trifluoroacetic acid (1 mL) was added and the solution stirred at room temperature for 1 hour. The solution was concentrated, neutralized with 10% KOH solution and extracted into 25 mL of dichloromethane. The organic layer was dried over sodium sulfate, filtered and concentrated to give 0.423 g (93%) of 1-(3-aminopropyl)-4-(2,4-dichlorophenyl)-piperidine-4-carbonitrile which was used as such for the subsequent step.

To 4-(3,4-difluorophenyl)-2-oxazolidinone-3-carboxylic acid 4-nitrophenyl ester (0.03 g, 0.0823 mmol) in dry THF (10 mL) was added 1-(3-aminopropyl)-4-(2,4-dichlorophenyl)piperidine-4-carbonitrile(0.03 g, 0.0823 mmol) and the solution was stirred at room temperature for 24 hours. The reaction mixture was concentrated and purified by column chromatography (hexanes:ethyl acetate 1:4) to yield 0.04 g (91%) of the product as a foamy syrup. To the syrup (0.040 g, 0.0744 mmol) in 4 mL of dichloromethane, 5 mL of 1N HCl in ether was added, and the solution concentrated under reduced pressure. Recrystallization of the residue from ether gave 0.040 g (94%) of the product as a white solid: mp 204°–206° C.; $[\alpha]_D$=48.8 (1.55 mg/mL MeOH). Anal. Calcd. for $C_{25}H_{25}F_2N_4O_3Cl_2.0.60\ CH_2Cl_2$: C, 49.21; H, 4.21; N, 8.97. Found: C, 49.44; H 4.39; N, 8.66.

EXAMPLE 49

(+)-3-(3-(4-Aminocarbonyl-4-(4-chloro)phenylpiperidin-1-yl)-propyl)aminocarbonyl-4-(3,4-difluoro)phenyl-2-oxazolidinone.

a. 3-(4-Cyano-4(4-chlorophenyl)piperidin-1-yl)propylcarbamic acid tert-butyl ester:

To bis(2-chloroethyl)-carbamic acid tert-butyl ester (1.0 g, 3.8 mmol) and (4-chloro)phenyl acetonitrile (0.624 g, 4.12 mmol) in DMF (35 mL) was added NaH (95%)(0.260 g, 10.30 mmol) in one lot at 0° C. The solution was stirred for 10 minutes at room temperature. When the foaming subsided, the solution was heated at 60° C. for 45 minutes. It was then quenched with water at 0° C., partitioned between ethyl acetate (25 mL) and brine (3×20 mL). The organic layer was dried over sodium sulfate, filtered and concentrated to yield 0.76 g (56%) of the crude product which was used as such for the subsequent step.

To 4-cyano-4-(4-chlorophenyl)piperidine-1-carboxylic acid tert-butyl ester (0.85 g, 2.64 mmol) in dichloromethane (2 mL) was added 2 mL of trifluoroacetic acid and the solution stirred at room temperature for 1 hour. The solution was concentrated, neutralized with 10% KOH solution and extracted into 25 mL of dichloromethane. The organic layer was dried over sodium sulfate, filtered and concentrated under reduced pressure. Purification of the residue by column chromatography (ethyl acetate:methanol:methanolic ammonia 8:1:1) yielded 0.482 g (82%) of the product as a syrup.

b. 3-(4-(4-Chlorophenyl)-4-cyanopiperidin-1-yl) propylcarbamic acid tert-butyl ester:

To a stirred solution of the 4-(4-chlorophenyl)piperidine-4-carbonitrile (0.482 g, 2.18 mmol) in acetone (20 mL) was added N-(tert-butoxycarbonyl)-3-bromopropylamine (0.572 g, 2.4 mmol, potassium carbonate (1.20 g, 8.7 mmol) and sodium iodide (0.655 g, 4.36 mmol) and the solution refluxed for 24 hours. The reaction mixture was cooled to room temperature, concentrated and partitioned between chloroform (20 mL) and water (5 mL). The organic layer was dried over sodium sulfate, filtered and concentrated. The crude product was purified by column chromatography (ethyl acetate) to yield 0.655 g (71%) of the required product as a colorless oil.

c. (+)-3-(3-(4-Aminocarbonyl-4-(4-chloro)phenylpiperidin-1-yl)-propyl)aminocarbonyl-4-(3,4-difluoro)phenyl-2-oxazolidinone: 3-(4-(4-chlorophenyl)-4-cyanopiperidin-1-yl)propylcarbamic acid tert-butyl ester (0.150 g, 5.39 mmol) in conc. $H_2SO_4$ (1 mL) was stirred at room temperature for 30 hours. The solution was concentrated, neutralized with 10% KOH solution and extracted into 25 mL of dichloromethane. The organic layer was dried over sodium sulfate, filtered and concentrated to give 0.185 g (79%) of 1-(3-aminopropyl)-4-(4-chlorophenyl)piperidine-4-carboxamide which was used as such for the subsequent step.

To 4-(3,4-difluorophenyl)-3-(4-nitrophenoxy)carbonyl-2-oxazolidinone (0.040 g, 0.109 mmol) in 10 mL of dry THF was added 1-(3-aminopropyl)-4-(4-chlorophenyl)-piperidine-4-carboxamide (0.042 g, 0.141 mmol) and the solution was stirred at room temperature for 24 hours. The reaction mixture was concentrated and purified by column chromatography (ethyl acetate: MeOH 9:1) to yield 0.025 g (44%) of the product as a foamy syrup. To the syrup (0.025 g, 0.048 mmol) in dichloromethane (2 mL) was added 1N HCl in ether (0.5 mL) and the solution concentrated under reduced pressure. Recrystallization of the residue from ether gave 0.021 g (80%) of the product as a white solid: mp 140°–142° C.; $[\alpha]_D$=−52.0(1.3 mg/mL MeOH). Anal. Calcd. for $C_{25}H_{27}Cl_2F_2N_4O_4$·1.7 $CH_2Cl_2$: C, 45.70; H, 4.51; N, 7.96. Found: C, 45.75; H 4.64; N,7.96.

EXAMPLE 50

(+)-3-(5-(4-Cyano-4-phenylpiperidin-1-yl)pent-2(E)-en-1-yl)-4-(3,4-difluoro)phenyl-2-oxazolidinone.

To a solution of 4-(3,4-difluorophenyl)-2-oxazolidinone (0.2 g, 1 mmol) and HMPA (0.18 g, 1 mmol) in THF (6 mL) was added NaH (44 mg, 1.1 mmol, 60% in mineral oil) at room temperature. After 30 min, 1,5-dibromo-2-pentene (0.34 g, 1.5 mmol) was added to the mixture. The mixture was stirred at room temperature for 4 h. After removal of solvent, the residue was flash chromatographed over silica gel (1:1 hexane-ethyl acetate) to give a mixture of two isomers in 40% yield as a yellow oil.

This oil (0.14 g, 0.4 mmol) was mixed with 4-cyano-4-phenylpiperidine hydrochloride (0.18 g, 0.8 mmol), potassium carbonate (0.2 g, 1.4 mmol), sodium iodide (61 mg, 0.4 mmol) in acetone (6 mL) and was refluxed overnight. After removal of the solvent, the residue was flash chromatographed over silica gel (ethyl acetate) to give a mixture of two isomers in 22% yield as a yellow oil. HPLC separation (column: Primesphere $SiO_2$ 5 μm, 21.2×250 mm, eluent: 75:25:0.1 ethyl acetate-hexane-triethylamine) gave the desired product (20 mg) as a yellow oil. It was treated with 1.0 equivalent of HCl to give a salt as a yellow solid: mp 168°–170° C.; ESMS m/e=452 (MH$^+$); $[\alpha]_D$=45.0 (0.4 mg/ML $CH_2Cl_2$). Anal. Calcd. for $C_{26}H_{27}F_2N_3O_2$·HCl·1.0$H_2O$: C, 61.72; H, 5.98; N, 8.30. Found: C, 61.79; H, 5.88; N, 8.26.

EXAMPLE 51 trans (+)-4-(3,4-Difluorophenyl)-5-methyl-2-oxo-oxazolidine-3-carboxylic acid{3-[4-(4-fluoro-2-methylphenyl)-piperidin-1-yl]propyl}amide a. 3-[4-(4-fluoro-2-methylphenyl)-piperidin-1-yl]-propylamine was synthesized as described in Example 22, Step c, and was used in the next step without further purification.

b. trans (+)-4-(3,4-Difluorophenyl)-5-methyl-2-oxo-oxazolidine-3-carboxylic acid{3-[4-(4-fluoro-2-methylphenyl)-piperidin-1-yl]propyl}amido As described in Example 18, step i, the trans (+)-4-(3,4-difluorophenyl)-5-methyl-2-oxo-oxazolidine-3-carboxylic acid-4-nitro-phenyl ester (0.03 g, 0.08 mmol) was converted into trans (+)-4-(3,4-difluorophenyl)-5-methyl-2-oxo-oxazolidine-3-carboxylic acid{3-[4-(4-fluoro-2-methylphenyl)-piperidin-1-yl]propyl}amide, using the side chain described in step a above, with 75% yield. It was converted into the hydrochloride salt. M.P.=80°–83° C.; $[\alpha]_D$=+23.0 (c=0.12, MeOH); Anal. Calcd. for $C_{25}H_{29}N_3O_3F_3Cl$·0.23 $H_2O$: C, 58.91; H, 5.98; N, 7.93. Found: C, 58.91; H, 6.37; N, 7.73.

EXAMPLE 52

(+)-8-(3,4-Difluorophenyl)-6-oxo-5-oxa-7-aza-spiro[3.4]octan-7-carboxylic acid-{3-[4-(4-fluoro)phenyl)-piperidin-1-yl]-propyl}-amide a. Benzhydrylindene-(3,4-difluoro-benzyl)-amine To a solution of 3,4-difluorobenzylamine (9.8 g, 69 mmol) and benzophenone (13.0 g, 71.0 mmol) in toluene (200 mL) was added a catalytic amount of $BF_3$·$OEt_2$ and the resulting solution was stirred at reflux for 12 h. The reaction mixture was concentrated in vacuo, yielding an oil (21 g, >95%), which was characterized by NMR analysis and subjected to the following reaction without any further purification.

b. 1-[(Benzhydryliden-amino)-(3,4-difluoro-phenyl) methyl]-cyclobutanol

To a solution of the imine (2.5 g, 8.1 mmol) in 50 mL of dry THF was added tert-butyllithium (1.7M, 6.2 mL) dropwise and the resulting solution was stirred at −78° C. for 0.5 h. To the solution was added cyclobutanone (0.74 ml, 9.9 mmol) in 10 ml of THF and the solution was stirred at −78° C. for 2 h and 25° C. for 1 h. The reaction was quenched by adding 1.0 mL of dilute acetic acid. Reaction mixture was diluted with 100 ml of $Et_2O$ and washed with brine. The organic layer was dried over $Na_2SO_4$ and concentrated in vacuo, yielding 1-[(benzhydryliden-amino)-(3,4-difluoro-phenyl)methyl]-cyclobutanol as an oil, which was subjected to the following reaction without purification.

c. 1-[Amino-(3,4-difluoro-phenyl)methyl]-cyclobutanol

The crude batch of 1-[(benzhydryliden-amino)-(3,4-difluoro-phenyl)methyl]-cyclobutanol obtained from the above reaction and $MeONH_2$·HCl (1.35 g, 16.2 mmol) was dissolved in 125.0 mL of MeOH and stirred for 12 h. The reaction mixture was concentrated in vacuo, yielding oily residue which was redissolved in 100 ml of EtOAc and was washed with 2.0M NaOH followed by brine. The organic layer was separated, dried over $Na_2SO_4$ and then concentrated in vacuo to give 1-[amino-(3,4-Difluoro-phenyl) methyl]-cyclobutanol as an oil which was used in the next step without any purification.

d. [(3,4-Difluorophenyl)-(1-hydroxy-cyclobutyl)-methyl]-carbamic acid-tert-butyl ester To a solution of 1-[amino-(3,4-difluoro-phenyl)methyl]-cyclobutanol (approximately 8.1 mmol) in $CH_2Cl_2$ (50 mL) at 0° C. was added a solution of di-tert-butyl dicarbonate (3.5 g, 16.2 mmol) in one portion and the resulting solution was stirred for 2 h at room temperature. The solvent was removed in vacuo and the residue was subjected to column chromatography on silica gel (9:1 cyclohexane-EtOAc followed by 4:1 cyclohexane-EtOAc) to obtain [(3,4-difluorophenyl)-(1-hydroxy-cyclobutyl)-methyl]-carbamic acid-tert-butyl ester as a viscous oil (1.0 g, 40% yield over four steps).

e. 8-(3,4-Difluorophenyl)-5-oxa-7-aza-spiro[3.4]octan-6-one

To a well stirred solution of [(3,4-difluorophenyl)-(1-hydroxy-cyclobutyl)-methyl]-carbamic acid-tert-butyl ester (1.0 g, 3.2 mmol) in THF (20 mL) was added 95% NaH (0.2 g, 8.3 mmol) at room temperature. The resulting suspension was stirred for 3 h at about 35° C. (warm water bath) and then quenched carefully with ice. The biphasic mixture was extracted with 100 mL of EtOAc, washed with brine, dried over $Na_2SO_4$, filtered and the solvent was removed in vacuo to yield 8-(3,4-difluorophenyl)-5-oxa-7-aza-spiro[3.4] octan-6-one in racemic form as a white solid.

The (+) and (−) enantiomers were separated by HPLC by using Chiralcel OD (4.6×250 mm) using 80% hexane/20% isopropyl alcohol/ 0.1% diethylamine as the eluting system (12 mL/min) under isothermal conditions (U.V. 254 nM). The retention times for the two isomers of were 12.1 min {$[\alpha]_D$=−20.0 (c=0.35, MeOH)} and 15.6 min {$[\alpha]_D$=+23.7 (c=0.52,MeOH)}respectively. The (−)-enantiomer was used in the next step (0.30 g, 35% yield).

f. (+)-8-(3,4-Difluorophenyl)-6-oxo-5-oxa-7-aza-spiro [3.4]octan-7-carboxylic acid-4-nitrophenylester To a solution of (−)-8-(3,4-difluorophenyl)-5-oxa-7-aza-spiro[3.4]octan-6-one (0.15 g, 0.63 mmol) in 10 mL THF was added a solution of n-butyllithium in hexane (0.47 mL, 0.76 mmol) dropwise via a syringe under argon atmosphere at −78° C. The resulting yellow solution was stirred at −78° C. for 50 min. This solution was then added dropwise via a cannula into another round bottom flask containing a solution of 4-nitrophenylchloroformate (0.15 g, 0.76 mmol) in 10 mL of THF, cooled at −78° C., over a period of 15 min. After five minutes, the flask was removed from the cooling bath and stirring was continued for 1 h. The reaction was quenched by adding ice and it was extracted with EtOAc. The organic extracts were washed with brine and the organic layer was dried over Na$_2$SO$_4$. The solvent was removed after filtration and the residue was purified by column chromatography on silica gel with 4:1 cyclohexane/EtOAc to obtain (+)-8-(3,4-difluorophenyl)-6-oxo-5-oxa-7-aza-spiro[3.4]octan-7-carboxylic acid-4-nitrophenyl]ester as a thick syrup which solidified upon standing (0.19 g, 75%). [α]$_D$=+42.0 (c=0.65, MeOH).

g. (+)-8-(3,4-Difluorophenyl)-6-oxo-5-oxa-7-aza-spiro[3.4]octan-7-carboxylic acid-{3-[4-(4-fluoro)phenyl)-piperidin-1-yl]-propyl}-amide To a solution of 3-[4-(4-fluorophenyl)piperidin-1-yl] propylamine (0.02 g, 0.08 mmol) in 10 mL of THF (+)-8-(3,4-difluorophenyl)-6-oxo-5-oxa-7-aza-spiro[3.4]octan-7-carboxylic acid-4-nitrophenyl]ester (0.02 g, 0.05 mmol) was added and the resulting yellow solution was stirred under argon atmosphere for 10 h at room temperature. The solvent was removed in vacuo and the residue was purified by column chromatography over silica gel with EtOAC followed by 15% MeOH in EtOAC as the eluting systems (R$_f$=0.4, 1:3 MeOH/EtOAC) to obtain (+)-8-(3,4-difluorophenyl)-6-oxo-5-oxa-7-aza-spiro[3.4]octan-7-carboxylic acid-{3-[4-(4-fluoro)phenyl)-piperidin-1-yl]-propyl}-amide as a pale yellow oil(0.02 g, 89%). It was converted into its hydrochloride salt by dissolving it into 5 mL of EtOAc and then treating it with 1.0 mL of HCl in Et$_2$O (1.0M). Mass spectrum showed M+1 peak.

EXAMPLE 53

(+)-5-Cyclopropyl-4-(3,4-difluorophenyl)-2-oxo-oxazolidine-3-carboxylic acid-{3-[4-(4-fluoro-2-methyl-phenyl)-piperidinl-yl]-propyl}-amide a. 2-(Benzhydryliden-amino)-1-cyclopropyl-2-(3,4-difluoro-phonyl)-ethanol To a solution of benzhydrylindene-(3,4-difluoro-benzyl)-amine (2.5 g, 8.1 mmol) in 50 mL of dry THF was added tert-butyllithium (1.7M, 6.2 mL) dropwise and the resulting solution was stirred at −78° C. for 0.5 h. To the solution was added cyclopropanecarboxaldehyde (0.90 ml, 12.0 mmol) in 10 ml of THF and the solution was stirred at −78° C. for 2 h and 25° C. for 1 h. The reaction was quenched by adding 1.0 mL of dilute acetic acid. Reaction mixture was diluted with 100 ml of Et$_2$O and washed with brine. The organic layer was dried over Na$_2$SO$_4$ and concentrated in vacuo, yielding 2-(benzhydryliden-amino)-1-cyclopropyl-2-(3,4-difluoro-phenyl)-ethanol as a yellow oil, which was subjected to the following reaction without purification.

b. 2-Amino-1-cyclopropyl-2-(3,4-difluoro-phenyl)-ethanol

The crude batch of 2-(benzhydryliden-amino)-1-cyclopropyl-2-(3,4-difluoro-phenyl)-ethanol obtained from the above reaction (approximately 16.2 mmol) and MeONH$_2$.HCl (4.0 g, 48.0 mmol) was dissolved in 125.0 mL of MeOH and stirred for 12 h. The reaction mixture was concentrated in vacuo, yielding oily residue which was redissolved in 100 ml of EtOAc and was washed with 2.0M NaOH followed by brine. The organic layer was separated, dried over Na$_2$SO$_4$ and then concentrated in vacuo to give the crude product as a yellow oil. It was purified by column chromatography over silica gel (95:5 CHCl$_3$/10% ammonia in MeOH) to yield 3.2 g (93% yield) of 2-amino-1-cyclopropyl-2-(3,4-difluoro-phenyl)-ethanol as a pale yellow oil.

c. [2-Cyclopropyl-1-(3,4-difluorophonyl)-2-hydroxy-ethyl]-carbanic acid-tert-butyl eater To a solution of 2-amino-1-cyclopropyl-2-(3,4-difluorophenyl)-ethanol (1.7 g, 8.1 mmol) in CH$_2$Cl$_2$ (50 mL) at 0° C. was added a solution of di-tert-butyl dicarbonate (3.5 g, 16.2 mmol) in one portion and the resulting solution was stirred for 2 h at room temperature. The solvent was removed in vacuo and the residue was subjected to column chromatography on silica gel (4:1 cyclohexane/EtOAc) to obtain [2-cyclopropyl-1-(3,4-difluorophenyl)- 2-hydroxy-ethyl]-carbamic acid-tert-butyl ester as a viscous oil (1.7 g, 68% yield).

e. 5-Cyclopropyl-4-(3,4-Difluorophenyl)-oxazolidin-2-one

To a well stirred solution of [2-cyclopropyl-1-(3,4-difluorophenyl)-2-hydroxy-ethyl]-carbamic acid-tert-butyl ester (1.7 g, 5.4 mmol) in THF (20 mL) was added 95% NaH (0.4 g, 16.2 mmol) at room temperature. The resulting suspension was stirred for 3 h at about 35° C. (warm water bath) and then quenched carefully with ice. The biphasic mixture was extracted with 100 mL of EtOAc, washed with brine, dried over Na$_2$SO$_4$, filtered and the solvent was removed in vacuo to yield 5-cyclopropyl-4-(3,4-difluorophenyl)-oxazolidin-2-one (1.3 g, 93% yield) as a 3:1 mixture of the trans:cis diastereomers. The diastereomers were separated by column chromatography over silica gel with 7:3 cyclohexane/ethyl acetate as the eluting system. The trans isomer eluted first (Rf=2.5, 0.65 g) followed by the cis isomer (R$_f$=2.0, 0.2 g). The relative streochemistry was assigned by comparing the $^1$H NMR of the two isomers of 5-cyclopropyl-4-(3,4-difluorophenyl)-oxazolidin-2-one to the corresponding isomers of 4-(3,4-difluorophenyl)-5-methyl-oxazolidin-2-one as described in Example 19.

The (+) and (−) enantiomers of the trans-isomer were separated by HPLC by using Chiralcel OD (4.6×250 mm) using 80% hexane/20% isopropyl alcohol/ 0.1% diethylamine as the eluting system (12 mL/min) under isothermal conditions (U.V. 254 nM). The retention times for the two enantiomers were 12.0 min {[α]$_D$=+1.8 (c=0.35, MeOH)} and 15.5 min respectively. The (+)-enantiomer was used in the next step.

f. (+)-5-Cyclopropyl-4-(3,4-difluorophenyl)-2-oxo-oxazolidine-3-carboxylic acid-4-nitrophenyl]ester To a solution of (+)-5-cyclopropyl-4-(3,4-Difluorophenyl)-oxazolidin-2-one (0.16 g, 0.66 mmol) in 10 mL THF was added a solution of n-butyllithium in hexane (0.49 mL, 0.79 mmol) dropwise via a syringe under argon atmosphere at −78° C. The resulting yellow solution was stirred at −78° C. for 50 min. This solution was then added dropwise via a cannula into another round bottom flask containing a solution of 4-nitrophenylchloroformate (0.16 g, 0.79 mmol) in 10 mL of THF, cooled at −78° C., over a period of 15 min. After five minutes, the flask was removed from the cooling bath and stirring was continued for 1 h. The reaction was quenched by adding ice and it was extracted with EtOAc. The organic extracts were washed with brine and the organic layer was dried over Na$_2$SO$_4$. The solvent was removed after filtration and the residue was purified by column chromatography on silica gel with 4:1 cyclohexane-ethyl acetate to obtain (+)-5-cyclopropyl-4-(3,4-difluorophenyl)-2-oxo-oxazolidine-3-carboxylic acid-4-nitrophenyl]ester as a thick syrup (0.17 mg, 58%).

g. (+)-5-Cyclopropyl-4-(3,4-difluorophenyl)-2-oxo-oxazolidine-3-carboxylic acid-{3-[4-(4-fluoro-2-methyl-phenyl)-piperidinl-yl]-propyl}-amide To a solution of 3-[4-(4-fluoro-2-methyl-phenyl)-piperidin-1-yl]propylamine (0.02 g, 0.05 mmol) in 10 mL of CH$_2$Cl$_2$, (+)-5-cyclopropyl-4-(3,4-difluorophenyl)-2-oxo-oxazolidine-3-carboxylic acid-4-nitrophenyl]ester(0.01 g, 0.03 mmol) was added and the resulting yellow solution was stirred for 10 h at room temperature. The solvent was removed in vacuo and the residue was purified by column chromatography over silica gel with EtOAC followed by 15% MeOH in EtOAC as the eluting systems (R$_f$=0.4, 1:3 MeOH/EtOAC) to obtain (+)-5-cyclopropyl-4-(3,4-difluorophenyl)-2-oxo-oxazolidine-3-carboxylic acid-{3-[4-(4-fluoro-2-methyl-phenyl)-piperidinl-yl]-propyl}-amide as a pale yellow oil (0.01 g, 80%). It was converted into its hydrochloride salt by dissolving it into 5 mL of EtOAc and then treating it with 1.0 mL of HCl in Et$_2$O (1.0M).

Mass spectrum showed M+1 peak.

EXAMPLE 54

Asymmetric Synthesis of 4-(3,4-Difluorophenyl)-5-methyl-oxazolidin-2-one a. 2-Hydroxy-1-pyrrolidin-1-yl-propan-1-one (The procedure reported by Vilarrasa et al. Tetrahedron Lett. 1997, 38, 1633 was used; see also Scheme 31) S-(+)-Methyl lactate (48.03 mmol, 5.0 g) and pyrrolidine (52.8 mmol, 4.4 mL) were mixed in a round bottom flask and the reaction mixture was allowed to stir at room temperature for four days. Methanol was distilled off using a short path distillation apparatus to obtain 2-hydroxy-1-pyrrolidin-1-yl-propan-1-one as a yellow oil. It was used in the next reaction without further purification.

b. 2-(tert-Butyl-dimethyl-silanyloxy)-1-pyrrolidin-1-yl-propan-1-one

To a solution of 2-hydroxy-1-pyrrolidin-1-yl-propan-1-one (47.0 mmol, 6.72 g) in DMF (25 mL) was added imidazole (70.5 mmol, 4.8 g), N,N-dimethyl-4-aminopyridine (4.7 mmol, 0.57 g) at room temperature. Tert-butyl-dimethylsilyl chloride (48.5 mmol, 7.31 g) was then added while stirring. Some exotherm was observed. The initial pale yellow solution turned brwn-red in color and some precipitate was observed after 30 min. The reaction mixture was allowed to stir overnight and then filtered through a sintered glass funnel. The solid was washed with some Et$_2$O. The filtrate was diluted with water (150 mL) and it was extracted with Et$_2$O (2×100 mL). The organic extrats were combined and washed successively with water (100 mL), sat. NH$_4$Cl solution and the organic layer was separated. It was dried over Na$_2$SO$_4$, filtered and the solvent was removed in vacuo to obtain 2-(tert-butyl-dimethyl-silanyloxy)-1-pyrrolidin-1-yl-propan-1-one as a golden yellow oil (10.4 g, 86% yield). The product was judged to be >95% pure by NMR and was used in next step without any purification.

c. 2-(tert-Butyl-dimethyl-silanyloxy)-1-(3,4-difluoro-phenyl)-1-yl-propan-1-one

To a round bottom flask containing 72.0 mL of THF at −78° C. was added a solution of n-butyllithium in hexane (72.0 mmol, 45.0 mL) under an argon atmosphere followed by 1-bromo-3,4-difluorobenzene (72.0 mmol, 8.1 mL). A solution of 2-(tert-butyl-dimethyl-silanyloxy)-1-pyrrolidin-1-yl-propan-1-one (60.0 mmol, 15.4 g) in 10.0 mL THF was then added ina steady stream and the orange colored solution was stirred for 35 min at −78° C. It was quenched with 20.0 mL of sat. NH$_4$Cl solution and was allowed to attain room temperature. The solution was extracted with Et$_2$O (2×50 mL), washed with brine and the organic layer was dried over Na$_2$SO$_4$. The solution was filtered and the solvent was removed in vacuo to obtain the product as an orange oil. The crude product was subjected to silica gel flash column chromatography (9:1 hexane/EtOAc to 4:1 hexane/EtOAc as the eluent system). 2-(tert-Butyl-dimethyl-silanyloxy)-1-(3,4-difluoro-phenyl)-1-yl-propan-1-one was obtained as a pale yellow oil (14.1 g, 78% yield, 96% based on the recovered starting material).

d. 2-(tert-Butyl-dimethyl-silanyloxy)-1-(3,4-difluoro-phenyl)-1-yl-propan-1-one-oxime To a solution of 2-(tert-Butyl-dimethyl-silanyloxy)-1-(3,4-difluoro-phenyl)-1-yl-propan-1-one (13.7 mmol, 4.1 g) in 60.0 mL of methanol was added sodium acetate (mmol, 3.76 g) and hydroxylamine hydrochloride (mmol, 1.24 g) and the resulting solution was stirred at room temperature overnight. Methanol was then removed in vacuo and the resultind residue was extracted with EtOAc (2×50 mL) and brine. The organic layer was separated, dried over Na$_2$SO$_4$, filtered and the solvent was removed in vacuo. 2-(tert-Butyl-dimethyl-silanyloxy)-1-(3,4-difluoro-phenyl)-1-yl-propan-1-one-oxime was obtained as a colorless oil (4.04 g, 94% yield). It was used in the next step without further purification.

e. 1-Amino-1-(3,4-difluorophonyl)-propan-2-ol

To a solution of 2-(tert-butyl-dimethyl-silanyloxy)-1-(3,4-difluoro-phenyl)-1-yl-propan-1-one-oxime (12.2 mmol, 3.84 g) in 20.0 mL of Et$_2$O was added a 1.0M solution of lithium aluminum hydride (25.0 mmol, 25.0 mL) at 0° C. under an argon atmosphere. After 1 h, the solution was heated to reflux for 2 h at which time some solid was observed. The reaction mixture was cooled to 0° C. and then quenched sequentially with water (1.0 mL), 1.0N KOH (1.0 mL) and water (3.0 mL). The residue was filtered and the solid was washed with warm Et$_2$O (20.0 mL). The filtrates were combined and dried over Na$_2$SO$_4$. The solution was filtered and the solvent was removed in vacuo to obtain 1-amino-1-(3,4-difluorophenyl)-propan-2-ol as a colorless oil as a mixture of two diastereomers which solidified into a low melting solid (2.1 g, 92% yield). It was used in the next step without purification.

It was converted into 4-(3,4-difluorophenyl)-5-methyl-oxazolidin-2-one by the general procedure as described before.

f. [1-(3,4-Difluorophenyl)-2-hydroxy-propyl]-carbamic acid-tert-butyl ester

To a solution of 1-amino-1-(3,4-difluorophenyl)-propan-2-ol (3.5 g, 19.1 mmol) in CHCl$_3$ (15 mL) at 0° C. was added a solution of di-tert-butyl dicarbonate (5.1 g, 23.6 mmol) in CHCl$_3$ (10 mL) in one portion and the resulting solution was stirred overnight at room temperature. The solvent was removed in vacuo and the residue was subjected to column chromatography on silica gel (2:1 hexane-EtOAc followed by EtOAc) to obtain [1-(3,4-difluorophenyl)-2-hydroxy-propyl]-carbamic acid-tert-butyl ester as a viscous oil (3.3 g, 60.2%).

g. 4-(3,4-Difluorophonyl)-S-methyl-oxazolidin-2-one

To a well stirred solution of [1-(3,4-difluorophenyl)-2-hydroxy-propyl]-carbamic acid-tert-butyl ester (0.43 g, 1.5 mmol) THF (20 mL) was added 95% NaH (0.09 g, 3.8 mmol) at room temperature. The resulting suspension was stirred for 3 h at about 35° C. (wary water bath) and then quenched carefully with ice. The biphasic mixture was extracted with 100 mL of EtOAc, washed with brine, dried over Na$_2$SO$_4$, filtered and the solvent was removed in vacuo. The two diastereomers were separated by column chromatography over silica gel (First isomer: 0.11 g, R$_f$=0.6, 3:1 hexane-EtOAc; second isomer: 0.23 g, R$_f$=0.5, 3:1 hexane-EtOAc). NOE experiment suggested that the first diastereomer had the methyl and the aryl group in trans configuration while the second diastereomer had cis relationship between the two groups.

Each diastereomer was subjected to chiral HPLC analysis using Chiralcel OD (4.6×250 mm) using 80% hexane/20% isopropyl alcohol/ 0.1% diethylamine as the eluting system (12 mL/min) under isothermal conditions (U.V. 254 nM). The retention time for the trans-oxazolidinone was 13.0 min. This corresponds to the (+)-isomer of the trans oxazolidinone that was synthesized by a separate method as described in Example 19 (the retention time for the (+)-trans-oxazolidinone was 12.1 min). The HPLC analysis also confimed that the enantiomeric purity of the diastereomer was >99% because no peak corresponding to (−)-isomer was observed. Since the absolute stereochemistry of the starting material [(S)-(+)-methyl lactate] is known, the absolute stereochemistry of the (+)-isomer of the trans-oxazolidinone must be (S,S) at the two stereocenters.

This enantiomerically pure oxazolidinone can be converted into the required final products by using similar methodology as described before in example 19.

General synthetic schemes. In addition to the specific examples of compounds described above, typical procedures for the synthesis of the compounds of this invention are shown in Schemes 32–35. In Scheme 34, the synthesis may be carried out using a procedure similar to Koo, J. (J. Am. Chem. Soc., 1953, 75, 723), Anderson, P. (Tetrahedron Lett., 1971, 2787), and Bean, N. P. et al. (Tetrahedron, 1993, 49, 3193). In Scheme 35, the synthesis may be carried out using a procedure similar to Belkon, Y. et al. (J. Chem. Soc. Perkin Trans. I, 1986, 1865), Novikov, M. S. et al. (Tetrahedron Lett., 1997, 38, 4187), and Meyers, A. et al. (J. Amer. Chem. Soc., 1984, 106, 1146).

EXAMPLE 55

As a specific embodiment of an oral composition of a compound of this invention, 100 mg of one of the compounds described herein is formulated with sufficient finely divided lactose to provide a total amount of 580 to 590 mg to fill a size 0 hard gel capsule.

Pharmacological Profiles of the Compounds in Cloned Human Adrenergic Receptors.

Binding affinities were measured for selected compounds of the invention at six cloned human alpha-1 and alpha-2 receptor subtypes, as well as at the L-type calcium channel. The protocols for these experiments are given below.

Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

$\alpha_{1D}$ Human Adronergic Receptor: The entire coding region of $\alpha_{1D}$ (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene (old nomenclature)) and the plasmid pGCcos3neo (plasmid containing the aminoglycoside transferase gene) into LM(tk-) cells using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

The cell line expressing the human $\alpha_{1D}$ receptor used herein was designated L-$\alpha_{1A}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure.

The cell line expressing the human $\alpha_{1D}$ receptor, was accorded ATCC Accession No. CRL 11138, and was deposited on Sep. 25, 1992.

$\alpha_{1B}$ Human Adrenergic Receptor: The entire coding region of α1B (1563 bp), including 200 base pairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above. The cell line used herein was designated L-$\alpha_{1B}$ and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line L-$\alpha_{1B}$ was accorded ATCC Accession No. CR 11139, on Sep. 29, 1992.

$\alpha_{1A}$ Human Adrenergic Receptor: The entire coding region of $\alpha_{1A}$ (1401 bp), including 400 base pairs of 5' untranslated sequence (5' UT) and 200 bp of 3' untranslated sequence (3' UT), was cloned into the KpnI site of the polylinker-modified pCEXV-3-derived is eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above. The stable cell line expressing the human $\alpha_{1A}$ receptor used herein was designated L-$\alpha_{1C}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure.

The cell line expressing the human $\alpha_{1A}$ receptor was accorded Accession No. CR 11140, on Sep. 25, 1992.

Radioligand Binding Assays: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000 x g for 20 min at 4°

C. The pellet was suspended in 50 mM Tris-HCl, 1 mM MgCl$_2$, and 0.1% ascorbic acid at pH 7.5. Binding of the α1 antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

α$_2$ Human Adronergic Receptors: To determine the potency of α$_1$ antagonists at the α$_2$ receptors, LM(tk-) cell lines stably transfected with the genes encoding the α$_{2A}$, α$_{2B}$, and α$_{2C}$ receptors were used. The cell line expressing the α$_{2A}$ receptor is designated L-α$_{2A}$, and was deposited on Nov. 6, 1992 under ATCC Accession No. CRL 11180. The cell line expressing the α$_{2B}$ receptor is designated L-NGC-α$_{2B}$, and was deposited on Oct. 25, 1989 under ATCC Accession No. CRL10275. The cell line expressing the α$_{2C}$ receptor is designated L-α$_{2C}$, and was deposited on Nov. 6, 1992 under ATCC Accession No. CRL-11181. All the cell lines were deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. Cell lysates were prepared as described above (see Radioligand Binding Assays), and suspended in 25 mM glycylglycine buffer (pH 7.6 at room temperature). Equilibrium competition binding assay were performed using [3H]rauwolscine (0.5 nM), and nonspecific binding was determined by incubation with 10 μM phentolamine. The bound radioligand was separated by filtration through GF/B filters using a cell harvester.

Determination of the Activity of α$_1$ Antagonists at Calcium Channels

The potency of α$_1$ antagonists at calcium channels may be determined in competition binding assays of [3H] nitrendipine to membrane fragments of rat cardiac muscle, essentially as described by Glossman and Ferry (Methods in Enzymology 109:513–550, 1985). Briefly, the tissue is minced and homogenized in 50 mM Tris-HCl (pH 7.4) containing 0.1 mM phenylmethylsulfonyl fluoride. The homogenates are centrifuged at 1000 g for 15 minutes, and the resulting supernatant centrifuged at 45,000 g for 15 minutes. The 45,000 g pellet is suspended in buffer and centrifuged a second time. Aliquots of membrane protein are then incubated for 30 minutes at 37° C. in the presence of [3H]nitrendipine (1 nM), and nonspecific binding determined in the presence of 10 μM nifedipine. The bound radioligand is separated by filtration through GF/B filters using a cell harvester.

The compounds described above were assayed using cloned human alpha adrenergic receptors. The preferred compounds were found to be selective α$_{1A}$ antagonists. The binding affinities of several compounds are illustrated in the following table.

Binding affinities of selected compounds of the present invention at cloned human α$_{1D}$, α$_{1B}$ and α$_{1A}$ receptors.

| Example | hα$_{1D}$ K$_i$ | hα$_{1B}$ K$_i$ | hα$_{1A}$ K$_i$ |
|---|---|---|---|
| 2 | 11 | 21 | 0.5 |
| 21 | 2455 | 891 | 21 |
| 28 | 3660 | 4012 | 0.7 | h = human

Scheme 1
General Synthesis of
Piperazine side chains

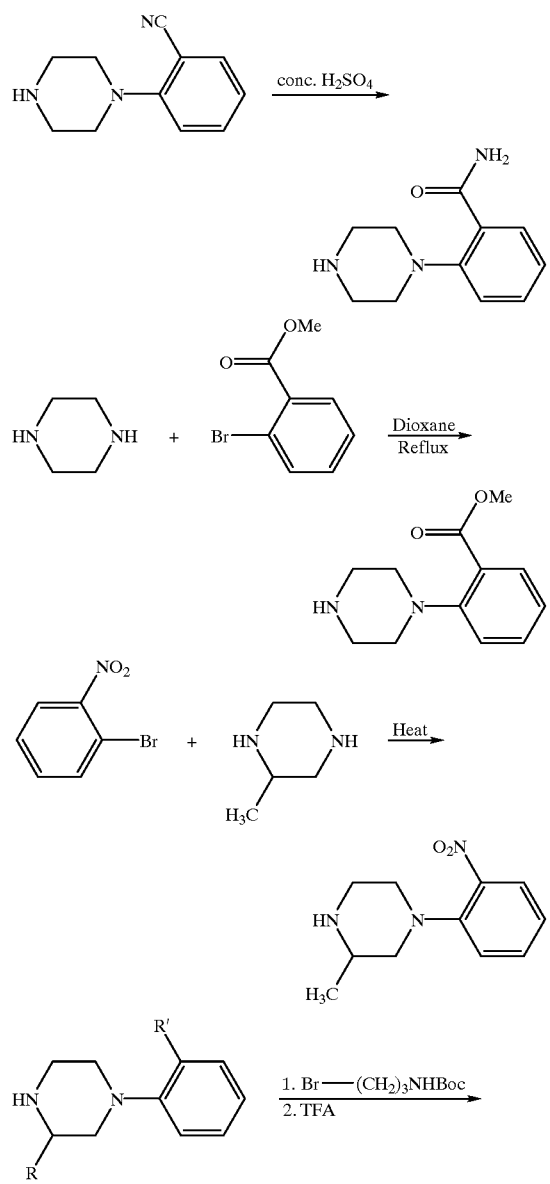

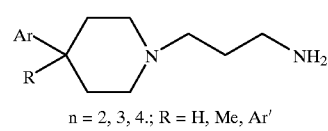
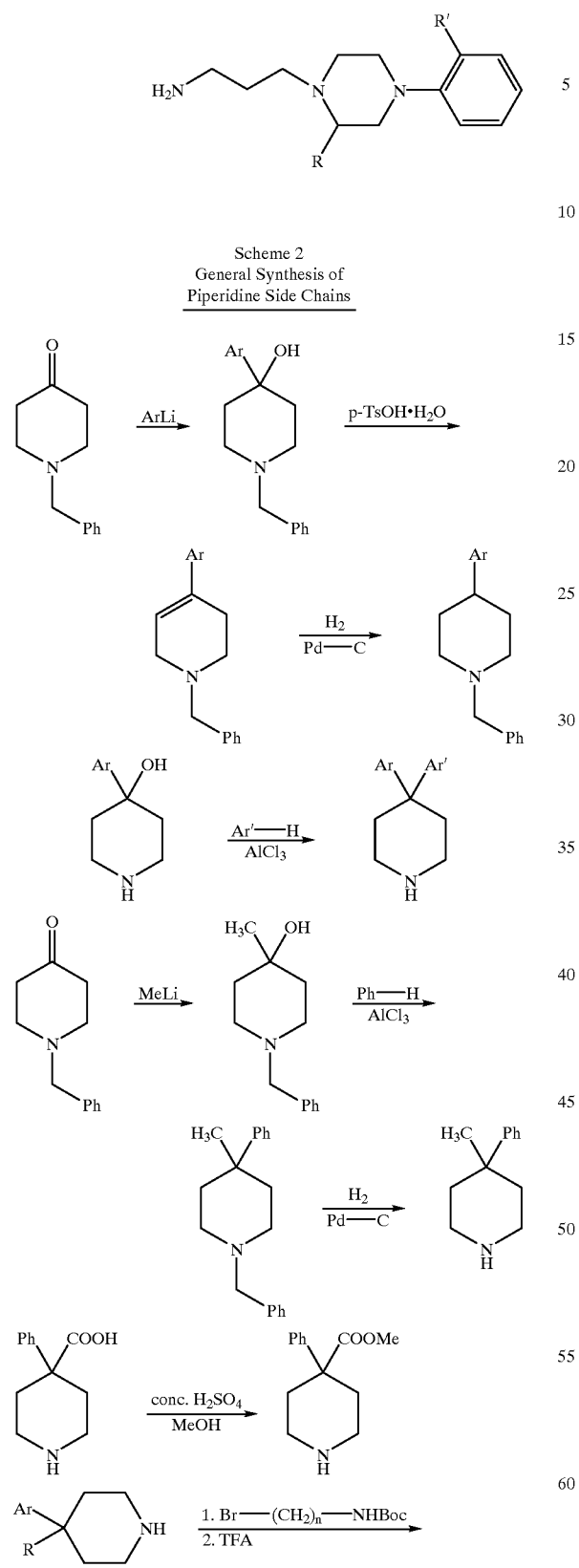

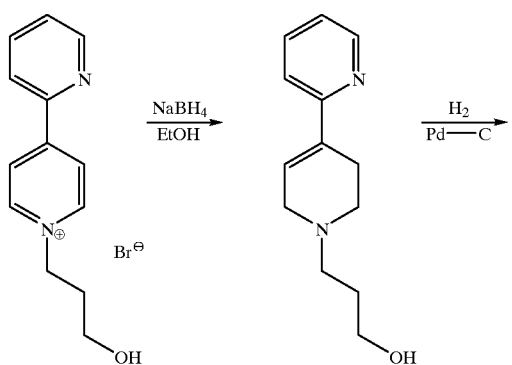
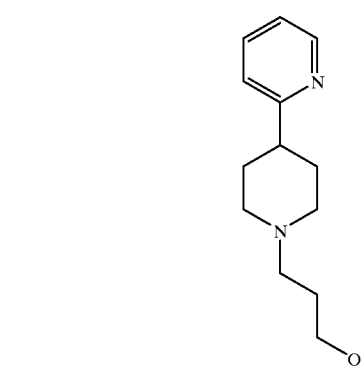
Scheme 4
Preparation of Example 2
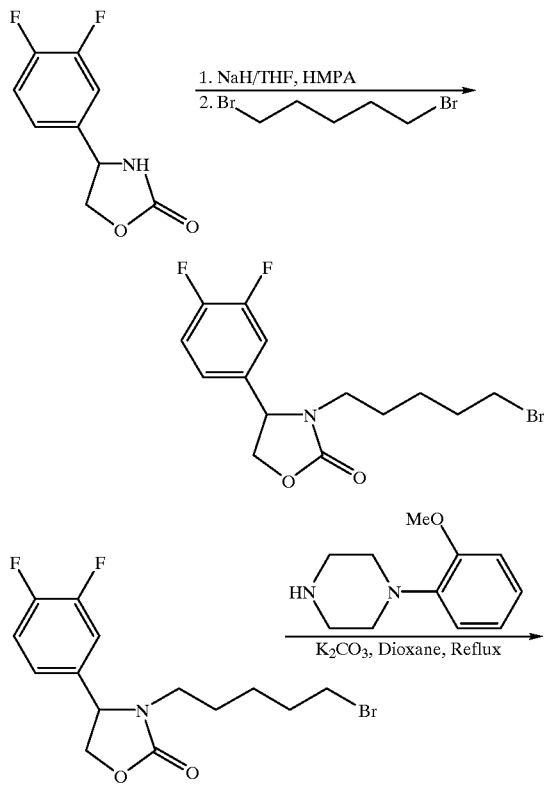
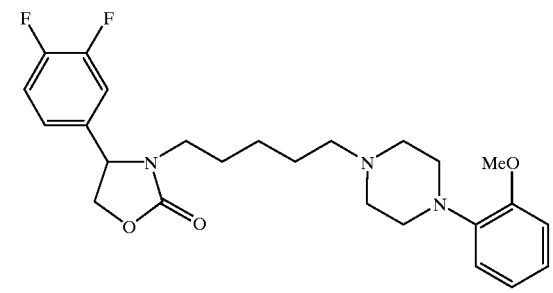
Scheme 5
General Synthesis of Oxazolidinones
(Examples 1, 3, 6, 7, 8, 10, 14 and 22)
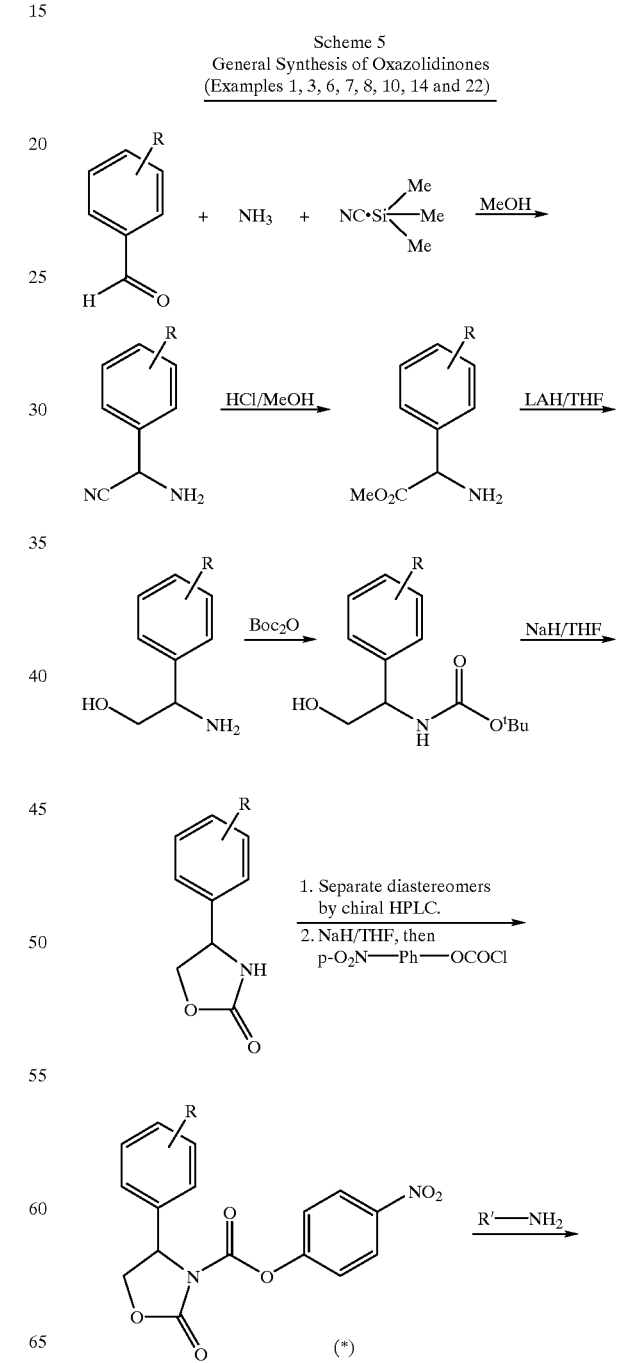
(*)

81
-continued
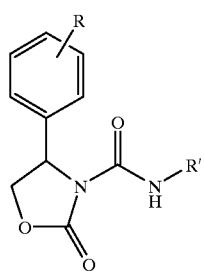
Scheme 6
Alternate Synthesis of Oxazolidinones described in Scheme 5
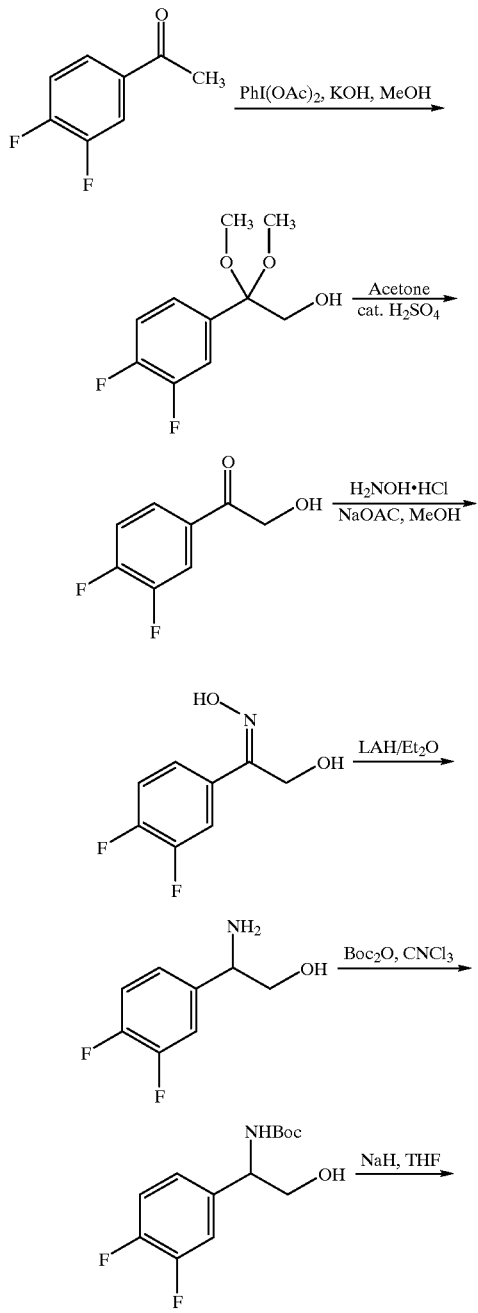
82
-continued
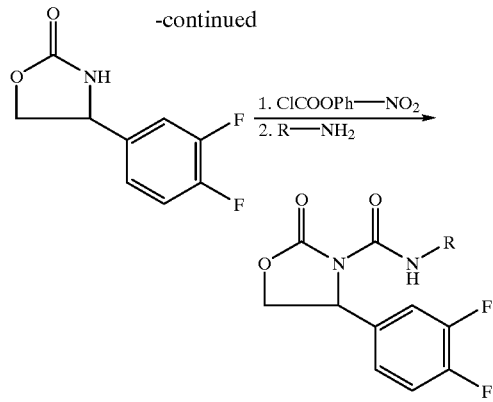
Scheme 7
General Synthesis of Oxazinones (Example 4)
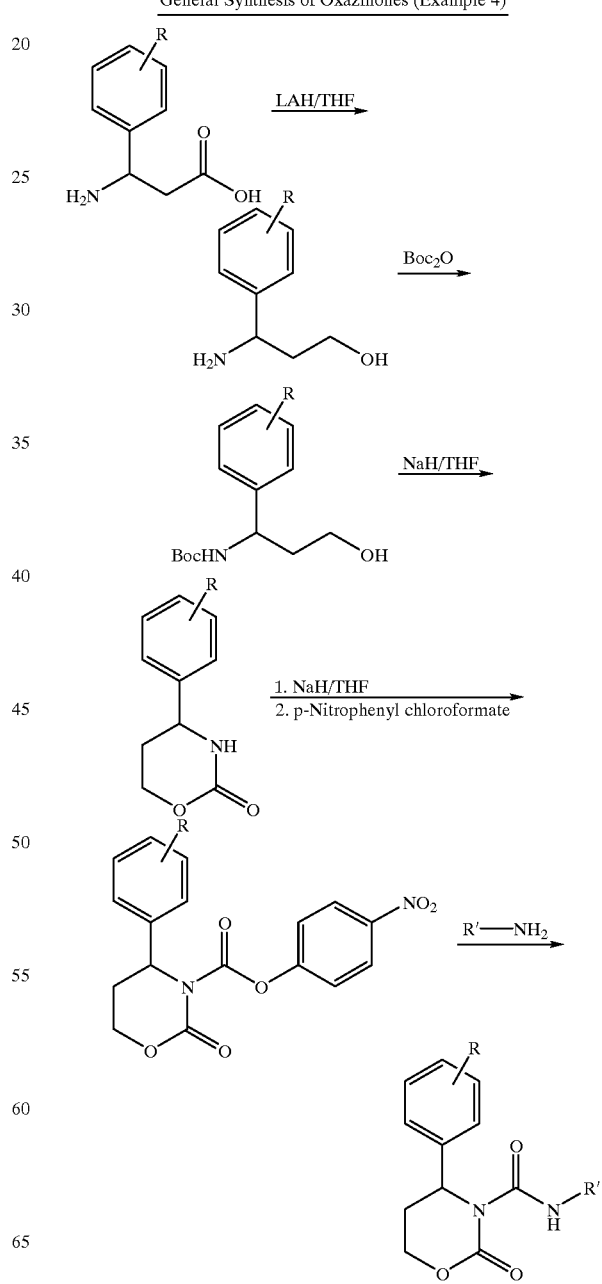

Scheme 8
Synthesis of Regioisomeric Oxazolidinones (Example 9)
Scheme 10
General Synthesis for Example 13
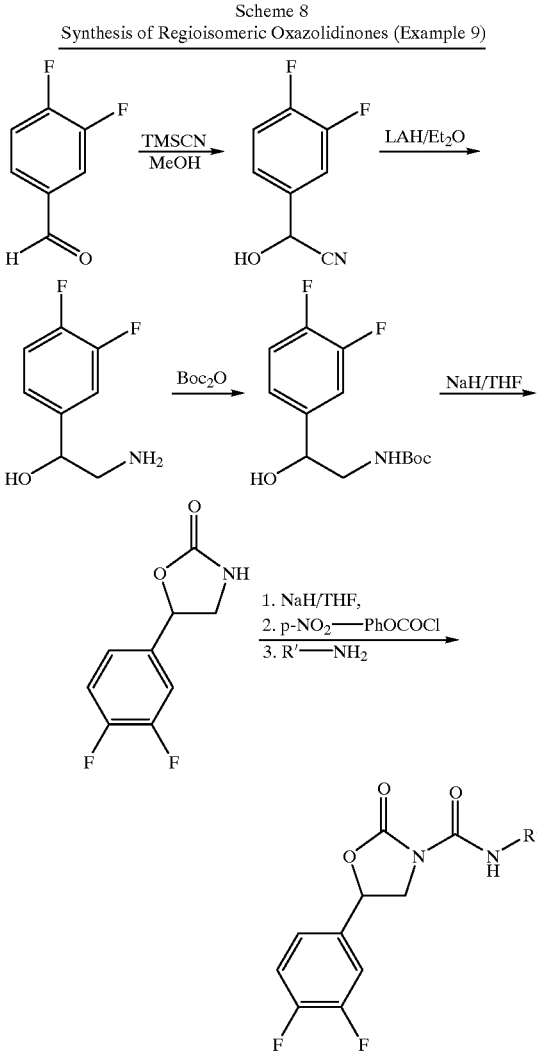
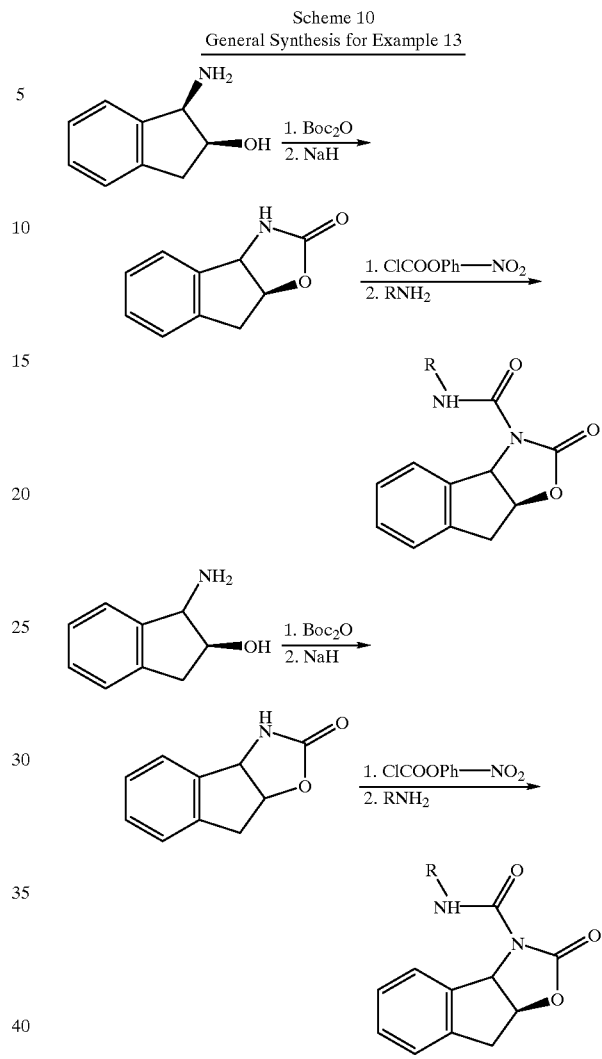
Scheme 9
Synthesis of Oxazolidin-thione and Thiazolidin-thione (Examples 11, 12)
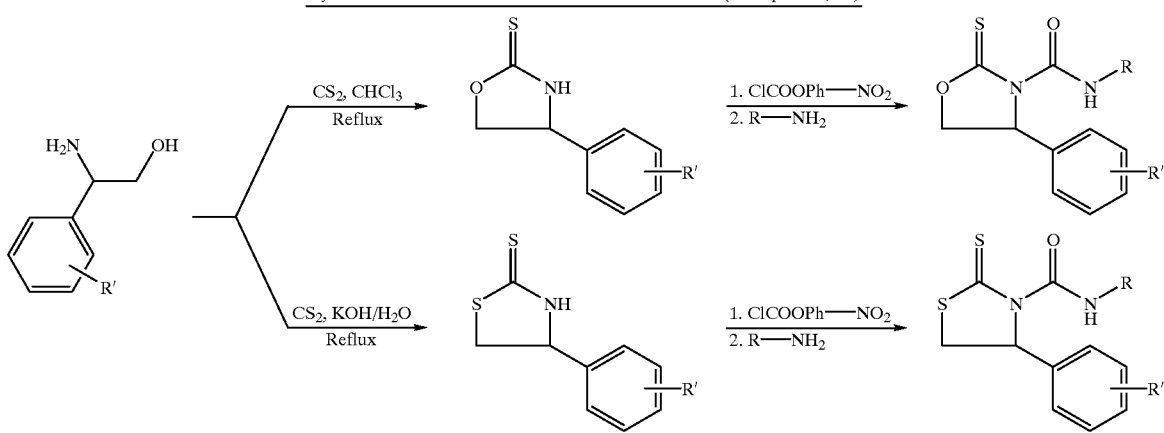

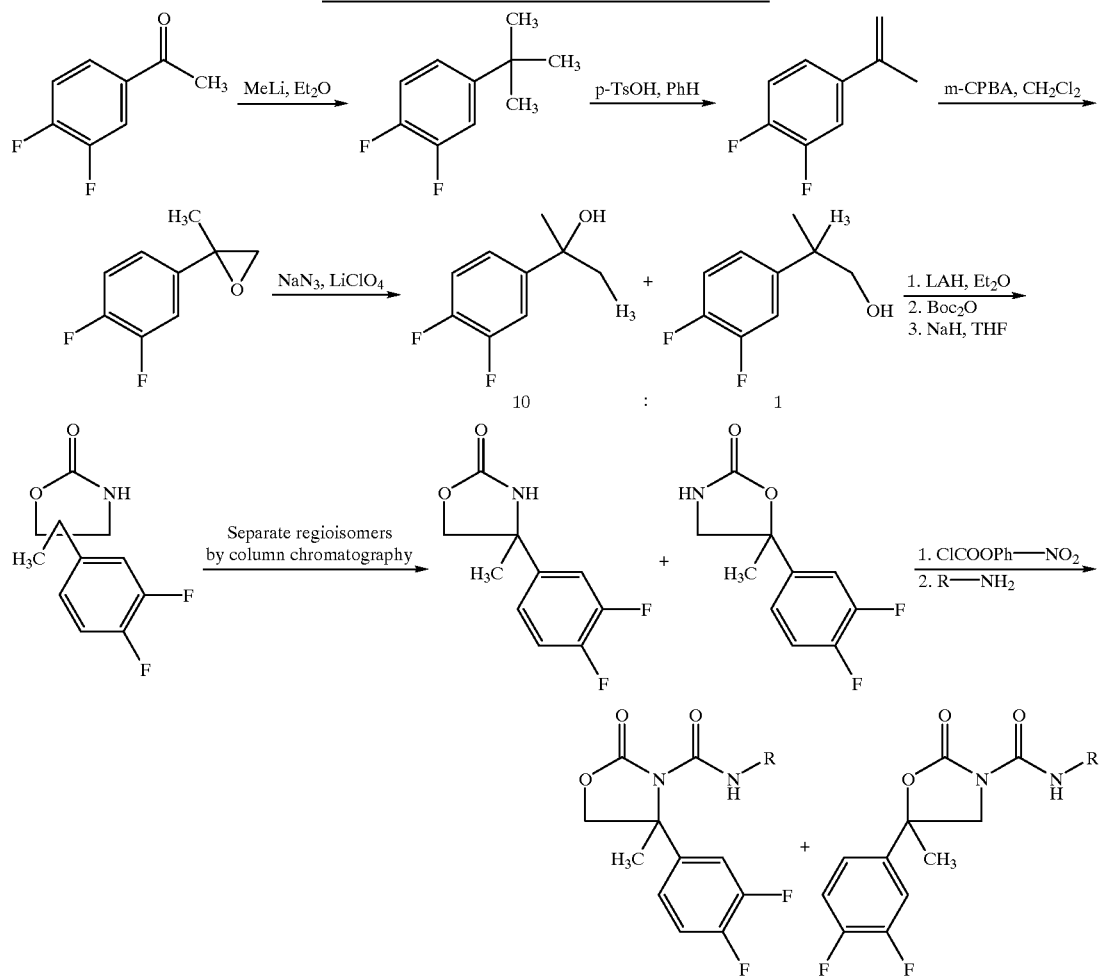
Scheme 11
Synthesis of Methylated Oxazolidinones (Examples 16, 17)
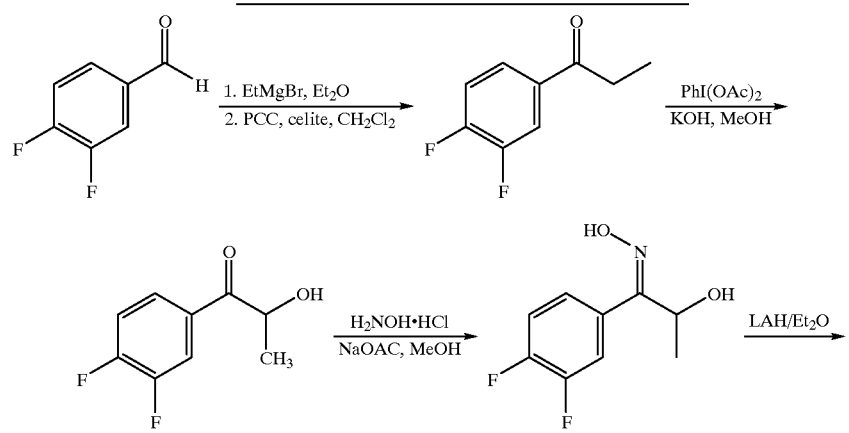
Scheme 12
Synthesis of Methylated Oxazolidinones (Examples 18, 19)

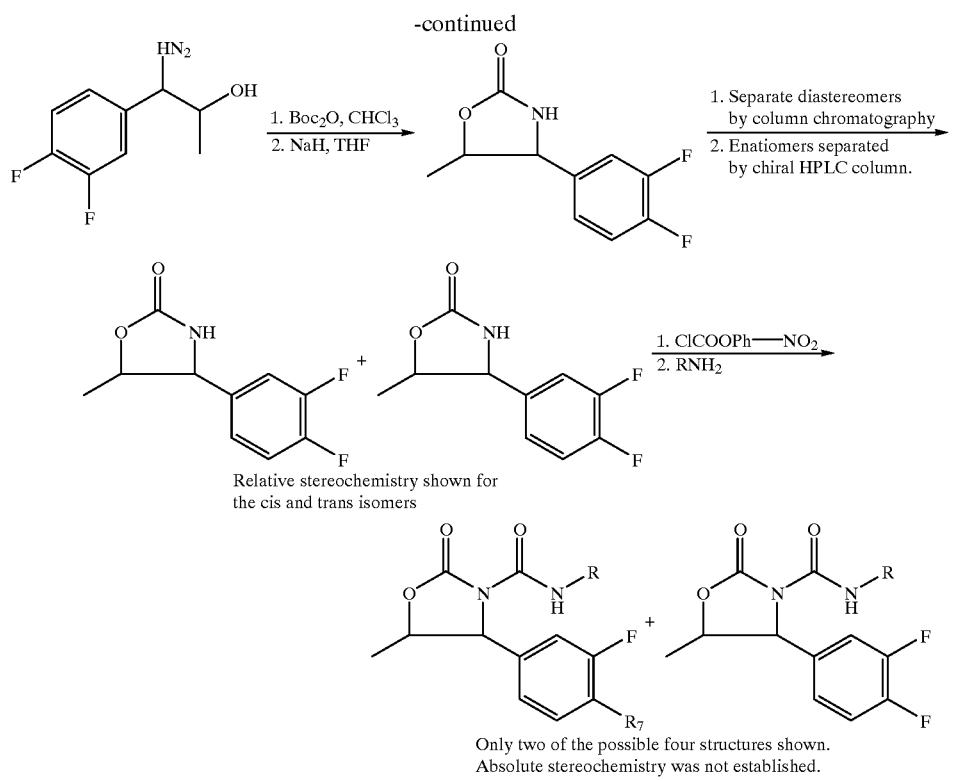
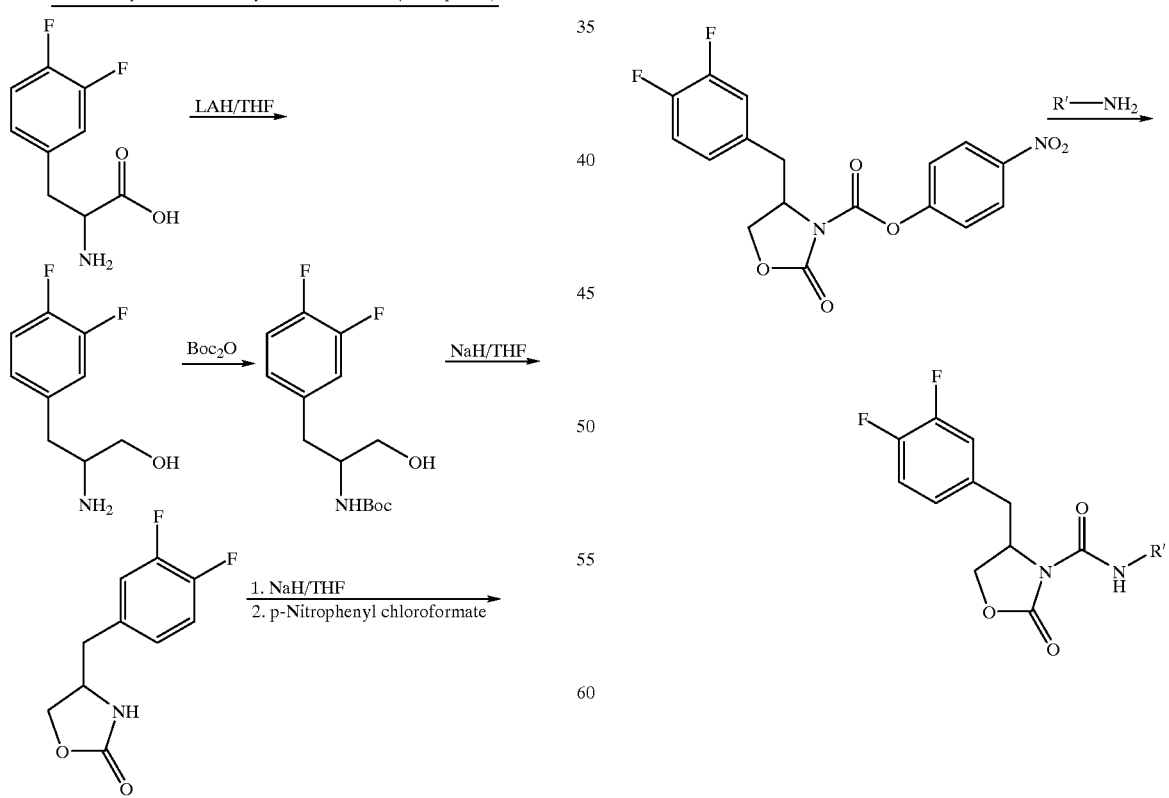
Scheme 13
General Synthesis of Benzyl Oxazolidinones (Example 20)

Scheme 14
Preparation of Examples 23 and 24
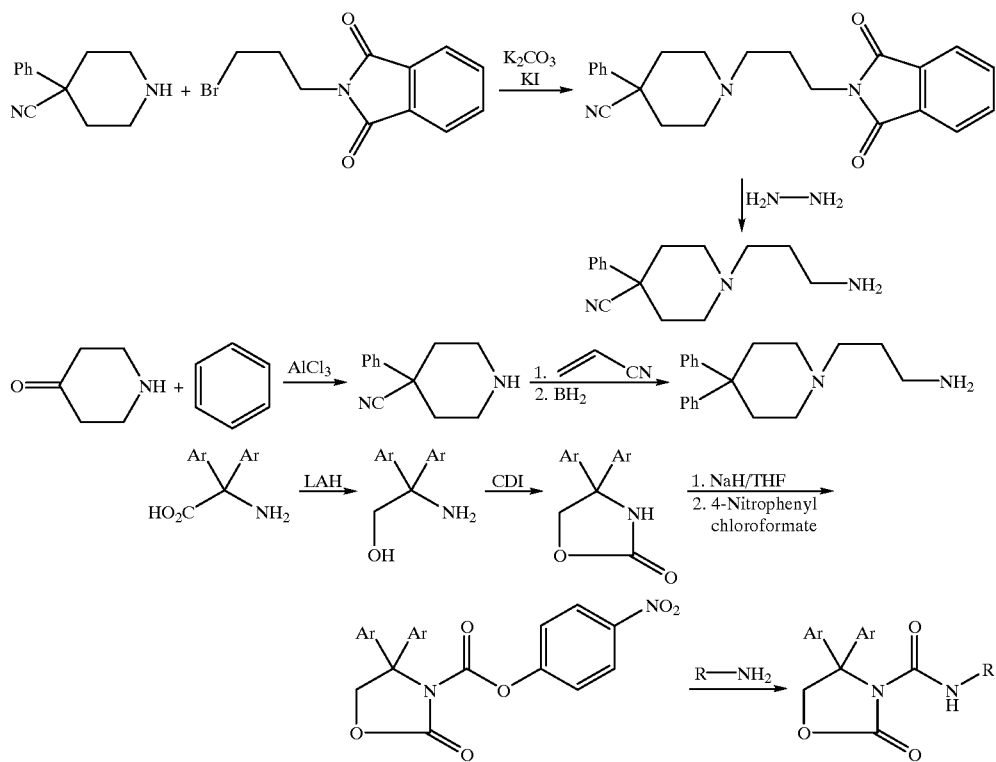
Scheme 15
Preparation of Side Chains
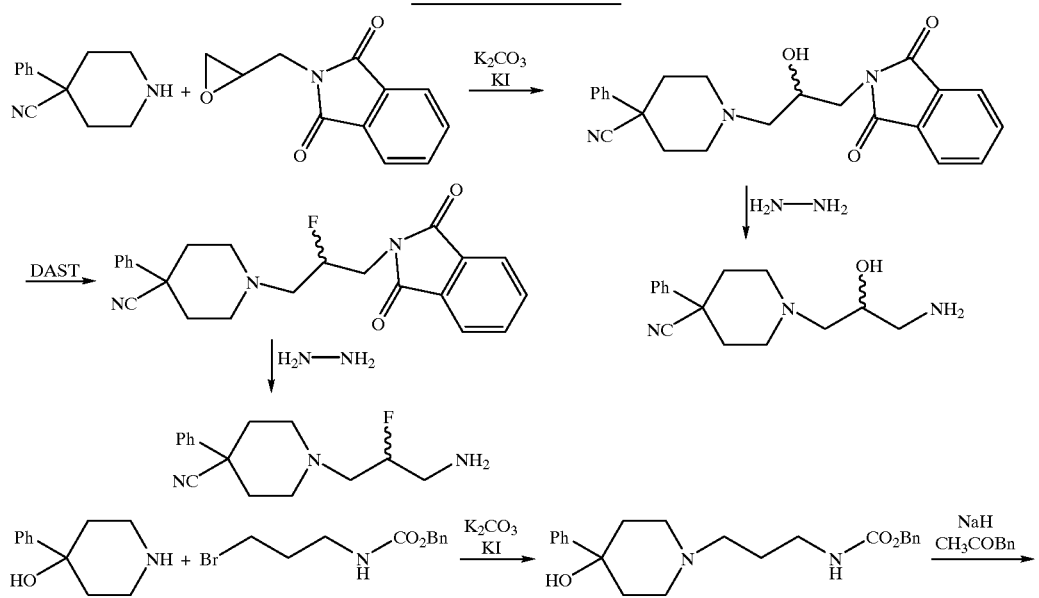

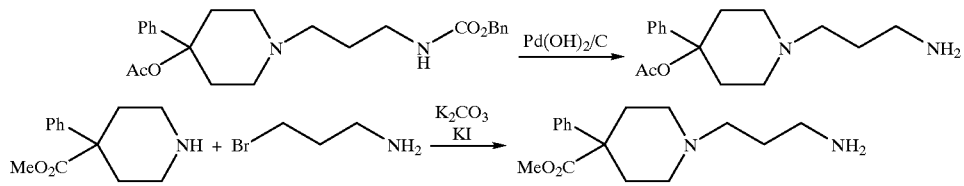
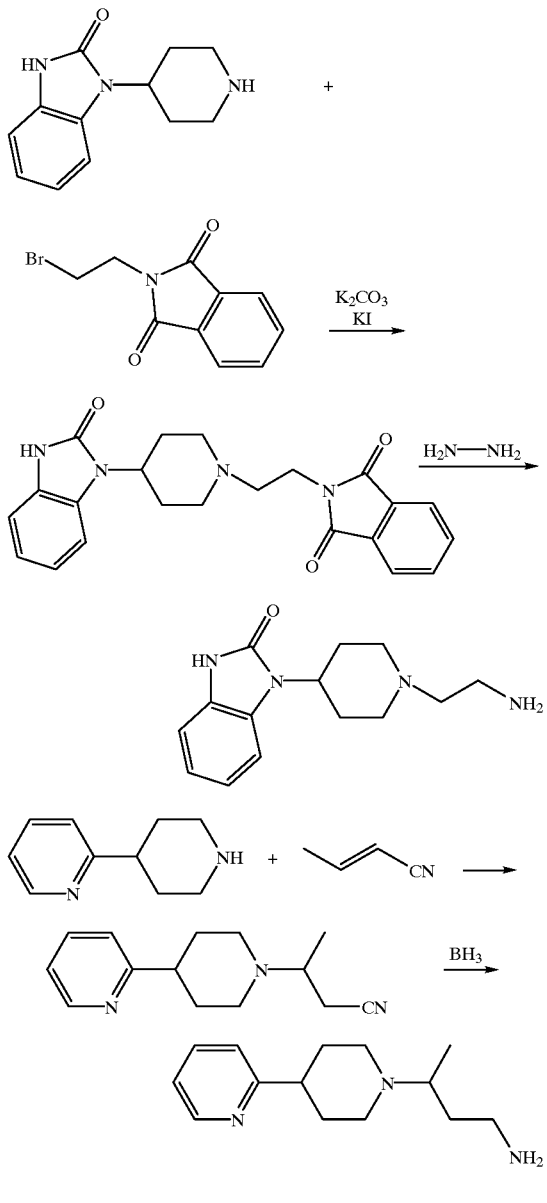
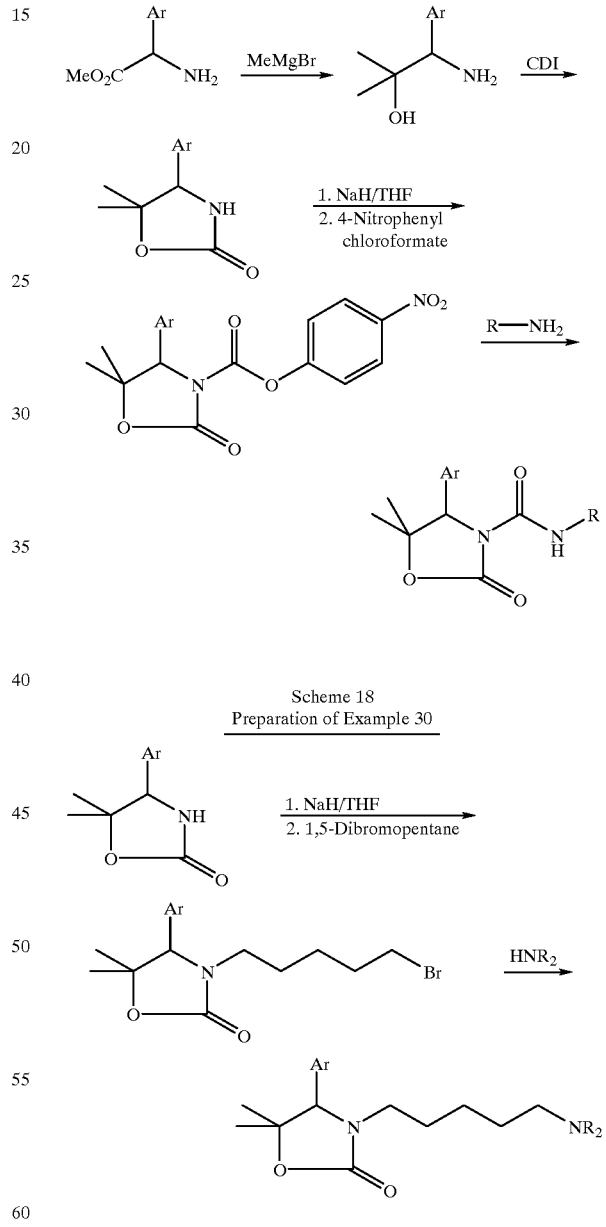

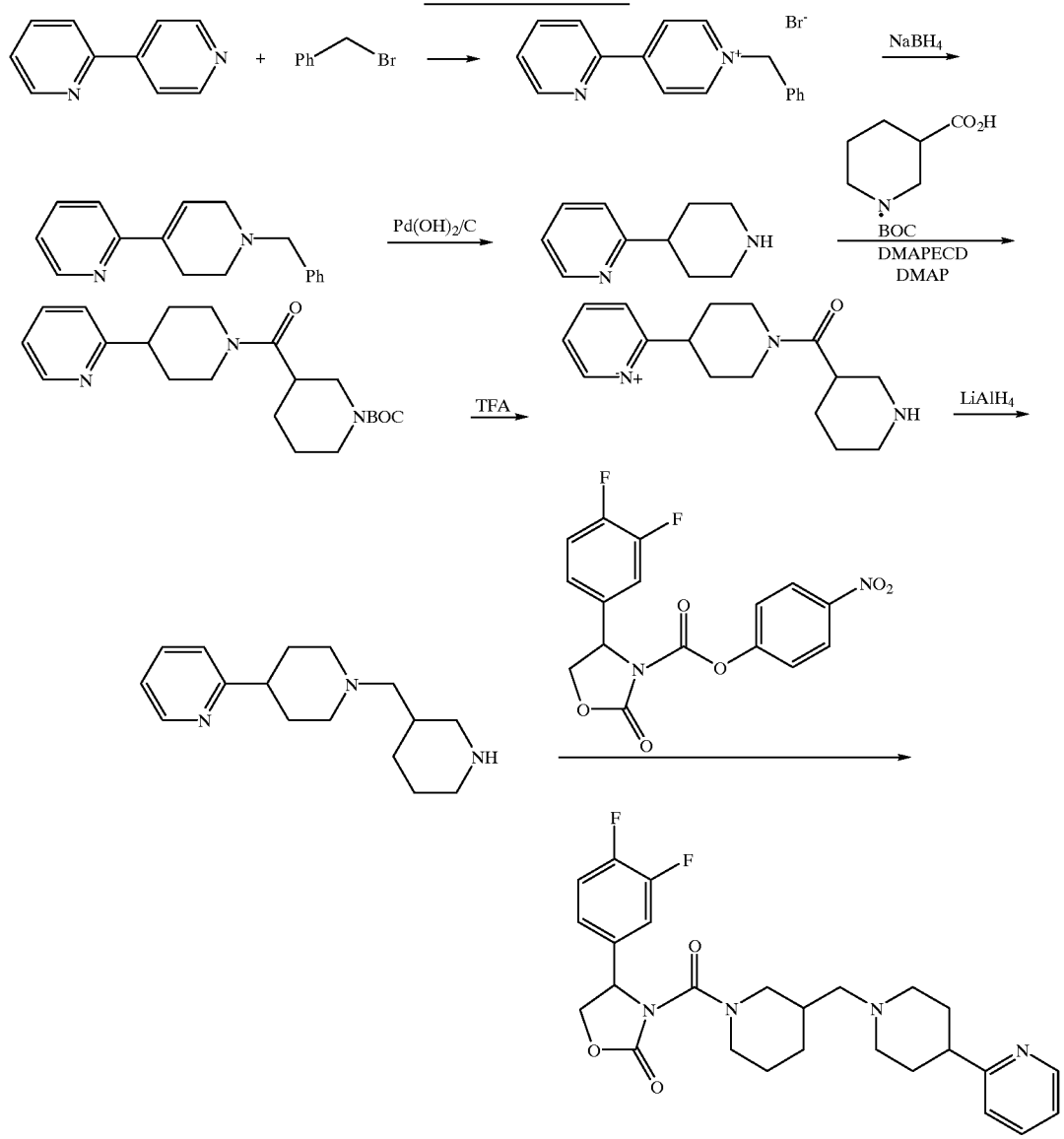
Scheme 19
Preparation of Example 32
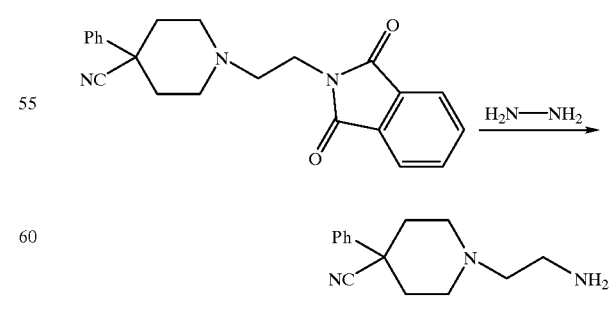
Scheme 20
Preparation of Side Chain

Scheme 21
Preparation of Example 33
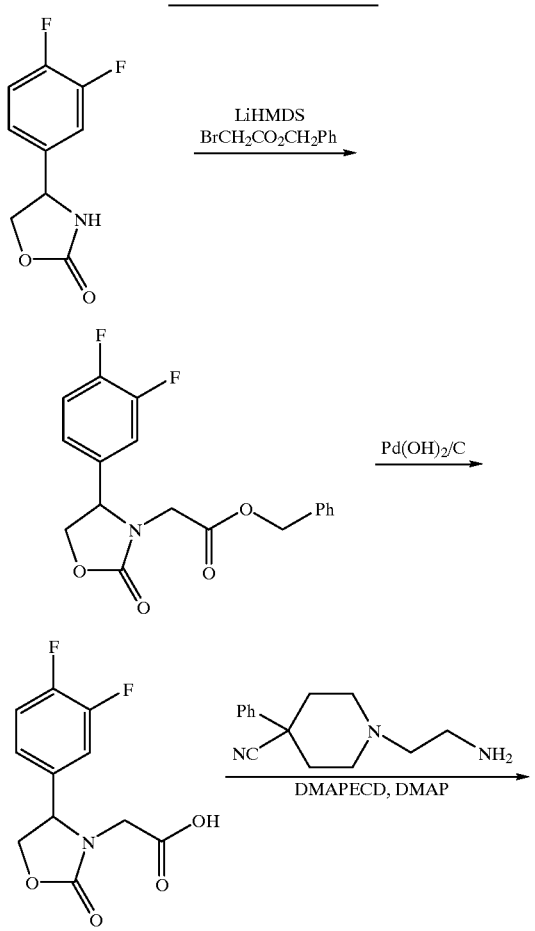
Scheme 22
Preparation of example 34
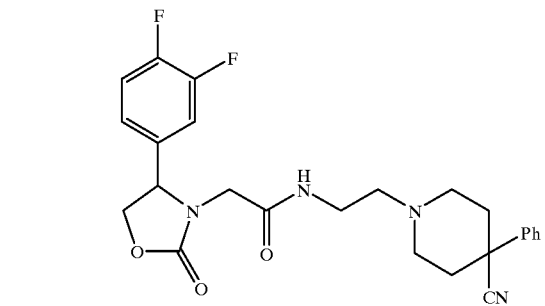
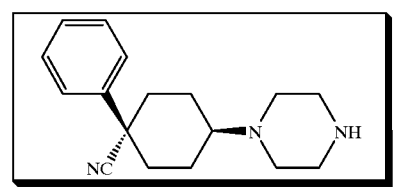
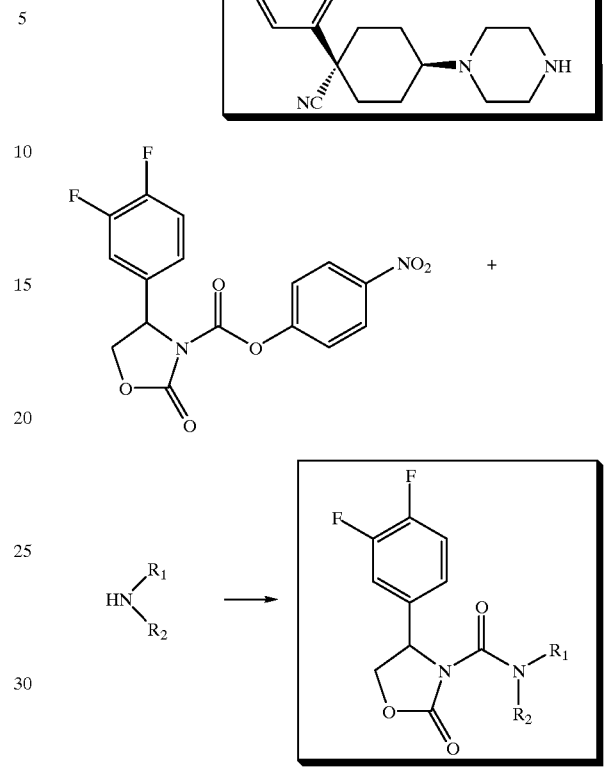
Scheme 23
Preparation of examples 35, 36 and 37
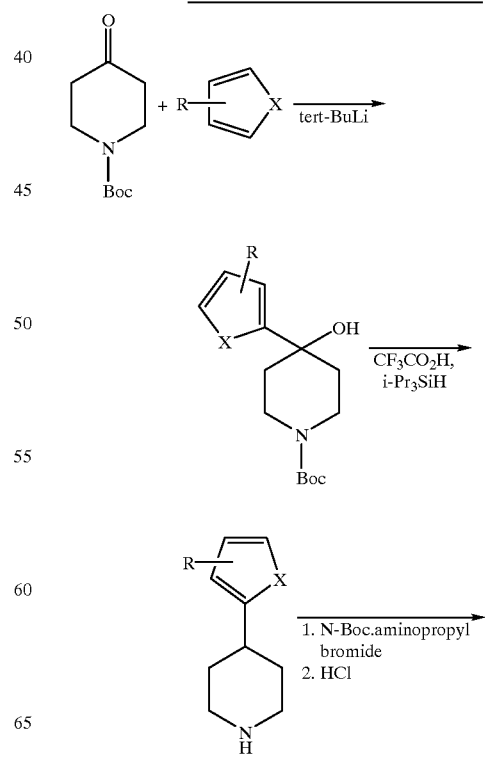

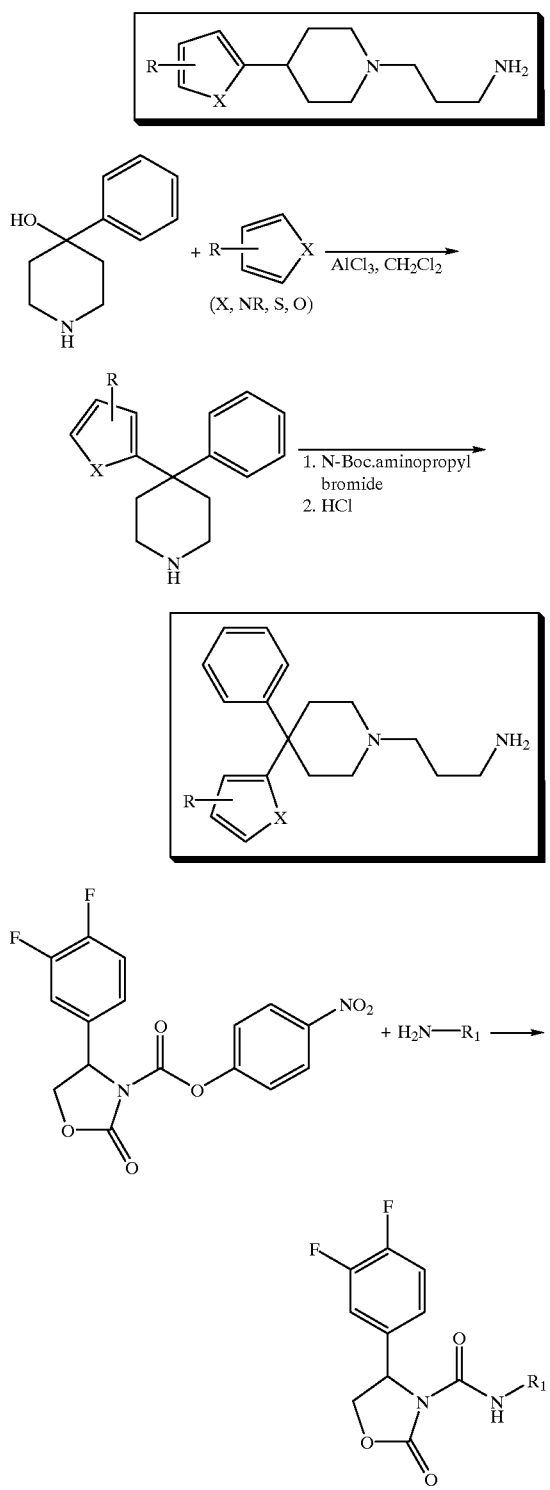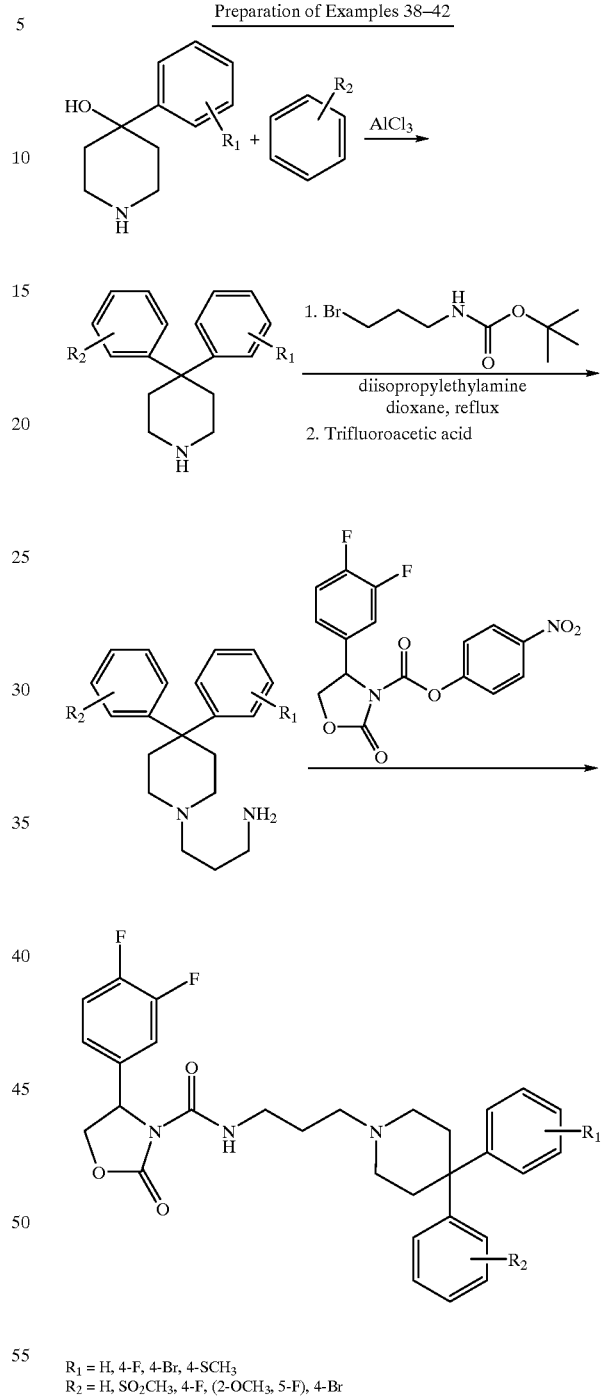

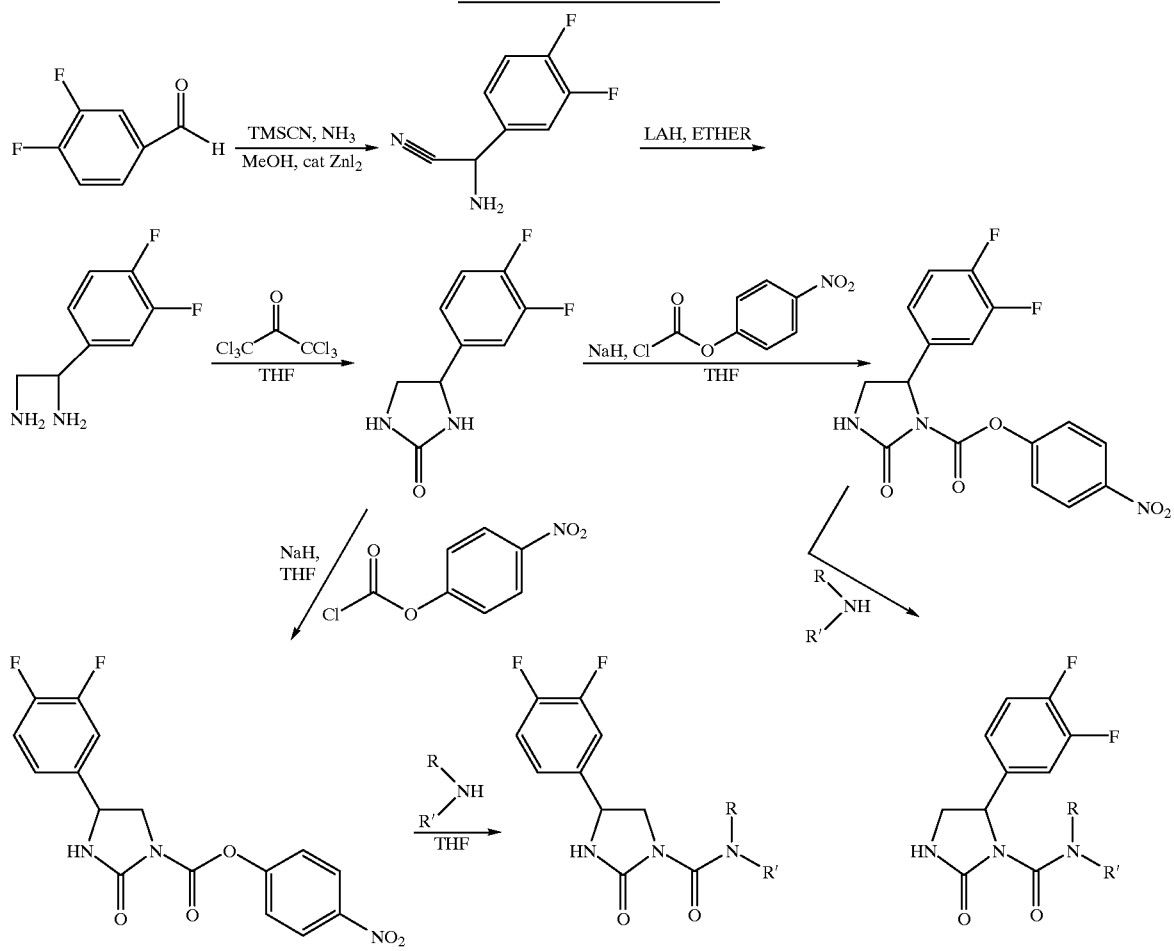
Scheme 25
Preparation of Examples 3 and 44.
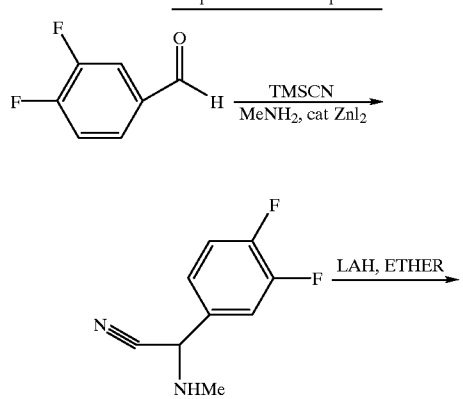
Scheme 26
Preparation of Example 45.
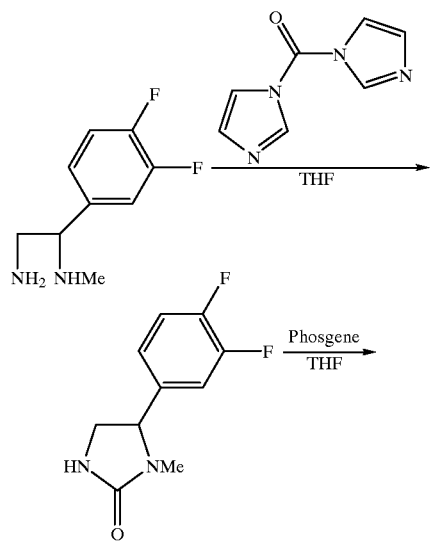
-continued

101
-continued
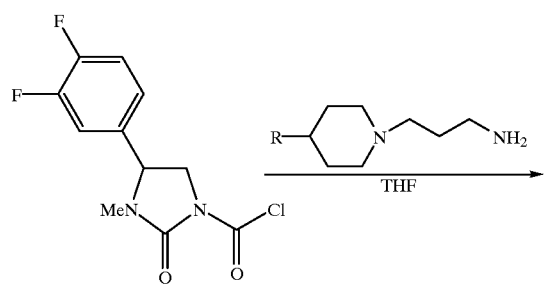
102
-continued
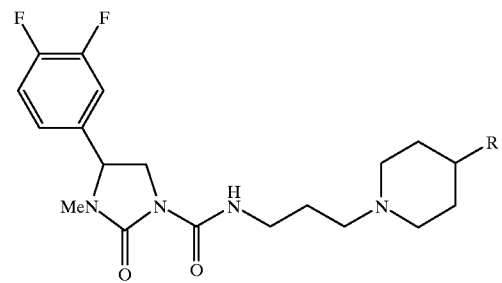
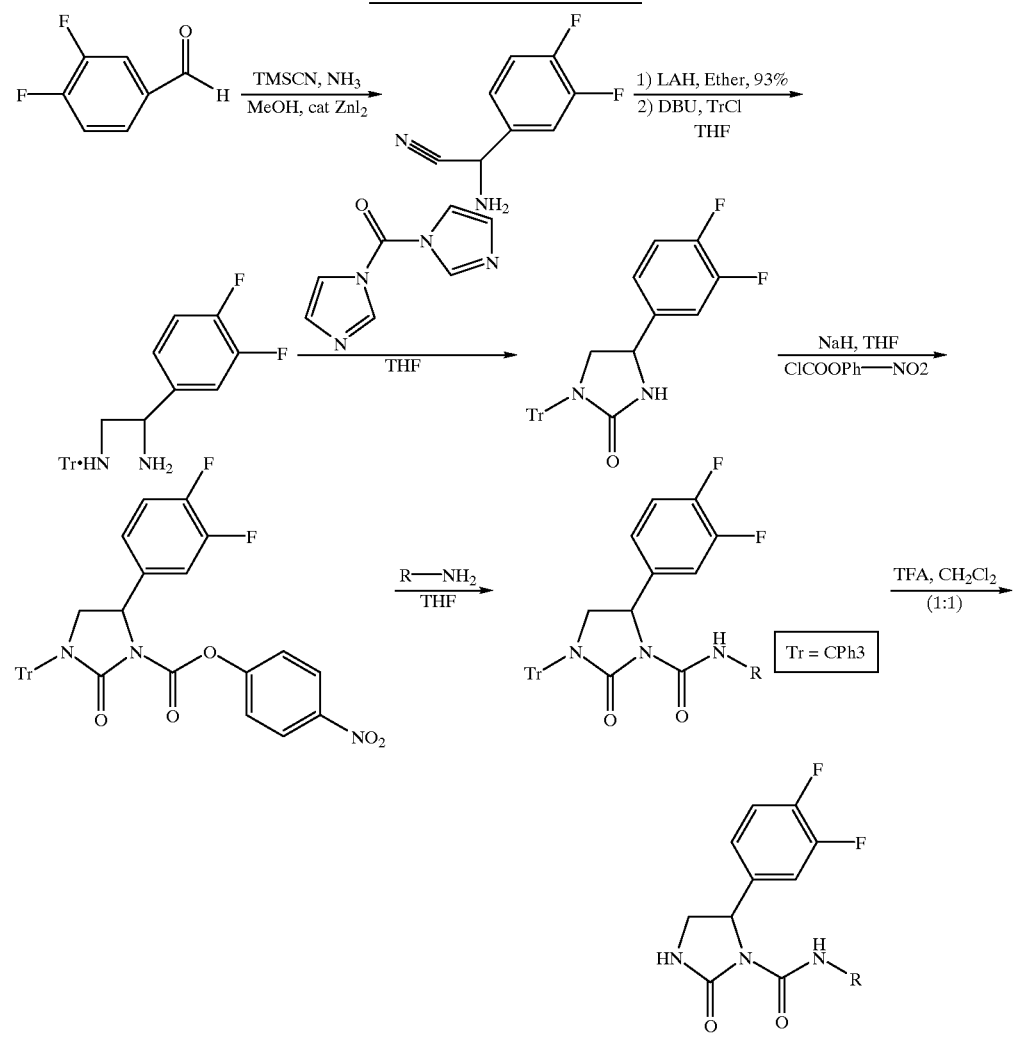

Scheme 28
Preparation of Example 50
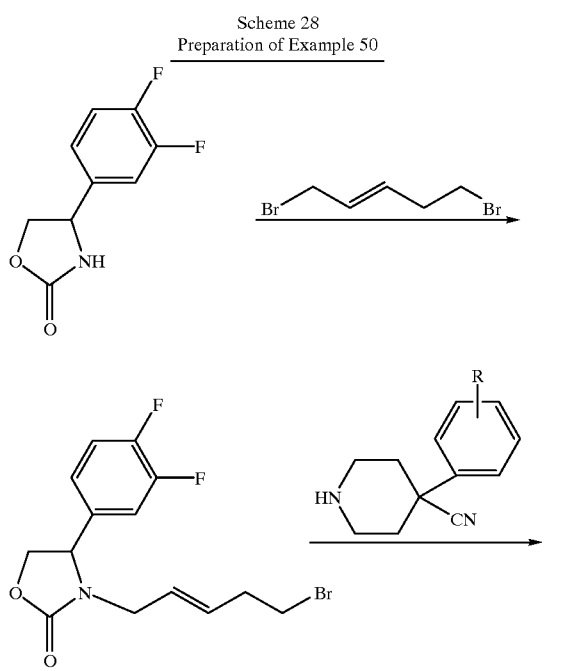
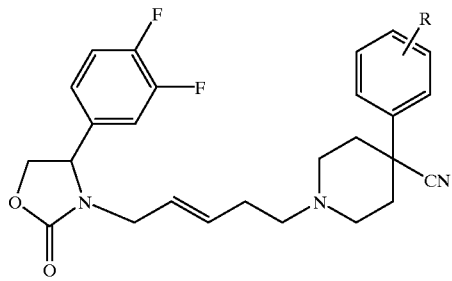
Scheme 29
Synthesis of Example 52 and related compounds
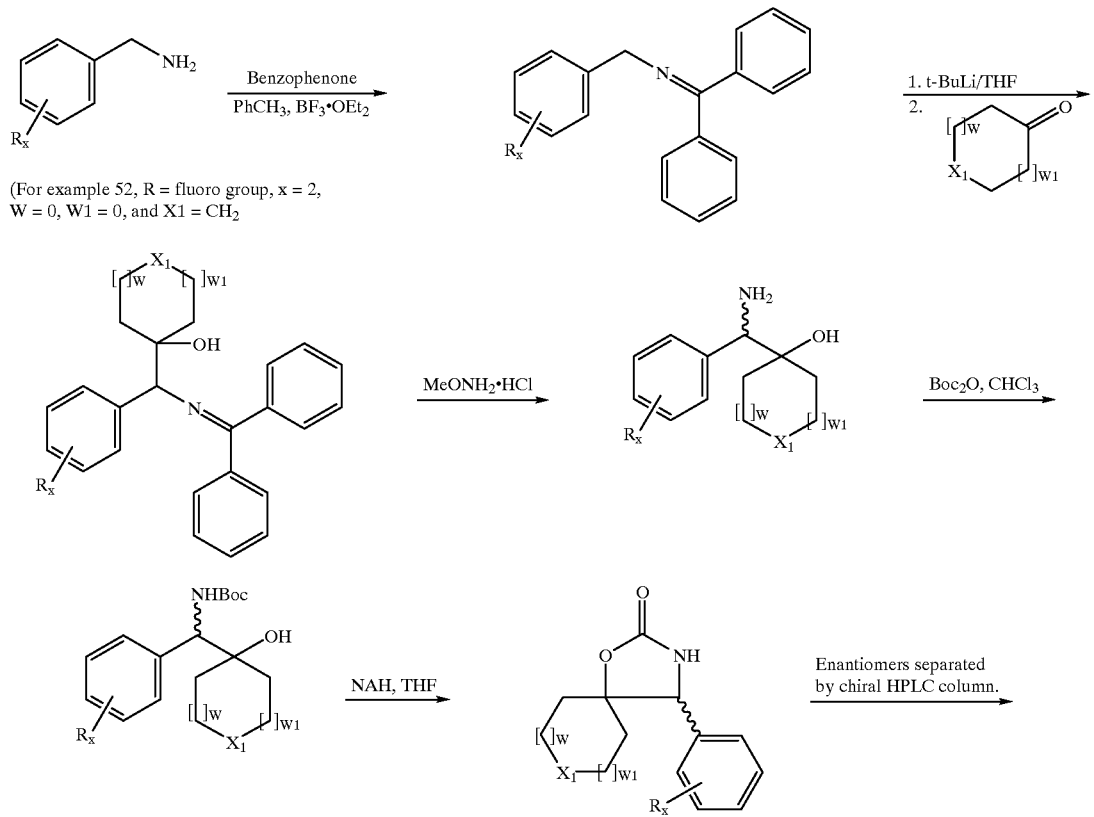
(For example 52, R = fluoro group, x = 2, W = 0, W1 = 0, and X1 = CH$_2$)
Enantiomers separated by chiral HPLC column.

105
106
-continued
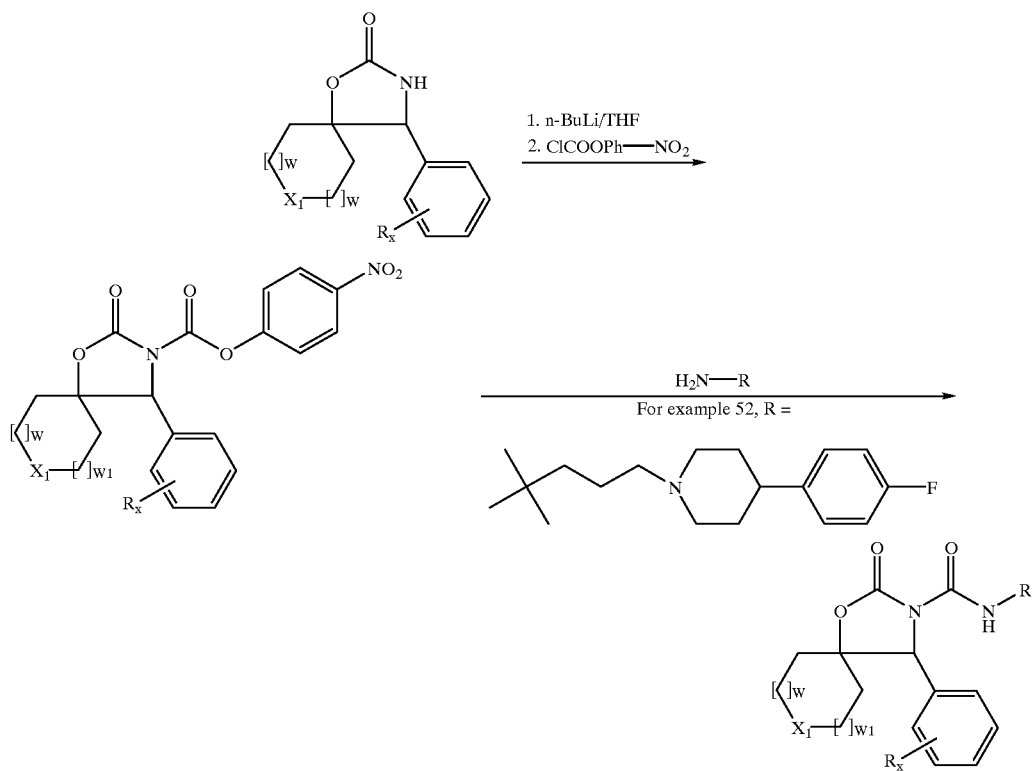
Scheme 30
Synthisis of Example 53
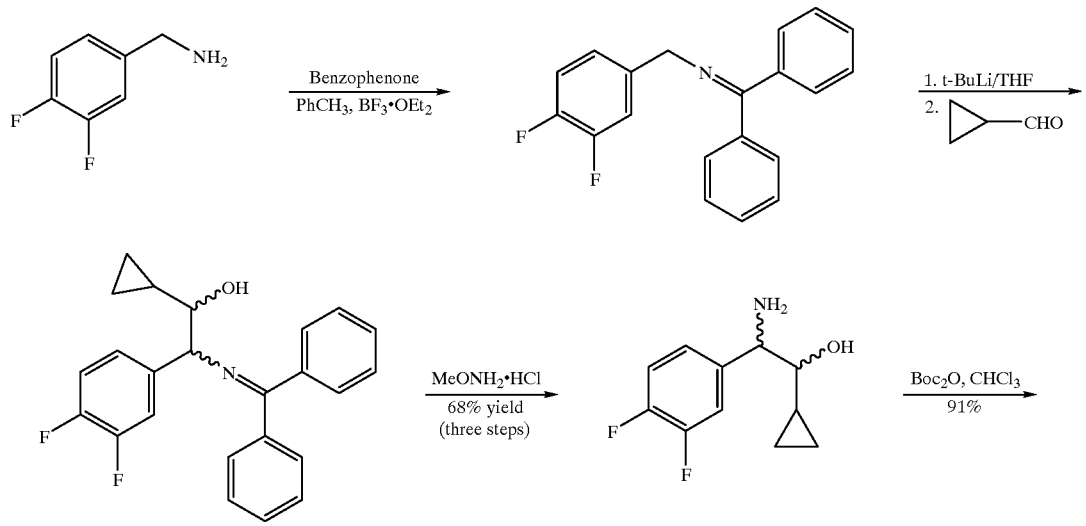

107
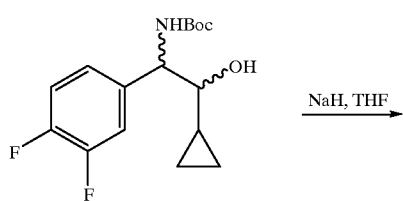
NaH, THF →
-continued
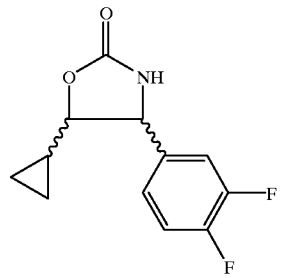
Diastereomers separated by chiral HPLC coloumn.
Enantiomers separated by chiral HPLC column. →
108
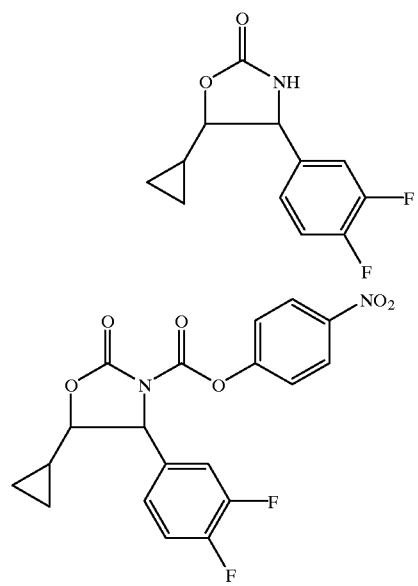
1. n-BuLi/THF
2. ClCOOPh—NO₂
→
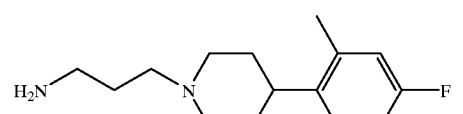
→
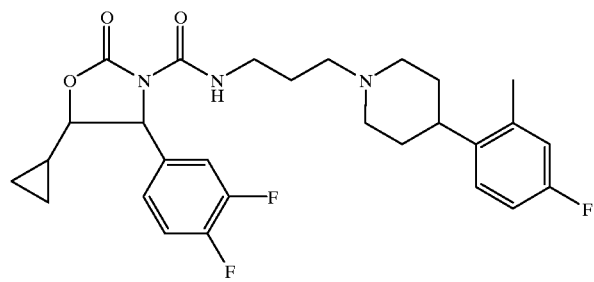
Scheme 31
General synthesis of methylated oxazolidinone
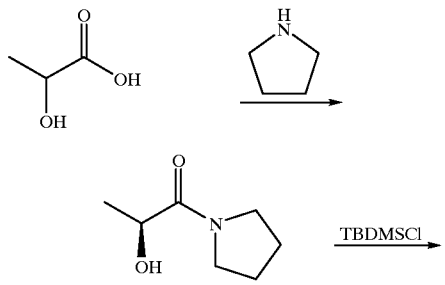
-continued
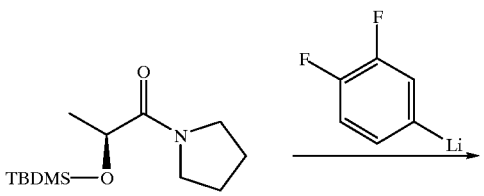
$H_2NOH \cdot HCl$ →
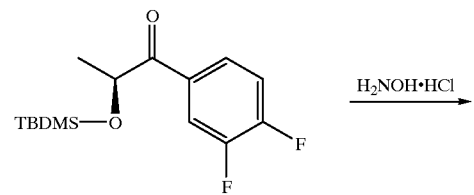

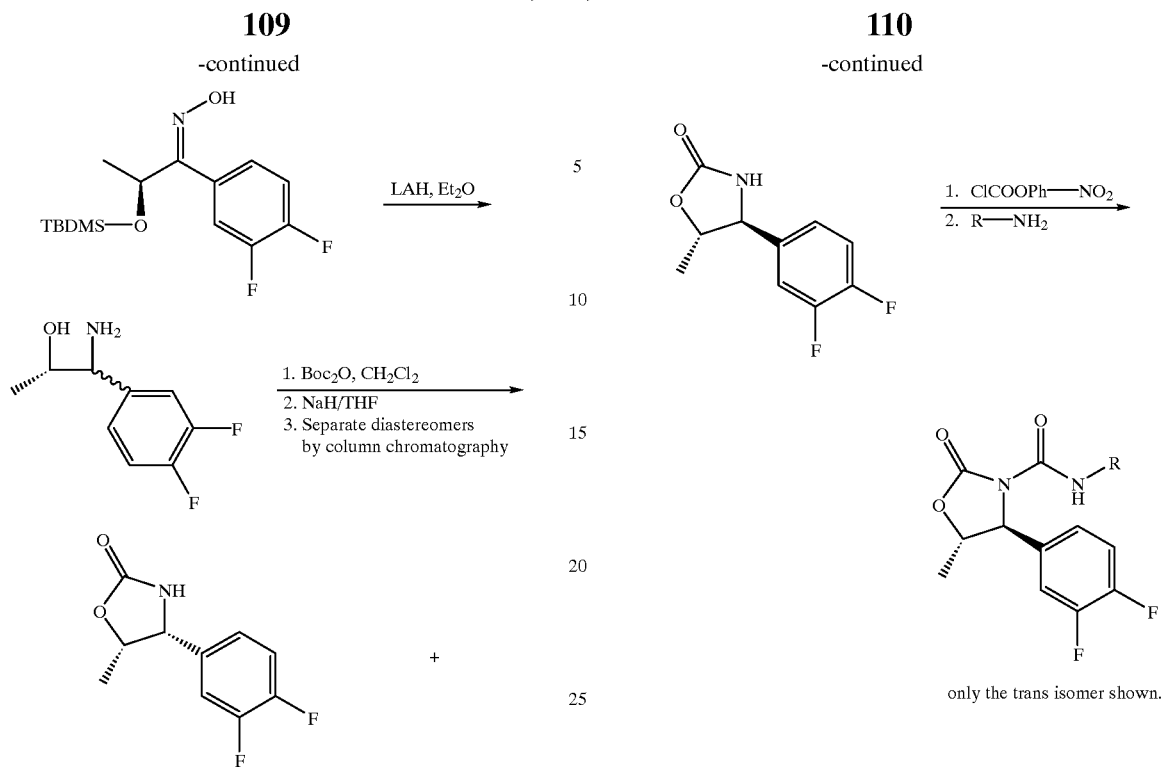
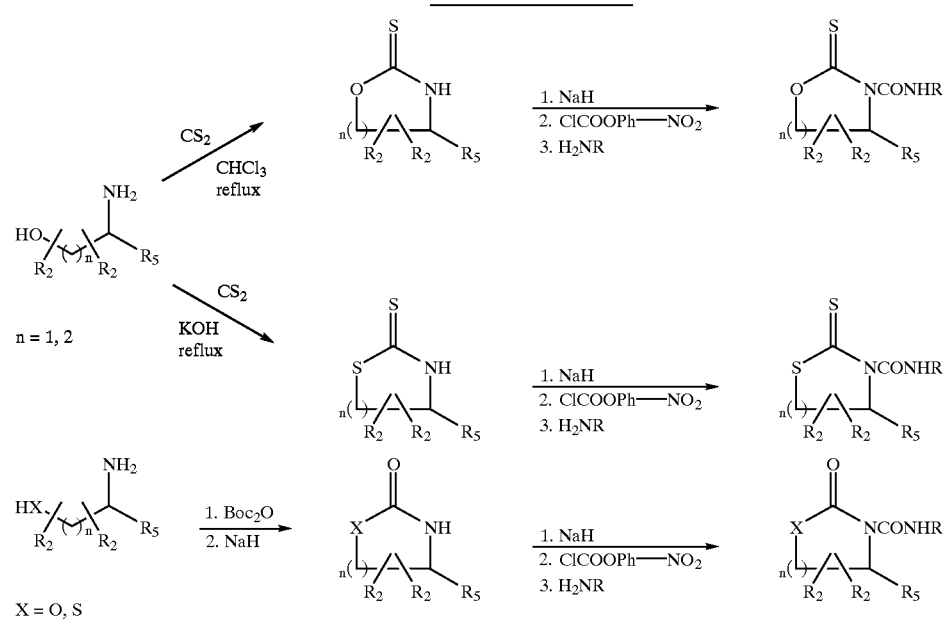
only the trans isomer shown.

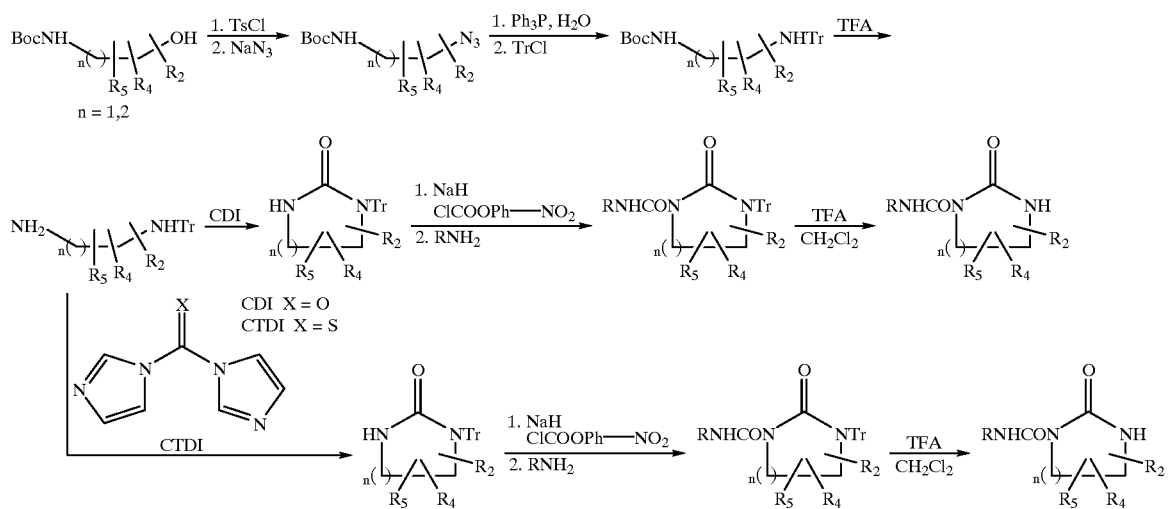
Scheme 33
General synthetic scheme
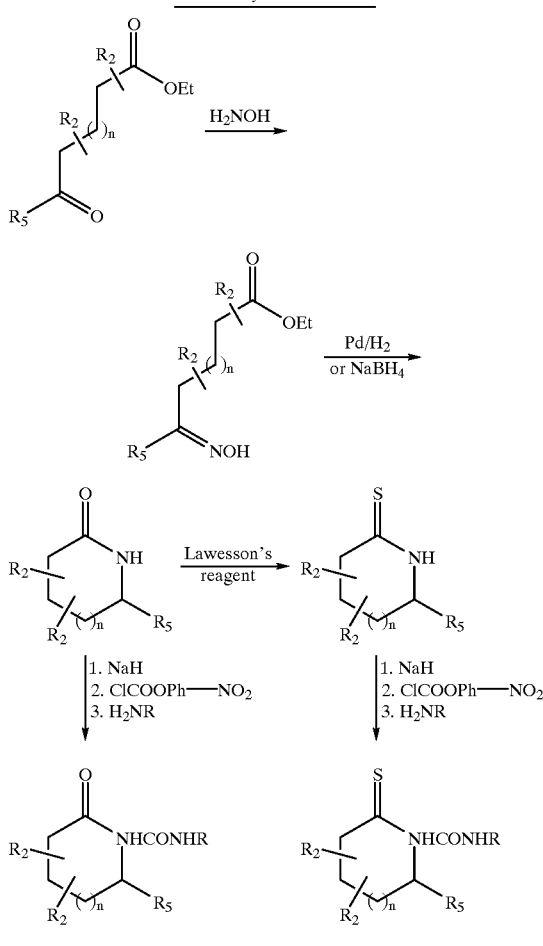
Scheme 34
General synthetic scheme
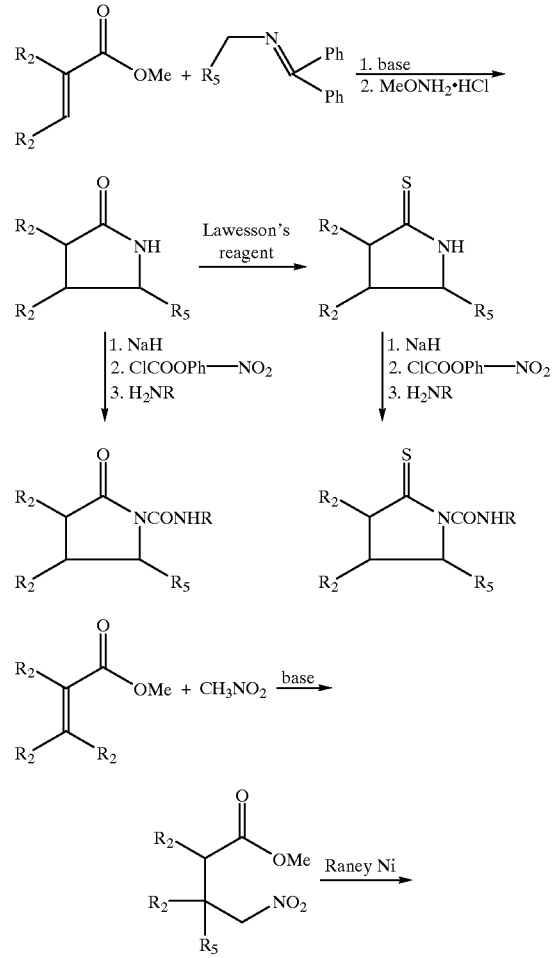
Scheme 35
General synthetic scheme

113

-continued

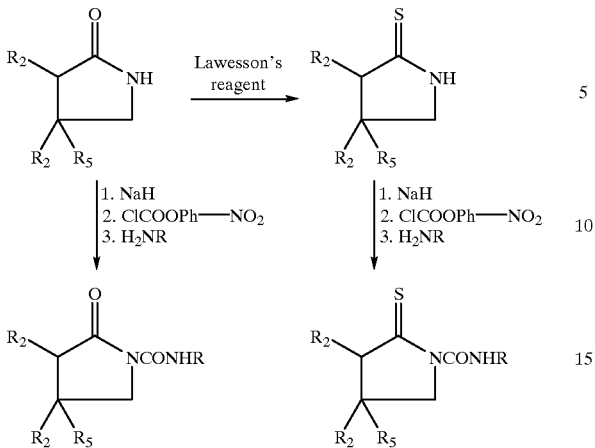

What is claimed is:
1. A compound having the structure:

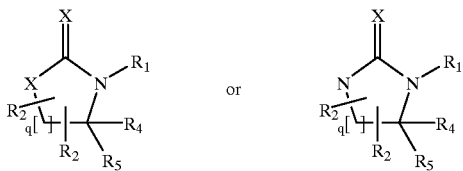

wherein each X is independently O or S;
wherein q is 1;
wherein each $R_2$ is independently H; —$(CH_2)_tXR_3$; —$(CH_2)_tC(X)NR_3$; —$(CH_2)_tCO_2R_3$; —$CO_2R_3$; straight chained or branched $C_1$–$C_7$ alkyl, aminoalkyl, carboxamidoalkyl; straight chained or branched $C_2$–$C_7$ alkenyl, or alkynyl; or $C_3$–$C_7$ cycloalkyl or $C_5$–$C_7$ cycloalkenyl;
wherein each t is an integer from 1 to 4 inclusive;
wherein each $R_3$ is independently H; straight chained or branched $C_1$–$C_7$ alkyl, straight chained or branched $C_2$–$C_7$ alkenyl, or alkynyl; or $C_3$–$C_7$ cycloalkyl or $C_5$–$C_7$ cycloalkenyl;
wherein $R_4$ is aryl, heteroaryl, $C_1$–$C_7$ alkyl substituted with one or two aryl, or $C_1$–$C_7$ alkyl substituted with one or two heteroaryl; wherein the aryl or heteroaryl may be substituted with one or more of F, Cl, Br, I, —CN, —$NO_2$, —$N(R_3)_2$, —$COR_3$, —$(CH_2)_nXR_3$, —$(CH_2)_nC(X)NR_3$, —$(CH_2)_nCO_2R_3$, straight chained or branched $C_1$–$C_7$ alkyl, monofluoroalkyl, polyfluoroalkyl or carboxamidoalkyl, or straight chained or branched $C_2$–$C_7$ aminoalkyl, alkenyl or alkynyl, or $C_3$–$C_7$ cycloalkyl or $C_5$–$C_7$ cycloalkenyl;
wherein each n independently is an integer from 0 to 7 inclusive;
wherein $R_5$ is H; aryl, $C_1$–$C_7$ alkyl substituted with aryl, heteroaryl, or $C_1$–$C_7$ alkyl substituted with heteroaryl; wherein the aryl or heteroaryl may be substituted with one or more of F, Cl, Br, I, —CN, —$NO_2$, —$N(R_3)_2$, —$COR_3$, —$(CH_2)_tXR_3$, —$(CH_2)_nC(X)NR_3$, —$(CH_2)_nCO_2R_3$, straight chained or branched $C_1$–$C_7$ alkyl, monofluoroalkyl, polyfluoroalkyl or carboxamidoalkyl, or straight chained or branched $C_2$–$C_7$ aminoalkyl, alkenyl or alkynyl, or $C_3$–$C_7$ cycloalkyl or $C_5$–$C_7$ cycloalkenyl;

114 where $R_5$ and one $R_2$ on adjacent carbon atoms together may form aryl, heteroaryl, indane or tetrahydronaphthyl, $C_3$–$C_7$ cycloalkyl, or heterocycloalkyl wherein one or two heteroatoms may be O, N or S;
wherein $R_1$ is

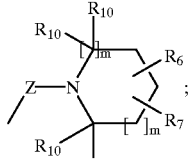

where each $R_6$ is independently aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;
where each $R_7$ is independently H; F; Cl; Br; I; —$COR_3$; —$CO_2R_3$; —$(CH_2)_nXR_3$; $(CH_2)_nC(X)N(R_3)_2$; —$(CH_2)_nCO_2R_3$; —CN; —$NO_2$; —$N(R_3)_2$; straight chained or branched $C_1$–$C_7$ alkyl, hydroxyalkyl, aminoalkyl, carboxamidoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or $C_5$–$C_7$ cycloalkenyl, wherein the alkyl, aminoalkyl, carboxamidoalkyl, alkenyl, alkynyl, cycloalkyl or cycloalkenyl may be substituted with one or more aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl; aryl or heteroaryl, wherein the aryl or heteroaryl may be substituted with one or more of F, Cl, Br, I, —$(CH_2)_nXR_3$, —$COR_3$, —$(CH_2)_nC(X)N(R_3)_2$, —$(CH_2)_nCO_2R_3$, —CN, —$NO_2$, —$N(R_3)_2$, —$SO_2R_3$, straight chained or branched $C_1$–$C_7$ alkyl, straight chained or branched $C_1$–$C_7$ monofluoroalkyl or polyfluoroalkyl, straight chained or branched $C_2$–$C_7$ alkenyl or alkynyl, or $C_3$–$C_7$ cycloalkyl, monofluorocycloalkyl, polyfluorocycloalkyl or $C_5$–$C_7$ cycloalkenyl;
wherein each $R_{10}$ is independently H; $(CH_2)_tXR_3$; $(CH_2)_tC(X)NR_3$; $(CH_2)_tCO_2R_3$; straight chained or branched $C_1$–$C_7$ alkyl or carboxamidoalkyl; straight chained or branched $C_2$–$C_7$ aminoalkyl, alkenyl, or alkynyl; or $C_3$–$C_7$ cycloalkyl or $C_5$–$C_7$ cycloalkenyl;
wherein $R_{11}$ is aryl, heteroaryl, $C_1$–$C_7$ alkyl substituted with one or two aryl, or $C_1$–$C_7$ alkyl substituted with one or two heteroaryl; wherein any aryl or heteroaryl independently may be substituted with one or more of F, Cl, Br, I, —CN, —$NO_2$, —$N(R_3)_2$, —$COR_3$, —$(CH_2)_nXR_3$, —$(CH_2)_nC(X)NR_3$, —$(CH_2)_nCO_2R_3$, straight chained or branched $C_1$–$C_7$ alkyl, monofluoroalkyl, polyfluoroalkyl, or carboxamidoalkyl, straight chained or branched $C_2$-$C_7$ aminoalkyl, alkenyl, or alkynyl, or $C_3$-$C_7$ cycloalkyl or $C_5$-$C_7$ cycloalkenyl;

wherein each m independently is an integer from 0 to 3 inclusive;

wherein Z is

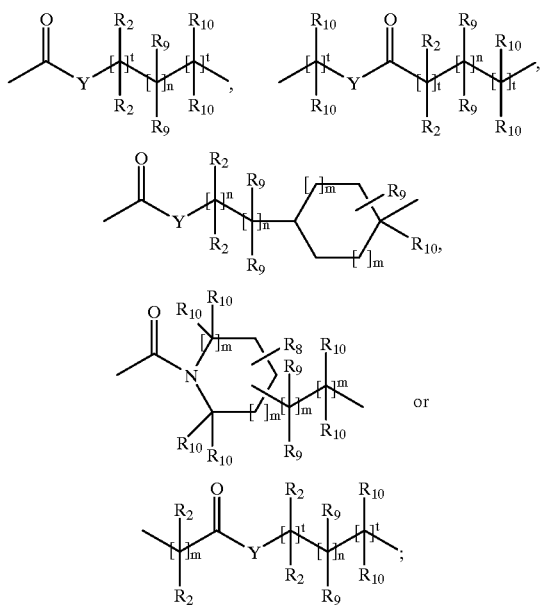

or $C_2$-$C_7$ alkenyl, wherein the $C_2$-$C_7$ alkenyl may be unsubstituted or substituted with one or more $R_9$ groups;

where $R_8$ is H; $(CH_2)_tXR_3$; $(CH_2)_tC(X)NR_3$; $(CH_2)_tCO_2R_3$; straight chained or branched $C_1$-$C_7$ alkyl, carboxamidoalkyl; straight chained or branched $C_2$-$C_7$ aminoalkyl, alkenyl, or alkynyl; or $C_3$-$C_7$ cycloalkyl or $C_5$-$C_7$ cycloalkenyl;

where each $R_9$ is independently H; F; Cl; Br; I; $(CH_2)_mXR_3$; $(CH_2)_mC(X)NR_3$; $(CH_2)_mCO_2R_3$; straight chained or branched $C_1$-$C_7$ alkyl, monofluoroalkyl, polyfluoroalkyl, aminoalkyl, or carboxamidoalkyl; straight chained or branched $C_2$-$C_7$ alkenyl, or alkynyl; or $C_3$-$C_7$ cycloalkyl or $C_5$-$C_7$ cycloalkenyl;

wherein Y is S, O, or $NR_3$;

or a pharmaceutically acceptable salt thereof.

2. The compound of claim 1, wherein the compound comprises the (+) enantiomer.

3. The compound of claim 1, wherein the compound comprises the (−) enantiomer.

4. The compound of claim 1, wherein the compound comprises a cis isomer.

5. The compound of claim 1, wherein the compound comprises a trans isomer.

6. The compound of claim 1, wherein $R_4$ is aryl or heteroaryl, wherein the aryl may be substituted with one or more of F, Cl, $(CH_2)_tOR_3$, $(CH_2)_nC(O)NR_3$, $(CH_2)_nCO_2R_3$, straight chained or branched $C_1$-$C_7$ alkyl or monofluoroalkyl; and Z is

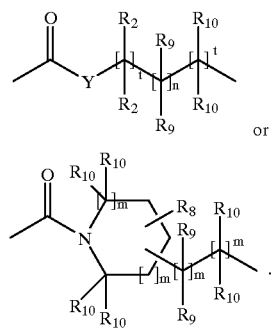

7. The compound of claim 6, wherein $R_4$ is pyridyl or phenyl, wherein the phenyl may be substituted with one or more of F, Cl, $-(CH_2)_tOR_3$, $-(CH_2)_nC(O)NR_3$, $-(CH_2)_nCO_2R_3$, straight chained or branched $C_1$-$C_7$ alkyl or monofluoroalkyl.

8. The compound of claim 7, wherein each $R_6$ is independently aryl or heteroaryl, wherein the aryl or heteroaryl may be substituted with one or more of F, Cl, Br, I, $-(CH_2)_nXR_3$, $-COR_3$, $-(CH_2)_nC(X)N(R_3)_2$, $-(CH_2)_nCO_2R_3$, $-CN$, $-NO_2$, $-N(R_3)_2$, $-SO_2R_3$, straight chained or branched $C_1$-$C_7$ alkyl, monofluoroalkyl or polyfluoroalkyl.

9. The compound of claim 8, wherein $R_7$ is H; $-CN$; $-CO_2R_3$; $-C(O)N(R_3)_2$; $-(CH_2)_mXR_3$; unsubstituted or substituted aryl; or $C_1$-$C_3$ alkyl.

10. The compound of claim 9, wherein the $R_4$ is phenyl, wherein the phenyl may be substituted with at least one of F or Cl.

11. The compound of claim 10 having the structure:

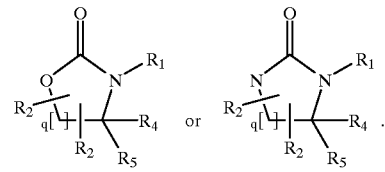

12. The compound of claim 11, wherein Z is:

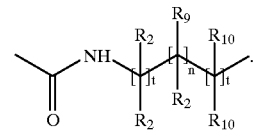

13. The compound of claim 12, wherein at least one $R_2$ is $C_1$-$C_3$ alkyl.

14. The compound of claim 12, wherein $R_4$ is phenyl substituted with at least one of F or Cl.

15. The compound of claim 14, wherein $R_4$ is phenyl substituted with at least two F.

16. The compound of claim 12, wherein $R_4$ is 3,4-difluorophenyl.

17. The compound of claim 12, wherein $R_6$ is pyridyl, phenyl, or phenyl substituted with one or more of F, Cl, Br, I, $-(CH_2)_nXR_3$, $-COR_3$, $-(CH_2)_nC(X)N(R_3)_2$, $-(CH_2)_nCO_2R_3$, $-CN$, $-NO_2$, $-N(R_3)_2$, $-SO_2R_3$, straight chained or branched $C_1$-$C_7$ alkyl, monofluoroalkyl or polyfluoroalkyl.

18. The compound of claim 12, wherein $R_7$ is H; —CN; or —CO$_2$R$_3$.

19. The compound of claim 12, wherein $R_9$ is F; —OH; C$_1$-C$_3$ alkyl; or —(CH$_2$)$_m$XR$_3$.

20. The compound of claim 17, wherein $R_6$ is 4-fluorophenyl.

21. A pharmaceutical composition comprising a therapeutically effective amount of the compound of claim 1 and a pharmaceutically acceptable carrier.

22. The pharmaceutical composition of claim 21 wherein the amount of the compound is an amount from about 0.01 mg to about 800 mg.

23. The pharmaceutical composition of claim 22 wherein the amount of the compound is an amount from about 0.01 mg to about 500 mg.

24. The pharmaceutical composition of claim 23 wherein the amount of the compound is an amount from about 0.01 mg to about 250 mg.

25. The pharmaceutical composition of claim 24 wherein the amount of the compound is from about 0.1 mg to about 60 mg.

26. The pharmaceutical composition of claim 25 wherein the amount of the compound is from about 1 mg to about 20 mg.

27. The pharmaceutical composition of claim 21, wherein the carrier is a liquid and the composition is a solution.

28. The pharmaceutical composition of claim 21, wherein the carrier is a solid and the composition is a tablet.

29. The pharmaceutical composition of claim 21, wherein the carrier is a gel and the composition is a suppository.

30. The pharmaceutical composition of claim 21, wherein the compound additionally does not cause a fall in blood pressure at dosages effective to alleviate benign prostatic hyperplasia.

31. A pharmaceutical composition comprising a therapeutically effective amount of the compound of claim 1 in combination with a therapeutically effective amount of finasteride and a pharmaceutically acceptable carrier.

32. The pharmaceutical composition of claim 31 wherein the compound is present in an amount from about 0.01 mg to about 500 mg and the therapeutically effective amount of the finasteride is about 5 mg.

33. The pharmaceutical composition of claim 32 wherein the compound is present in an amount from about 0.1 mg to about 60 mg and the therapeutically effective amount of finasteride is about 5 mg.

34. The pharmaceutical composition of claim 33 wherein the compound is present in an amount from about 1 mg to about 20 mg and the therapeutically effective amount of finasteride is about 5 mg.

35. A trans (+) isomer of the compound of claim 20, wherein the compound has the structure:

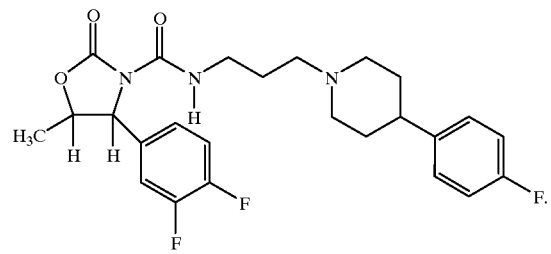

36. The compound of claim 1, wherein the compound has the structure:

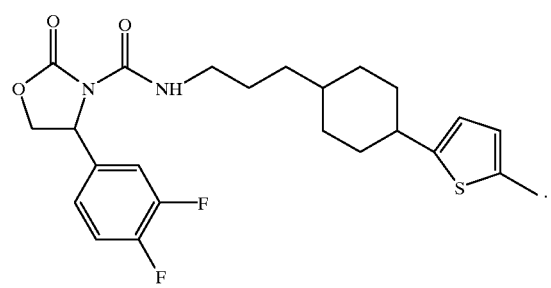

37. The compound of claim 1, wherein the compound has the structure:

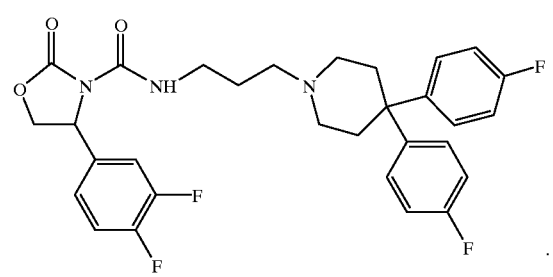

38. The compound of claim 1, wherein the compound has the structure:

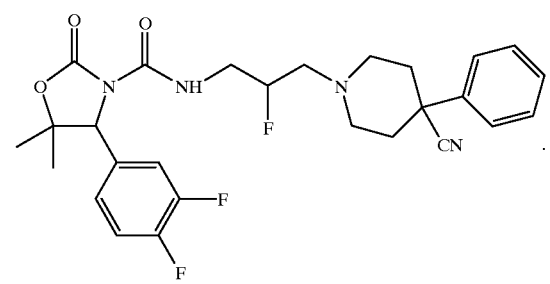

* * * * *